United States Patent
Ahn et al.

(10) Patent No.: US 12,250,874 B2
(45) Date of Patent: Mar. 11, 2025

(54) ORGANIC ELECTROLUMINESCENCE DEVICE AND ORGANOMETALLIC COMPOUND FOR ORGANIC ELECTROLUMINESCENCE DEVICE

(71) Applicant: Samsung Display Co., Ltd., Yongin-si (KR)

(72) Inventors: Eunsoo Ahn, Jinju-si (KR); Soo-Byung Ko, Yongin-si (KR); Haejin Kim, Hwaseong-si (KR); Sujin Shin, Hwaseong-si (KR); Hyunjung Lee, Hwaseong-si (KR); Junghoon Han, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 643 days.

(21) Appl. No.: 17/447,249

(22) Filed: Sep. 9, 2021

(65) Prior Publication Data
US 2022/0199918 A1    Jun. 23, 2022

(30) Foreign Application Priority Data

Dec. 15, 2020    (KR) .......... 10-2020-0175439

(51) Int. Cl.
| | |
|---|---|
| *H10K 85/30* | (2023.01) |
| *C07F 15/00* | (2006.01) |
| *C09K 11/06* | (2006.01) |
| *H10K 50/11* | (2023.01) |
| *H10K 85/40* | (2023.01) |

(Continued)

(52) U.S. Cl.
CPC ....... *H10K 85/346* (2023.02); *C07F 15/0086* (2013.01); *C09K 11/06* (2013.01); *H10K 85/322* (2023.02); *H10K 85/40* (2023.02); *C09K 2211/1029* (2013.01); *C09K 2211/1044* (2013.01); *C09K 2211/185* (2013.01); *H10K 50/11* (2023.02); *H10K 2101/10* (2023.02); *H10K 2101/90* (2023.02)

(58) Field of Classification Search
CPC .......... H10K 2101/10; C09K 2211/185; C07F 15/0086
See application file for complete search history.

(56) References Cited

U.S. PATENT DOCUMENTS

| | | | |
|---|---|---|---|
| 7,381,479 B2 | 6/2008 | Lamansky et al. | |
| 7,393,599 B2 | 7/2008 | Thompson et al. | |
| 7,585,573 B2 | 9/2009 | Lee et al. | |

(Continued)

FOREIGN PATENT DOCUMENTS

| | | | | |
|---|---|---|---|---|
| CN | 104370974 A | 2/2015 | | |
| EP | 3750898 A1 * | 12/2020 | .......... | C07F 15/0086 |

(Continued)

*Primary Examiner* — Vu A Nguyen
(74) *Attorney, Agent, or Firm* — Womble Bond Dickinson (US) LLP

(57) ABSTRACT

An organic electroluminescence device is provided and including a first electrode, a hole transport region disposed on the first electrode, an emission layer disposed on the hole transport region, an electron transport region disposed on the emission layer, and a second electrode disposed on the electron transport region, wherein the emission layer may include an organometallic compound, thereby exhibiting high luminous efficiency and long service life characteristics.

20 Claims, 6 Drawing Sheets

(51) Int. Cl.
*H10K 101/00* (2023.01)
*H10K 101/10* (2023.01)

(56) References Cited

U.S. PATENT DOCUMENTS

| | | | |
|---|---|---|---|
| 7,768,894 B2 | 8/2010 | Kimmelmann et al. | |
| 7,776,458 B2 | 8/2010 | Ragini et al. | |
| 8,106,199 B2 | 1/2012 | Jabbour et al. | |
| 8,389,725 B2 | 3/2013 | Li et al. | |
| 8,669,364 B2 | 3/2014 | Li et al. | |
| 8,680,760 B2 | 3/2014 | Cheng et al. | |
| 8,816,080 B2 | 8/2014 | Li et al. | |
| 8,846,940 B2 | 9/2014 | Li et al. | |
| 8,946,417 B2 | 2/2015 | Jian et al. | |
| 9,051,344 B2 | 6/2015 | Lin et al. | |
| 9,076,974 B2 | 7/2015 | Li et al. | |
| 9,203,039 B2 | 12/2015 | Li et al. | |
| 9,221,857 B2 | 12/2015 | Li et al. | |
| 9,224,963 B2 | 12/2015 | Li et al. | |
| 9,238,668 B2 | 1/2016 | Li et al. | |
| 9,312,502 B2 | 4/2016 | Li et al. | |
| 9,324,957 B2 | 4/2016 | Li et al. | |
| 9,382,273 B2 | 7/2016 | Li et al. | |
| 9,425,415 B2 | 8/2016 | Li et al. | |
| 9,698,359 B2 | 7/2017 | Li et al. | |
| 9,899,614 B2 | 2/2018 | Li et al. | |
| 9,972,793 B2 | 5/2018 | Wu et al. | |
| 2005/0287394 A1 | 12/2005 | Yang et al. | |
| 2008/0018221 A1 | 1/2008 | Egen et al. | |
| 2012/0121936 A1 | 5/2012 | Baek et al. | |
| 2014/0309428 A1 | 10/2014 | Egen et al. | |
| 2019/0119312 A1 | 4/2019 | Chen et al. | |
| 2019/0225636 A1 | 7/2019 | Bae et al. | |
| 2019/0280222 A1 | 9/2019 | Kim et al. | |
| 2019/0296254 A1* | 9/2019 | Ko | H10K 85/346 |
| 2020/0099001 A1 | 3/2020 | Kim et al. | |
| 2020/0199164 A1 | 6/2020 | Kim et al. | |
| 2020/0280003 A1 | 9/2020 | Min et al. | |

FOREIGN PATENT DOCUMENTS

| | | |
|---|---|---|
| JP | 4729516 B2 | 7/2011 |
| KR | 10-0730115 B1 | 6/2007 |
| KR | 10-2019-0089626 A | 7/2019 |
| KR | 10-2019-0107264 A | 9/2019 |
| KR | 10-2020-0034900 A | 4/2020 |
| KR | 10-2020-0076583 A | 6/2020 |
| KR | 10-2020-0095395 A | 8/2020 |
| WO | WO 2012/121936 A2 | 9/2012 |

\* cited by examiner

ORGANIC ELECTROLUMINESCENCE DEVICE AND ORGANOMETALLIC COMPOUND FOR ORGANIC ELECTROLUMINESCENCE DEVICE

CROSS-REFERENCE TO RELATED APPLICATION

This application claims priority to and the benefit of Korean Patent Application No. 10-2020-0175439, filed on Dec. 15, 2020, the entire content of which is hereby incorporated by reference.

BACKGROUND

1. Field

One or more embodiments of the present disclosure herein relate to an organic electroluminescence device and an organometallic complex for the organic electroluminescence device, and for example, to an organic electroluminescence device including an organometallic compound in an emission layer.

2. Description of the Related Art

Recently, the development of an organic electroluminescence display as an image display has been investigated. Unlike liquid crystal display apparatuses and the like, the organic electroluminescence display is a so-called self-luminescent display apparatus in which holes and electrons injected from a first electrode and a second electrode recombine in an emission layer, and thus a luminescent material including an organic compound in the emission layer emits light to implement display (e.g., to display one or more images).

In the application of an organic electroluminescence device to a display apparatus, there is a demand for an organic electroluminescence device having a low driving voltage, high luminous efficiency, and a long service life (lifespan), and the development on materials, for an organic electroluminescence device, capable of stably attaining such characteristics may be required.

Meanwhile, development on an organometallic compound used as a dopant material has also been investigated in the development of an emission layer material, but development on a dopant material exhibiting high efficiency in a blue emitting region may still be needed.

SUMMARY

Aspects of embodiments of the present disclosure are directed toward an organic electroluminescence device exhibiting excellent luminous efficiency and long service life characteristics by including an organometallic compound.

Aspects of embodiments of the present disclosure are directed toward an organometallic compound which may be a material for an organic electroluminescence device and which may improve luminous efficiency and service life characteristics.

Embodiments of the present disclosure provide an organic electroluminescence device including a first electrode, a hole transport region disposed on the first electrode, an emission layer disposed on the hole transport region, an electron transport region disposed on the emission layer, and a second electrode disposed on the electron transport region, wherein the emission layer may include an organometallic compound represented by Formula 1 below:

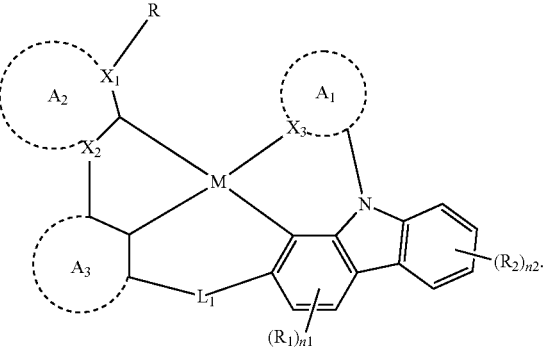

Formula 1

In Formula 1 above, M may be Pt, Pd, Ni, Au, Ag, Be, Mg, Al, Ca, Ti, Mn, Co, Zn, Ga, Zr, Ru, Rh, or Cu, $L_1$ may be $CR_3R_4$, $NR_5$, O, $SiR_6R_7$, $BR_8$, or $PR_9$, $X_1$ to $X_3$ may be each independently $CR_{10}$ or N, ring $A_1$ to ring $A_3$ may be each independently a substituted or unsubstituted monocyclic or polycyclic hydrocarbon ring group having 6 to 30 ring-forming carbon atoms, or a substituted or unsubstituted monocyclic or polycyclic heterocyclic group having 2 to 30 ring-forming carbon atoms, $R_1$ to $R_{10}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, n1 may be an integer of 0 to 2, n2 may be an integer of 0 to 4, and R may be represented by Formula 2 below:

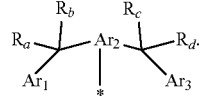

Formula 2

In Formula 2 above, $Ar_1$ and $Ar_3$ may be each independently a substituted or unsubstituted aryl group having 6 to 30 ring-forming carbon atoms, or a substituted or unsubstituted heteroaryl group having 2 to 30 ring-forming carbon atoms, $Ar_2$ may be a substituted or unsubstituted trivalent aryl group having 6 to 30 ring-forming carbon atoms, and $R_a$ to $R_d$ may be each independently a substituted or unsubstituted amine group, a substituted or unsubstituted alkoxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and $R_a$ and $R_b$ may be bonded to each other to form a ring, $R_c$ and $R_d$ may be bonded to each other to form a ring, and "—*" may be a bonding position with Formula 1.

In one or more embodiments, the emission layer may be to emit phosphorescence.

In one or more embodiments, the emission layer may include a host and a dopant, and the dopant may include the organometallic compound represented by Formula 1 above.

In one or more embodiments, Formula 2 above may be represented by Formula 2-1 or Formula 2-2 below:

Formula 2-1

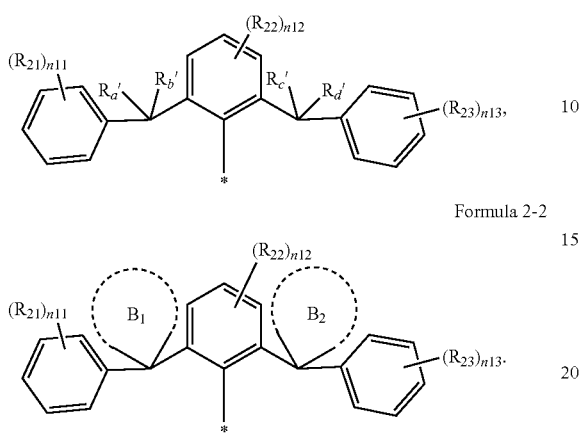

Formula 2-2

In Formula 2-1 and Formula 2-2 above, $R_{21}$ to $R_{23}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, $R_{a'}$ to $R_{d'}$ may be each independently a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, ring $B_1$ and ring $B_2$ may be each independently a substituted or unsubstituted cycloalkyl having 3 to 20 carbon atoms, a substituted or unsubstituted hetero cycloalkyl having 2 to 20 carbon atoms, a substituted or unsubstituted bicycloalkyl having 4 to 20 carbon atoms, a substituted or unsubstituted hetero bicycloalkyl having 3 to 20 carbon atoms, a substituted or unsubstituted tricycloalkyl having 6 to 20 carbon atoms, or a substituted or unsubstituted hetero tricycloalkyl having 5 to 20 carbon atoms, n11 and n13 may be each independently an integer of 0 to 5, and n12 may be an integer of 0 to 3.

In one or more embodiments, ring $B_1$ and ring $B_2$ above may be each independently represented by any one among Formula 3-1 to Formula 3-5 below:

Formula 3-1

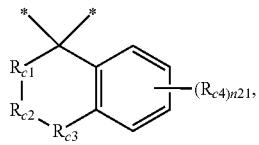

Formula 3-2

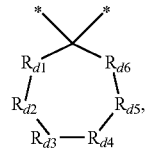

Formula 3-3

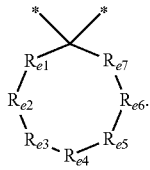

Formula 3-4

Formula 3-5

In Formula 3-1 to Formula 3-5 above, $R_{a1}$ to $R_{a4}$, $R_{b1}$ to $R_{b5}$, $R_{c1}$ to $R_{c3}$, $R_{d1}$ to $R_{d6}$, and $R_{e1}$ to $R_{e7}$ may be each independently $CR_{31}R_{32}$, or $NR_{33}$, $R_{31}$ and $R_{32}$ may be each independently a hydrogen atom, a deuterium atom, a halogen atom, a substituted or unsubstituted alkyl group having 1 to 30 carbon atoms, a substituted or unsubstituted amine group, a substituted or unsubstituted aryl group having 6 to 30 ring-forming carbon atoms, or a substituted or unsubstituted heteroaryl group having 2 to 30 ring-forming carbon atoms, $R_{33}$ and $R_{c4}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, at least any two groups among $R_{a1}$ to $R_{a4}$, at least any two groups among $R_{b1}$ to $R_{b5}$, at least any two groups among $R_{c1}$ to $R_{c3}$, at least any two groups among $R_{d1}$ to $R_{d6}$, or at least any two groups among $R_{e1}$ to $R_{e7}$ may be bonded to each other to form bicycloalkyl, hetero bicycloalkyl, tricycloalkyl, or hetero tricycloalkyl, and n21 may be an integer of 0 to 4.

In one or more embodiments, Formula 1 above may be represented by Formula 4 below:

Formula 4

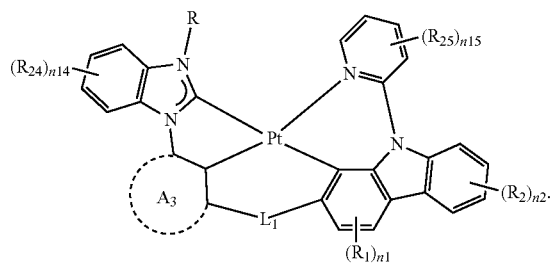

In Formula 4 above, $R_{24}$ and $R_{25}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted

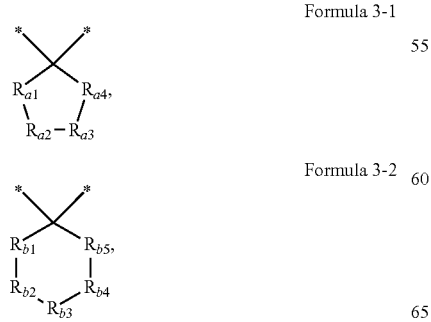

or unsubstituted heteroaryl group having 2 to 30 ring-forming carbon atoms, n14 and n15 may be each independently an integer of 0 to 4, and $L_1$, ring $A_3$, R, $R_1$, $R_2$, n1, and n2 may be the same as defined in Formula 1.

In one or more embodiments, Formula 4 above may be represented by Formula 5 below:

Formula 5

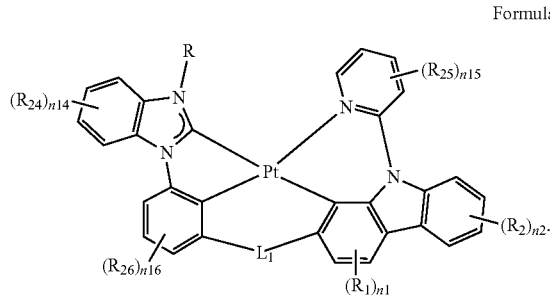

In Formula 5 above, $R_{26}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, n16 may be an integer of 0 to 3, and $L_1$, R, $R_1$, $R_2$, n1, n2, $R_{24}$, $R_{25}$, n14, and n15 may be the same as defined in Formula 1 and Formula 4.

In one or more embodiments, the host may include a first host represented by Formula 6 below or a second host represent by Formula 7 below:

Formula 6

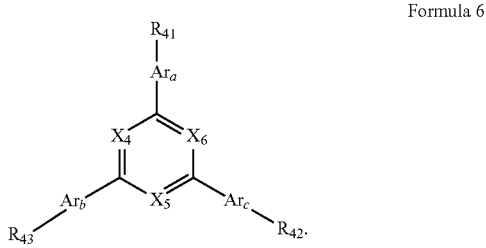

In Formula 6 above, $X_4$ to $X_6$ may be each independently N or $CR_{44}$, but at least one among $X_4$ to $X_6$ may be N, $Ar_a$ to $Ar_c$ may be each independently a direct linkage, a substituted or unsubstituted arylene group having 6 to 30 ring-forming carbon atoms, a substituted or unsubstituted hetero arylene group having 2 to 30 ring-forming carbon atoms, and/or bonded to an adjacent group to form a ring, $R_{41}$ to $R_{43}$ may be each independently a hydrogen atom, a deuterium atom, a halogen atom, a substituted or unsubstituted silyl group, a substituted or unsubstituted oxy group, a substituted or unsubstituted alkyl group having 1 to 30 carbon atoms, a substituted or unsubstituted aryl group having 6 to 30 ring-forming carbon atoms, a substituted or unsubstituted heteroaryl group having 2 to 30 ring-forming carbon atoms, and/or bonded to an adjacent group to form a ring, and $R_{44}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

Formula 7

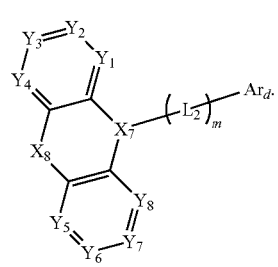

In Formula 7 above, $Y_1$ to $Y_8$ may be each independently $CR_{51}$ or N, $X_7$ may be N or $CR_{52}$, $X_8$ may be a direct linkage, $SiR_{53}R_{54}$, or $CR_{55}R_{56}$, $R_{51}$ may be a hydrogen atom, a deuterium atom, a halogen atom, a cyano group, a substituted or unsubstituted silyl group, a substituted or unsubstituted oxy group, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, and/or bonded to an adjacent group to form a ring, $R_{52}$ to $R_{56}$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, $L_2$ may be a direct linkage, a substituted or unsubstituted arylene group having 6 to 30 ring-forming carbon atoms, a substituted or unsubstituted heteroarylene group having 2 to 30 ring-forming carbon atoms, and/or bonded to an adjacent group to form a ring, $Ar_d$ may be a substituted or unsubstituted silyl group, a substituted or unsubstituted phosphine oxide group, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, and/or bonded to an adjacent group to form a ring, and m may be an integer of 0 to 2.

In one or more embodiments, the emission layer may further include a thermally activated delayed fluorescence dopant, and the thermally activated delayed fluorescence dopant may be represented by Formula 8 below:

Formula 8

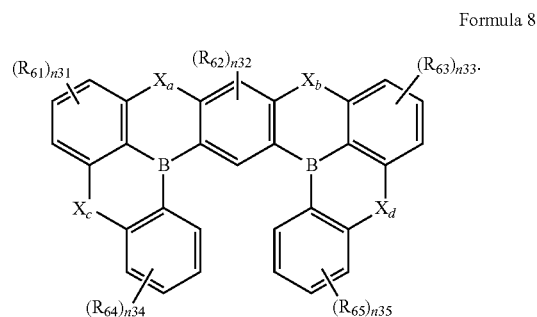

In Formula 8 above, $X_a$ to $X_d$ may be each independently $NR_{66}$, O, or S, $R_{61}$ to $R_{65}$ may be each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, and/or bonded to an adjacent group to form a ring, $R_{66}$ may be a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, and/or bonded to an adjacent group to form a ring, n31 and n33 may be each independently an integer of 0 to 3, n32 may be an integer of 0 to 2, and n34 and n35 may be each independently an integer of 0 to 4.

In one or more embodiments, the dopant represented by Formula 1 above may be any one among the compounds represented by Compound Group 1.

In one or more embodiments, the first host represented by Formula 6 above may be any one among the compounds represented by Compound Group 2.

In one or more embodiments, the second host represented by Formula 7 above may be any one among the compounds represented by Compound Group 3.

In one or more embodiments, the thermally activated delayed fluorescence dopant represented by Formula 8 above may be any one among the compounds represented by Compound Group 4.

In one or more embodiments of the present disclosure, an organometallic compound may be represented by Formula 1 above.

BRIEF DESCRIPTION OF THE DRAWINGS

The accompanying drawings are included to provide a further understanding of the present disclosure, and are incorporated in and constitute a part of this specification. The drawings illustrate non-limiting embodiments of the present disclosure and, together with the description, serve to explain principles of the present disclosure. In the drawings.

DETAILED DESCRIPTION

Figure 1:
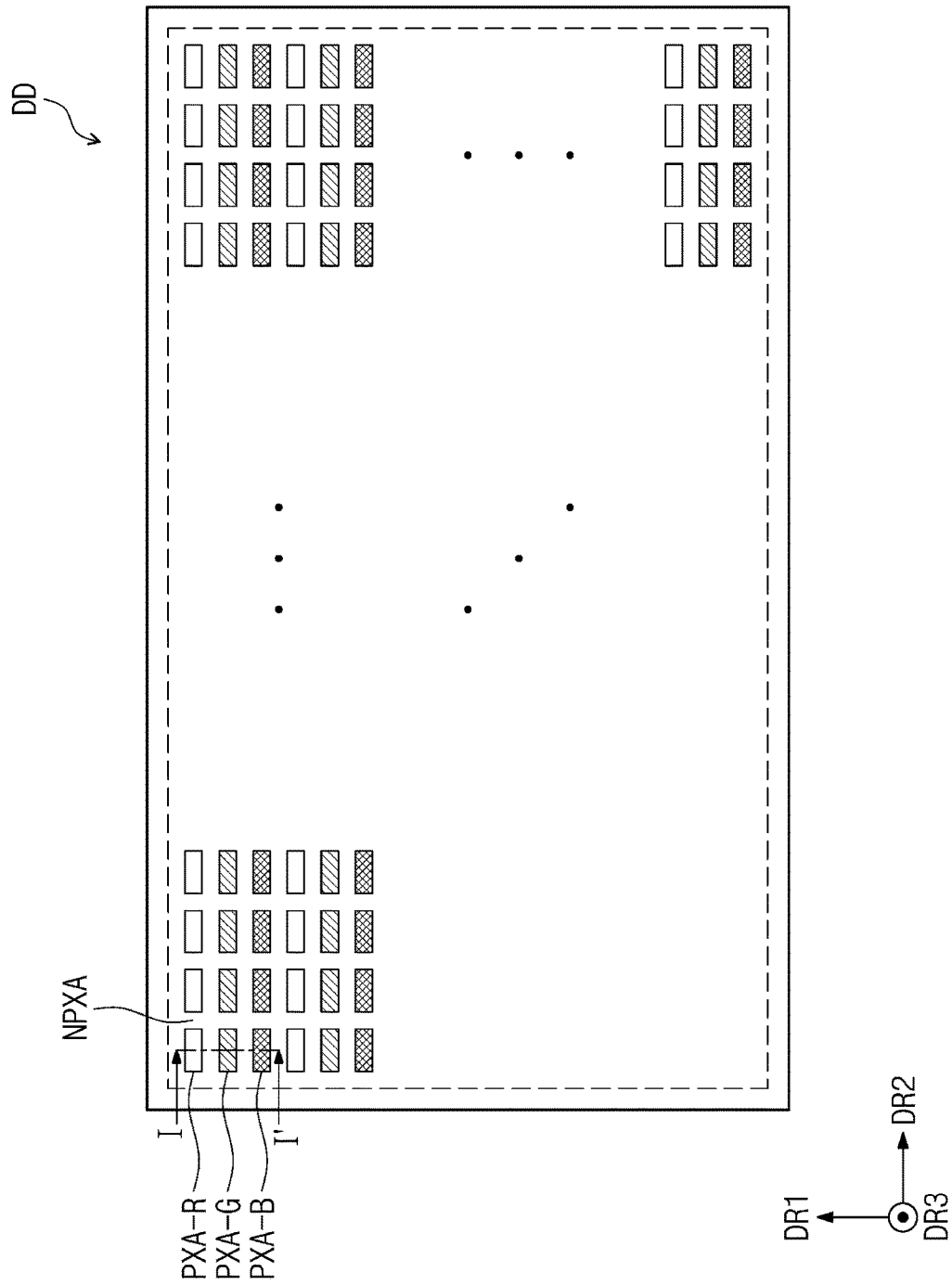
FIG. 1 is a plan view of a display apparatus according to an embodiment of the present disclosure.

The present disclosure may be modified in many alternate forms, and thus specific embodiments will be exemplified in the drawings and described in detail. It should be understood, however, that it is not intended to limit the present disclosure to the particular forms disclosed, but rather, is intended to cover all modifications, equivalents, and alternatives falling within the spirit and scope of the invention.

When explaining each of drawings, like reference numbers are used for referring to like elements. In the accompanying drawings, the dimensions of each structure may be exaggeratingly illustrated for clarity of the present disclosure. It will be understood that, although the terms "first," "second," etc. may be used herein to describe various elements, these elements should not be limited by these terms. These terms are only used to distinguish one element from another. For example, a first element may be referred to as a second element, and, similarly, the second element may be referred to as the first element, without departing from the scope of the present disclosure. The singular forms include the plural forms unless the context clearly indicates otherwise.

In the present application, it will be understood that the terms "include," "have" etc., specify the presence of a feature, a fixed number, a step, an operation, an element, a component, or a combination thereof disclosed in the specification, but do not exclude the possibility of presence or addition of one or more other features, fixed numbers, steps, operations, elements, components, or combination thereof.

In the present application, when a part such as a layer, a film, a region, or a plate is referred to as being "on" or "above" another part, it can be directly on (without any intervening layers therebetween) the other part, or an intervening part may also be present. Similarly, when a part such as a layer, a film, a region, or a plate is referred to as being "under" or "below" another part, it can be directly under the other part (without any intervening layers therebetween), or an intervening part may also be present. In addition, it will be understood that when a part is referred to as being "on" another part, it can be disposed (e.g. provided) on the other part, or disposed (e.g. provided) under the other part as well.

As used herein, the terms "use," "using," and "used" may be considered synonymous with the terms "utilize," "utilizing," and "utilized," respectively.

As used herein, expressions such as "at least one of", "one of", and "selected from", when preceding a list of elements, modify the entire list of elements and do not modify the individual elements of the list.

As used herein, the term "and/or" includes any and all combinations of one or more of the associated listed items.

Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may refer to within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Hereinafter, embodiments of the present disclosure will be described with reference to the accompanying drawings.

Figure 2:
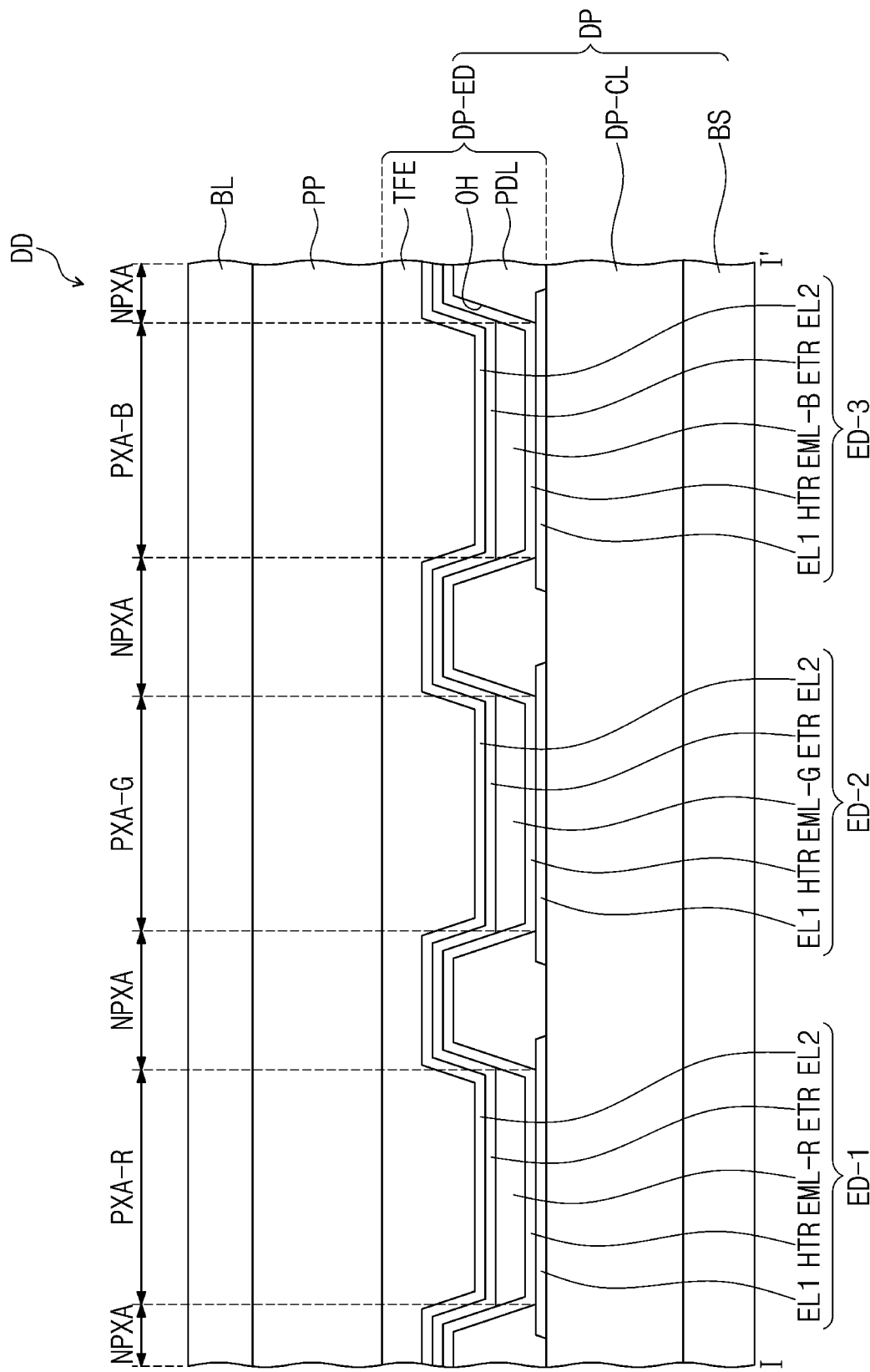
FIG. 2 is a cross-sectional view of a display apparatus according to an embodiment of the present disclosure.

FIG. 1 is a plan view illustrating one or more embodiments of a display apparatus DD. FIG. 2 is a cross-sectional view of the display apparatus DD of the embodiment. FIG. 2 is a cross-sectional view illustrating a part taken along line I-I' of FIG. 1.

The display apparatus DD may include a display panel DP and an optical layer PP disposed on the display panel DP. The display panel DP may include organic electroluminescence devices ED-1, ED-2, and ED-3. The display apparatus DD may include a plurality of organic electroluminescence devices ED-1, ED-2, and ED-3. The optical layer PP may be disposed on the display panel DP and control reflected light in the display panel DP due to external light. The optical layer PP may include, for example, a polarization layer and/or a color filter layer. Meanwhile, unlike the view illustrated in the drawing, the optical layer PP may be omitted from the display apparatus DD of one or more embodiments.

A base substrate BL may be disposed on the optical layer PP. The base substrate BL may be a member which provides a base surface on which the optical layer PP disposed. The base substrate BL may be a glass substrate, a metal substrate, a plastic substrate, etc. However, the embodiments of the present disclosure are not limited thereto, and the base substrate BL may be an inorganic layer, an organic layer, or a composite material layer. In one or more embodiments, the base substrate BL may be omitted.

The display apparatus DD according to one or more embodiments may further include a filling layer. The filling layer may be disposed between a display device layer DP-ED and the base substrate BL. The filling layer may be an organic material layer. The filling layer may include at least one of an acrylic-based resin, a silicone-based resin, or an epoxy-based resin.

The display panel DP may include a base layer BS, a circuit layer DP-CL provided on the base layer BS, and a display device layer DP-ED. The display device layer DP-ED may include a pixel defining film PDL, the organic electroluminescence devices ED-1, ED-2, and ED-3 disposed between portions of the pixel defining film PDL, and an encapsulation layer TFE disposed on the organic electroluminescence devices ED-1, ED-2, and ED-3.

The base layer BS may be a member which provides a base surface on which the display device layer DP-ED may be disposed. The base layer BS may be a glass substrate, a metal substrate, a plastic substrate, etc. However, the embodiments of the present disclosure are not limited thereto, and the base layer BS may be an inorganic layer, an organic layer, or a composite material layer.

In one or more embodiments, the circuit layer DP-CL may be disposed on the base layer BS, and the circuit layer DP-CL may include a plurality of transistors. Each of the transistors may include a control electrode, an input electrode, and an output electrode. For example, the circuit layer DP-CL may include a switching transistor and a driving transistor in order to drive the organic electroluminescence devices ED-1, ED-2, and ED-3 of the display device layer DP-ED.

Each of the organic electroluminescence devices ED-1, ED-2, and ED-3 may have a structure of an organic electroluminescence device ED of one or more embodiments according to FIGS. 3 to 6, which will be described later. Each of the organic electroluminescence devices ED-1, ED-2 and ED-3 may include a first electrode EL1, a hole transport region HTR, a corresponding one of emission layers EML-R, EML-G and EML-B, an electron transport region ETR, and a second electrode EL2.

FIG. 2 illustrates one or more embodiments in which the emission layers EML-R, EML-G, and EML-B of the organic electroluminescence devices ED-1, ED-2, and ED-3 may be disposed in the openings OH defined in the pixel defining film PDL, and the hole transport region HTR, the electron transport region ETR, and the second electrode EL2 may be provided as a common layer in the entire organic electroluminescence devices ED-1, ED-2, and ED-3. However, embodiments of the present disclosure are not limited thereto, for example, the hole transport region HTR and the electron transport region ETR in an embodiment may be provided by being patterned inside the openings (e.g., holes) OH defined in the pixel defining film PDL. For example, the hole transport region HTR, the emission layers EML-R, EML-G, and EML-B, and the electron transport region ETR of the organic electroluminescence devices ED-1, ED-2, and ED-3 in one or more embodiments may be provided by being patterned in an inkjet printing method.

The encapsulation layer TFE may cover the organic electroluminescence devices ED-1, ED-2 and ED-3. The encapsulation layer TFE may seal the display device layer DP-ED. The encapsulation layer TFE may be a thin film encapsulation layer. The encapsulation layer TFE may be formed by laminating one layer or a plurality of layers. The encapsulation layer TFE may include at least one insulation layer. The encapsulation layer TFE according to one or more embodiments may include at least one inorganic film (hereinafter, an encapsulation-inorganic film). The encapsulation layer TFE according to one or more embodiments may also include at least one organic film (hereinafter, an encapsulation-organic film) and at least one encapsulation-inorganic film.

The encapsulation-inorganic film protects the display device layer DP-ED from moisture/oxygen, and the encapsulation-organic film protects the display device layer DP-ED from foreign substances such as dust particles. The encapsulation-inorganic film may include silicon nitride, silicon oxynitride, silicon oxide, titanium oxide, aluminum oxide, and/or the like, but the embodiments of the present disclosure are not particularly limited thereto. The encapsulation-organic film may include an acrylic-based compound, an epoxy-based compound, and/or the like. The encapsulation-organic film may include a photopolymerizable organic material, but the embodiments of the present disclosure are not particularly limited thereto.

The encapsulation layer TFE may be disposed on the second electrode EL2 and may be disposed filling the opening OH.

Referring to FIGS. 1 and 2, the display apparatus DD may include a non-light emitting region NPXA and light emitting regions PXA-R, PXA-G and PXA-B. The light emitting regions PXA-R, PXA-G and PXA-B each may be a region which emits light generated from the organic electroluminescence devices ED-1, ED-2 and ED-3, respectively. The light emitting regions PXA-R, PXA-G, and PXA-B may be spaced apart from each other in a plane.

Each of the light emitting regions PXA-R, PXA-G, and PXA-B may be a region divided by the pixel defining film PDL. The non-light emitting regions NPXA may be regions between the adjacent light emitting regions PXA-R, PXA-G, and PXA-B, which correspond to portions of the pixel defining film PDL. Meanwhile, in the specification, each of the light emitting regions PXA-R, PXA-G, and PXA-B may correspond to a pixel. The pixel defining film PDL may separate the organic electroluminescence devices ED-1, ED-2 and ED-3. The emission layers EML-R, EML-G and EML-B of the organic electroluminescence devices ED-1, ED-2 and ED-3 may be disposed in openings OH defined by the pixel defining film PDL and separated from each other.

The light emitting regions PXA-R, PXA-G and PXA-B may be divided into a plurality of groups according to the color of light generated from the organic electroluminescence devices ED-1, ED-2 and ED-3. In the display apparatus DD of one or more embodiments shown in FIGS. 1 and 2, three light emitting regions PXA-R, PXA-G, and PXA-B which emit red light, green light, and blue light, respectively are illustrated. For example, the display apparatus DD of one or more embodiments may include the red light emitting region PXA-R, the green light emitting region PXA-G, and the blue light emitting region PXA-B which may be separated from one another.

In the display apparatus DD according to one or more embodiments, the plurality of organic electroluminescence devices ED-1, ED-2 and ED-3 may emit light having wavelengths different from one another. For example, in one or more embodiments, the display apparatus DD may include a first organic electroluminescence device ED-1 that emits red light, a second organic electroluminescence device ED-2 that emits green light, and a third organic electroluminescence device ED-3 that emits blue light. That is, the red light emitting region PXA-R, the green light emitting region PXA-G, and the blue light emitting region PXA-B of the display apparatus DD may correspond to the first organic electroluminescence device ED-1, the second organic electroluminescence device ED-2, and the third organic electroluminescence device ED-3, respectively.

However, the embodiments of the present disclosure are not limited thereto, and the first to third organic electroluminescence devices ED-1, ED-2, and ED-3 may emit light in the same wavelength range or at least one organic electroluminescence device may emit a light in a wavelength range different from the others. For example, the first to third organic electroluminescence devices ED-1, ED-2, and ED-3 may all emit blue light.

The light emitting regions PXA-R, PXA-G, and PXA-B in the display apparatus DD according to one or more embodiments may be arranged in a stripe form. Referring to FIG. 1, the plurality of red light emitting regions PXA-R may be arranged with each other along a second directional DR2, the plurality of green light emitting regions PXA-G may be arranged with each other along the second directional DR2, and the plurality of blue light emitting regions PXA-B may be arranged with each other along the second directional DR2. In one or more embodiments, a red light emitting region PXA-R, a green light emitting region PXA-G, and a blue light emitting region PXA-B may be alternately arranged in this order along a first directional DR1.

FIGS. 1 and 2 illustrate that all the light emitting regions PXA-R, PXA-G, and PXA-B have similar area, but the embodiments of the present disclosure are not limited thereto, and the light emitting regions PXA-R, PXA-G, and PXA-B may have different areas from each other according to a wavelength range of the emitted light. In this case, the areas of the light emitting regions PXA-R, PXA-G, and PXA-B may refer to areas when viewed in a plane defined by the first directional DR1 and the second directional DR2 (e.g., in a plan view).

Meanwhile, the arrangement form of the light emitting regions PXA-R, PXA-G, and PXA-B are not limited to the feature illustrated in FIG. 1, and the order in which the red light emitting region PXA-R, the green light emitting region PXA-G, and the blue light emitting region PXA-B may be arranged may be variously combined and provided according to characteristics of a display quality desired in the display apparatus DD. For example, the arrangement form of the light emitting regions PXA-R, PXA-G, and PXA-B may be a PenTile®/PENTILE® arrangement (PENTILE® is a registered trademark owned by Samsung Display Co., Ltd.), or a diamond arrangement form.

In one or more embodiments, the areas of the light emitting regions PXA-R, PXA-G, and PXA-B may be different from each other. For example, in one or more embodiments, the area of the green light emitting region PXA-G may be smaller than that of the blue light emitting region PXA-B, but the embodiments of the present disclosure are not limited thereto.

Hereinafter, FIGS. 3 to 6 are cross-sectional views schematically illustrating organic electroluminescence devices according to embodiments. Each of the organic electroluminescence devices ED according to embodiments may include a first electrode EL1, a hole transport region HTR, an emission layer EML, an electron transport region ETR, and a second electrode EL2 that may be sequentially stacked.

The organic electroluminescence device ED of one or more embodiments may include an organometallic compound of one or more embodiments, which will be further described below, in the emission layer EML disposed between the first electrode EL1 and the second electrode EL2. However, the embodiments of the present disclosure are not limited thereto, and the organic electroluminescence device ED of one or more embodiments may include the organometallic compound according to one or more embodiments described below in the hole transport region HTR or the electron transport region ETR which may be one of the plurality of functional layers disposed between the first electrode EL1 and the second electrode EL2, or may include the organometallic compound according to one or more embodiments described below in the capping layer CPL disposed on the second electrode EL2, as well as also being in the emission layer EML.

Figure 3:
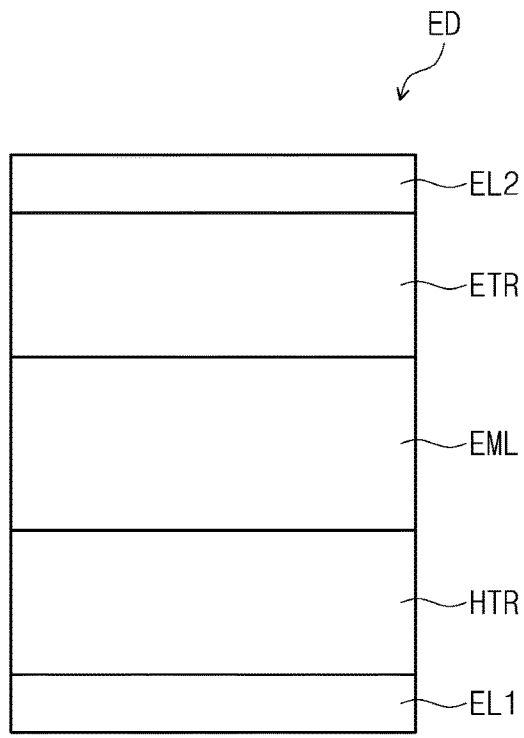
FIG. 3 is a cross-sectional view schematically illustrating an organic electroluminescence device according to an embodiment of the present disclosure.
Figure 4:
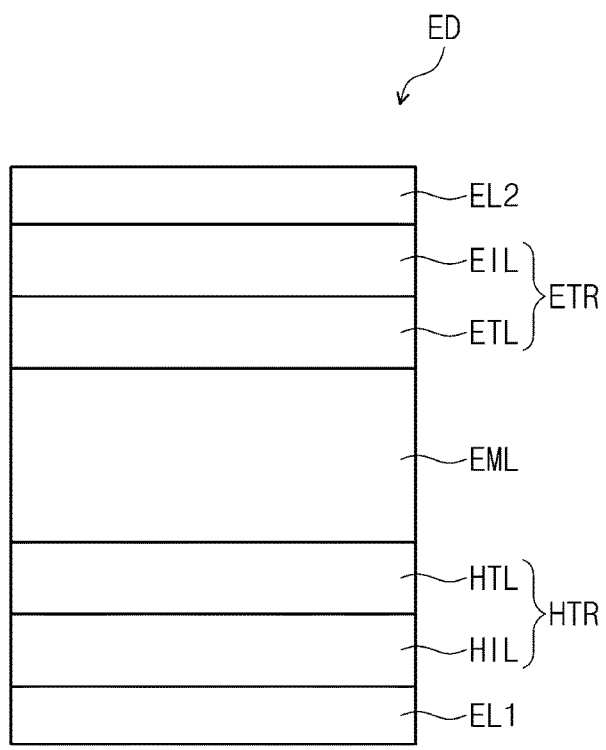
FIG. 4 is a cross-sectional view schematically illustrating an organic electroluminescence device according to an embodiment of the present disclosure.
Figure 5:
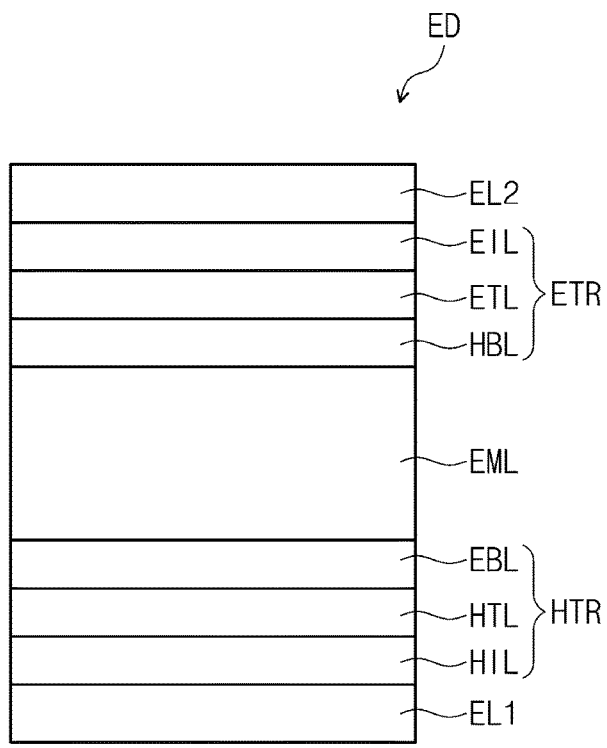
FIG. 5 is a cross-sectional view schematically illustrating an organic electroluminescence device according to one or more embodiments of the present disclosure.
Figure 6:
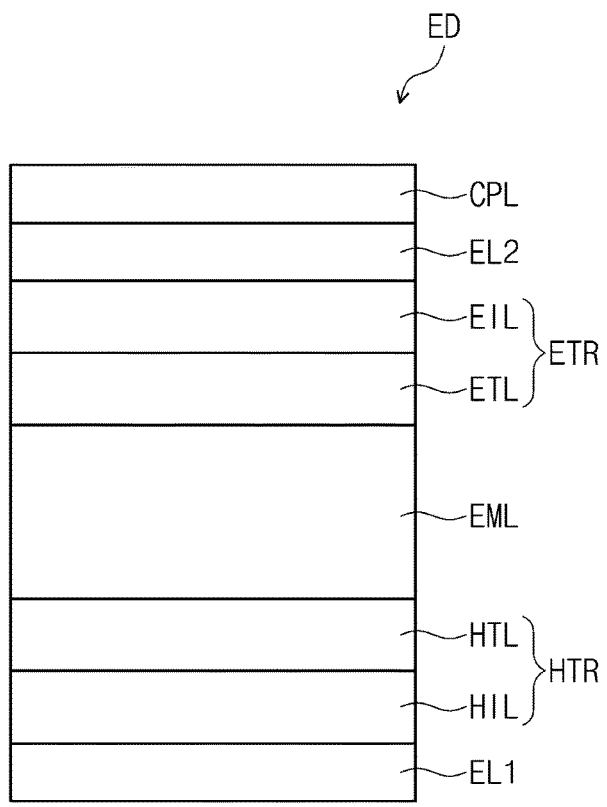
FIG. 6 is a cross-sectional view schematically illustrating an organic electroluminescence device according to one or more embodiments of the present disclosure.

FIGS. 3-4 illustrates a cross-sectional view of an organic electroluminescence device ED of one or more embodiments, in which a hole transport region HTR may include a hole injection layer HIL and a hole transport layer HTL, and an electron transport region ETR may include an electron injection layer EIL and an electron transport layer ETL. FIGS. 3-5 illustrates a cross-sectional view of an organic electroluminescence device ED of one or more embodiments, in which a hole transport region HTR may include a hole injection layer HIL, a hole transport layer HTL, and an electron blocking layer EBL, and an electron transport region ETR may include an electron injection layer EIL, an electron transport layer ETL, and a hole blocking layer HBL. FIGS. 4-6 illustrate a cross-sectional view of an organic electroluminescence device ED of one or more embodiments including a capping layer CPL disposed on a second electrode EL2.

The first electrode EL1 has conductivity. The first electrode EL1 may be formed of a metal material, a metal alloy, or a conductive compound. The first electrode EL1 may be an anode or a cathode. However, the embodiments of the present disclosure are not limited thereto. In one or more embodiments, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EU may include Ag, Mg, Cu, Al, Pt, Pd, Au, Ni, Nd, Ir, Cr, Li, Ca, LiF/Ca, LiF/Al, Mo, Ti, W, a compound thereof, or a mixture thereof (e.g., a mixture of Ag and Mg). In some embodiments, the first electrode EL1 may have a multilayer structure including a reflective film or a transflective film formed of one or more of the above-described materials, and a transparent conductive film formed of ITO, IZO, ZnO, ITZO, etc. For example, the first electrode EL1 may have a three-layer structure of ITO/Ag/ITO, but the embodiments of the present disclosure are not limited thereto For example, the first electrode EL1 may include one or more of the above-described metal materials, combinations of at least two metal materials of the above-described metal materials, one or more oxides of the above-described metal materials, and/or the like. The thickness of the first electrode EL1 may be from about 700 Å to about 10,000 Å. For example, the thickness of the first electrode EL1 may be from about 1,000 Å to about 3,000 Å.

The hole transport region HTR may be provided on the first electrode EL1. The hole transport region HTR may include at least one of a hole injection layer HIL, a hole transport layer HTL, a buffer layer and/or an emission-auxiliary layer, or an electron blocking layer EBL. The thickness of the hole transport region HTR may be, for example, from about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of the hole injection layer HIL or the hole transport layer HTL, and may have a single layer structure formed of a hole injection material and a hole transport material. In one or more embodiments, the hole transport region HTR may have a single layer structure formed of a plurality of different materials, or a structure in which a hole injection layer HIL/hole transport layer HTL, a hole injection layer HIL/hole transport layer HTL/buffer layer, a hole injection layer HIL/buffer layer, a hole transport layer HTL/buffer layer, or a hole injection layer HIL/hole transport layer HTL/electron blocking layer EBL may be stacked in order from the first electrode EL1, but the embodiments of the present disclosure are not limited thereto.

The hole transport region HTR may be formed using one or more of various methods such as a vacuum deposition method, a spin coating method, a cast method, a Langmuir-Blodgett (LB) method, an inkjet printing method, a laser printing method, and/or a laser induced thermal imaging (LITI) method.

The hole transport region HTR may include a compound represented by Formula H-1 below:

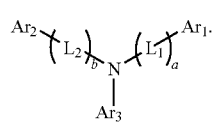

Formula H-1

In Formula H-1 above, $L_1$ and $L_2$ may be each independently a direct linkage, a substituted or unsubstituted arylene group having 6 to 30 ring-forming carbon atoms, or a substituted or unsubstituted heteroarylene group having 2 to 30 ring-forming carbon atoms, and a and b may be each independently an integer of 0 to 10. Meanwhile, when a orb is an integer of 2 or greater, a plurality of $L_1$'s and $L_2$'s may be each independently a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may be each independently a substituted or unsubstituted aryl group having 6 to 30 ring-forming carbon atoms, or a substituted or unsubstituted heteroaryl group having 2 to 30 ring-forming carbon atoms. In one or more embodiments, in Formula H-1, $Ar_3$ may be a substituted or unsubstituted aryl group having 6 to 30 ring-forming carbon atoms.

The compound represented by Formula H-1 above may be a monoamine compound. In some embodiments, the compound represented by Formula H-1 above may be a diamine compound in which at least one among $Ar_1$ to $Ar_3$ may include the amine group as a substituent. In one or more embodiments, the compound represented by Formula H-1 above may be a carbazole-based compound including a substituted or unsubstituted carbazole group in at least one of $Ar_1$ or $Ar_2$, or a fluorene-based compound including a substituted or unsubstituted fluorene group in at least one of $Ar_1$ or $Ar_2$.

The compound represented by Formula H-1 may be represented by any one among the compounds of Compound Group H below. However, the compounds listed in Compound Group H below are examples, and the compounds represented by Formula H-1 are not limited to those represented by Compound Group H below:

Compound Group H

H-1-1

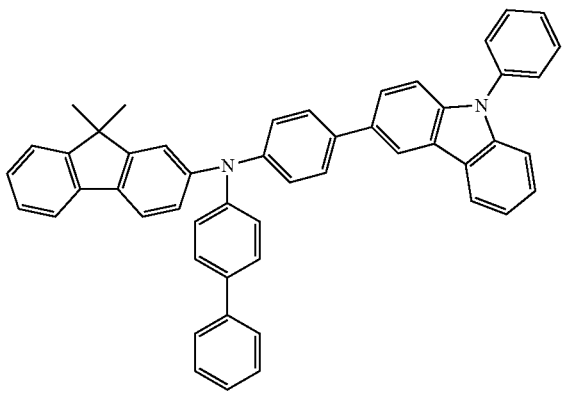

-continued
H-1-2
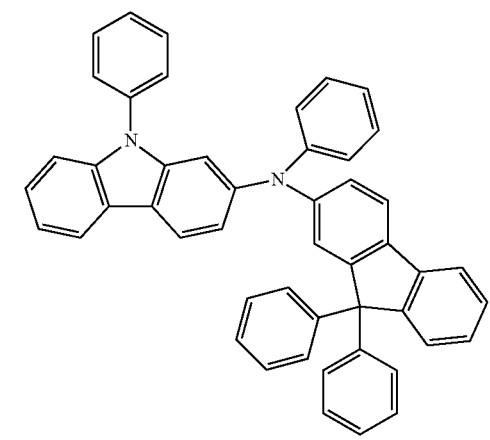
H-1-3
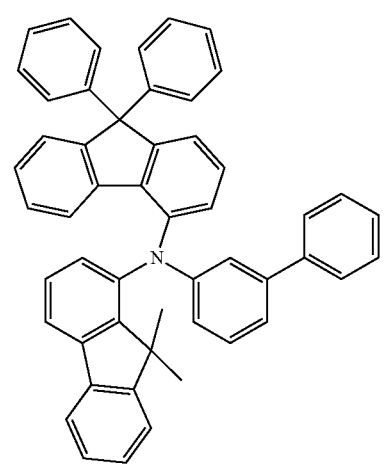
H-1-4
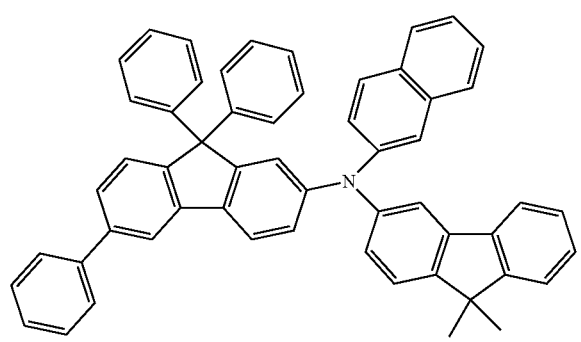
H-1-5
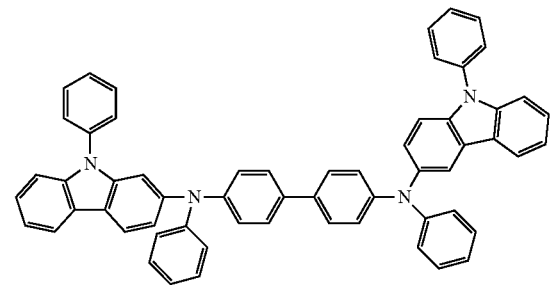
-continued
H-1-6
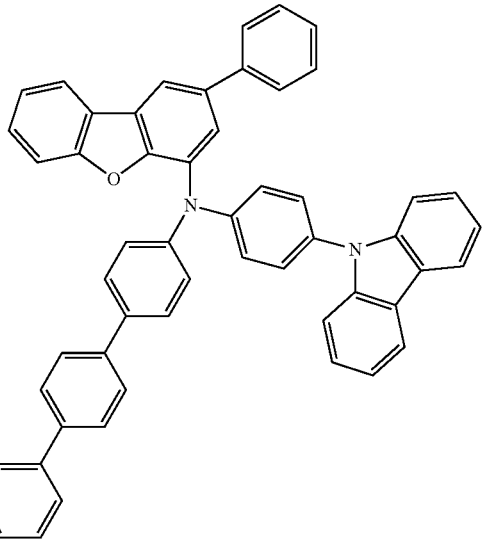
H-1-7
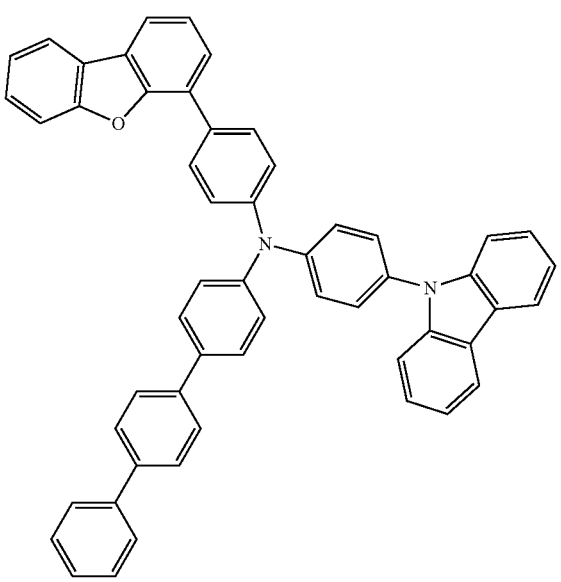
H-1-8
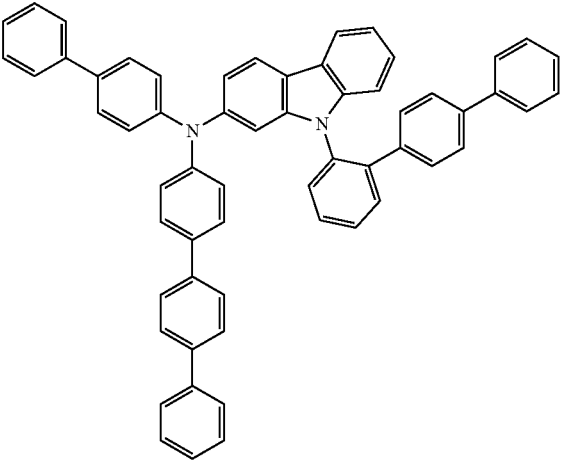

-continued
H-1-9
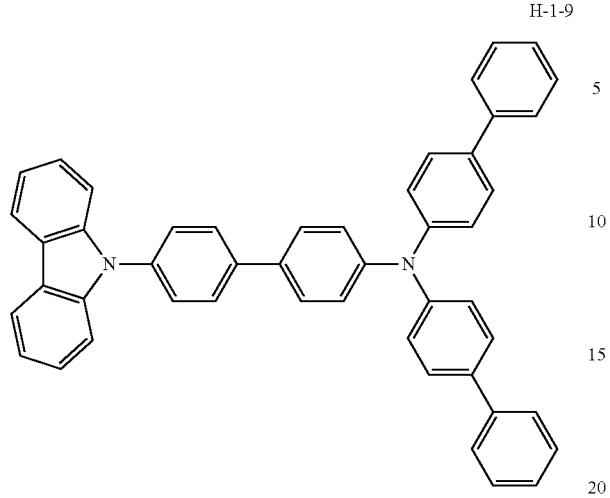
H-1-10
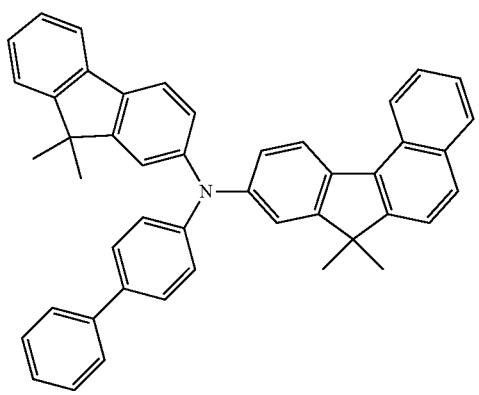
H-1-11
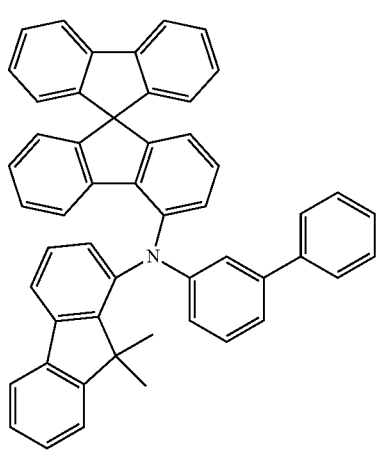
-continued
H-1-12
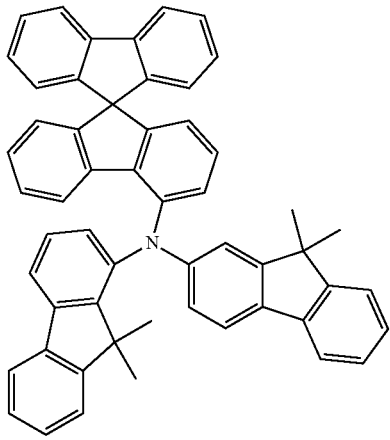
H-1-13
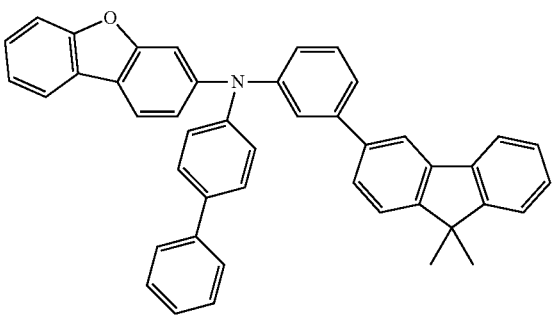
H-1-14
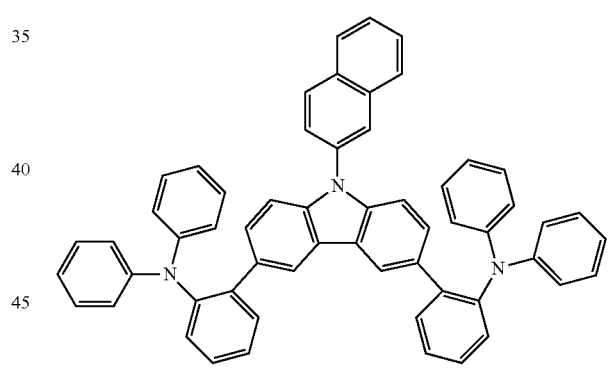
H-1-15
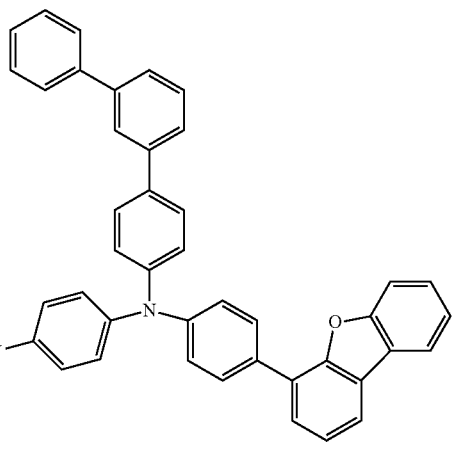

H-1-16

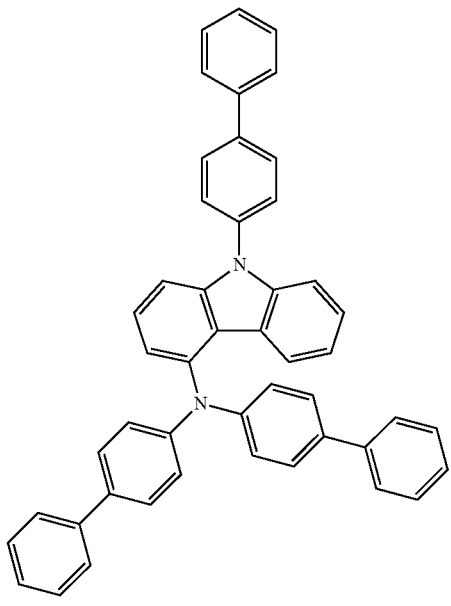

H-1-17

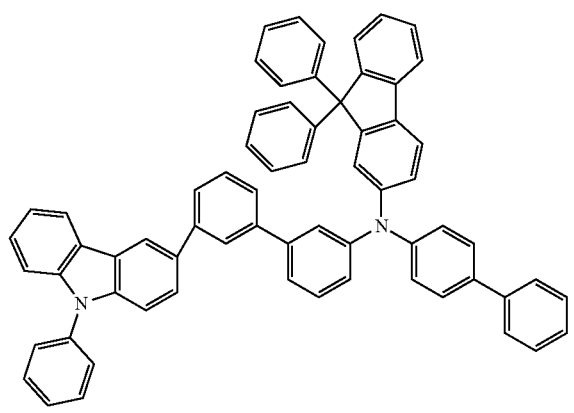

H-1-18

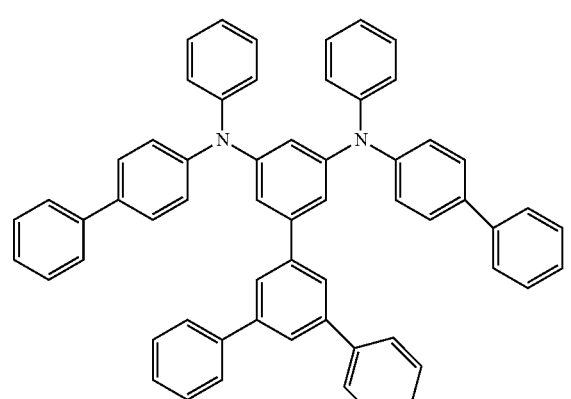

H-1-19

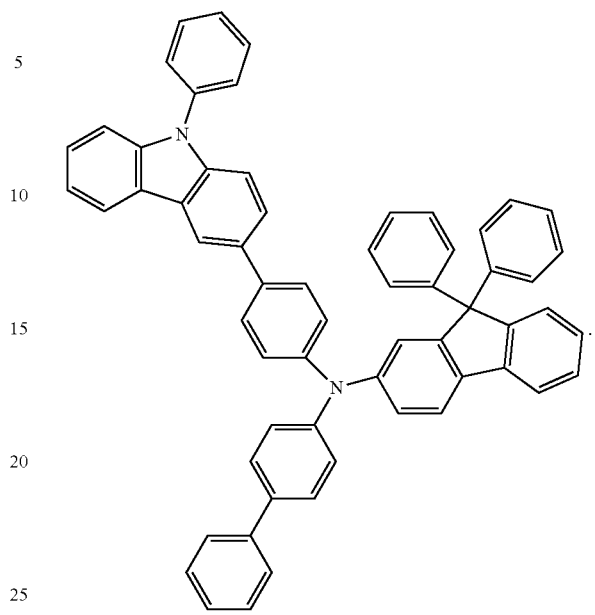

The hole transport region HTR may include a phthalocyanine compound such as copper phthalocyanine; $N^1,N^{1'}$-([1,1'-biphenyl]-4,4'-diyl)bis($N^1$-phenyl-$N^4$,$N^4$-di-m-tolyl-benzene-1,4-diamine) (DNTPD), 4,4',4"-[tris(3-methylphenyl)phenylamino] triphenylamine (m-MTDATA), 4,4'4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], dipyrazino[2,3-f: 2',3'-h]quinoxaline-2,3,6,7,10,11-hexacarbonitrile (HATCN), etc.

The hole transport region HTR may include carbazole derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl) triphenylamine (TCTA), N,N'-di(naphthalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis (N-carbazolyl)benzene (mCP), etc.

In one or more embodiments, the hole transport region HTR may further include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the above-described compound of the hole transport region in at least one of a hole injection layer HIL, a hole transport layer HTL, or an electron blocking layer EBL.

The thickness of the hole transport region HTR may be from about 100 Å to about 10,000 Å, for example, from about 100 Å to about 5,000 Å. When the hole transport region HTR includes the hole injection layer HIL, the hole injection layer HIL may have, for example, a thickness of about 30 Å to about 1,000 Å. When the hole transport region HTR includes the hole transport layer HTL, the hole transport layer HTL may have a thickness of about 30 Å to about 1,000 Å. For example, when the hole transport region HTR includes the electron blocking layer EBL, the electron blocking layer EBL may have a thickness of about 10 Å to about 1,000 Å. If the thicknesses of the hole transport region HTR, the hole injection layer HIL, the hole transport layer HTL and the electron blocking layer EBL satisfy the above-described ranges, satisfactory hole transport characteristic may be achieved without a substantial increase in a driving voltage.

The hole transport region HTR may further include a charge generating material to increase conductivity in addition to the above-described materials. The charge generating material may be dispersed uniformly (e.g. substantially uniformly) or non-uniformly in the hole transport region HTR. The charge generating material may be, for example, a p-dopant. The p-dopant may include at least one of a halogenated metal compound, a quinone derivative, a metal oxide, or a cyano group-containing compound, but the embodiments of the present disclosure are not limited thereto. For example, the p-dopant may include metal halides such as CuI and RbI, quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide and molybdenum oxide, cyano group-containing compounds such as dipyrazino[2,3-f: 2',3'-h] quinoxaline-2,3,6,7,10,11-hexacarbonitrile (HATCN), 4-[[2,3-bis[cyano-(4-cyano-2,3,5,6-tetrafluorophenyl)methylidene]cyclopropylidene]-cyanomethyl]-2,3,5,6-tetrafluorobenzonitrile, etc., but the embodiments of the present disclosure are not limited thereto.

As described above, the hole transport region HTR may further include at least one of the buffer layer or the electron blocking layer EBL in addition to the hole injection layer HIL and the hole transport layer HTL. The buffer layer may compensate a resonance distance according to the wavelength of light emitted from the emission layer EML and may thus increase light emission efficiency. Materials which may be included in the hole transport region HTR may be used as materials to be included in the buffer layer. The electron blocking layer EBL may be a layer that serves to prevent or reduce the electron injection from the electron transport region ETR to the hole transport region HTR.

The emission layer EML may be provided on the hole transport region HTR. The emission layer EML may have a thickness of, for example, about 100 Å to about 1,000 Å or about 100 Å to about 300 Å. The emission layer EML may have a single layer formed of a single material, a single layer formed of a plurality of different materials, or a multilayer structure having a plurality of layers formed of a plurality of different materials.

The emission layer EML may emit one of red, green, blue, white, yellow or cyan light. The emission layer EML may include a phosphorescence-emitting material, a fluorescence-emitting material, or a thermally activated delayed fluorescence material.

In one or more embodiments, the emission layer EML may be a phosphorescence emission layer. For example, a portion of light emitted from the emission layer may be by emitting phosphorescence. For example, the emission layer EML may include a luminescent component that emits phosphorescence, In one or more embodiments, the emission layer EML may be an emission layer that emits phosphorescence emitting blue light. However, the embodiments of the present disclosure are not limited thereto, and the emission layer may be a thermally activated delayed fluorescence emission layer.

The organic electroluminescence device ED of one or more embodiments may include the organometallic compound according to one or more embodiments of the present disclosure. For example, the emission layer EML of the organic electroluminescence device ED of one or more embodiments may include the organometallic compound according to one or more embodiments of the present disclosure. The emission layer EML may include one kind of organometallic compound. However, the embodiments of the present disclosure are not limited thereto, and the emission layer EML may include two kinds of different organometallic compounds.

In one or more embodiments, the emission layer EML may include a host and a dopant. In this case, the organometallic compound according to one or more embodiments may be included as a dopant material of the emission layer EML. For example, the organometallic compound of one or more embodiments described later may be used as a phosphorescence dopant.

In the specification, the term "substituted or unsubstituted" may refer to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In one or more embodiments, each of the substituents exemplified above may be substituted or unsubstituted. For example, a biphenyl group may be interpreted as an aryl group or a phenyl group substituted with a phenyl group.

In the specification, the phrase "bonded to an adjacent group to form a ring" may indicate that one is bonded to an adjacent group to form a substituted or unsubstituted hydrocarbon ring, or a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may be monocyclic or polycyclic. In one or more embodiments, the rings formed by being bonded to each other may be connected to another ring to form a spiro structure.

In the specification, the term "adjacent group" may refer to a substituent substituted for an atom which is directly bonded to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other. In one or more embodiments, two methyl groups in 4,5-dimethylphenanthrene may be interpreted as "adjacent groups" to each other.

In the specification, examples of the halogen atom may include a fluorine atom, a chlorine atom, a bromine atom, or an iodine atom.

In the specification, the alkyl group may be a linear or branched type. The number of carbon atoms in the alkyl group is 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, an n-nonyl group, an n-decyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octylodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but the embodiments of the present disclosure are not limited thereto.

In the specification, the cycloalkyl may be an alkyl group in a cyclic structure. The number of carbon atoms in the cycloalkyl group may be 3 to 30, 3 to 20, or 3 to 10. Examples of the cycloalkyl group may include cyclopropyl, cyclobutyl, cyclopentyl, cyclohexyl, cycloheptyl, cyclooctyl, 1-methylcyclopropyl, 1-pentylcyclopropyl, 1,2-diethylcyclobutyl, 1-methylcyclobutyl, 1-butylcyclobutyl, 1,3-dimethylcyclobutyl, 1-methylcyclopentyl, 1-butylcyclopentyl, 1-methylcyclohexyl, 1-ethylcyclopentyl, cyclopentenyl, cyclohexenyl, cycloheptenyl, cyclooctenyl, etc., but the embodiments of the present disclosure are not limited thereto.

The hetero cycloalkyl herein means any functional group or substituent derived from an alkyl group in a non-aromatic cyclic structure including at least one of B, O, N, P, Si, or S as a heteroatom. The number of ring-forming carbon atoms in the hetero cycloalkyl group may be 2 to 30, 2 to 20, or 2 to 10. If the hetero cycloalkyl group may include two or more heteroatoms, the two or more heteroatoms may be the same as or different from each other. Examples of the cycloalkyl group may include a substituted or unsubstituted hexahydropyrimidine, etc., but the embodiments of the present disclosure are not limited thereto.

In the specification, the bicycloalkyl or the tricycloalkyl may represent a kind of cyclic structure. The bicycloalkyl may refer to being formed by two rings that share one or more atoms which are not adjacent, like C-1 to C-4 below, and the tricycloalkyl may refer to being formed by three rings that share two or more atoms which are not adjacent, like C-5 below. Also, the bicycloalkyl may include a spiro group and a fused ring group. The number of ring-forming carbon atoms in the bicycloalkyl and the tricycloalkyl may be 5 to 30, 5 to 20, or 5 to 10. Examples of the bicycloalkyl may include bicyclo[2.1.1]hexyl, bicyclo[2.2.1]heptyl, bicyclo[2.2.2]octyl, bicyclo[3.3.1]nonyl, bicyclo[4.2.1]nonyl, bicyclo[3.3.2]decyl, bicyclo[4.2.2]decyl, bicyclo[4.3.1]decyl, bicyclo[3.3.3]undecyl, bicyclo[4.3.2]undecyl, bicyclo[4.3.3]dodecyl, etc. but the embodiments of the present disclosure are not limited thereto. Examples of the tricycloalkyl may include an adamantanyl group, etc., but the embodiments of the present disclosure are not limited thereto.

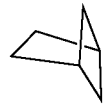

C-1

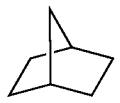

C-2

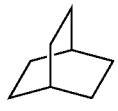

C-3

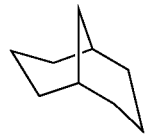

C-4

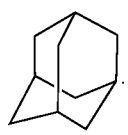

C-5

The hetero bicycloalkyl herein may be an alkyl group in a cyclic structure including two non-aromatic rings, the rings may share one or two atoms, and at least one of the rings may include at least one of B, O, N, P, Si, or S. In one or more embodiments, the hetero bicycloalkyl may include a spiro group and a fused ring group unless otherwise indicated. If the hetero bicycloalkyl group may include two or more heteroatoms, the two or more heteroatoms may be the same as or different from each other. The number of ring-forming carbon atoms in the hetero bicycloalkyl group may be 3 to 30, 3 to 20, or 3 to 10.

The hetero tricycloalkyl herein may be an alkyl group in a cyclic structure including three non-aromatic rings, the rings may share two or more atoms, and at least one of the rings may include at least one of B, O, N, P, Si, or S. In one or more embodiments, the hetero bicycloalkyl may include a spiro group and a fused ring group unless otherwise indicated. For example, two ring of the three rings may share one or two atoms, and the rest one ring may share one or two atoms with one or more rings of the two rings. If the hetero tricycloalkyl group may include two or more heteroatoms, the two or more heteroatoms may be the same as or different from each other. The number of ring-forming carbon atoms in the hetero tricycloalkyl group may be 6 to 30, 6 to 20, or 6 to 10.

The hydrocarbon ring group herein means any functional group or substituent derived from an aliphatic hydrocarbon ring and an aromatic hydrocarbon ring. The hydrocarbon ring group may be a saturated hydrocarbon ring group having 5 to 20 ring-forming carbon atoms or an unsaturated hydrocarbon ring group having 2 to 20 ring-forming carbon atoms. The aliphatic hydrocarbon ring and the aromatic heterocycle may be monocyclic or polycyclic.

The aryl group herein means any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but the embodiments of the present disclosure are not limited thereto.

The heterocyclic group herein means any functional group or substituent derived from a ring including at least one of B, O, N, P, Si, or Se as a heteroatom. The heterocyclic group may include an aliphatic heterocyclic group and an aromatic heterocyclic group. The aromatic heterocyclic group may be a heteroaryl group. The aliphatic heterocycle and the aromatic heterocycle may be monocyclic or polycyclic.

In the specification, the heterocyclic group may include at least one of B, O, N, P, Si or S as a heteroatom. If the heterocyclic group may include two or more heteroatoms, the two or more heteroatoms may be the same as or different from each other. The heterocyclic group may be a monocyclic heterocyclic group or a polycyclic heterocyclic group and has the concept including a heteroaryl group. The number of ring-forming carbon atoms in the heterocyclic group may be 2 to 30, 2 to 20, or 2 to 10.

In the specification, the aliphatic heterocyclic group may include one or more among B, O, N, P, Si, and S as a heteroatom. The number of ring-forming carbon atoms in the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but the embodiments of the present disclosure are not limited thereto.

The heteroaryl group herein may include at least one of B, O, N, P, Si, or S as a heteroatom. When the heteroaryl group contains two or more heteroatoms, the two or more heteroatoms may be the same as or different from each other. The heteroaryl group may be a monocyclic heteroaryl group or polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but the embodiments of the present disclosure are not limited thereto.

In the specification, the above description with respect to the aryl group may be applied to an arylene group except that the arylene group is a divalent group. The explanation on the aforementioned heteroaryl group may be applied to the heteroarylene group except that the heteroarylene group is a divalent group.

In the specification, the silyl group may include an alkylsilyl group and an arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, one or more embodiments of the present disclosure are not limited thereto.

The thio group herein may include an alkylthio group and an arylthio group. The thio group may refer to that a sulfur atom is bonded to the alkyl group or the aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, but the embodiments of the present disclosure are not limited thereto.

The oxy group herein may refer to that an oxygen atom is bonded to the alkyl group or the aryl group as defined above. The oxy group may include an alkoxy group and an aryl oxy group. The alkoxy group may be a linear chain, a branched chain or a ring chain. The number of carbon atoms in the alkoxy group is not specifically limited, but may be, for example, 1 to 20 or 1 to 10. Examples of the oxy group include methoxy, ethoxy, n-propoxy, isopropoxy, butoxy, pentyloxy, hexyloxy, octyloxy, nonyloxy, decyloxy, benzyloxy, etc., but the embodiments of the present disclosure are not limited thereto.

In the specification, the alkenyl group may be linear or branched. The number of carbon atoms in the alkenyl group is not specifically limited, but may be 2 to 30, 2 to 20, or 2 to 10. Examples of the alkenyl group include a vinyl group, a 1-butenyl group, a 1-pentenyl group, a 1,3-butadienyl aryl group, a styrenyl group, a styryl vinyl group, etc., but the embodiments of the present disclosure are not limited thereto.

In the specification, the number of carbon atoms in an amine group is not specifically limited, but may be 1 to 30. The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., but the embodiments of the present disclosure are not limited thereto.

A direct linkage herein may refer to a single bond.

Meanwhile, "—*" herein means a position to be connected.

An organometallic compound according to one or more embodiments may be represented by Formula 1 below.

Formula 1

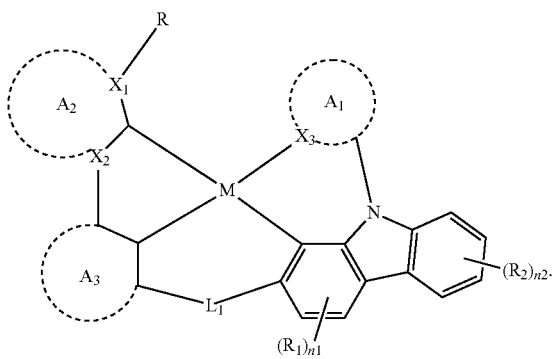

In Formula 1, M may be platinum (Pt), palladium (Pd), nickel (Ni), gold (Au), silver (Ag), beryllium (Be), magnesium (Mg), aluminum (Al), calcium (Ca), titanium (Ti), manganese (Mn), cobalt (Co), zinc (Zn), gallium (Ga), zirconium (Zr), ruthenium (Ru), rhodium (Rh), osmium (Os), or copper (Cu).

In Formula 1, $L_1$ may be $CR_3R_4$, $NR_5$, O, $SiR_6R_7$, $BR_8$, or $PR_9$, and $X_1$ to $X_3$ may be each independently $CR_{10}$ or N.

In Formula 1, ring $A_1$ to ring $A_3$ may be each independently a substituted or unsubstituted monocyclic or polycyclic hydrocarbon ring group having 6 to 30 ring-forming carbon atoms, or a substituted or unsubstituted monocyclic or polycyclic heterocyclic group having 2 to 30 ring-forming carbon atoms.

In Formula 1, $R_1$ to $R_{10}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In Formula 1, n1 may be an integer of 0 to 2. Meanwhile, when n1 is 2, a plurality of $R_1$'s may be the same as or different from each other.

In Formula 1, n2 may be an integer of 0 to 4. Meanwhile, when n2 is 2 or more, a plurality of $R_2$'s may be the same as or different from each other.

In Formula 1, R may be represented by Formula 2 below.

Formula 2

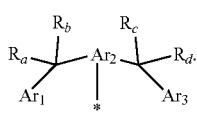

In Formula 2, $Ar_1$ and $Ar_3$ may be each independently a substituted or unsubstituted aryl group having 6 to 30 ring-forming carbon atoms, or a substituted or unsubstituted heteroaryl group having 2 to 30 ring-forming carbon atoms.

In Formula 2, $Ar_2$ may be a substituted or unsubstituted trivalent aryl group having 6 to 30 ring-forming carbon atoms, or a substituted or unsubstituted trivalent heteroaryl group having 2 to 30 ring-forming carbon atoms.

In Formula 2, $R_a$ to $R_d$ may be each independently a substituted or unsubstituted amine group, a substituted or unsubstituted alkoxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 2, $R_a$ and $R_b$ may be bonded to each other to form a ring, $R_c$ and $R_d$ may be bonded to each other to form a ring, and "—*" is the bonding position with N.

In one or more embodiments, $M_1$ in Formula 1 may be a metal atom which is bonded to a tetradentate ligand. M may be a metal atom, such as platinum (Pt), palladium (Pd), copper (Cu), or osmium (Os), and for example, M may be platinum (Pt).

In one or more embodiments, $X_1$ to $X_3$ in Formula 1 may all be N.

In one or more embodiments, $Ar_1$ and $Ar_3$ in Formula 2 may be each independently a substituted or unsubstituted aryl group. For example, $Ar_1$ and $Ar_3$ may both (e.g. simultaneously) be substituted or unsubstituted phenyl groups.

In one or more embodiments, $Ar_2$ in Formula 2 may be a substituted or unsubstituted trivalent aryl group. For example, $Ar_2$ may be a substituted or unsubstituted trivalent phenyl group, or a substituted or unsubstituted trivalent biphenyl group.

In one or more embodiments, Formula 2 may be represented by Formula 2-1 or Formula 2-2 below.

Formula 2-1

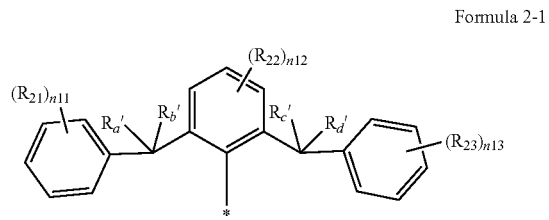

Formula 2-2

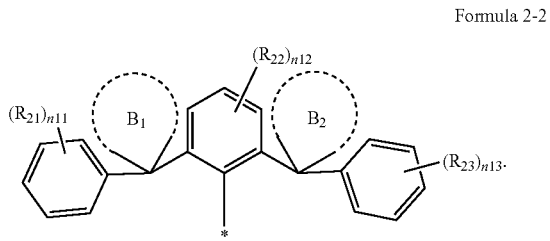

In Formula 2-1 and Formula 2-2, $R_{21}$ to $R_{23}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In Formula 2-1, $R_{a'}$ to $R_{d'}$ may be each independently a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In Formula 2-2, ring $B_1$ and ring $B_2$ may be each independently a substituted or unsubstituted cycloalkyl having 3 to 30 carbon atoms, a substituted or unsubstituted hetero cycloalkyl having 2 to 20 carbon atoms, a substituted or unsubstituted bicycloalkyl having 4 to 20 carbon atoms, a substituted or unsubstituted hetero bicycloalkyl having 3 to 20 carbon atoms, a substituted or unsubstituted tricycloalkyl having 6 to 20 carbon atoms, or a substituted or unsubstituted hetero tricycloalkyl having 5 to 20 carbon atoms.

In Formula 2-1 and Formula 2-2, n11 is an integer of 0 to 5. Meanwhile, when n11 is 2 or more, a plurality of $R_{21}$'s may be the same as or different from each other.

In Formula 2-1 and Formula 2-2, n12 may be an integer of 0 to 3. Meanwhile, when n12 is 2 or more, a plurality of $R_{22}$'s may be the same as or different from each other.

In Formula 2-1 and Formula 2-2, n13 may be an integer of 0 to 5. Meanwhile, when n13 is 2 or more, a plurality of $R_{23}$'s may be the same as or different from each other.

In one or more embodiments, $R_a{'}$ to $R_d{'}$ may be each independently a substituted or unsubstituted alkyl group having 1 to 10 carbon atoms. For example, $R_{a'}$ to $R_{d'}$ may be each independently any one selected from among Formulae A-1 to A-40 below. However, the embodiments of the present disclosure are not limited thereto. In one or more embodiments, any one among Formulae A-1 to A-40 below may be one in which at least one hydrogen is substituted with deuterium.

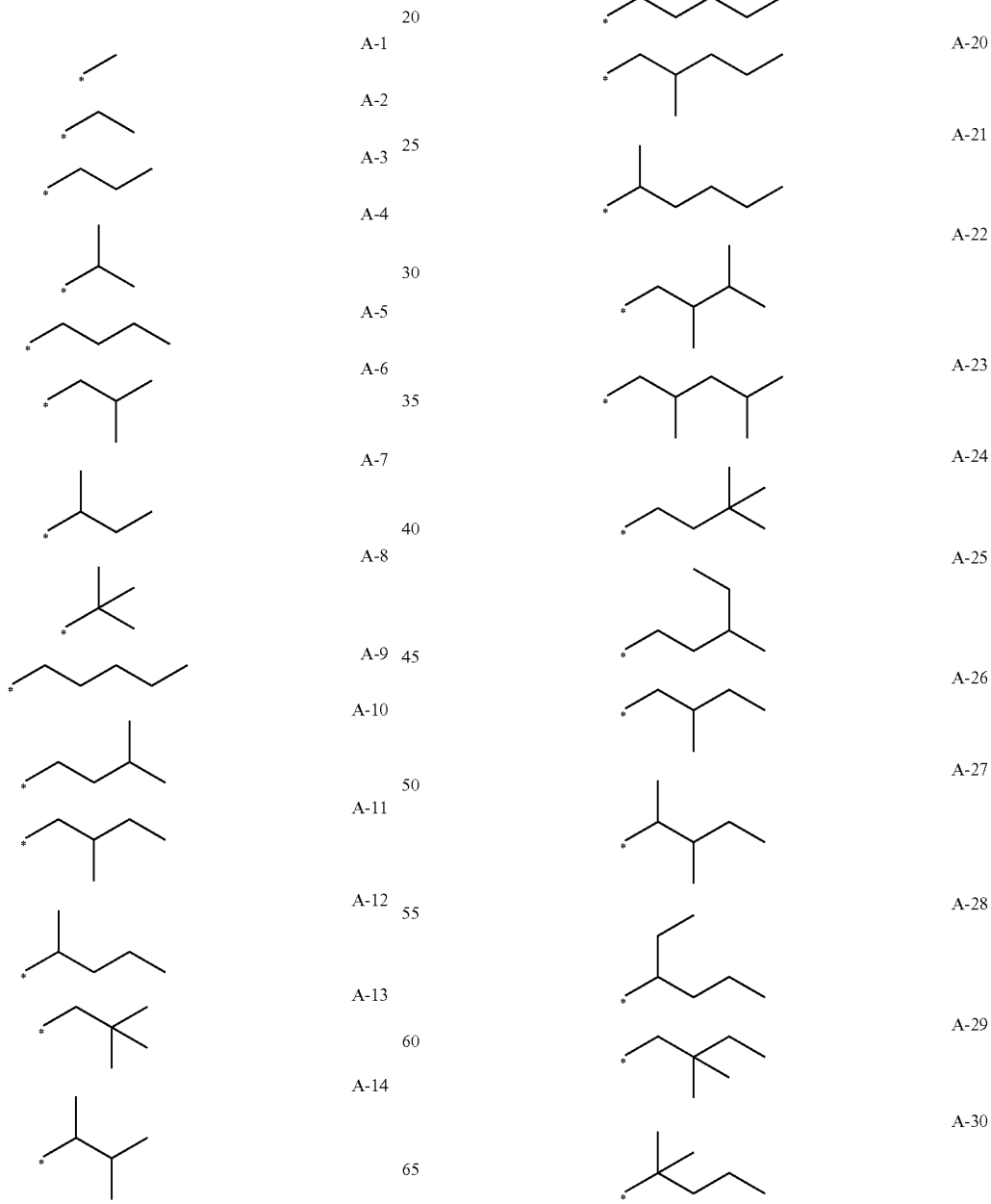

| | |
|---|---|
| A-31 | 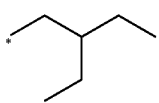 |
| A-32 | 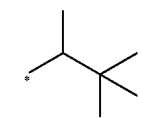 |
| A-33 | 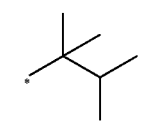 |
| A-34 | 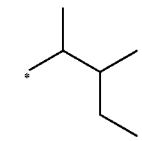 |
| A-35 | 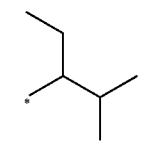 |
| A-36 | 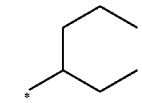 |
| A-37 | 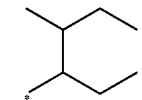 |
| A-38 | 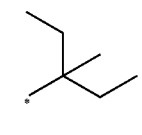 |
| A-39 | 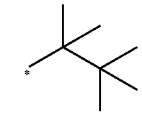 |
| A-40 | 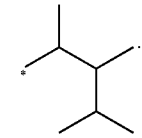 |

In one or more embodiments, $R_{a'}$ to $R_{d'}$ may be each independently a methyl group, a methyl group substituted with deuterium, an ethyl group, an n-propyl group, an isopropyl group, or a tert-butyl group.

In one or more embodiments, ring $B_1$ and ring $B_2$ may be each independently represented by any one among Formula 3-1 to Formula 3-5 below.

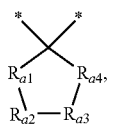
Formula 3-1

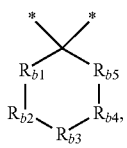
Formula 3-2

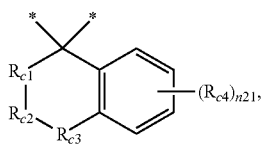
Formula 3-3

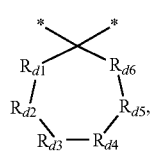
Formula 3-4

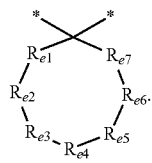
Formula 3-5

In Formula 3-1 to Formula 3-5, $R_{a1}$ to $R_{a4}$, $R_{b1}$ to $R_{b5}$, $R_{c1}$ to $R_{c3}$, $R_{d1}$ to $R_{d6}$, and $R_{e1}$ to $R_{e1}$ may be each independently $CR_{31}R_{32}$ or $NR_{33}$, and $R_{31}$ and $R_{32}$ may be each independently a hydrogen atom, a deuterium atom, a halogen atom, a substituted or unsubstituted alkyl group having 1 to 30 carbon atoms, a substituted or unsubstituted amine group, a substituted or unsubstituted aryl group having 6 to 30 ring-forming carbon atoms, or a substituted or unsubstituted hetero aryl group having 2 to 30 ring-forming carbon atoms.

In Formula 3-1 to Formula 3-5, $R_{33}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted hetero aryl group having 2 to 30 ring-forming carbon atoms.

In Formula 3-3, $R_{c4}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted hetero aryl group having 2 to 30 ring-forming carbon atoms.

In Formula 3-1, any two or more groups among $R_{a1}$ to $R_{a4}$ may be bonded to each other to form bicycloalkyl, hetero bicycloalkyl, tricycloalkyl, or hetero tricycloalkyl.

In Formula 3-2, any two or more groups among $R_{b1}$ to $R_{b5}$ may be bonded to each other to form bicycloalkyl, hetero bicycloalkyl, tricycloalkyl, or hetero tricycloalkyl.

In Formula 3-3, any two or more groups among $R_{c1}$ to $R_{c3}$ may be bonded to each other to form bicycloalkyl, hetero bicycloalkyl, tricycloalkyl, or hetero tricycloalkyl.

In Formula 3-4, any two or more groups among $R_{d1}$ to $R_{d6}$ may be bonded to each other to form bicycloalkyl, hetero bicycloalkyl, tricycloalkyl, or hetero tricycloalkyl.

In Formula 3-5, any two or more groups among $R_{e1}$ to $R_{e7}$ may be bonded to each other to form bicycloalkyl, hetero bicycloalkyl, tricycloalkyl, or hetero tricycloalkyl.

In Formula 3-3, n21 may be an integer of 0 to 4. Meanwhile, when n21 is 2 or more, a plurality of $R_{c4}$'s may be the same as or different from each other.

Meanwhile, in the specification, the expression "any two or more groups are bonded to each other to form bicycloalkyl, hetero bicycloalkyl, tricycloalkyl, or hetero tricycloalkyl" means that two or more groups, which are not adjacent, are bonded to each other to form two or more rings that share the two or more groups. That is, two groups, which are not adjacent to each other, may be bonded to each other to form bicycloalkyl or hetero bicycloalkyl, or two or more groups, which are not adjacent to each other, may be bonded to each other to form tricycloalkyl or hetero tricycloalkyl. For example, $R_{e1}$ and $R_{e5}$ in Formula 3-5 above may be bonded to each other to form bicyclo[3.3.1]nonyl, or $R_{e1}$ and $R_{e5}$ may be bonded to each other and $R_{e3}$ and $R_{e7}$ may be bonded to each other to form tricyclo[3.3.1.1³,⁷]decane.

In one or more embodiments, ring $B_1$ and ring $B_2$ may be each independently a substituted or unsubstituted cyclopentane, a substituted or unsubstituted cyclohexane, a substituted or unsubstituted hexahydropyrimidine, a substituted or unsubstituted cycloheptane, a substituted or unsubstituted tetraline, a substituted or unsubstituted bicyclo[3.3.1]nonyl, or a substituted or unsubstituted tricyclo[3.3.1.1³,⁷]decane.

In one or more embodiments, Formula 1 may be represented by Formula 4 below.

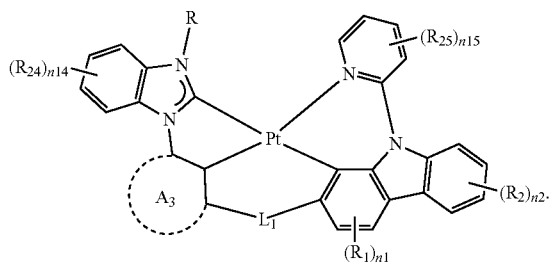

Formula 4

In Formula 4, $R_{24}$ and $R_{25}$ may be each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In Formula 4, n14 may be an integer of 0 to 4. Meanwhile, when n14 is 2 or more, a plurality of $R_{24}$'s may be the same as or different from each other.

In Formula 4, n15 may be an integer of 0 to 4. Meanwhile, when n15 is 2 or more, a plurality of $R_{25}$'s may be the same as or different from each other.

In Formula 4, $L_1$, ring $A_3$, R, $R_1$, $R_2$, n1, and n2 may be the same as defined in Formula 1.

In one or more embodiments, Formula 4 may be represented by Formula 5 below.

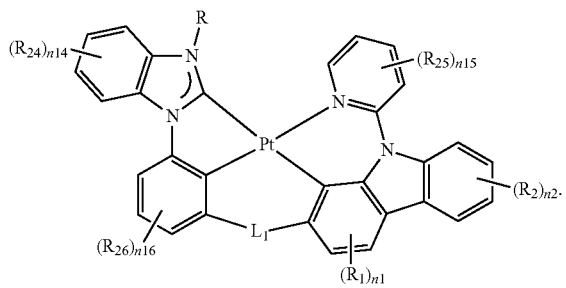

Formula 5

In Formula 5, $R_{26}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In Formula 5, n16 may be an integer of 0 to 3. Meanwhile, when n16 is 2 or more, a plurality of $R_{26}$'s may be the same as or different from each other.

In Formula 5, $L_1$, R, $R_1$, $R_2$, n1, n2, $R_{24}$, $R_{25}$, n14, and n15 may be the same as defined in Formula 4.

In one or more embodiments, the dopant represented by Formula 1 may be any one selected from among the compounds represented by Compound Group 1 below. However, the embodiments of the present disclosure are not limited thereto.

Compound Group 1

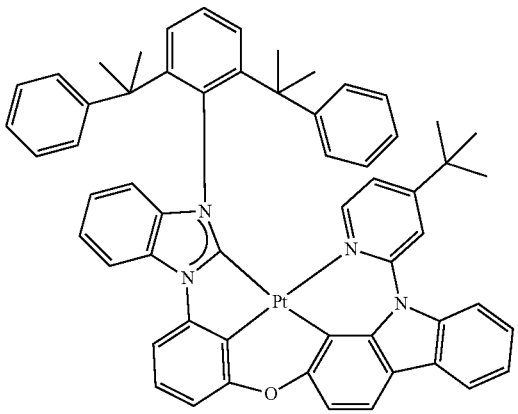

BD1

BD2
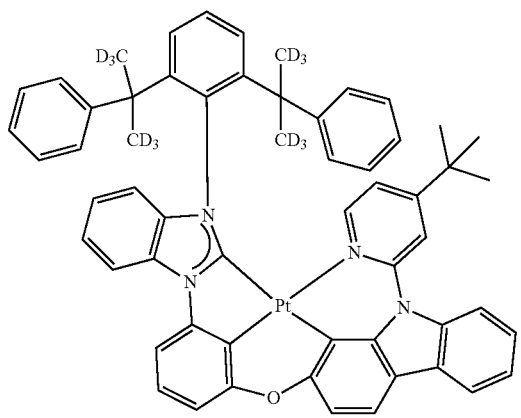
BD5
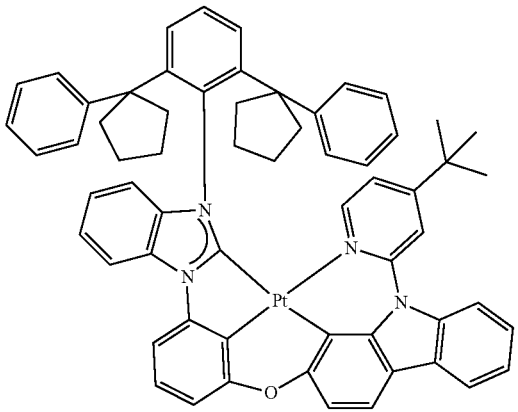
BD3
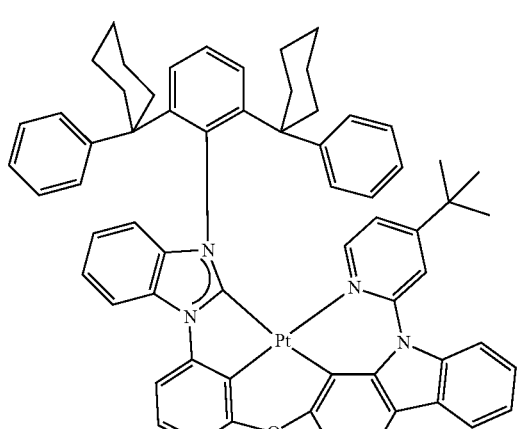
BD6
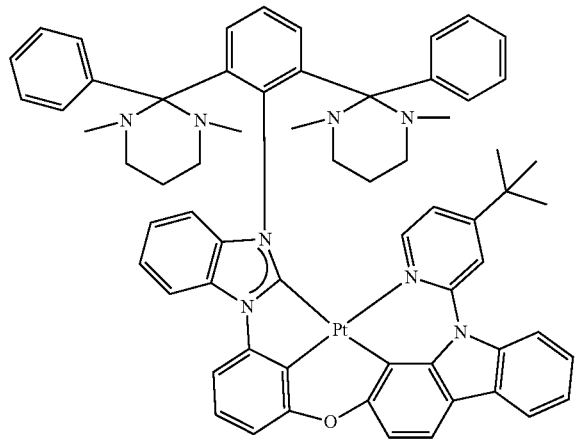
BD4
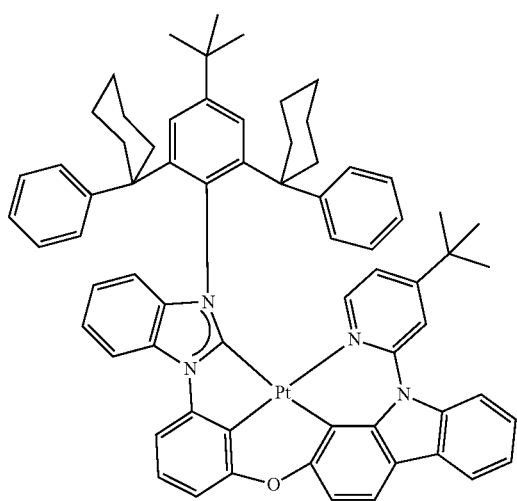
BD7

BD8
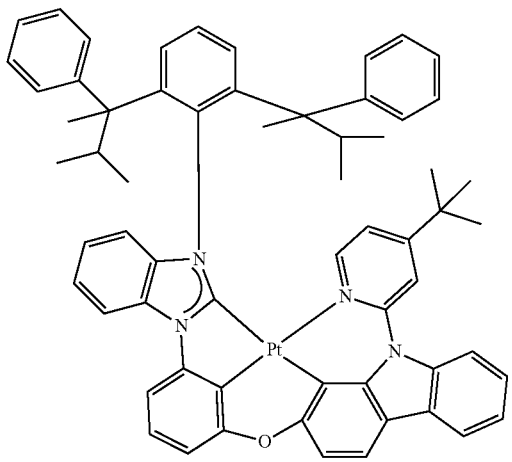
BD11
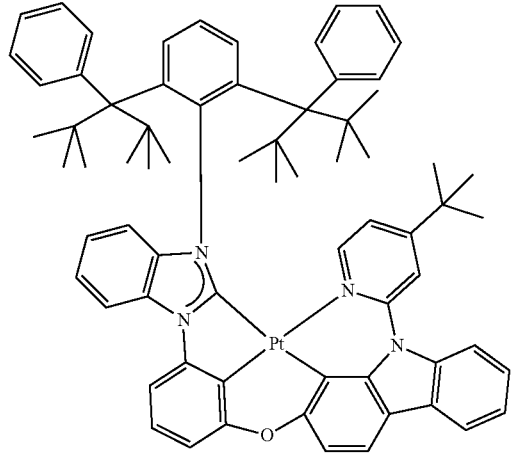
BD9
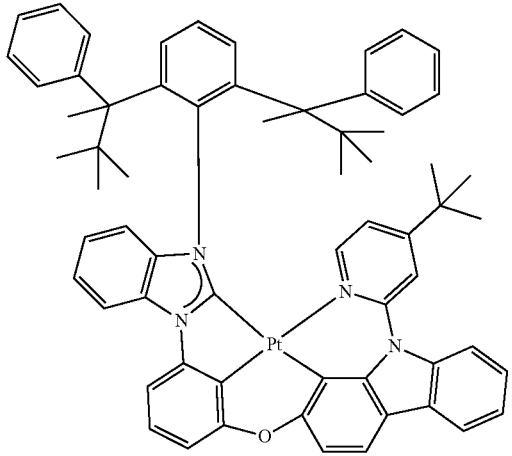
BD12
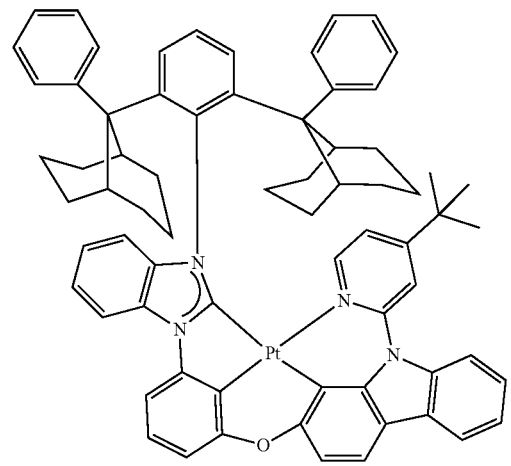
BD10
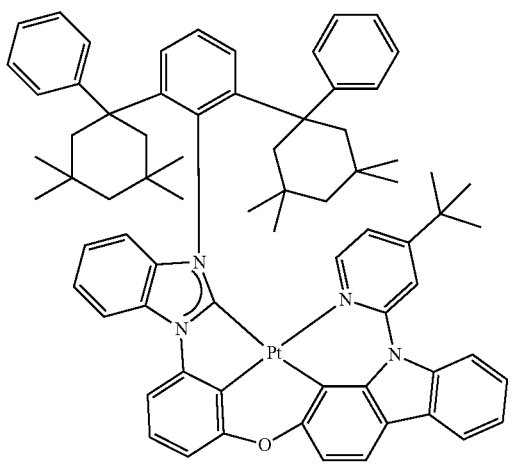
BD13
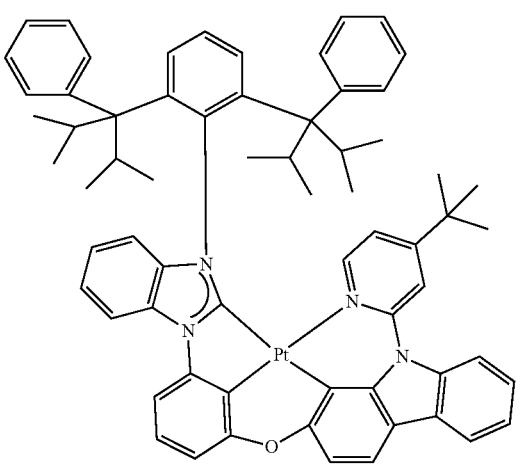

BD14
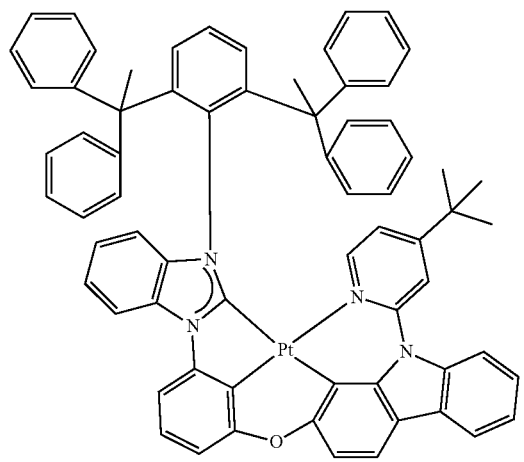
BD17
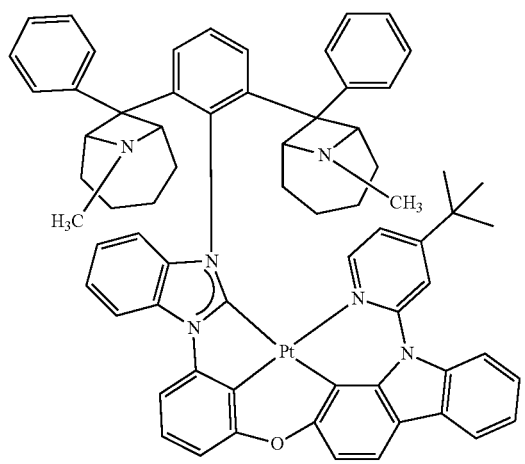
BD15
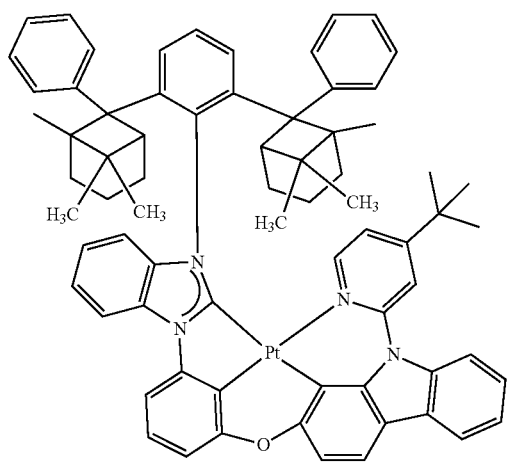
BD18
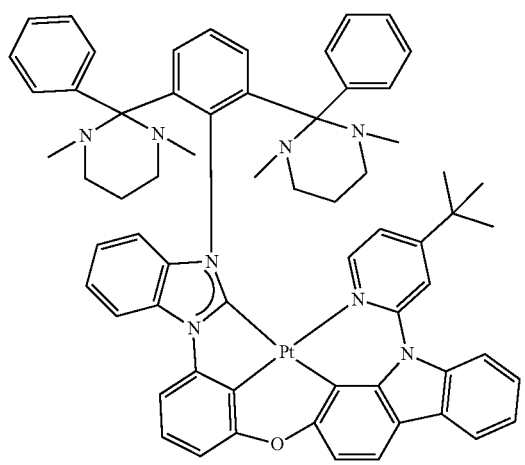
BD16
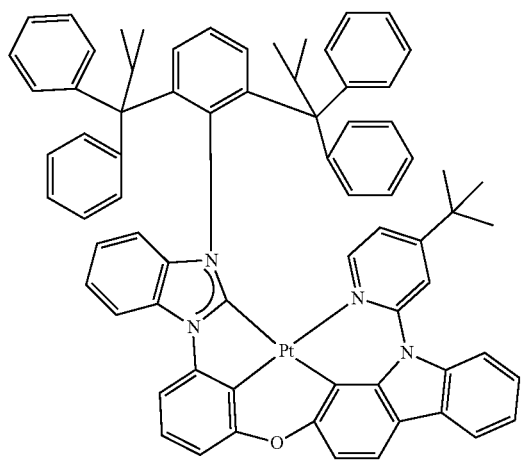
BD19
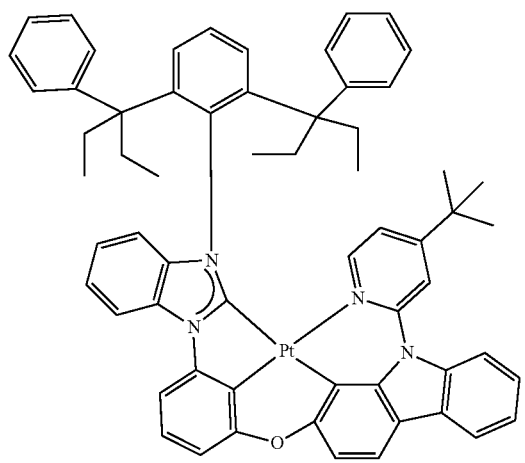

BD20
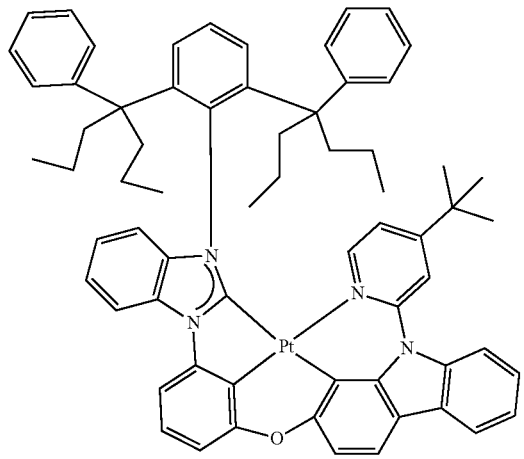
BD23
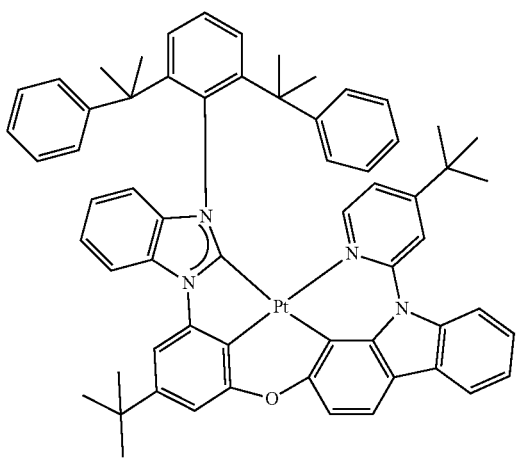
BD21
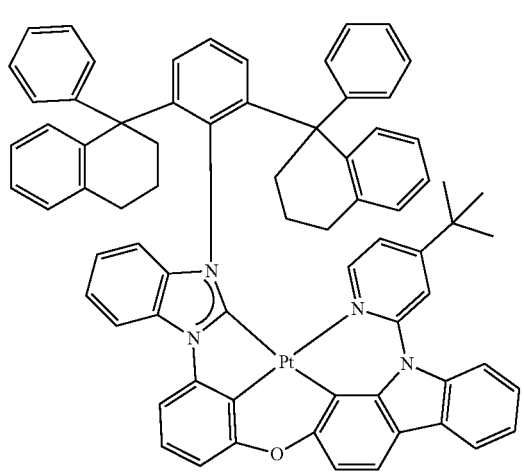
BD24
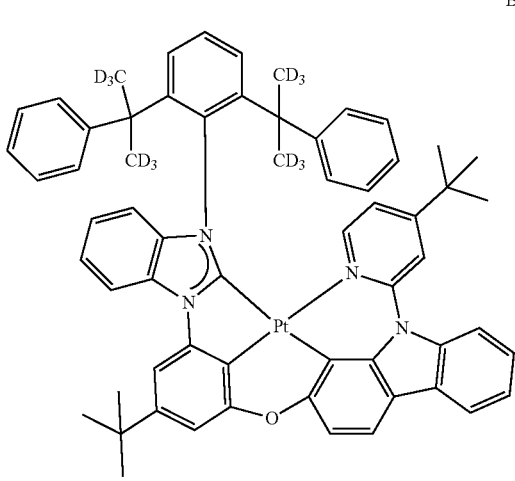
BD22
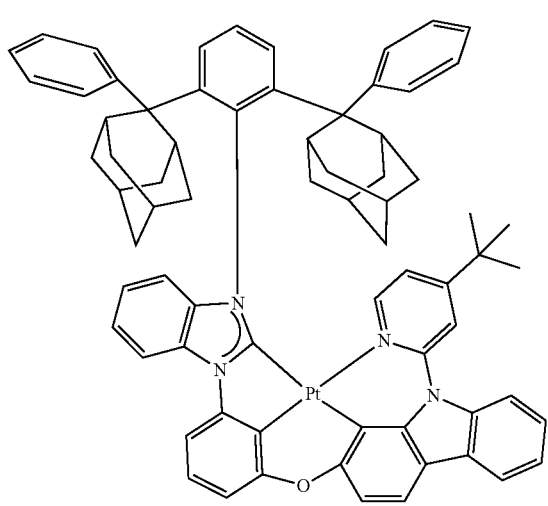
BD25
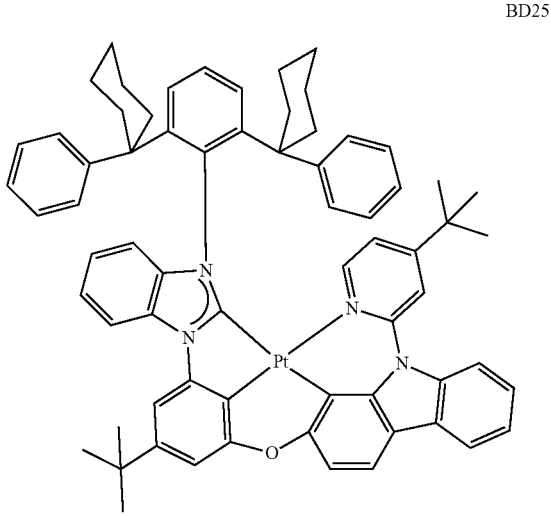

BD26
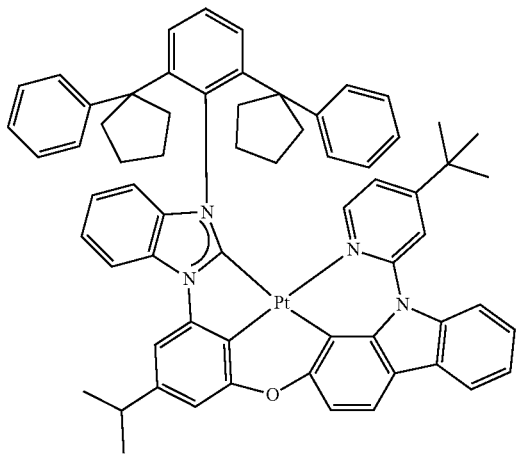
BD29
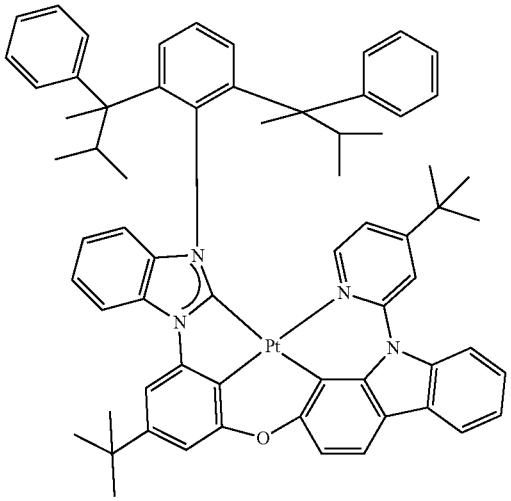
BD27
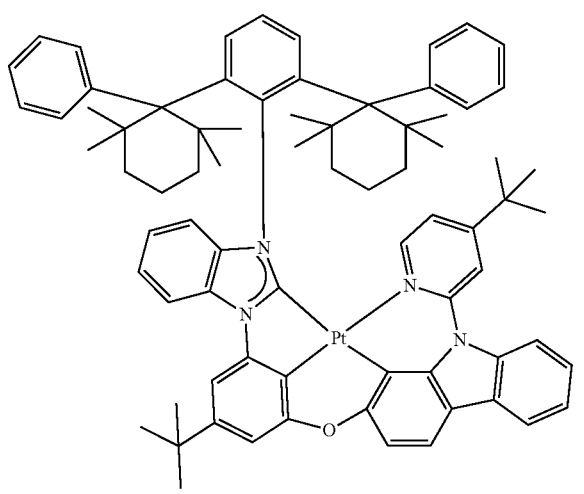
BD30
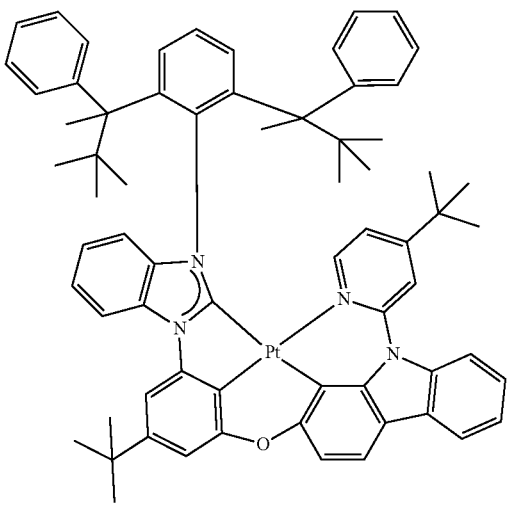
BD28
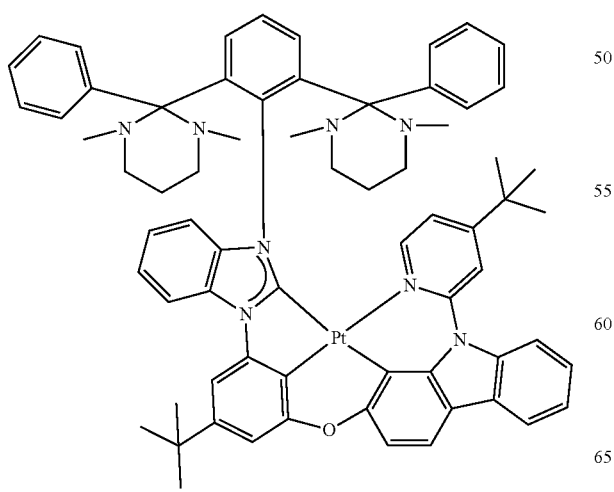
BD31
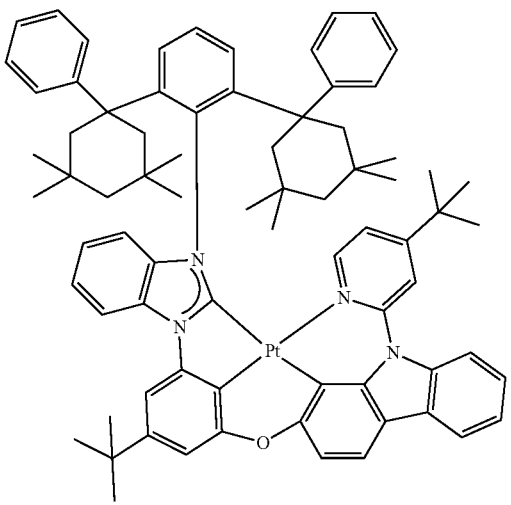

BD32
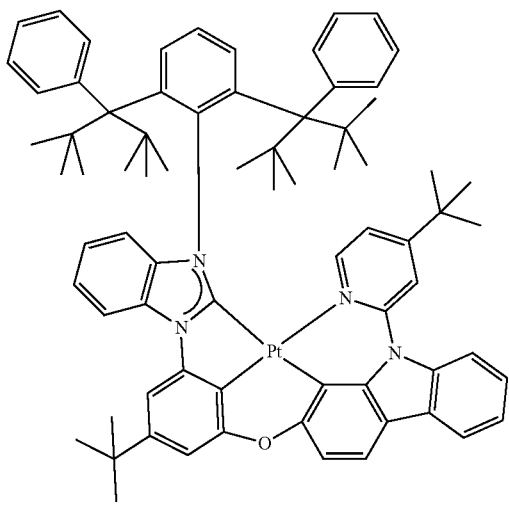
BD33
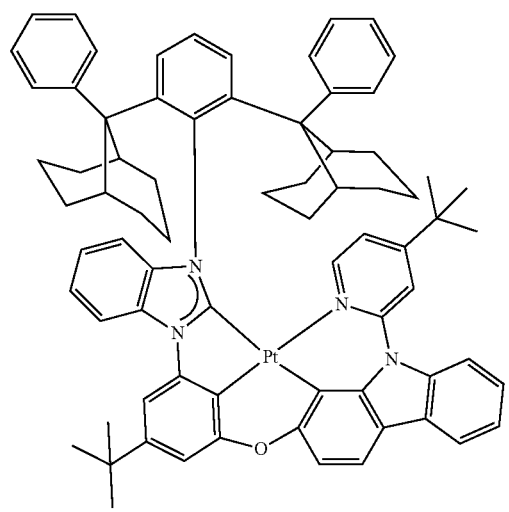
BD34
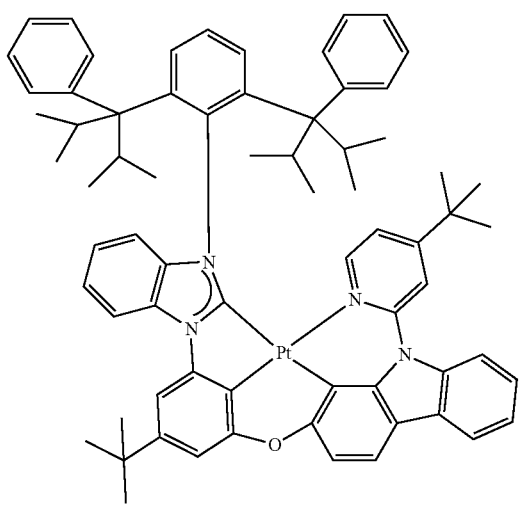
BD35
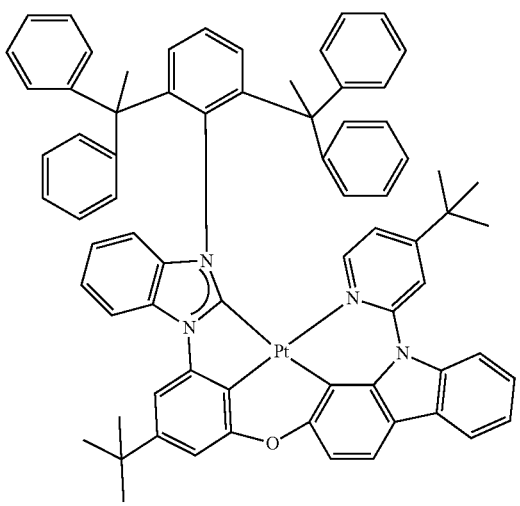
BD36
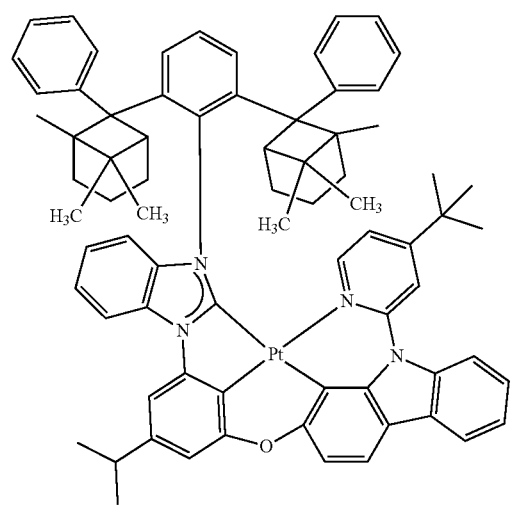
BD37
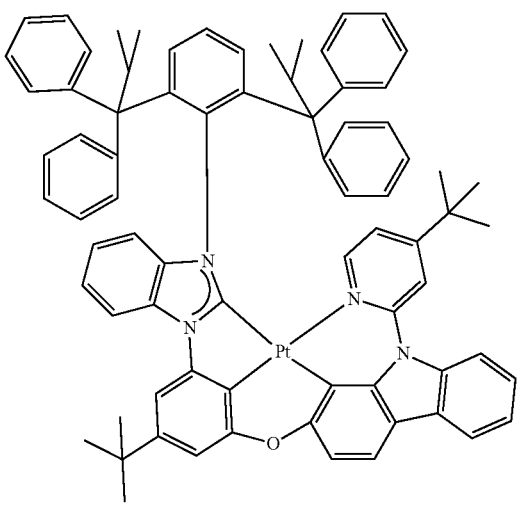

BD38
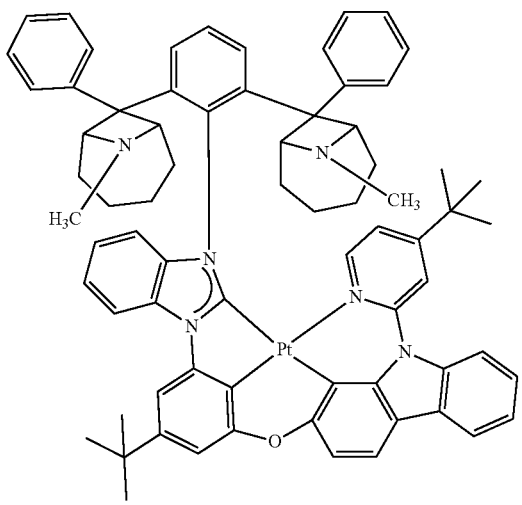
BD41
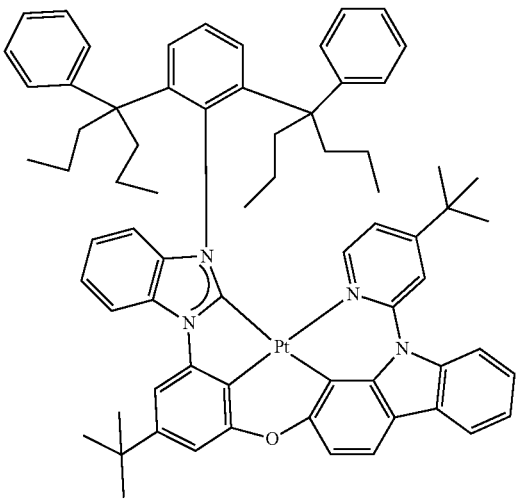
BD39
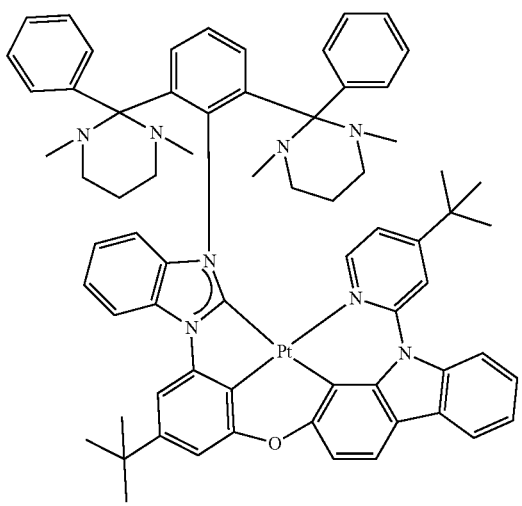
BD42
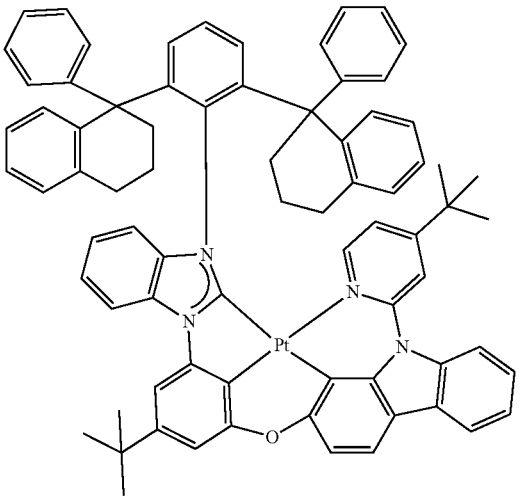
BD40
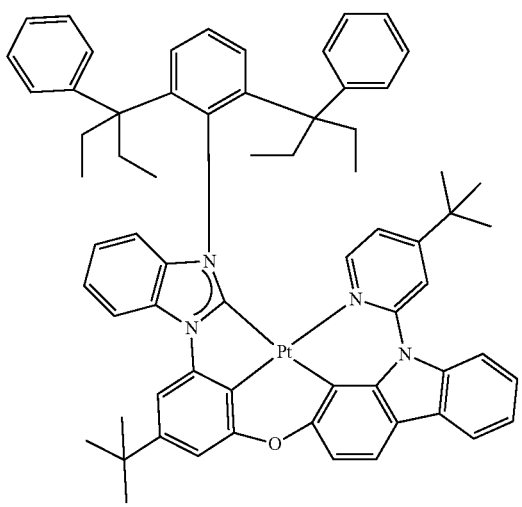
BD43
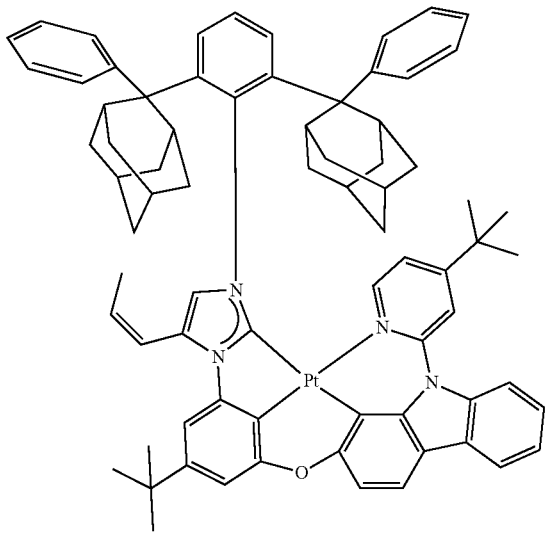

BD44
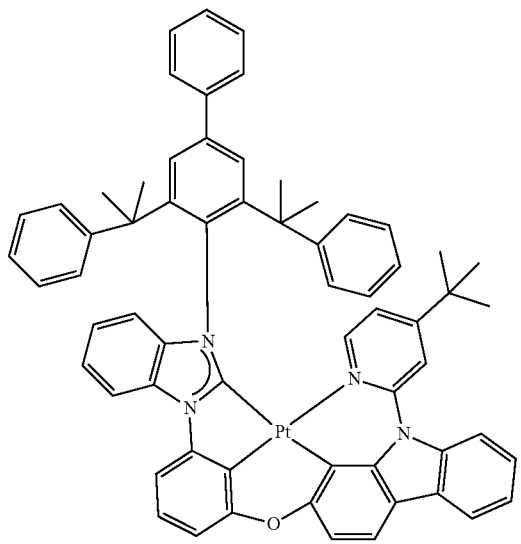
BD46
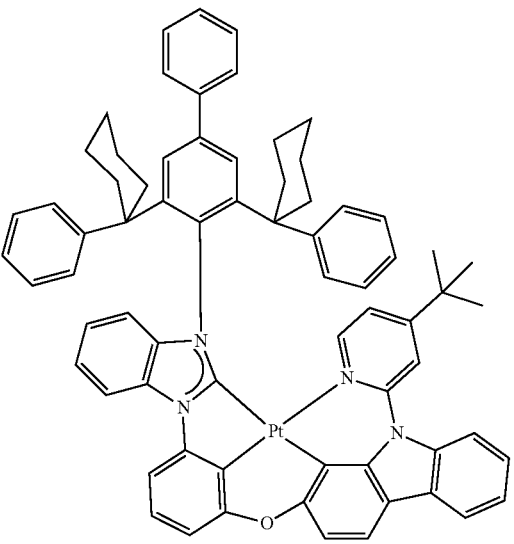
BD45
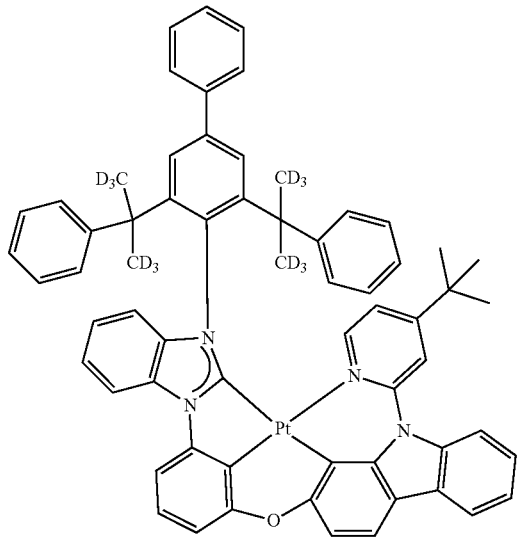
BD47
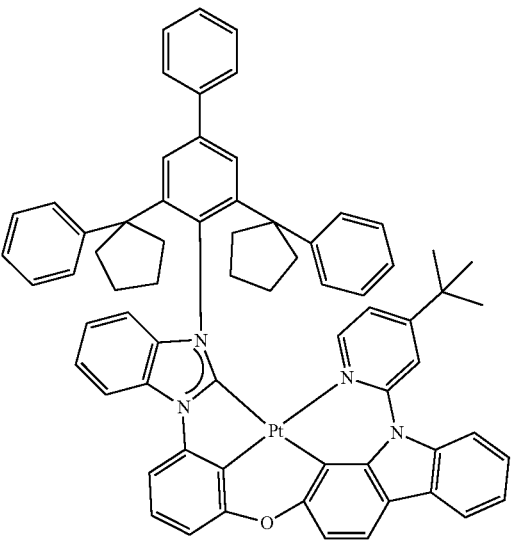

BD48
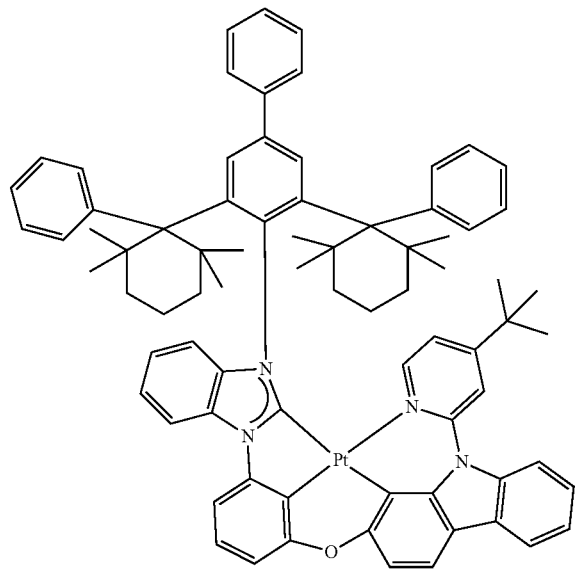
BD50
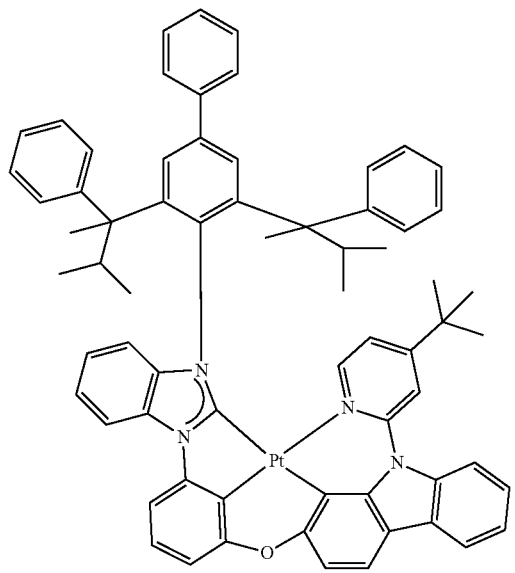
BD49
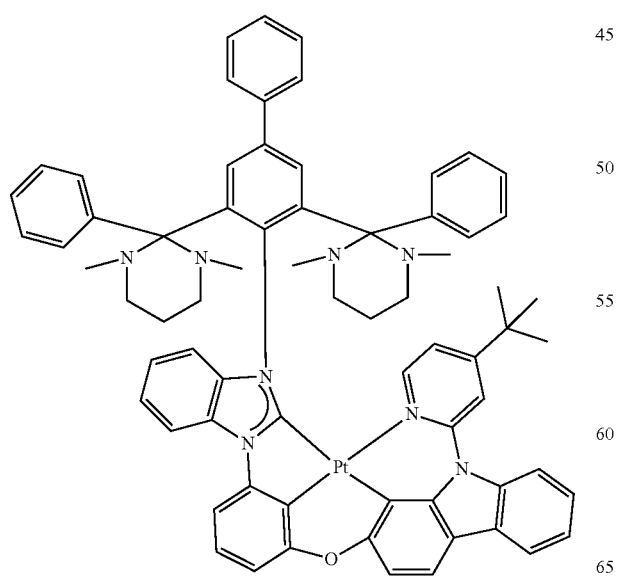
BD51
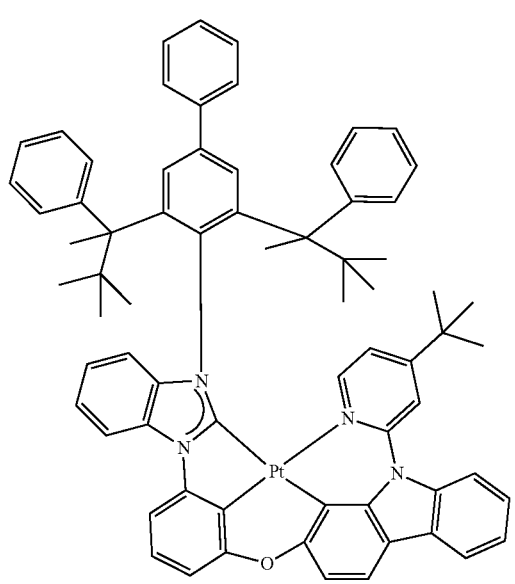

BD52
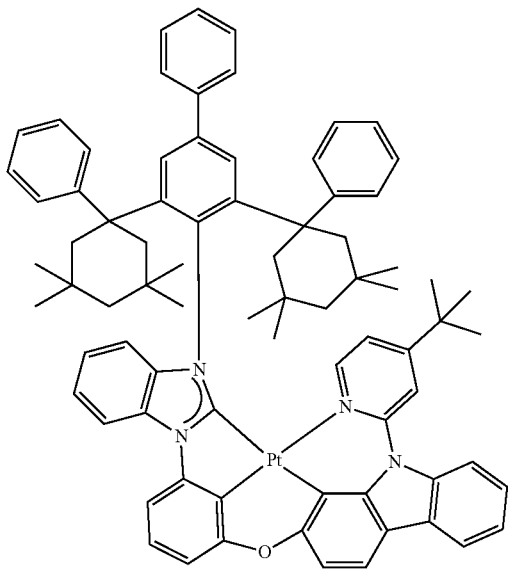
BD54
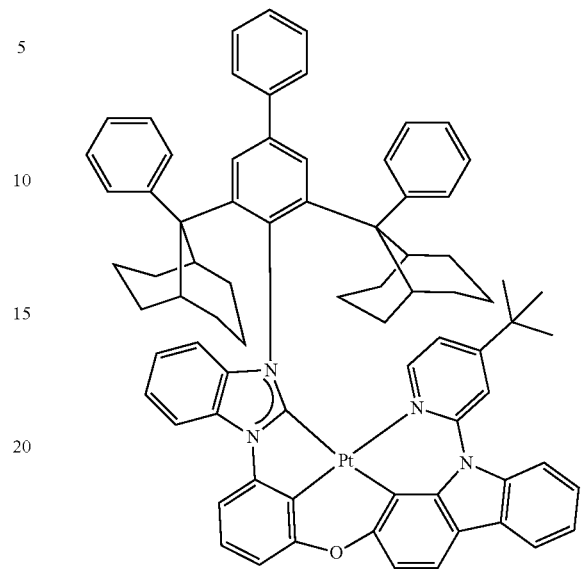
BD53
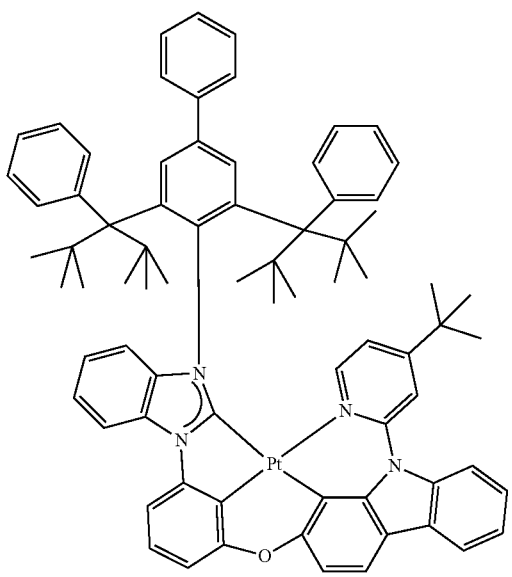
BD55
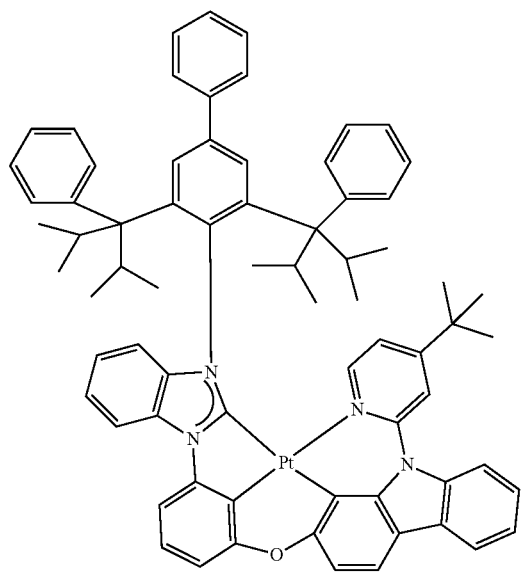

BD56
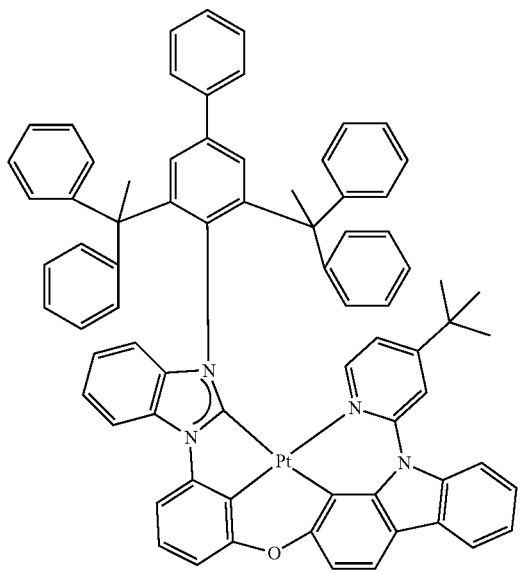
BD58
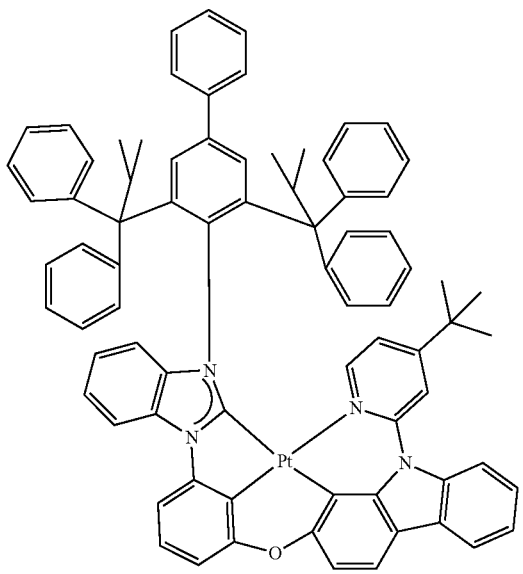
BD57
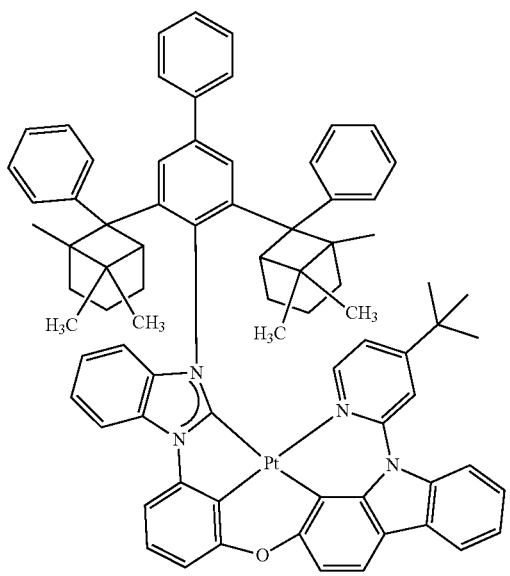
BD59
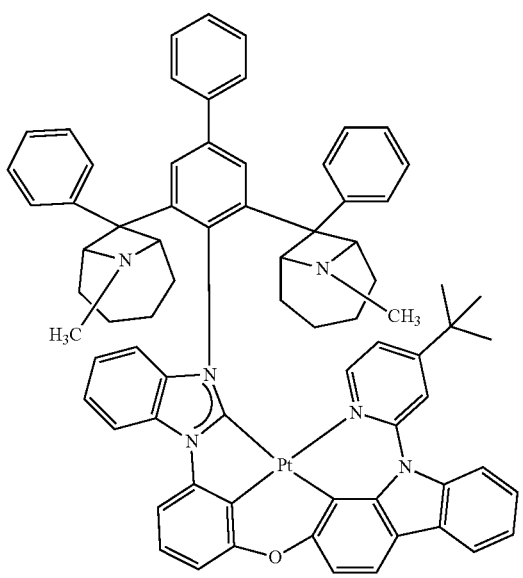

BD60

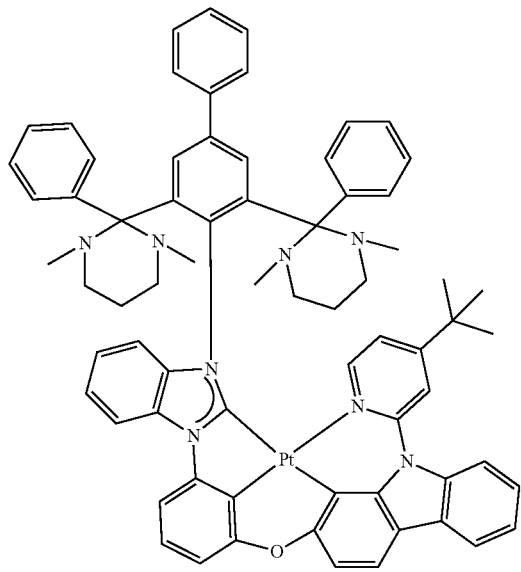

BD61

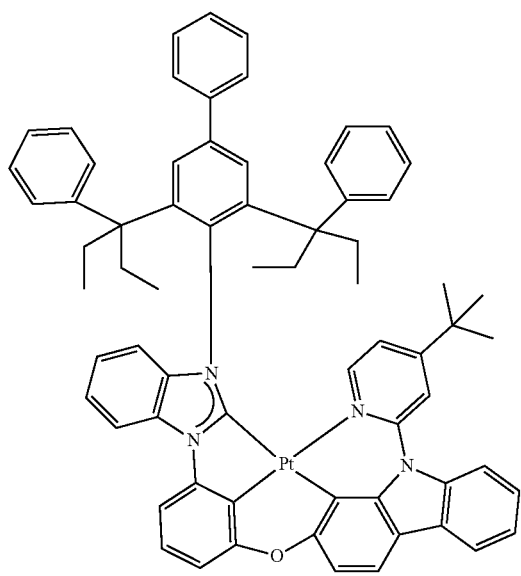

In one or more embodiments, the emission layer EML may include a host. For example, the emission layer EML may include at least one kind of host. In one or more embodiments, the emission layer EML may include a first host having an electron transport property.

In one or more embodiments, the first host may be represented by Formula 6 below.

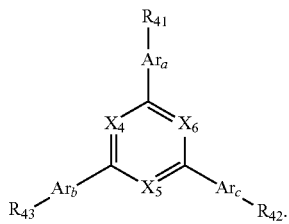

Formula 6

In Formula 6, $X_4$ to $X_6$ may be each independently N or $CR_{44}$, but at least one among $X_4$ to $X_6$ may be N.

In Formula 6, $Ar_a$ to $Ar_c$ may be each independently a direct linkage, a substituted or unsubstituted arylene group having 6 to 30 ring-forming carbon atoms, or a substituted or unsubstituted heteroarylene group having 2 to 30 ring-forming carbon atoms, and/or bonded to an adjacent group to form a ring.

In Formula 6, $R_{41}$ to $R_{43}$ may be each independently a hydrogen atom, a deuterium atom, a halogen atom, a substituted or unsubstituted silyl group, a substituted or unsubstituted oxy group, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 6, $R_{44}$ may be a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms.

In one or more embodiments, the first host represented by Formula 6 may be any one selected from among the compounds represented by Compound Group 2 below. However, the embodiments of the present disclosure are not limited thereto.

Compound Group 2

ETH1

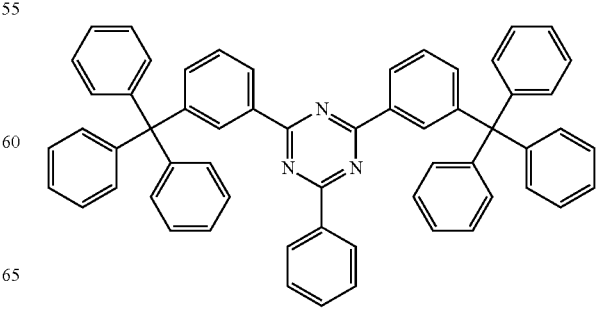

ETH2
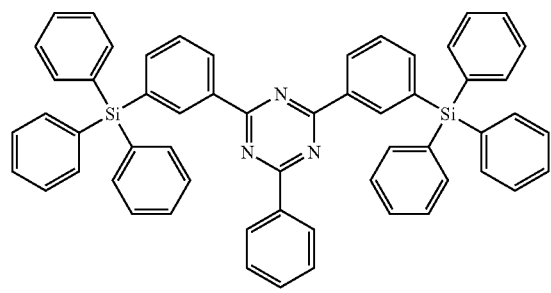
ETH3
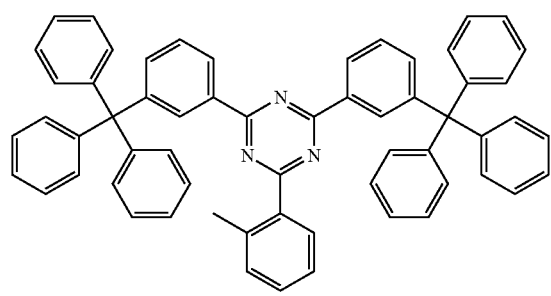
ETH4
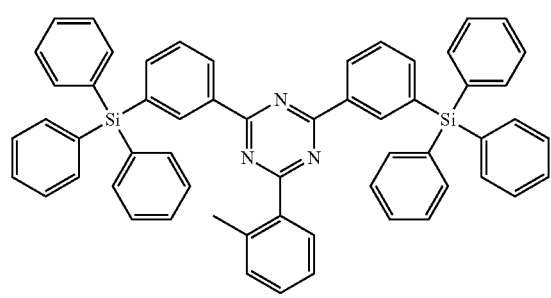
ETH5
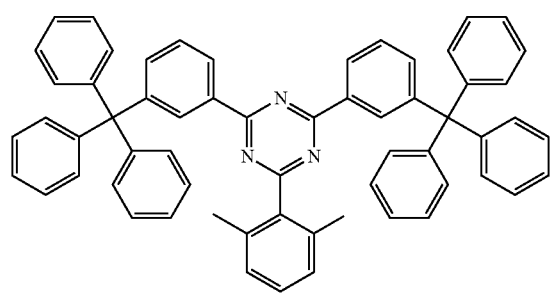
ETH6
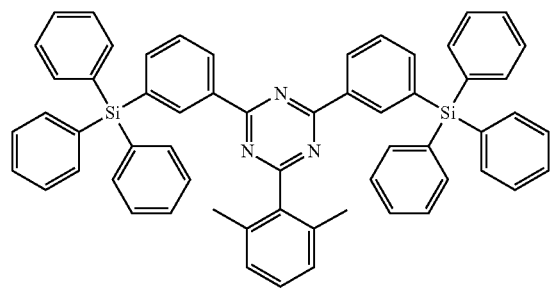
ETH7
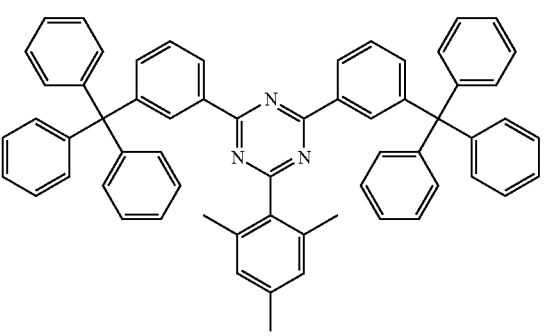
ETH8
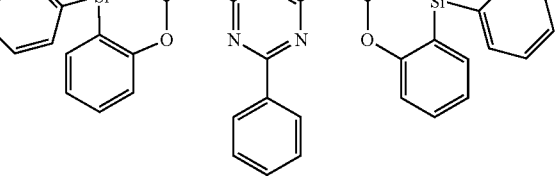
ETH9
ETH10
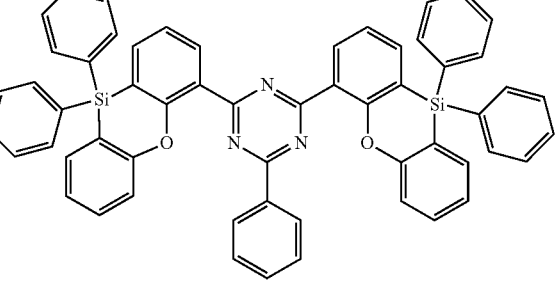

ETH11
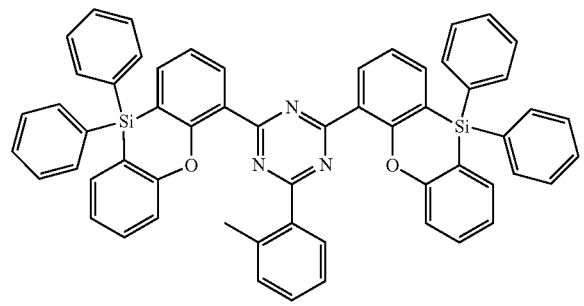
ETH15
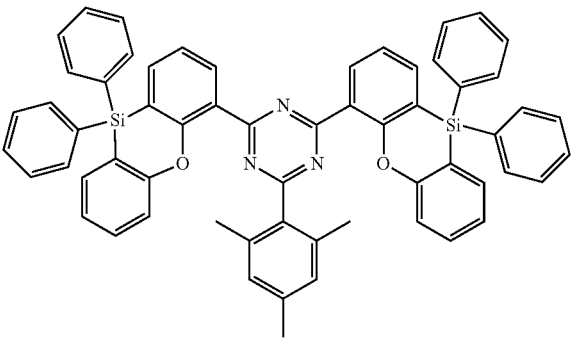
ETH12
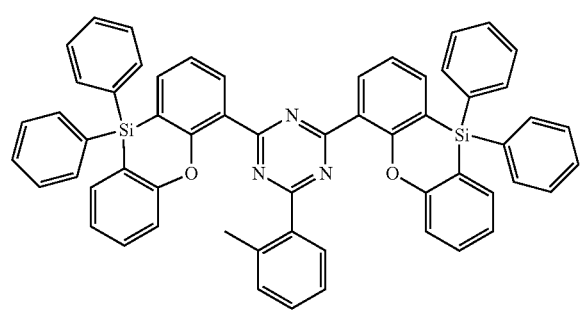
ETH16
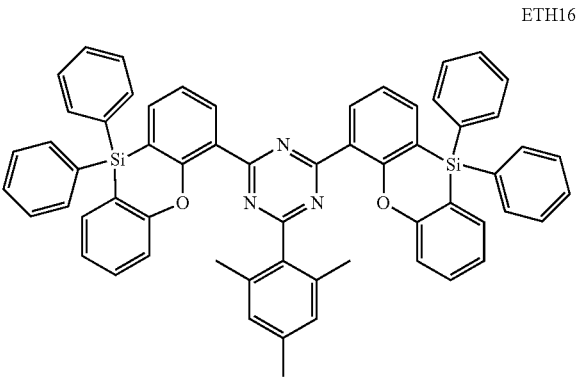
ETH13
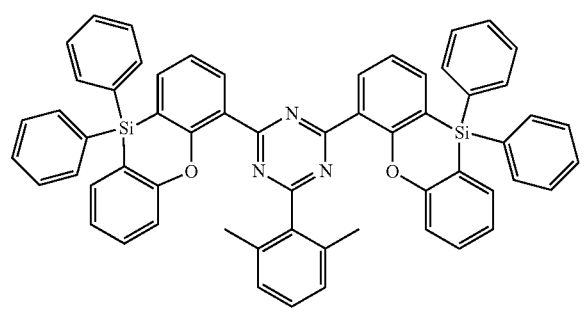
ETH17
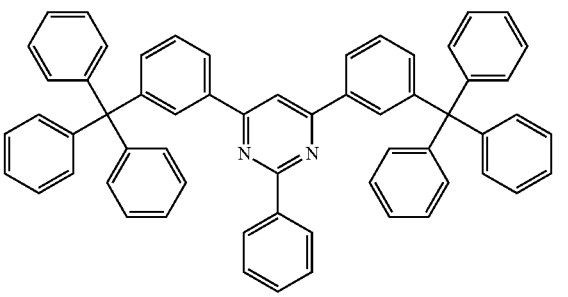
ETH14
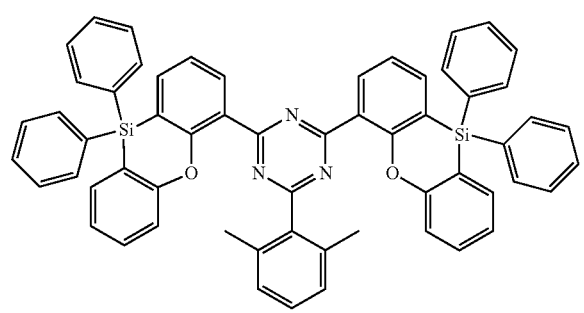
ETH18
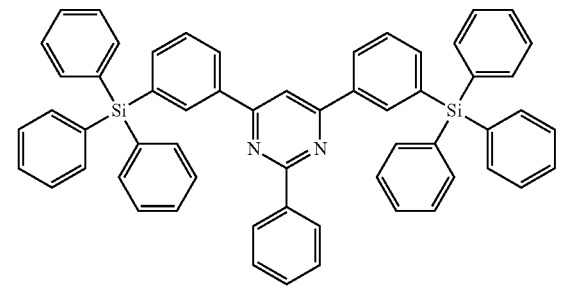

ETH19
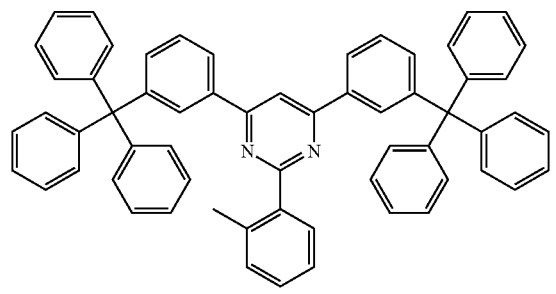
ETH20
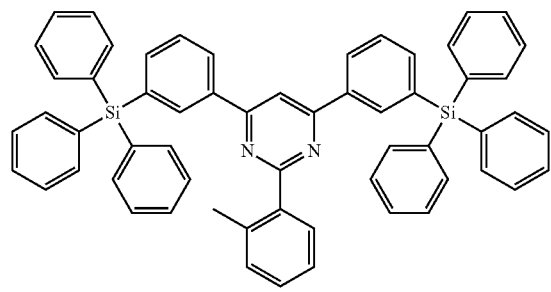
ETH21
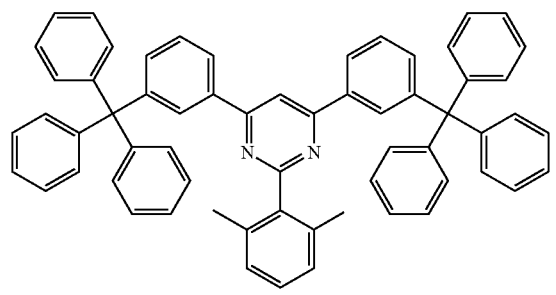
ETH22
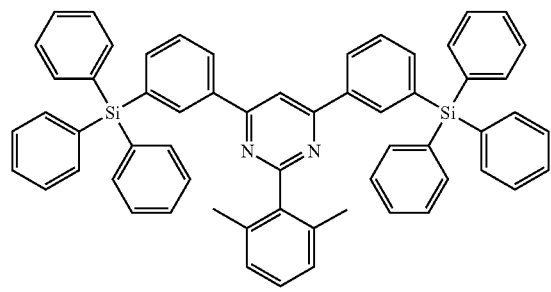
ETH23
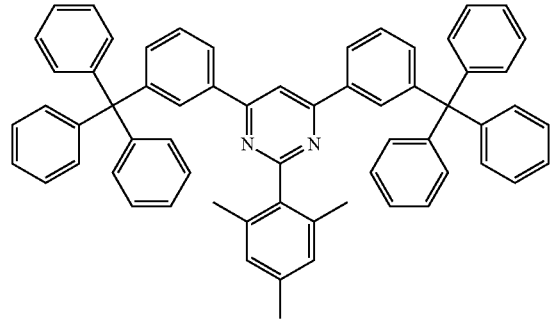
ETH24
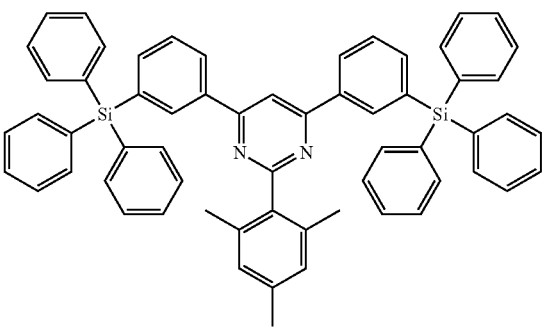
ETH25
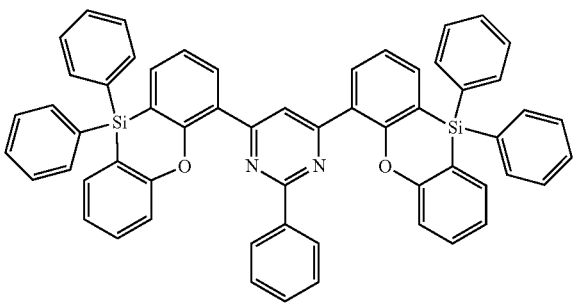
ETH26
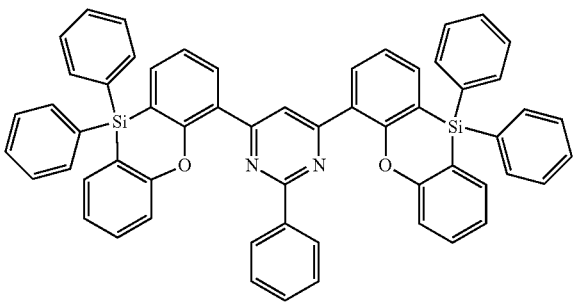
ETH27
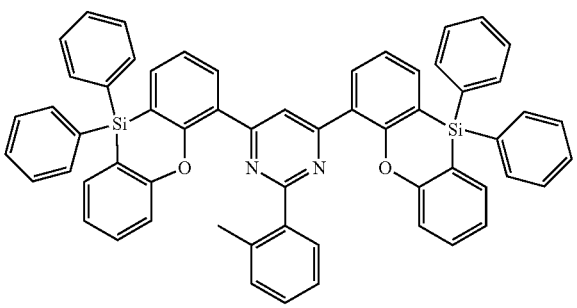

ETH28
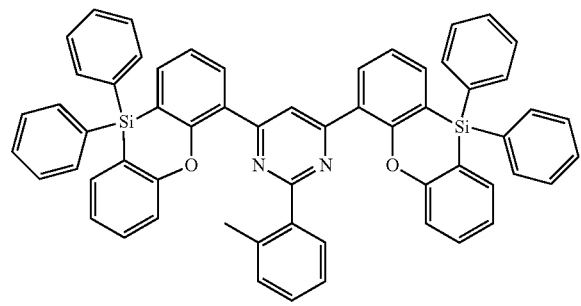
ETH29
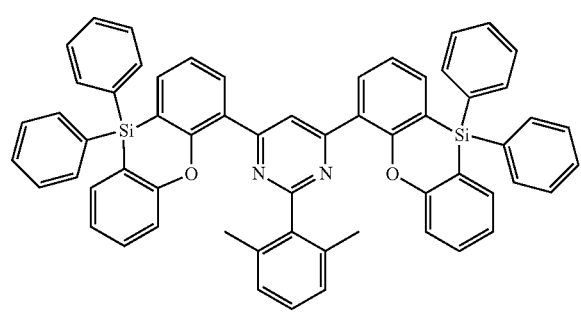
ETH30
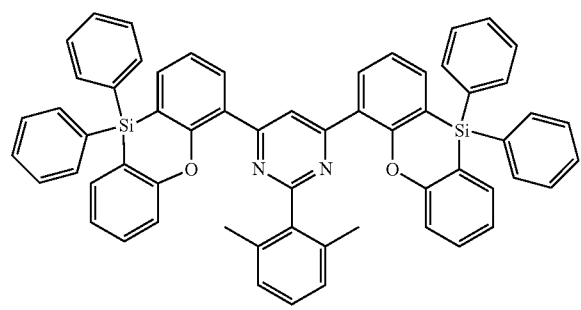
ETH31
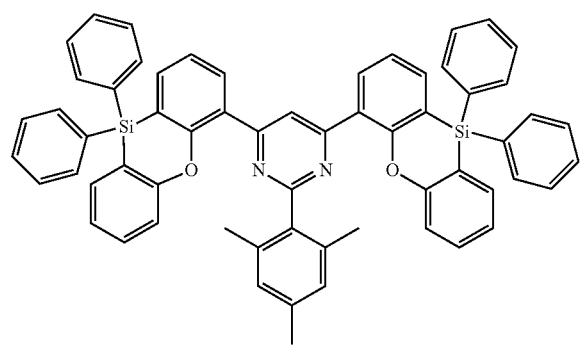
ETH32
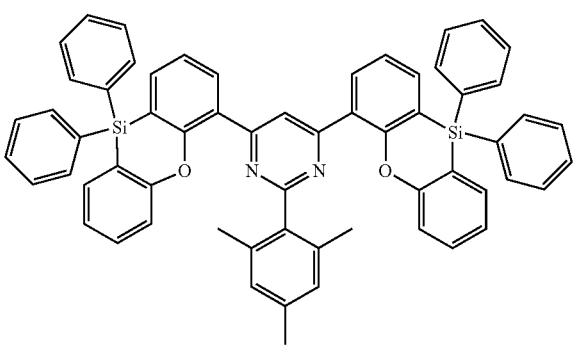
ETH33
ETH34
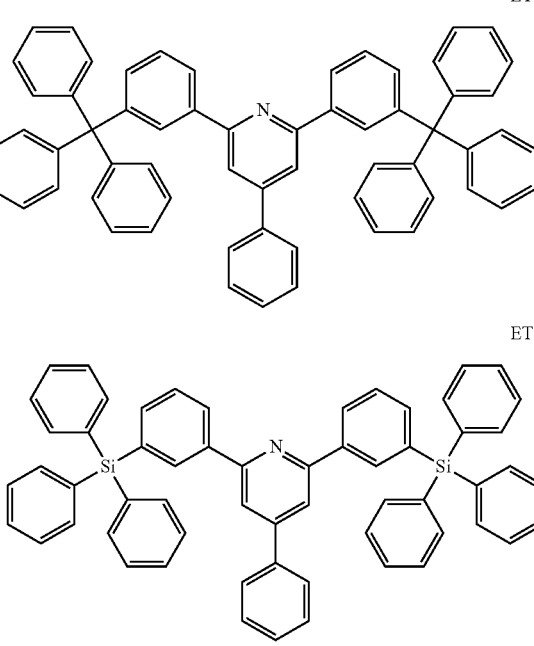
ETH35
ETH36
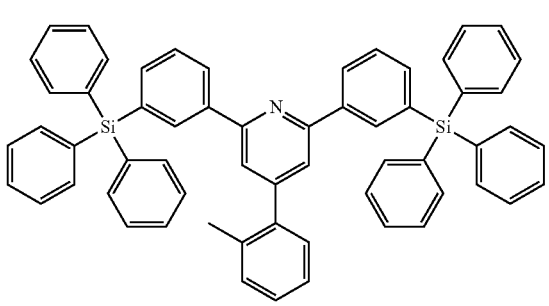

ETH37
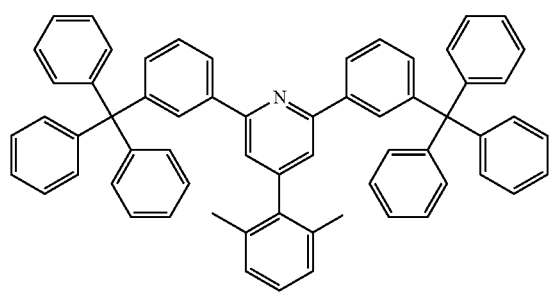
ETH42
ETH38
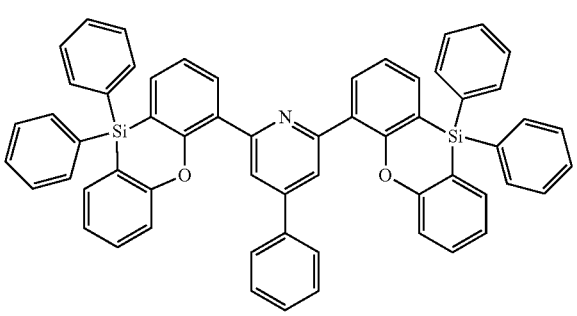
ETH43
ETH39
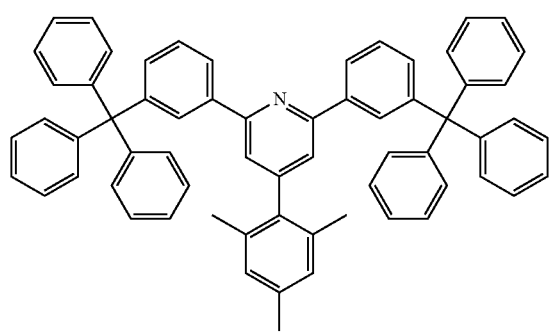
ETH44
ETH40
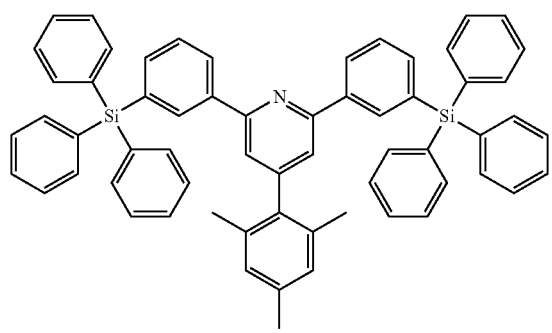
ETH45
ETH41
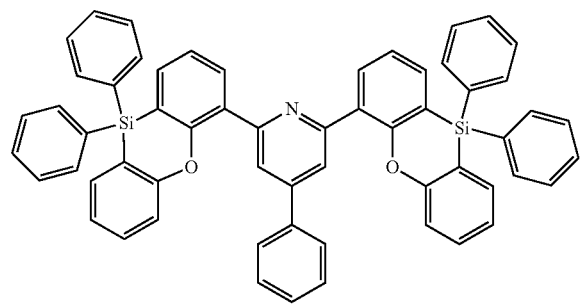
ETH46

ETH47
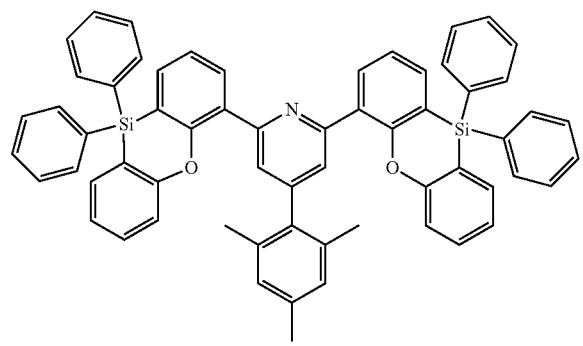
ETH51
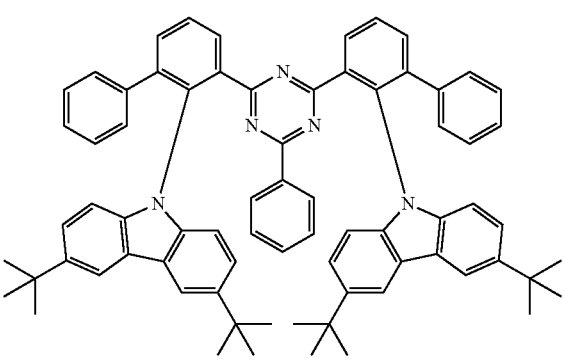
ETH48
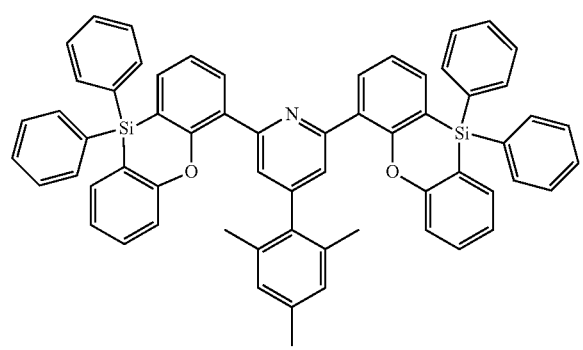
ETH52
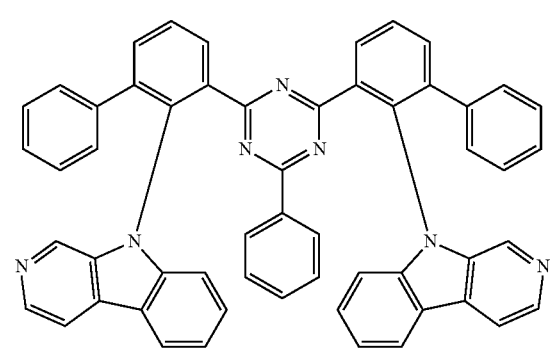
ETH49
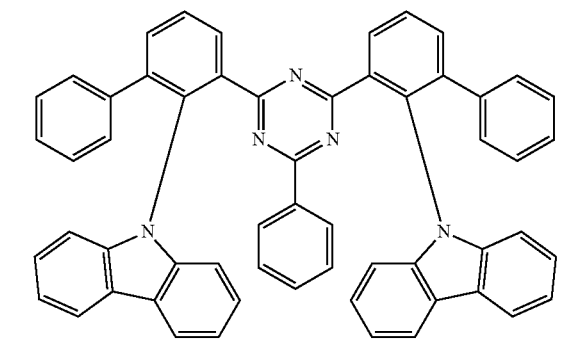
ETH53
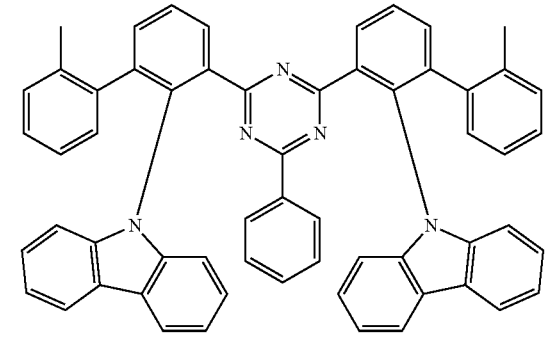
ETH50
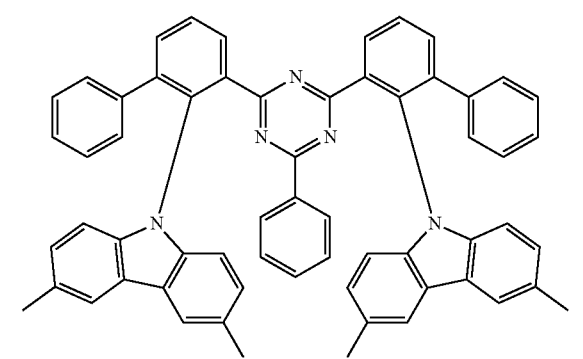
ETH54
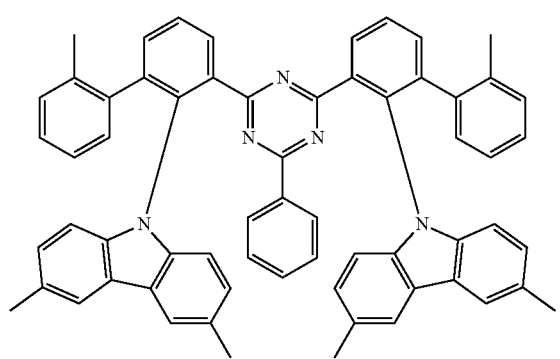

-continued
ETH55
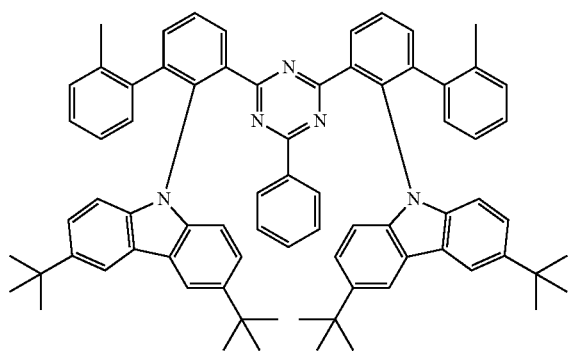
ETH56
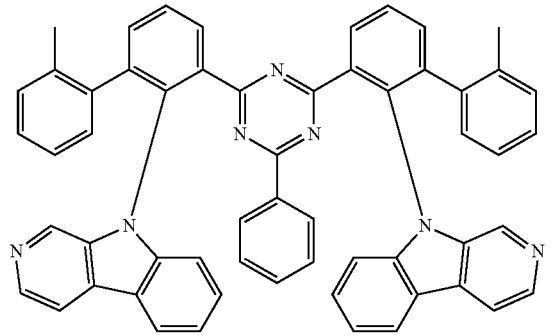
ETH57
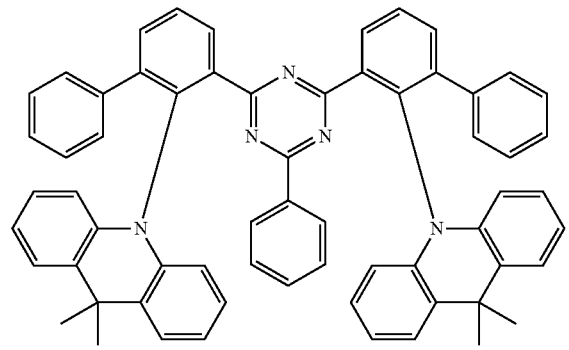
ETH58
-continued
ETH59
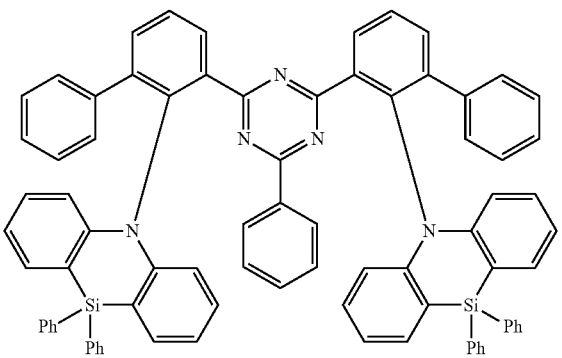
ETH60
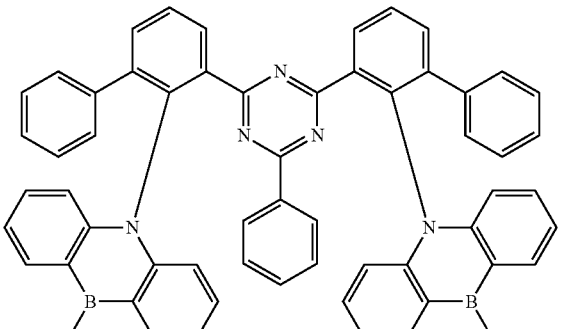
ETH61
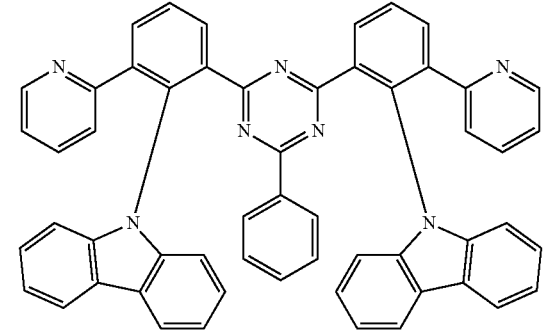
ETH62
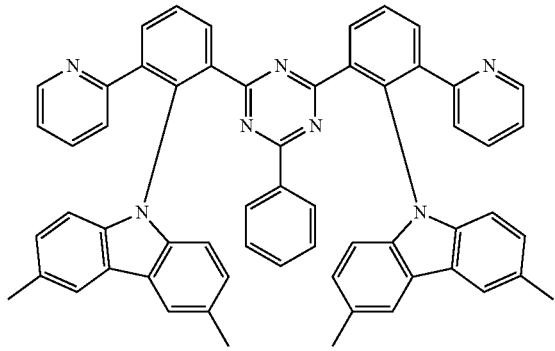

ETH63
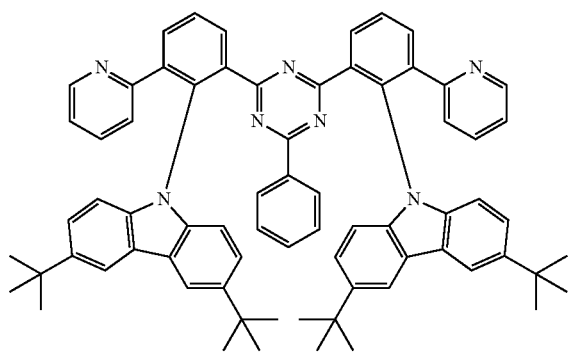
ETH67
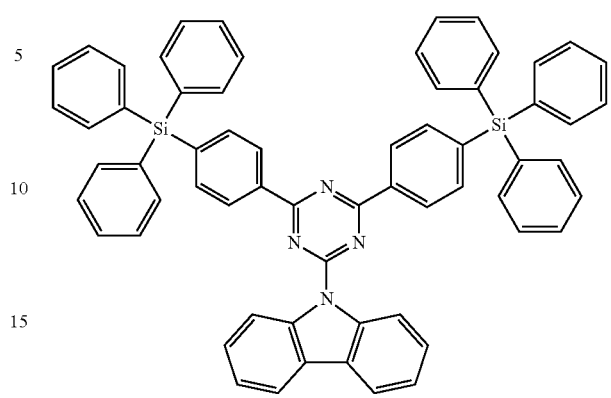
ETH64
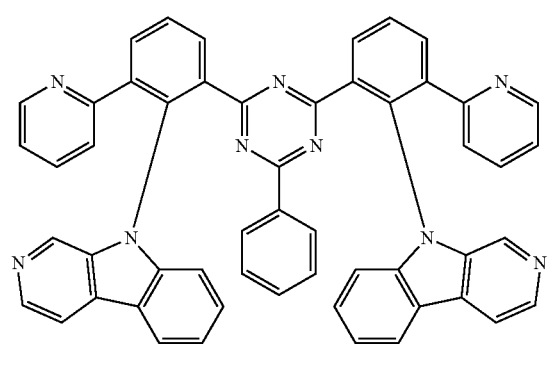
ETH68
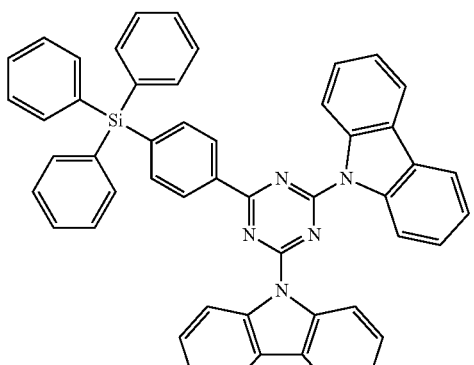
ETH65
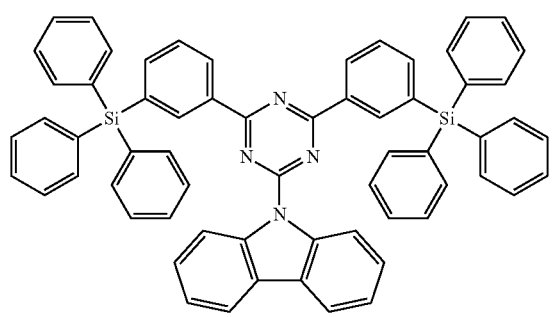
ETH69
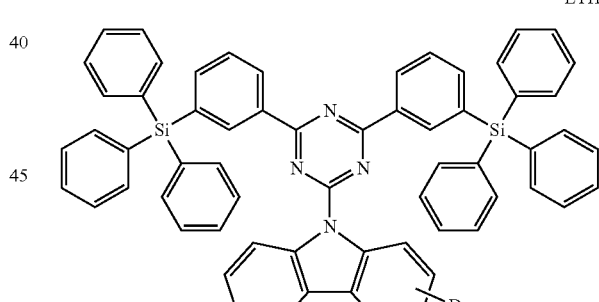
ETH66
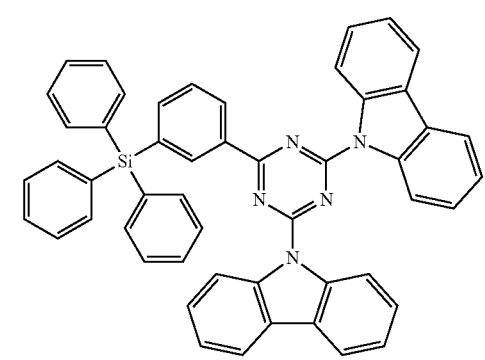
ETH70
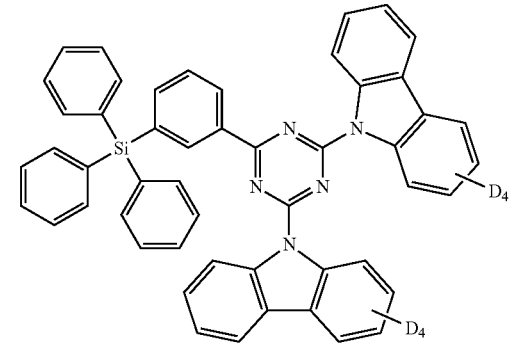

-continued
ETH71
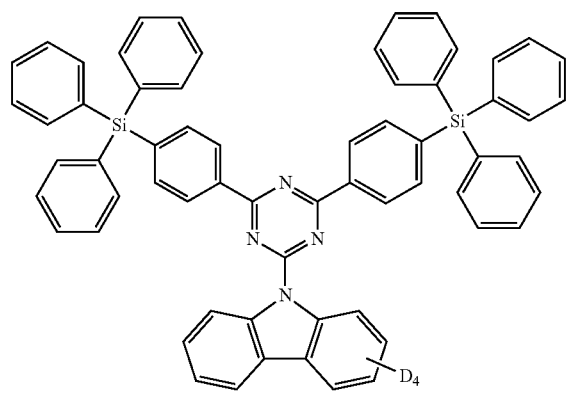
ETH72
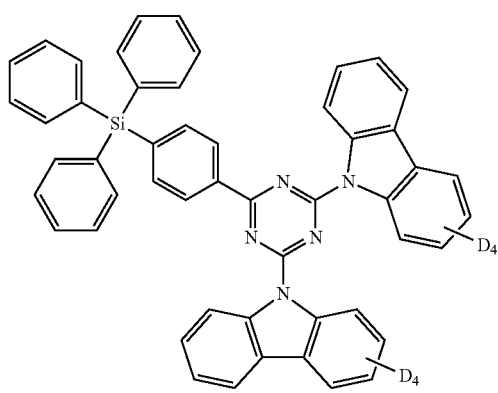
ETH73
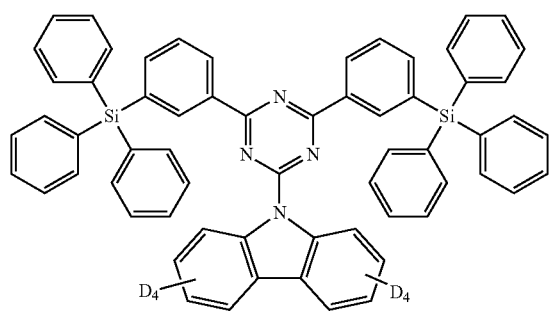
ETH74
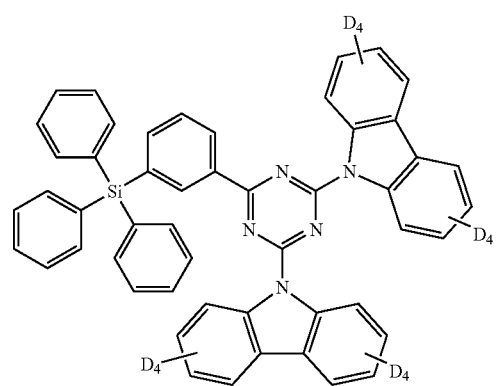
-continued
ETH75
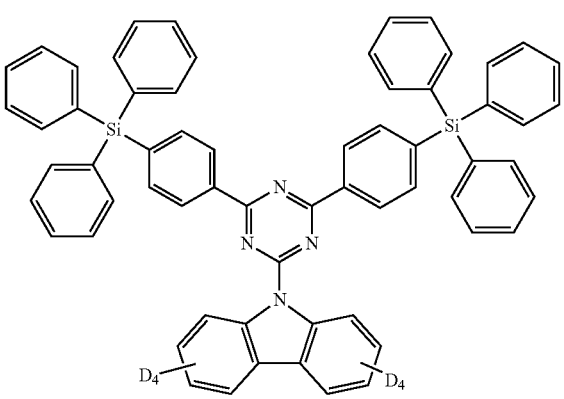
ETH76
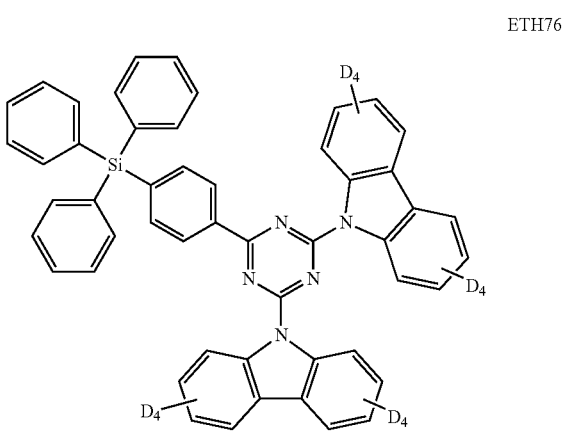
ETH77
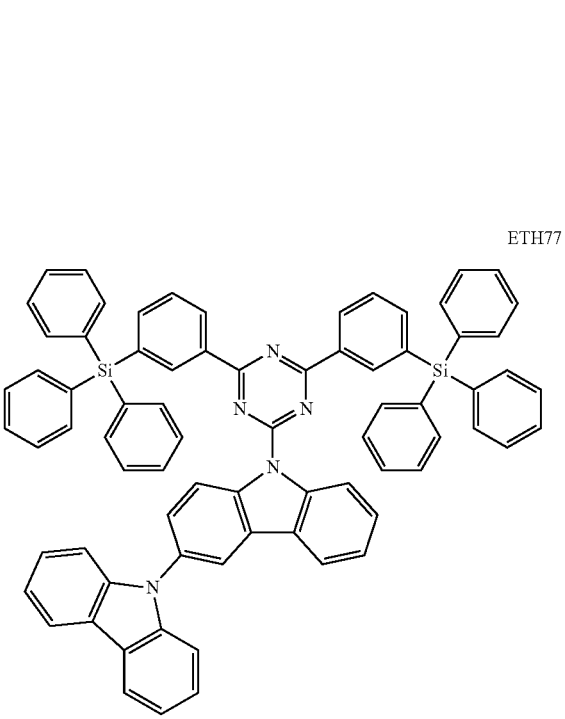

ETH78
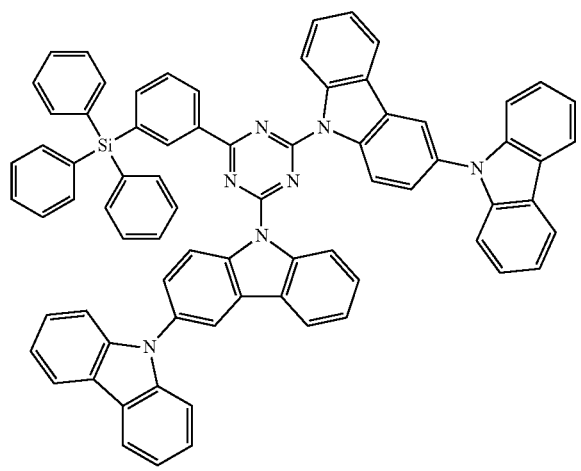
ETH79
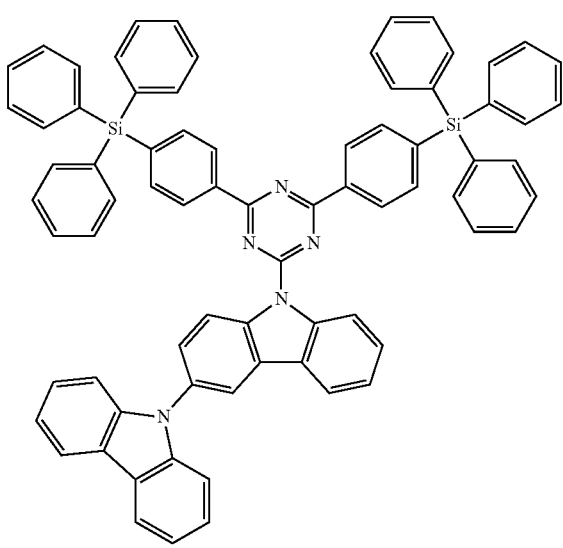
ETH80
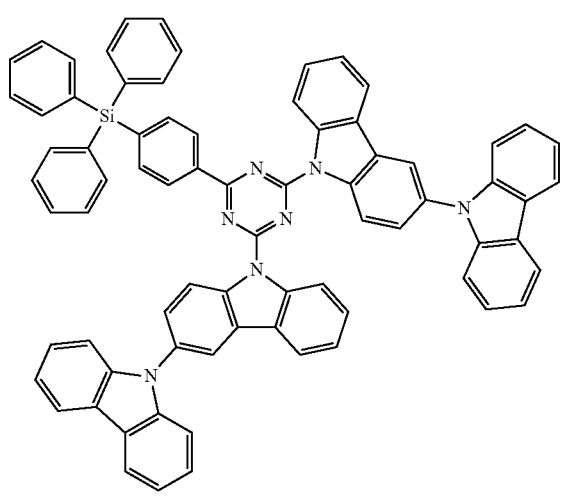
ETH81
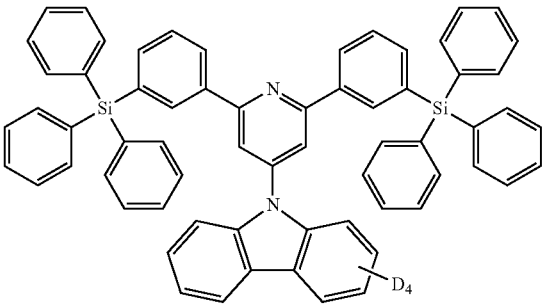
ETH82
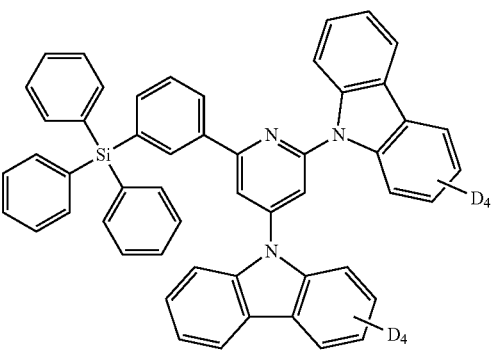
ETH83
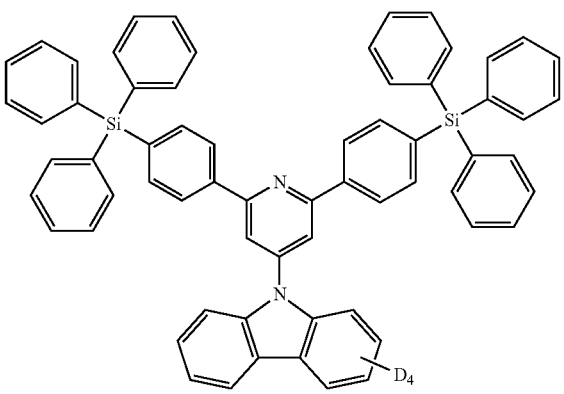
ETH84
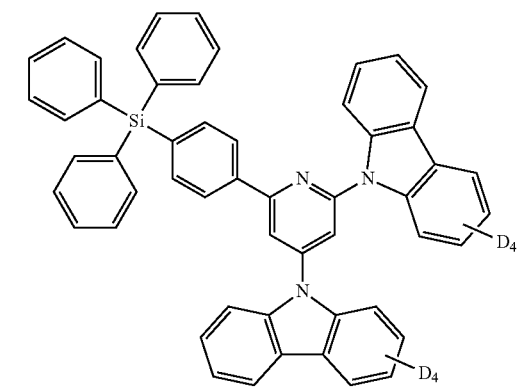
In one or more embodiments, the emission layer EML may further include a second host having a hole transport property. When the first host having the electron transport property and the second host having the hole transport property may be included in the emission layer EML, holes and electrons may be easily injected into the emission layer EML. Also, a charge balance in the emission layer EML may be increased, and thus high luminous efficiency and long service life characteristics may be exhibited.

In one or more embodiments, the second host may be represented by Formula 7 below.

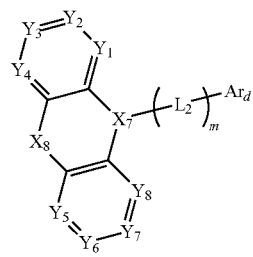

Formula 7

In Formula 7, $Y_1$ to $Y_8$ may be each independently $CR_{51}$ or N, $X_7$ may be N or $CR_{52}$, and $X_8$ may be a direct linkage, $SiR_{53}R_{54}$, or $CR_{55}R_{56}$.

In Formula 7, $R_{51}$ may be a hydrogen atom, a deuterium atom, a halogen atom, a cyano group, a substituted or unsubstituted silyl group, a substituted or unsubstituted oxy group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 7, $R_{52}$ to $R_{56}$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 7, $L_2$ may be a direct linkage, a substituted or unsubstituted arylene group having 6 to 30 ring-forming carbon atoms, or a substituted or unsubstituted heteroarylene group having 2 to 30 ring-forming carbon atoms, and/or bonded to an adjacent group to form a ring.

In Formula 7, $Ar_d$ may be a substituted or unsubstituted silyl group, a substituted or unsubstituted phosphine oxide group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 7, m may be an integer of 0 to 2. Meanwhile, when m is 2 or more, a plurality of $L_2$'s may be the same as or different from each other.

The second host represented by Formula 7 above may be any one selected from among the compounds represented by Compound Group 3 below. However, the embodiments of the present disclosure are not limited thereto.

Compound Group 3

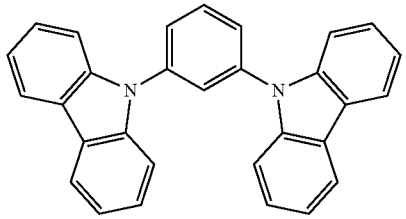

HTH1

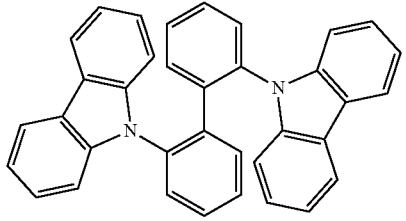

HTH2

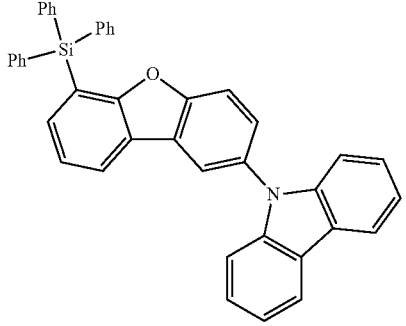

HTH3

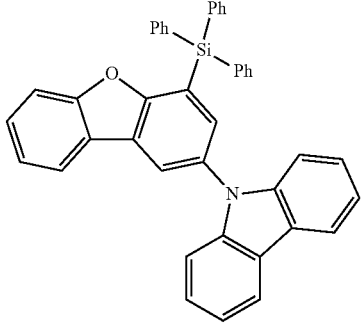

HTH4

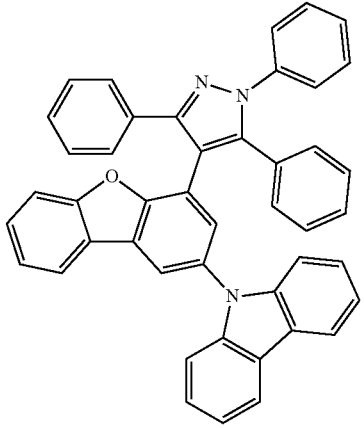

HTH5

-continued
HTH6
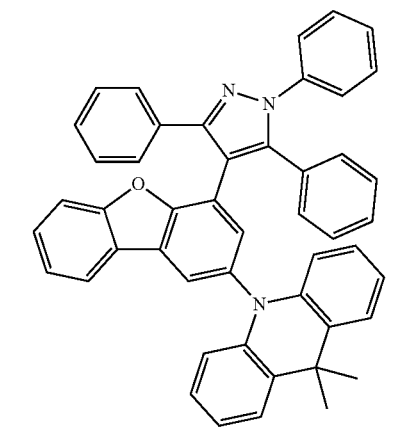
HTH7
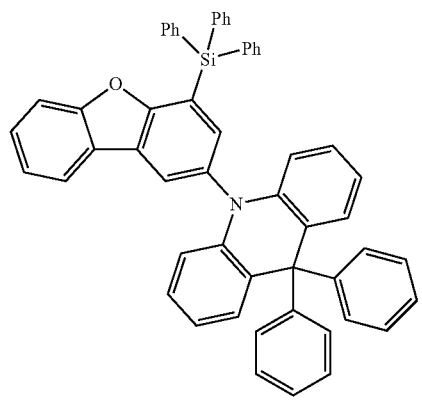
HTH8
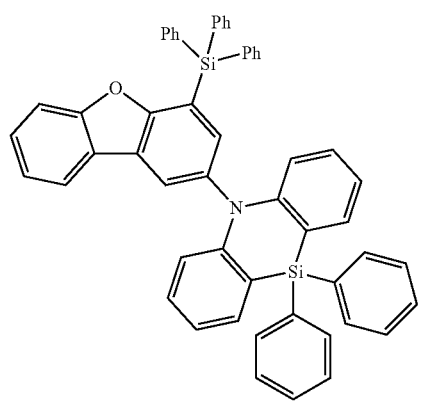
-continued
HTH9
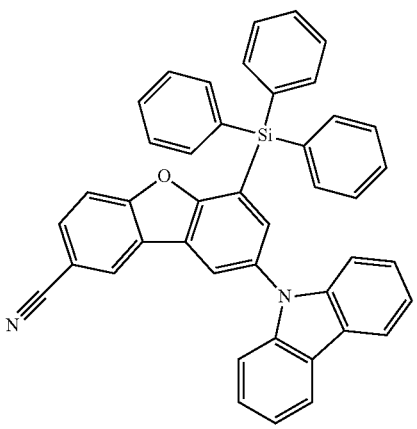
HTH10
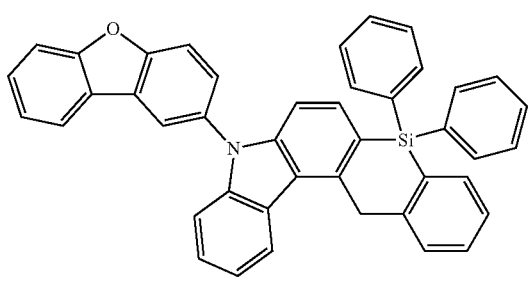
HTH11
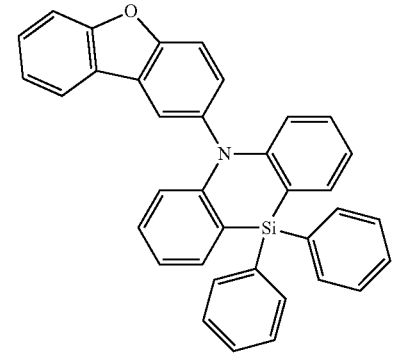
HTH12
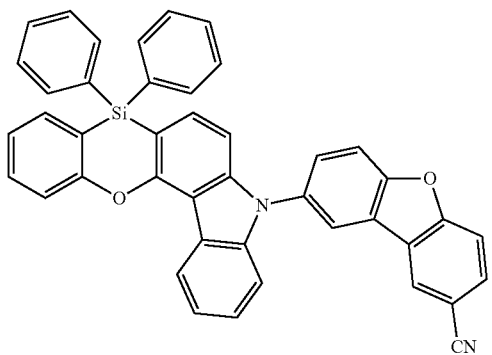

HTH13
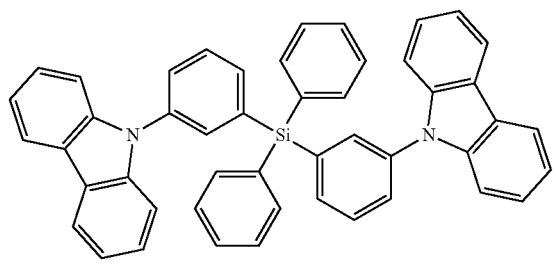
HTH14
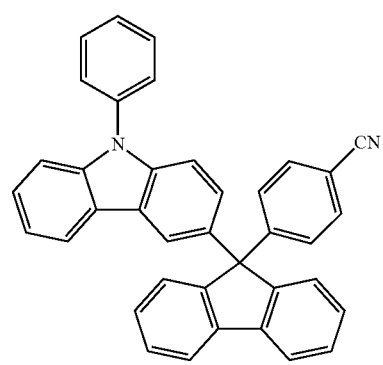
HTH15
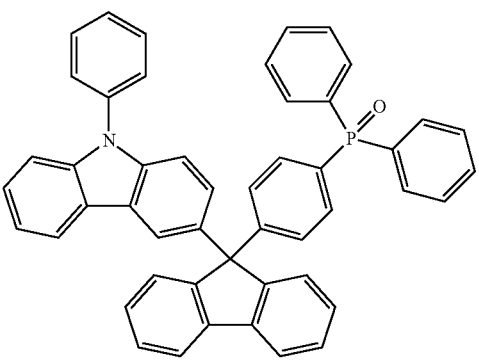
HTH16
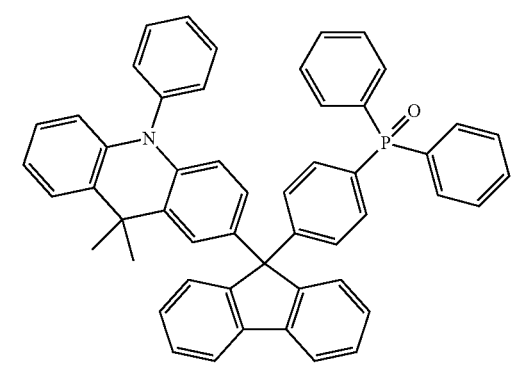
HTH17
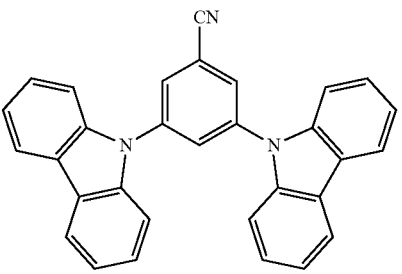
HTH18
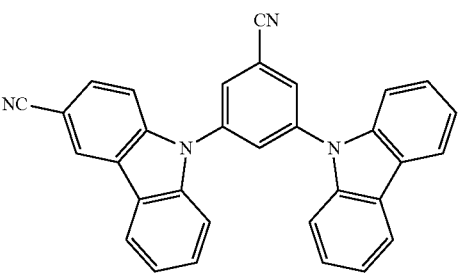
HTH19
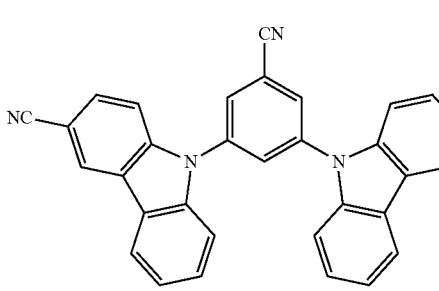
HTH20
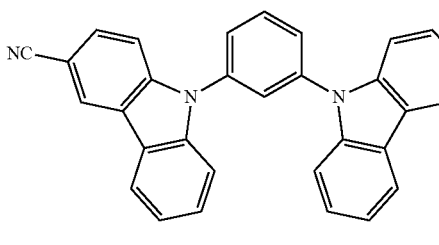
HTH21
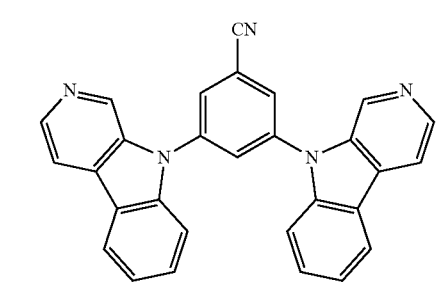
HTH22
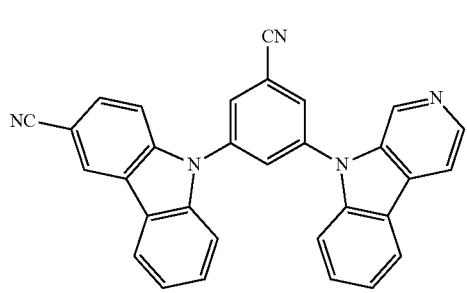

HTH23
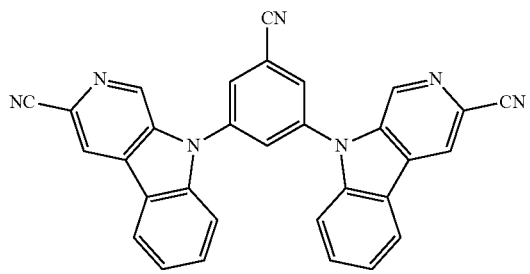
HTH24
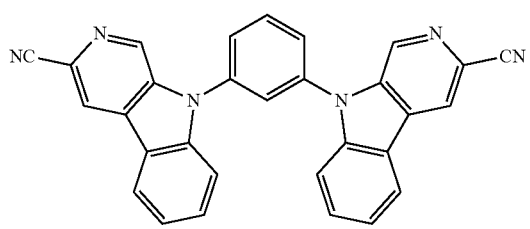
HTH25
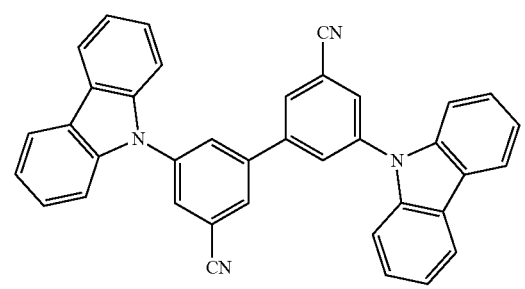
HTH26
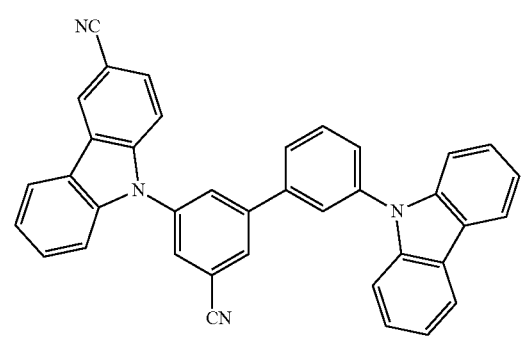
HTH27
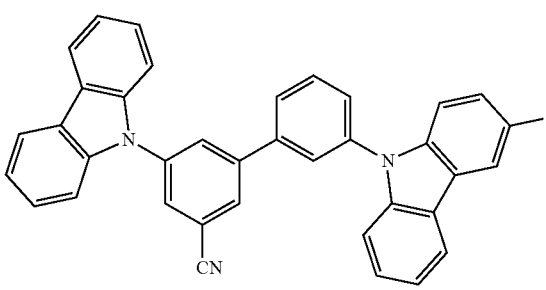
HTH28
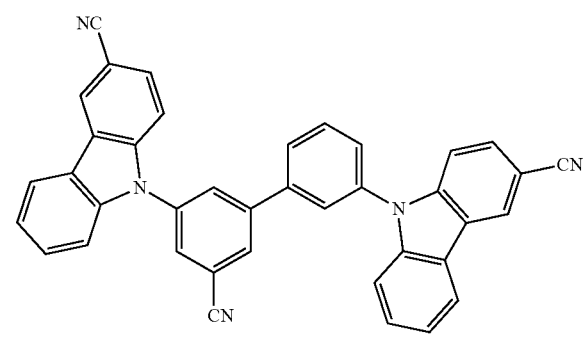
HTH29
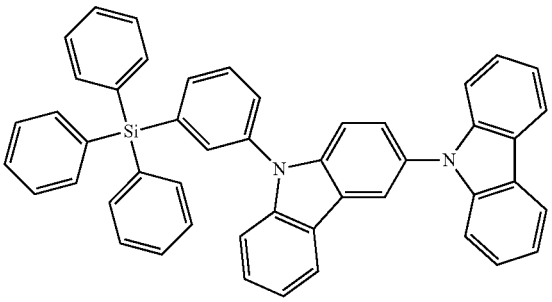
HTH30
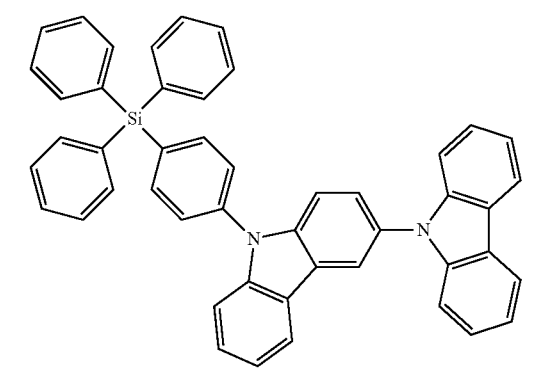
HTH31
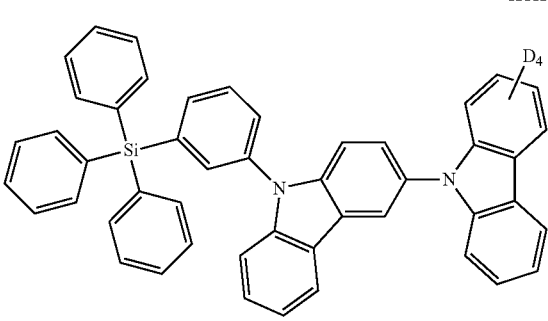

HTH32
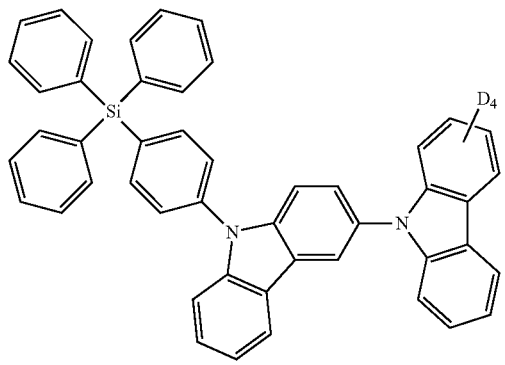
HTH35
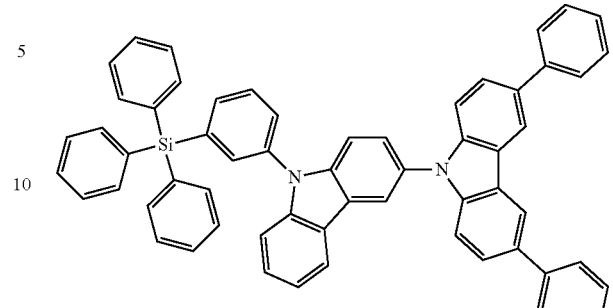
HTH33
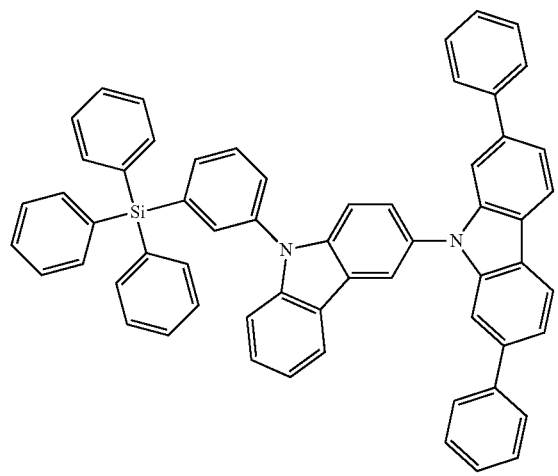
HTH36
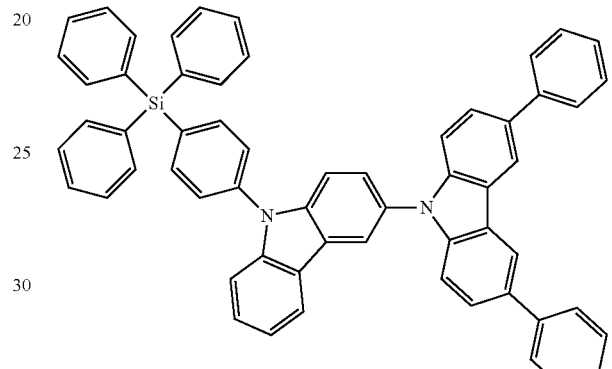
HTH37
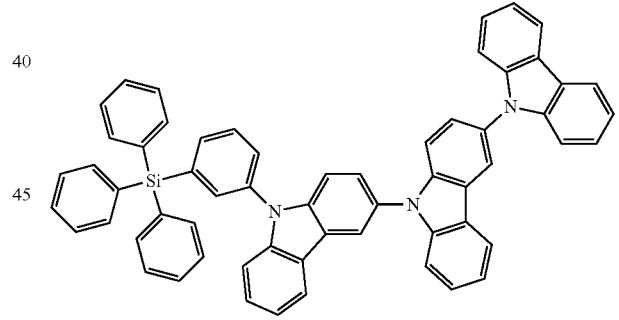
HTH34
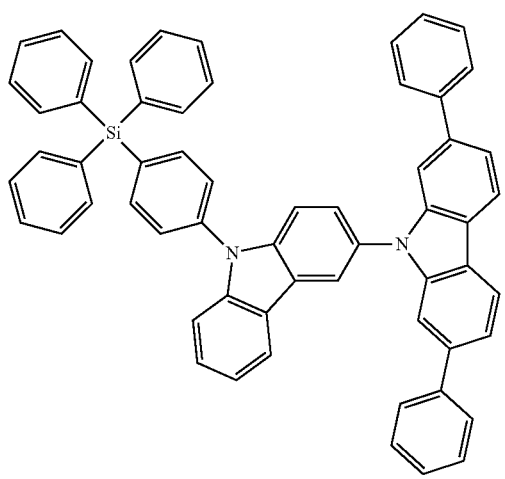
HTH38
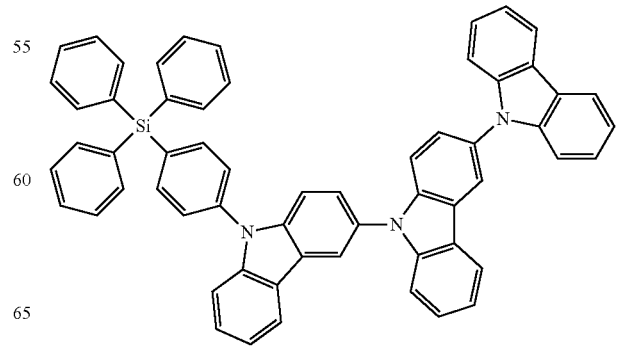

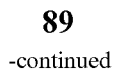
HTH39
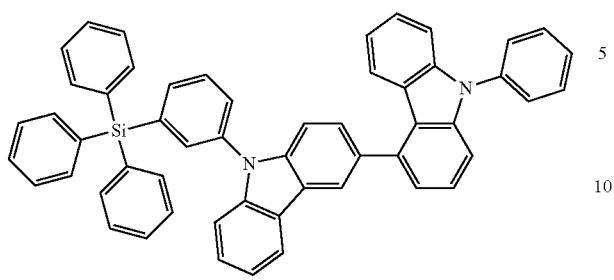
HTH40
HTH41
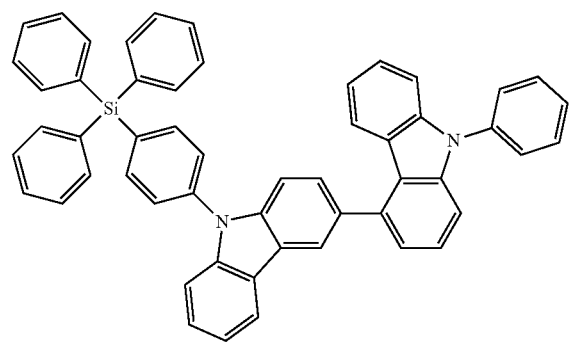
HTH42
HTH43
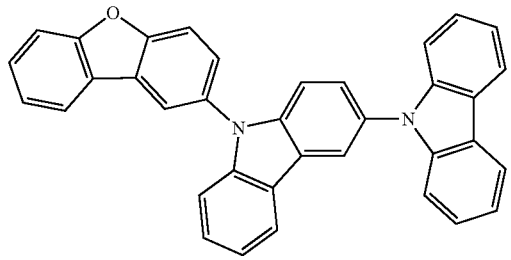
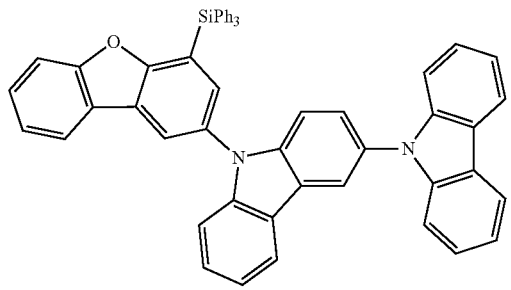
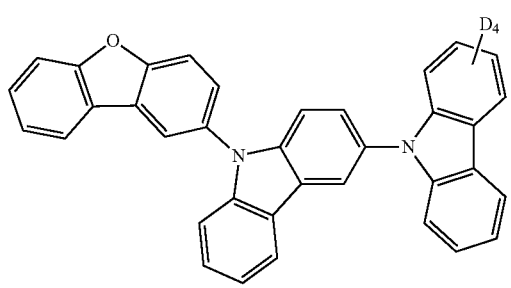
HTH44
HTH45
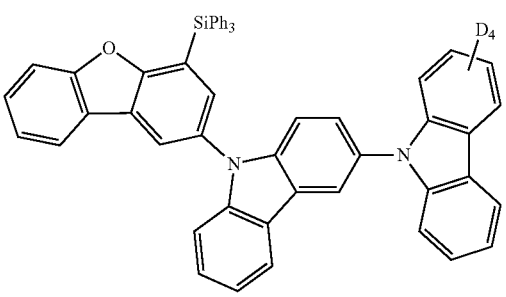
HTH46
HTH47
HTH48

HTH49

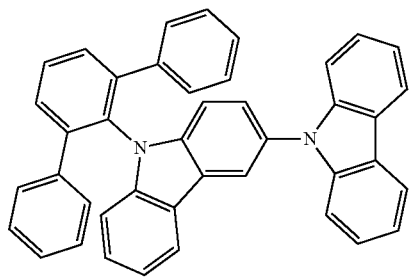

HTH50

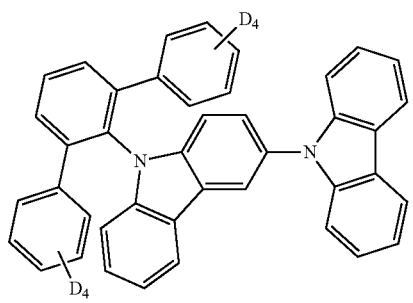

HTH51

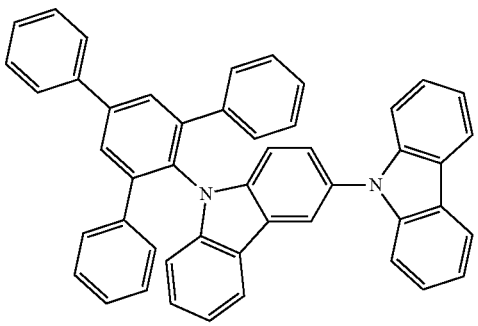

HTH52

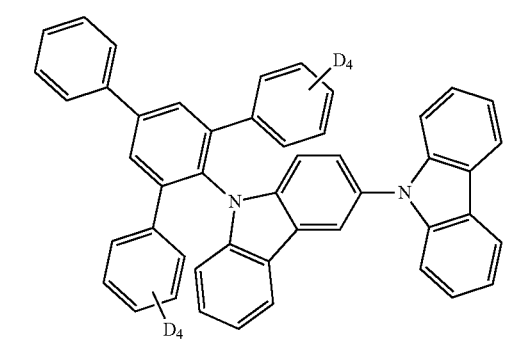

In one or more embodiments, the emission layer EML may further include a thermally activated delayed fluorescence dopant. For example, the emission layer EML may include a host and a phosphorescence dopant represented by Formula 1, and may further include a thermally activated delayed fluorescence dopant. In this case, an excitation energy generated by the host may be captured by the phosphorescence dopant that may be an organometallic compound, and may be transferred to the thermally activated delayed fluorescence dopant, or a triplet excitation energy formed by the direct recombination in the phosphorescence dopant may be transferred to the thermally activated delayed fluorescence dopant, and finally, the thermally activated delayed fluorescence may be emitted.

The structure of the thermally activated delayed fluorescence dopant may be represented by Formula 8 below. However, the structure of the thermally activated delayed fluorescence dopant is not limited by Formula 8 below.

Formula 8

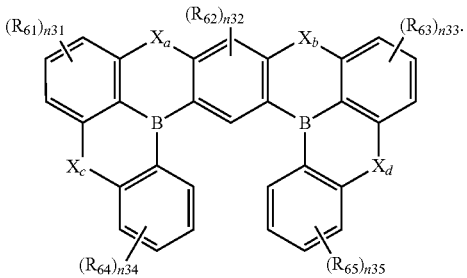

In Formula 8, $X_a$ to $X_d$ may be each independently $NR_{66}$, O or S.

In Formula 8, $R_{61}$ to $R_{65}$ may be each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 8, $R_{66}$ may be a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula 8, n31 may be an integer of 0 to 3. Meanwhile, when n31 is 2 or more, a plurality of $R_{61}$'s may be the same as or different from each other.

In Formula 8, n32 may be an integer of 0 to 2. Meanwhile, when n32 is 2, a plurality of $R_{62}$'s may be the same as or different from each other.

In Formula 8, n33 may be an integer of 0 to 3. Meanwhile, when n33 is 2 or more, a plurality of $R_{63}$'s may be the same as or different from each other.

In Formula 8, n34 may be an integer of 0 to 4. Meanwhile, when n34 is 2 or more, a plurality of $R_{64}$'s may be the same as or different from each other.

In Formula 8, n35 may be an integer of 0 to 4. Meanwhile, when n35 is 2 or more, a plurality of $R_{65}$'s may be the same as or different from each other.

In one or more embodiments, the thermally activated delayed fluorescence dopant represented by Formula 8 may be any one selected from among the compounds represented by Compound Group 4. However, the embodiments of the present disclosure are not limited thereto.

Compound Group 4
DFD1
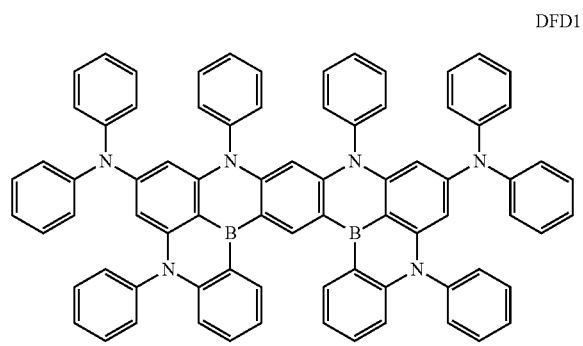
DFD2
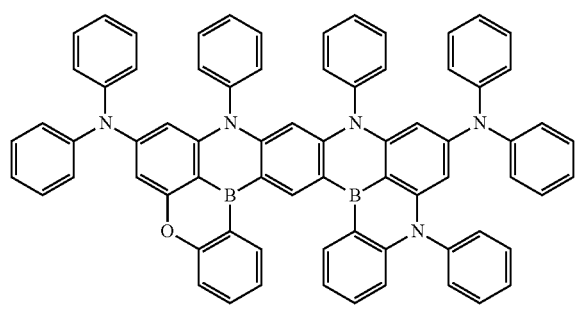
DFD3
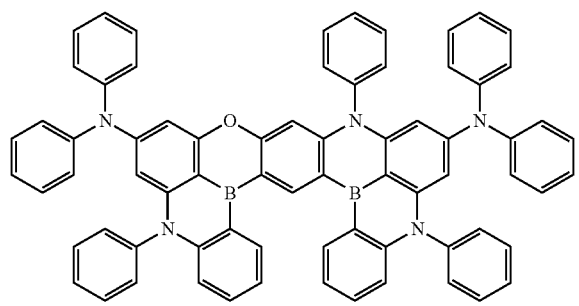
DFD4
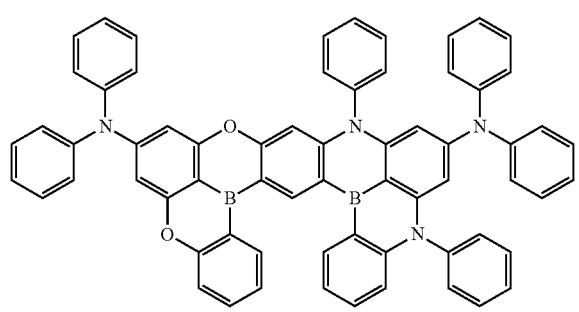
DFD5
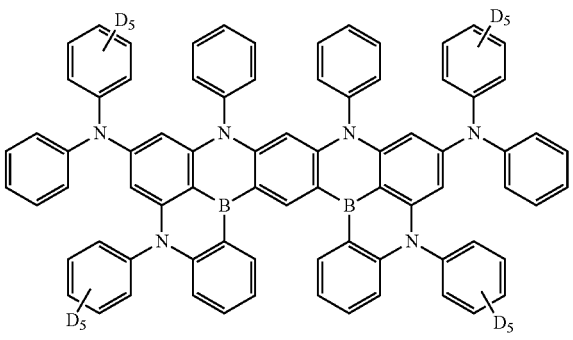
DFD6
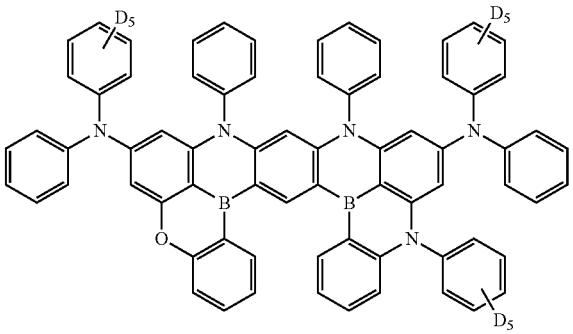
DFD7
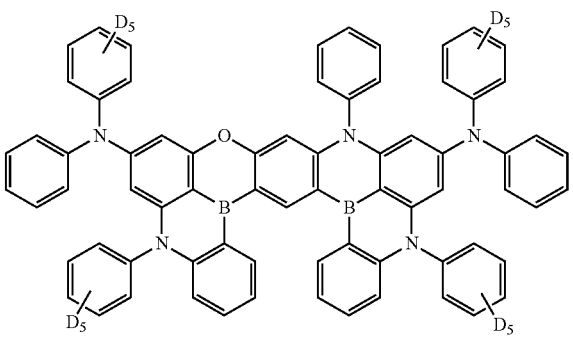
DFD8
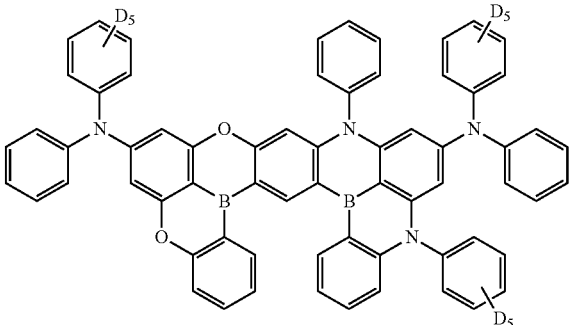

-continued

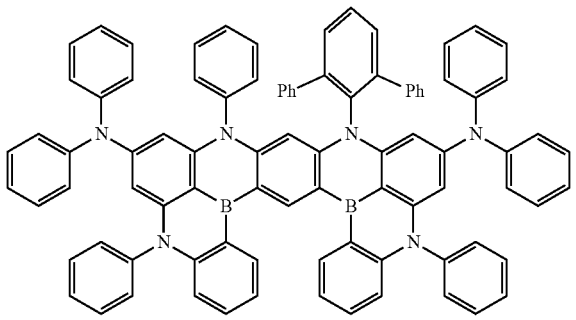
DFD9

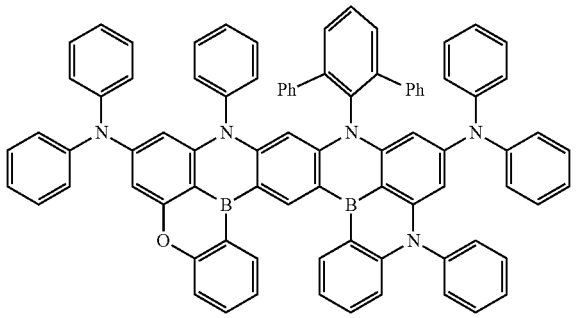
DFD10

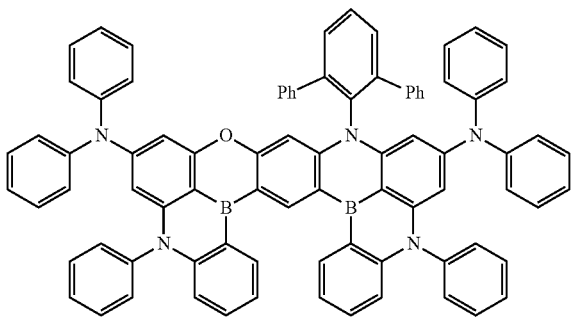
DFD11

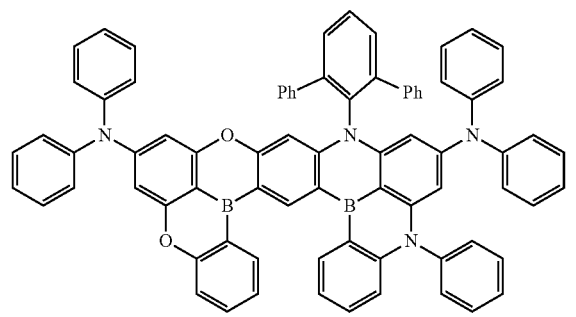
DFD12

The organometallic compound represented by Formula 1 according to one or more embodiments may include a group represented by Formula 2 in a particular position, and thus a deep blue emission color may be provided.

The group represented by Formula 2 may include a substituent having an electron donor property between $Ar_1$ and $Ar_2$ and between $Ar_2$ and $Ar_3$, and may be located in the position corresponding to LUMO of the organometallic compound, and thus the organometallic compound represented by Formula 1 above may be allowed to have a high LUMO energy level. Therefore, the organometallic compound represented by Formula 1 above may have a high triplet energy level due to the widened band gap, and thus may provide a deep blue luminous color. Moreover, according to the electron donor property of Formula 2 above, an emission wavelength of about several nanometers to about several score nanometers may be easily controlled.

In one or more embodiments, the group represented by Formula 2 may include a bulky substituent between $Ar_1$ and $Ar_2$ and/or between $Ar_2$ and $Ar_3$. The group represented by Formula 2 having such a structure may be substituted at the organometallic compound and causes a steric hindrance, and thus may hinder excimer or exciplex formation by the interaction between dopants or between a dopant and a host. Accordingly, a light emission due to the excimer or exciplex may be suppressed to thus be blue-shifted, as well as, may have a small full width at half maximum (FWHM), and thus if the organometallic compound is applied as an emission layer dopant of the organic electroluminescence device, high luminous efficiency and high color purity may be achieved.

In the organic electroluminescence device ED of one or more embodiments, the emission layer EML may further include one or more of anthracene derivatives, pyrene derivatives, fluoranthene derivatives, chrysene derivatives, dehydrobenzanthracene derivatives, and/or triphenylene derivatives. For example, the emission layer EML may further include one or more anthracene derivatives and/or one or more pyrene derivatives.

In each organic electroluminescence device ED of embodiments illustrated in FIGS. 3 to 6, the emission layer EML may further include a host and a dopant, and the emission layer EML may include a compound represented by Formula E-1 below. The compound represented by Formula E-1 below may be used as a fluorescence host material.

Formula E-1

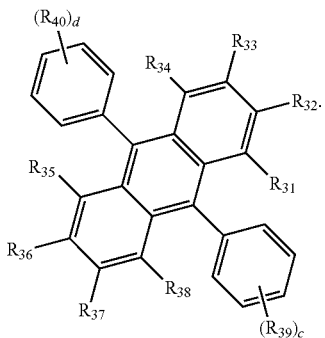

In Formula E-1, $R_{31}$ to $R_{40}$ may be each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. Meanwhile, $R_{31}$ to $R_{40}$ may be bonded to an adjacent group to form a saturated hydrocarbon ring or an unsaturated hydrocarbon ring.

In Formula E-1, c and d may be each independently an integer of 0 to 5.

Formula E-1 may be represented by any one among Compound E1 to Compound E19 below.
E1
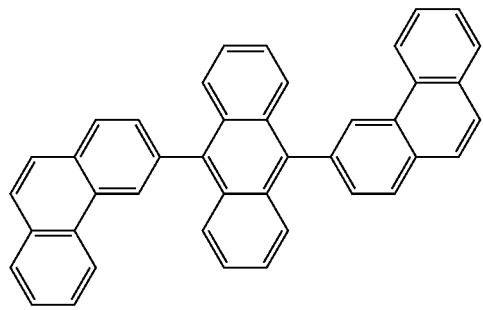
E2
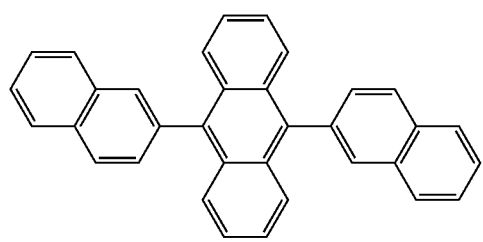
E3
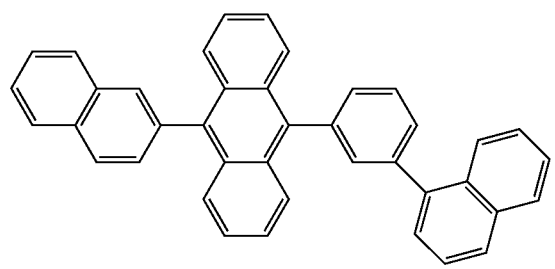
E4
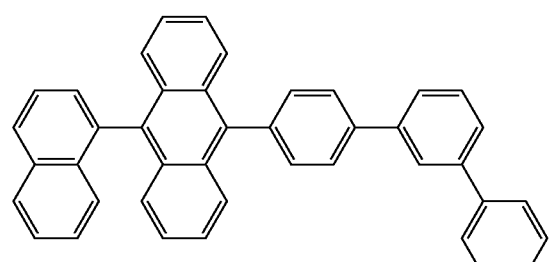
E5
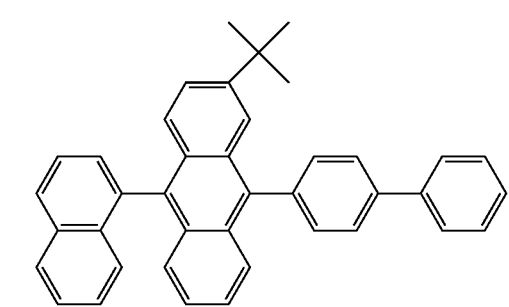
E6
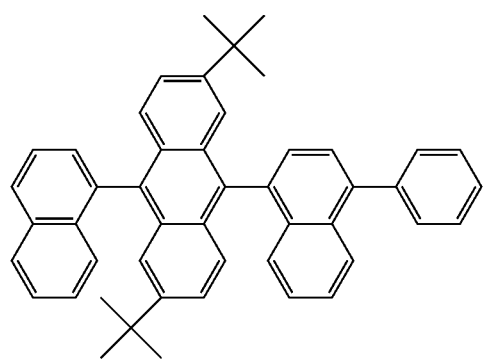
E7
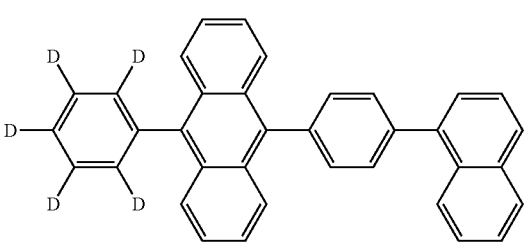
E8
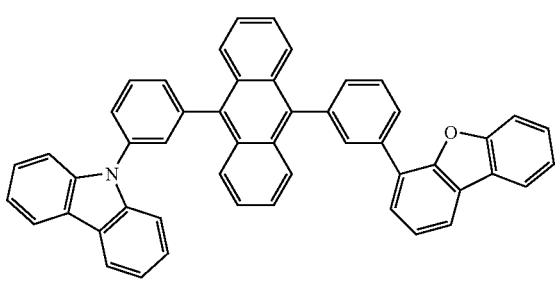
E9
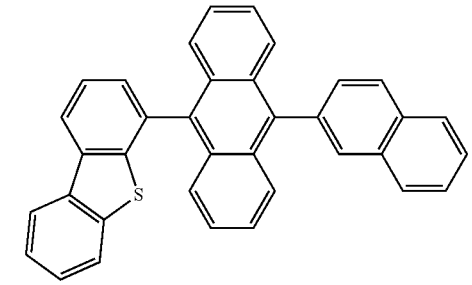
E10
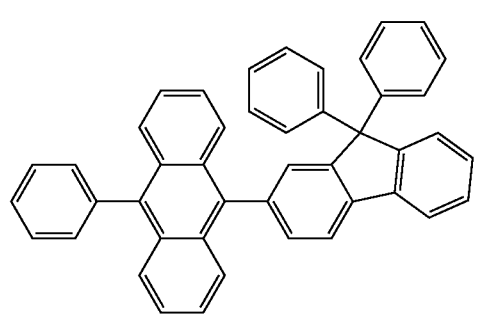

E11
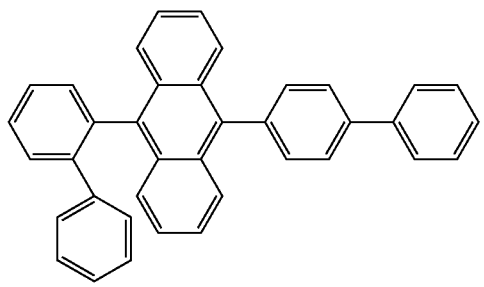
E12
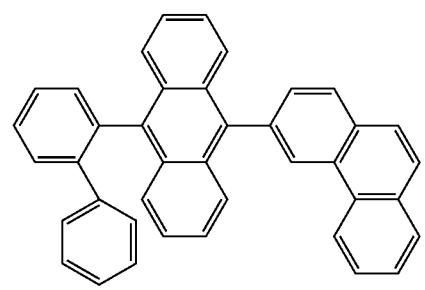
E13
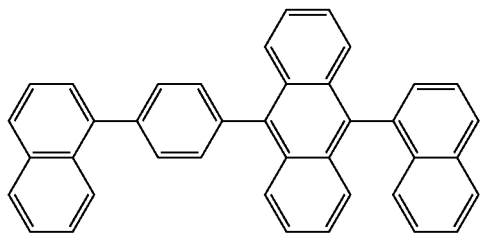
E14
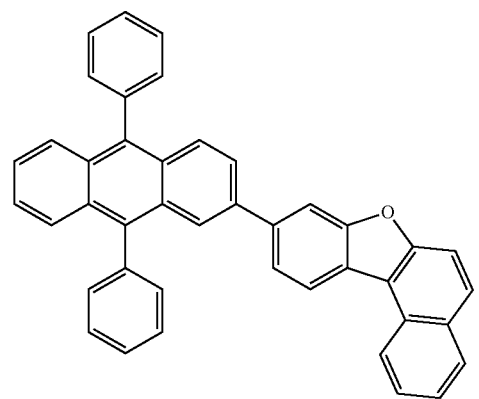
E15
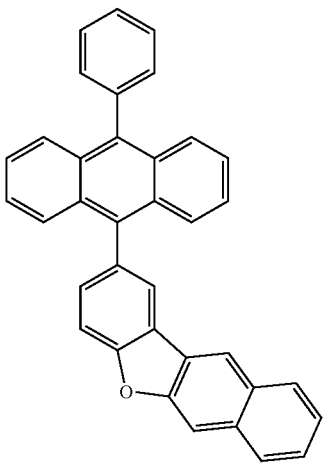
E16
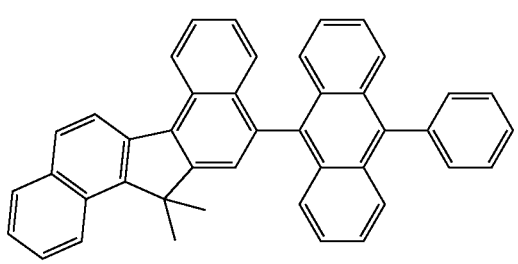
E17
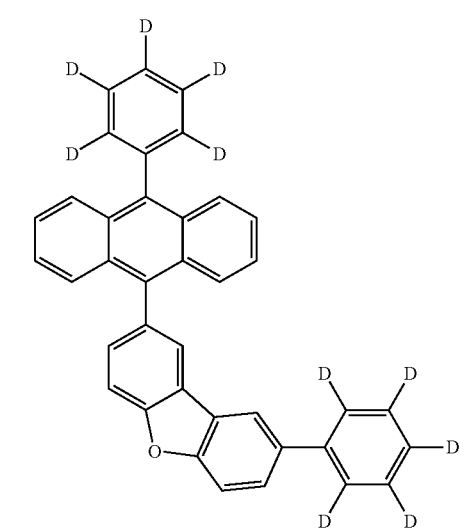
E18
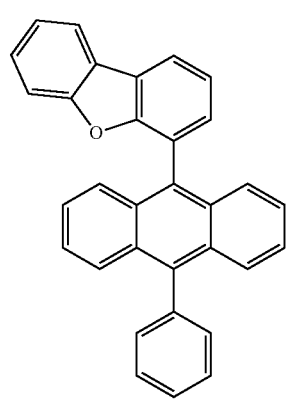

E19

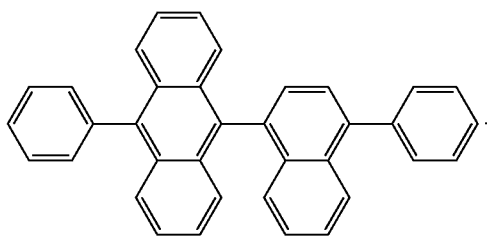

In one or more embodiments, the emission layer EML may further include a compound represented by Formula E-2a or Formula E-2b below. The compound represented by Formula E-2a or Formula E-2b below may be used as a phosphorescence host material.

Formula E-2a

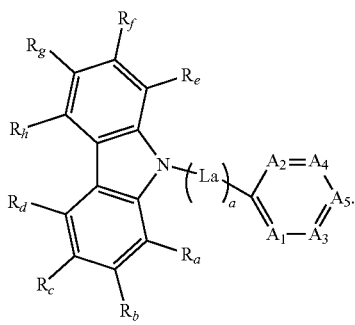

In Formula E-2a, a may be an integer of 0 to 10, La may be a direct linkage, a substituted or unsubstituted arylene group having 6 to 30 ring-forming carbon atoms, or a substituted or unsubstituted heteroarylene group having 2 to 30 ring-forming carbon atoms. Meanwhile, when a is an integer of 2 or more, a plurality of La's may be each independently a substituted or unsubstituted arylene group having 6 to 30 ring-forming carbon atoms, or a substituted or unsubstituted heteroarylene group having 2 to 30 ring-forming carbon atoms.

In one or more embodiments, in Formula E-2a, $A_1$ to $A_5$ may be each independently N or $CR_i$. $R_a$ to $R_i$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. $R_a$ to $R_i$ may be bonded to an adjacent group to form a hydrocarbon ring or a heterocycle containing N, O, S, etc. as a ring-forming atom.

Meanwhile, in Formula E-2a, two or three selected from among $A_1$ to $A_5$ may be N, and the rest may be $CR_i$.

Formula E-2b (Cbz1)₋ₐ(L_b)₋_b−Cbz2).

In Formula E-2b, Cbz1 and Cbz2 may be each independently an unsubstituted carbazole group, or a carbazole group substituted with an aryl group having 6 to 30 ring-forming carbon atoms. $L_b$ may be a direct linkage, a substituted or unsubstituted arylene group having 6 to 30 ring-forming carbon atoms, or a substituted or unsubstituted heteroarylene group having 2 to 30 ring-forming carbon atoms. Meanwhile, b may be an integer of 0 to 10, and when b is an integer of 2 or more, a plurality of $L_b$'s may be each independently a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be represented by any one among the compounds of Compound Group E-2 below. However, the compounds listed in Compound Group E-2 below are examples, the compound represented by Formula E-2a or Formula E-2b is not limited to those represented by Compound Group E-2 below.

Compound Group E-2

E-2-1

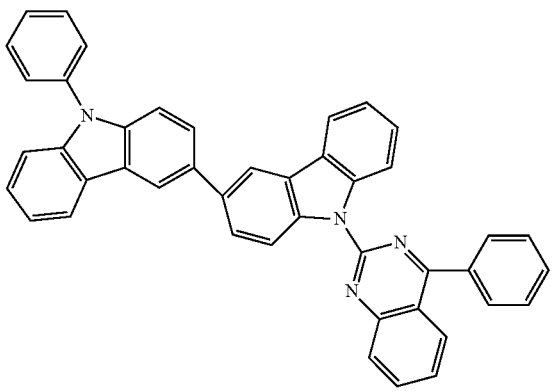

E-2-2

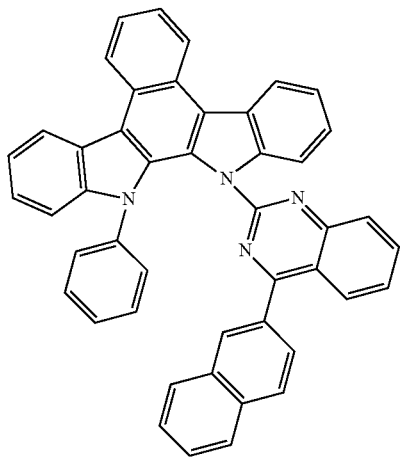

E-2-3
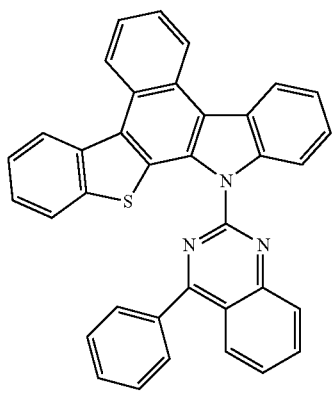
E-2-4
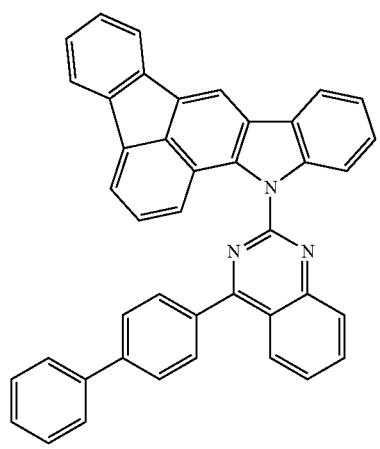
E-2-5
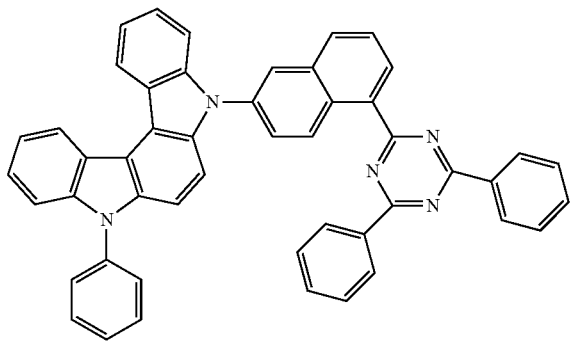
E-2-6
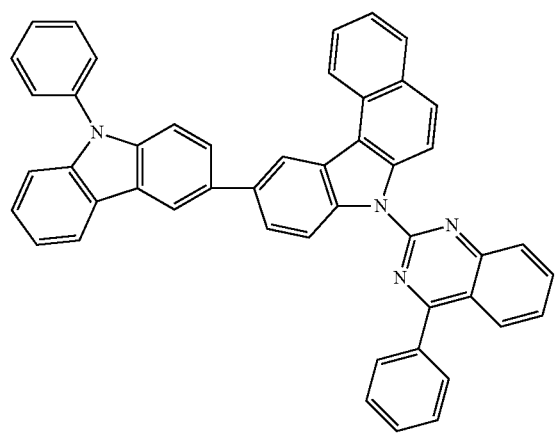
E-2-7
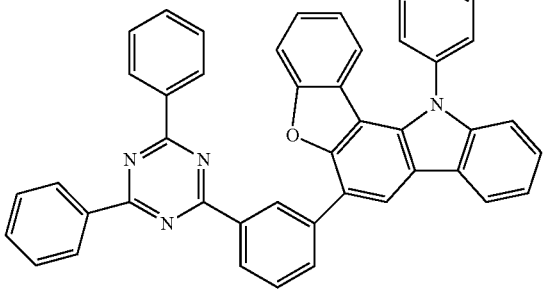
E-2-8
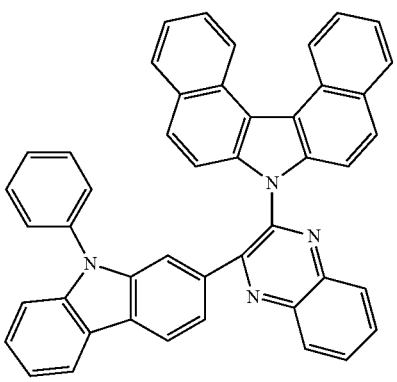
E-2-9
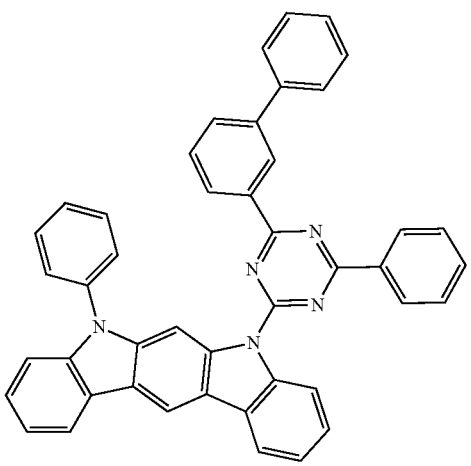

E-2-10
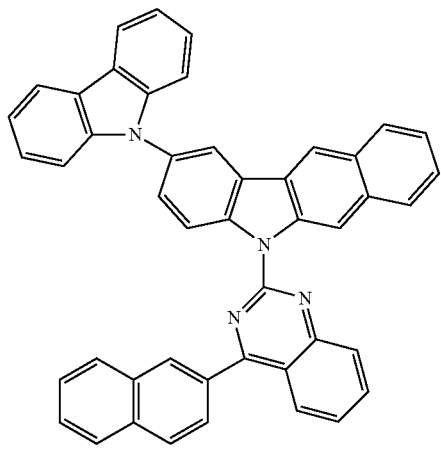
E-2-13
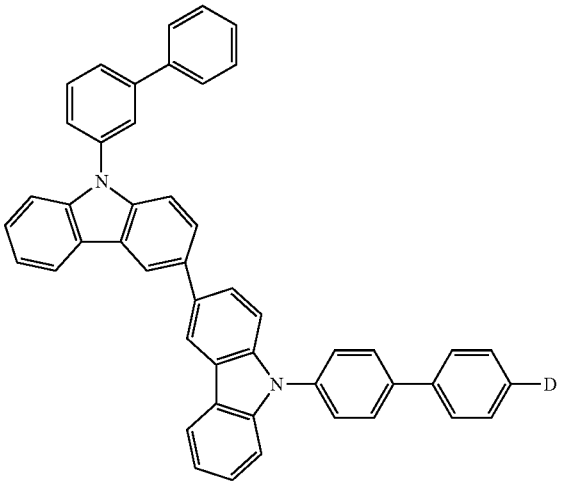
E-2-11
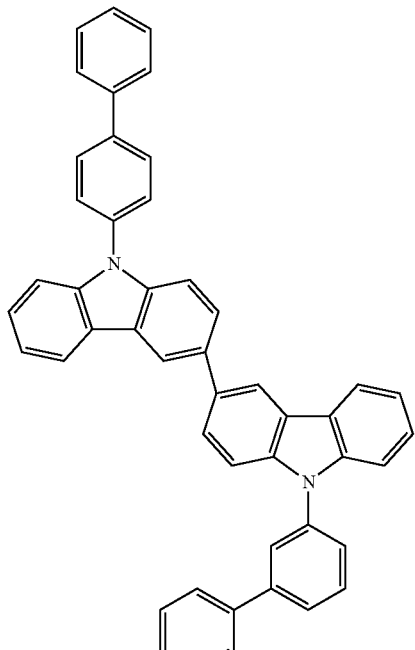
E-2-14
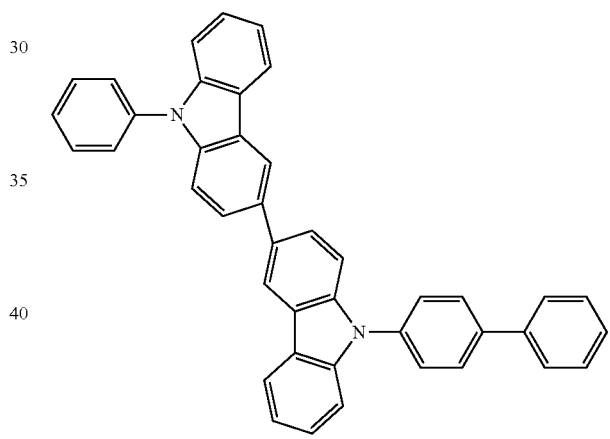
E-2-12
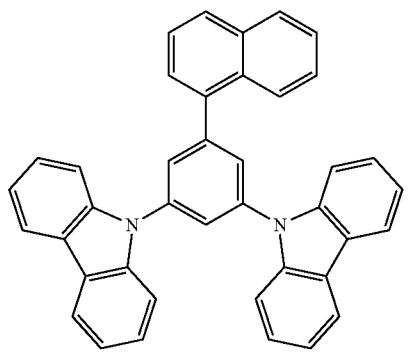
E-2-15
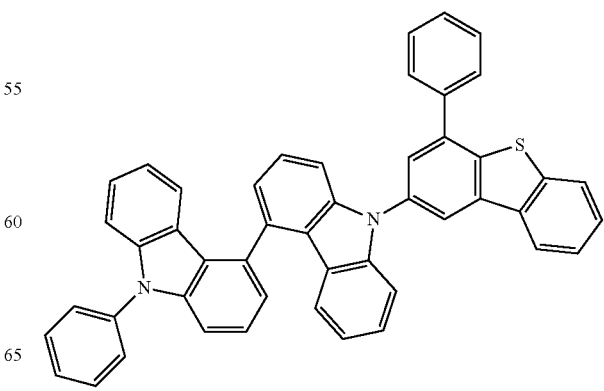

E-2-16
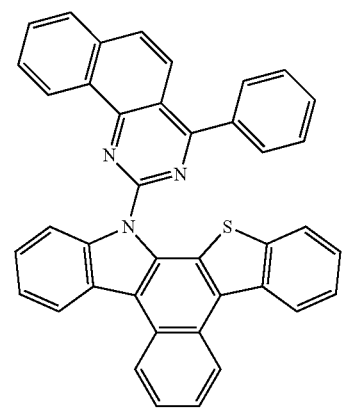
E-2-17
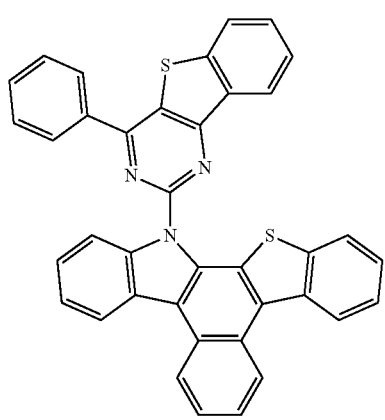
E-2-18
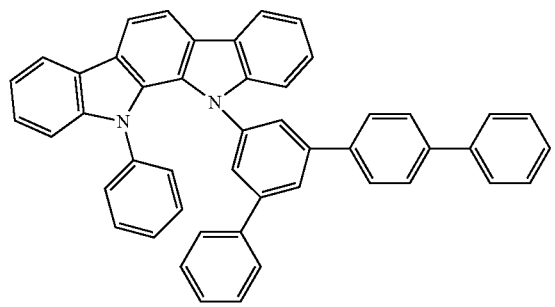
E-2-19
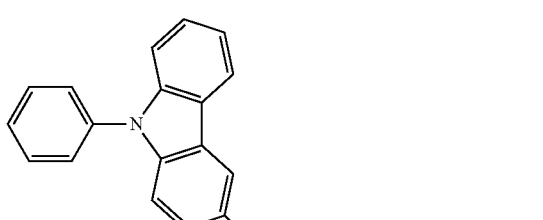
E-2-20
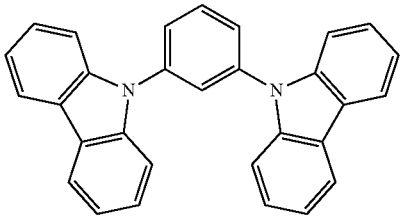
E-2-21
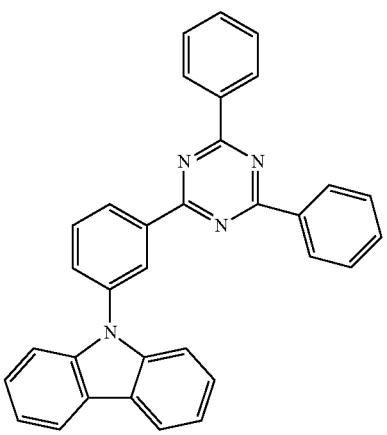
E-2-22
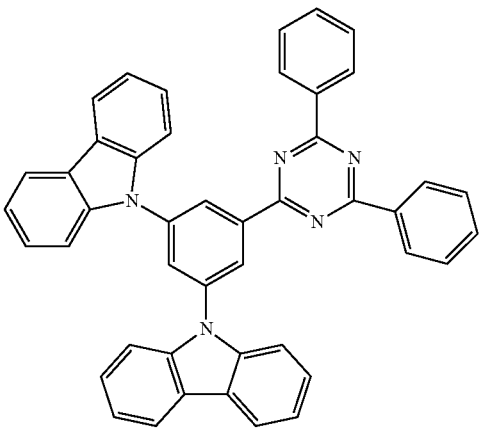
E-2-23
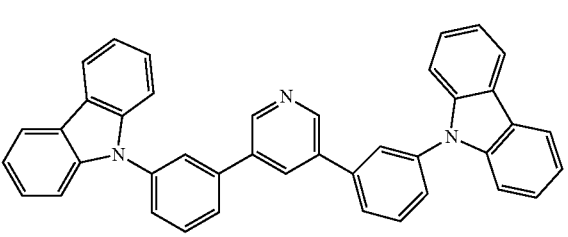

-continued

E-2-24

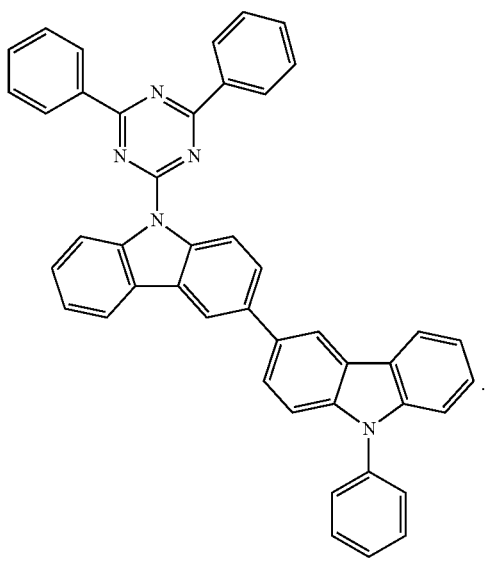

The emission layer EML may further include any suitable material as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TCTA), or 1,3,5-tris(1-phenyl-1H-benzo[d]imidazole-2-yl)benzene (TPBi). However, the embodiments of the present disclosure are not limited thereto, and for example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be used as a host material.

The emission layer EML may further include a compound represented by Formula M-a or Formula M-b below. The compound represented by Formula M-a or Formula M-b below may be used as a phosphorescence dopant material.

Formula M-a

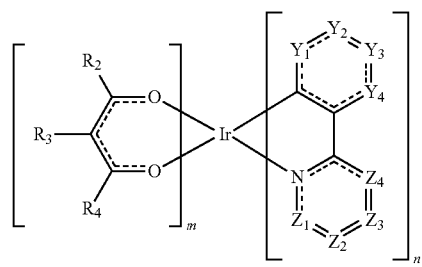

In Formula M-a above, $Y_1$ to $Y_4$ and $Z_1$ to $Z_4$ may be each independently $CR_1$ or N, $R_1$ to $R_4$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a red phosphorescence dopant or a green phosphorescence dopant.

The compound represented by Formula M-a may be represented by any one among Compound M-a1 to Compound M-a19 below. However, Compounds M-a1 to M-a19 below are examples, and the compound represented by Formula M-a is not limited to those represented by Compounds M-a1 to M-a19 below.

Compounds M-a1 to M-a19

M-a1

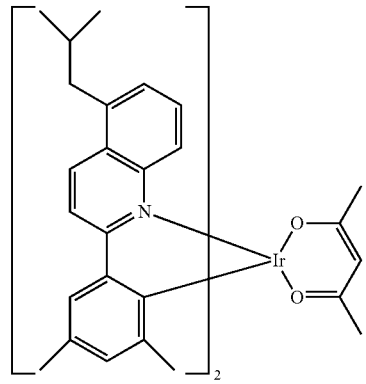

M-a2

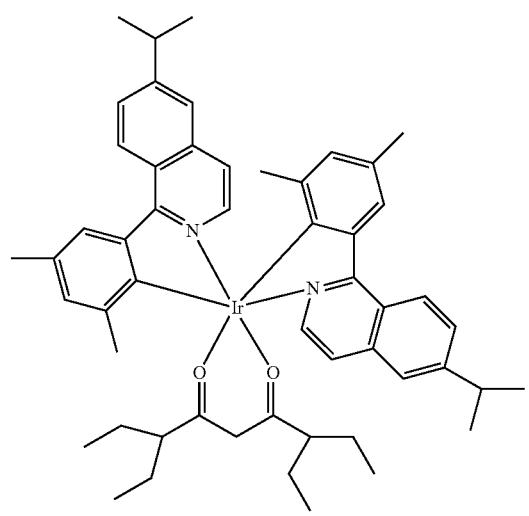

M-a3
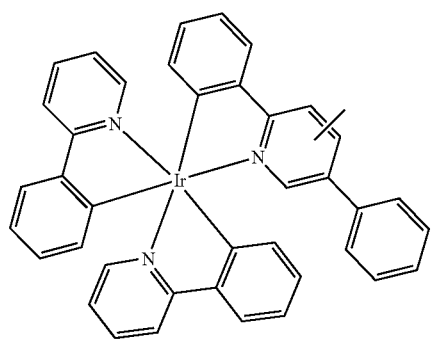
M-a4
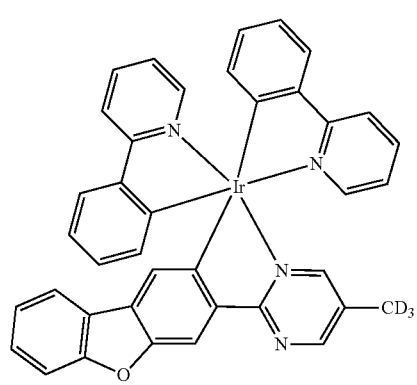
M-a5
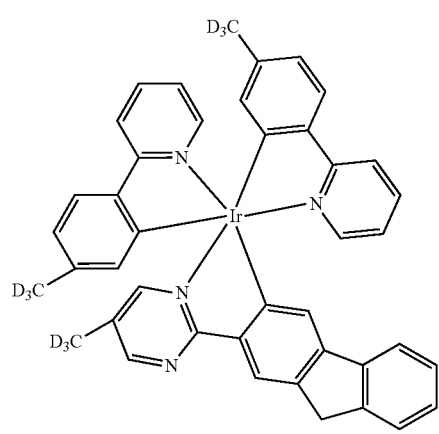
M-a6
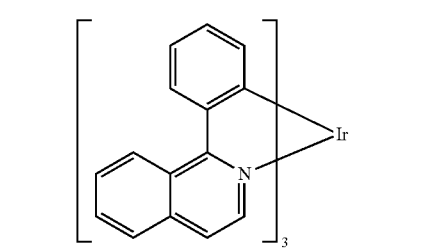
M-a7
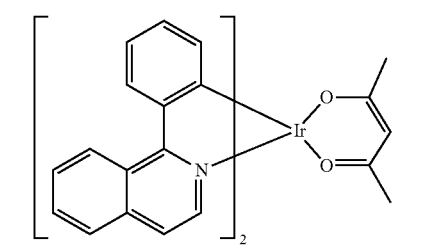
M-a8
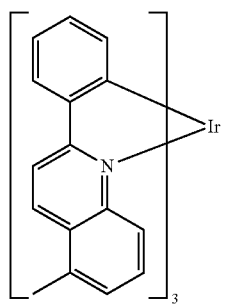
M-a9
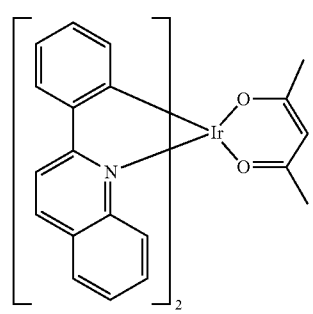
M-a10
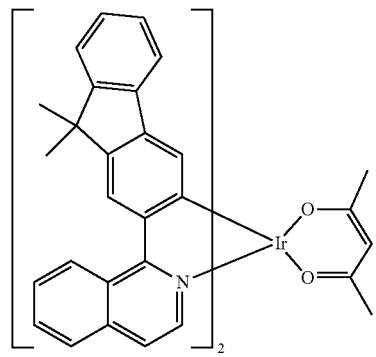
M-a11
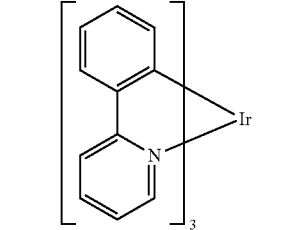
M-a12
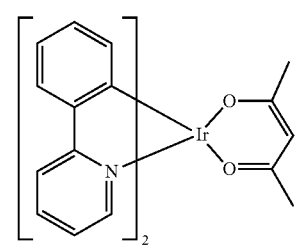

M-a13

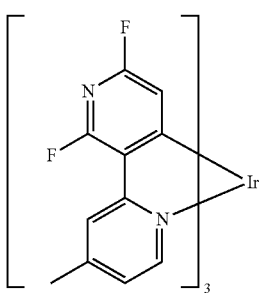

M-a14

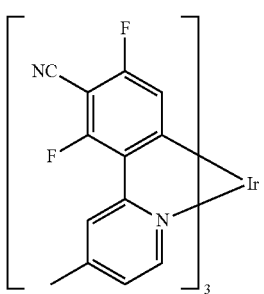

M-a15

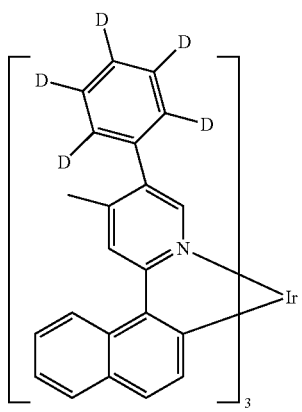

M-a16

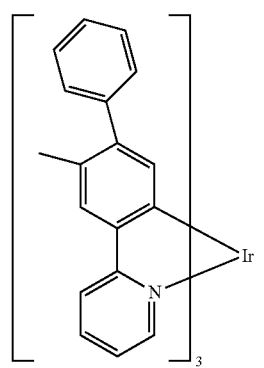

M-a17

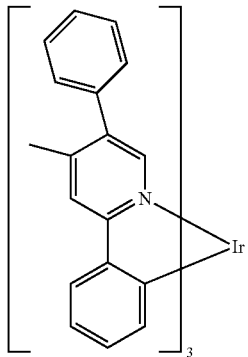

M-a18

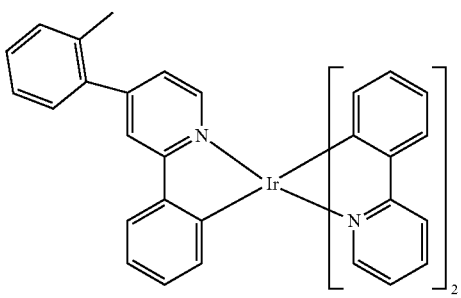

M-a19

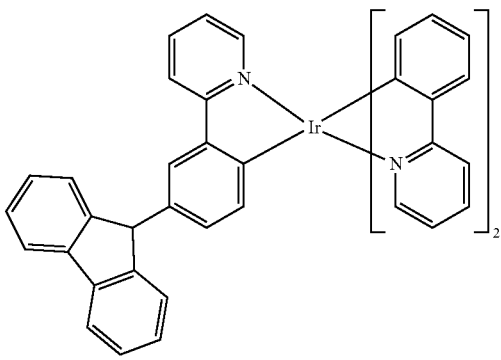

Compound M-a1 and Compound M-a2 may be used as a red dopant material, and Compound M-a3 to Compound M-a5 may be used as a green dopant material.

Formula M-b

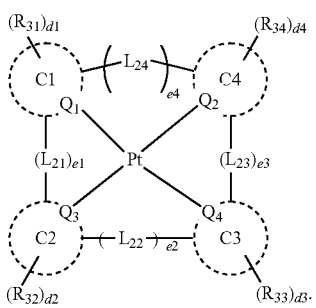

In Formula M-b, $Q_1$ to $Q_4$ may be each independently C or N, and C1 to C4 may be each independently a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may be each independently a direct linkage,

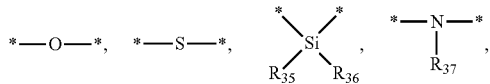

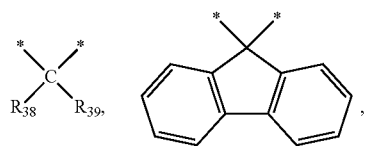

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may be each independently 0 or 1. $R_{31}$ to $R_{39}$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring, and d1 to d4 may be each independently an integer of 0 to 4.

The compound represented by Formula M-b may be used as a blue phosphorescence dopant or a green phosphorescence dopant.

The compound represented by Formula M-b may be represented by any one among the compounds below. However, the compounds below are examples, and the compound represented by Formula M-b are not limited to those represented by the compounds below.

Compounds M-b-1 to M-b-14

M-b-1

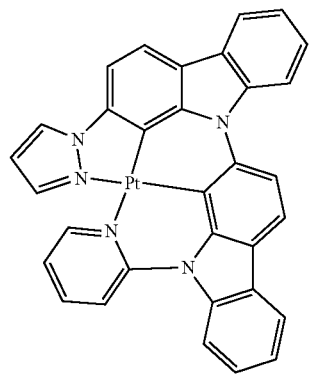

M-b-2

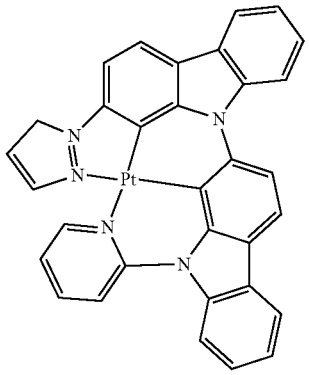

M-b-3

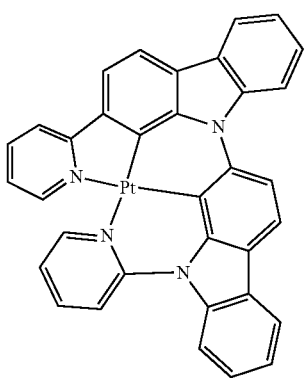

M-b-4

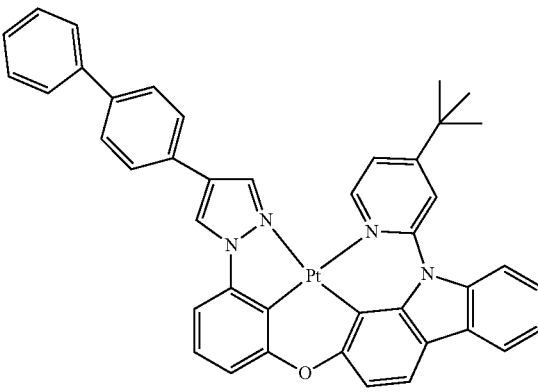

M-b-5

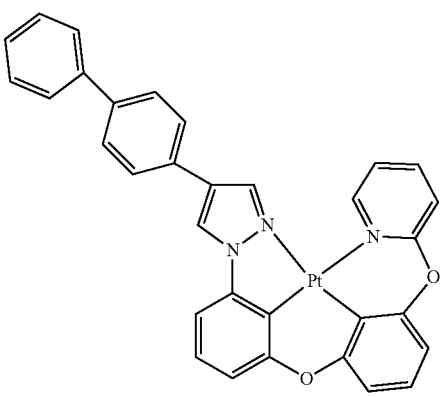

M-b-6
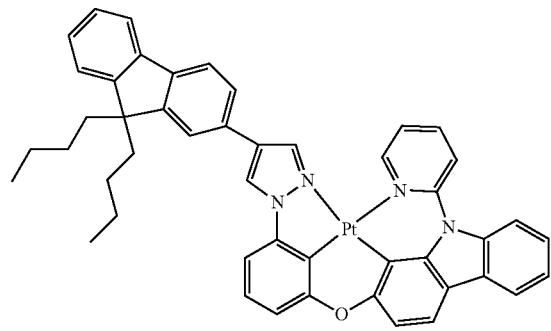
M-b-7
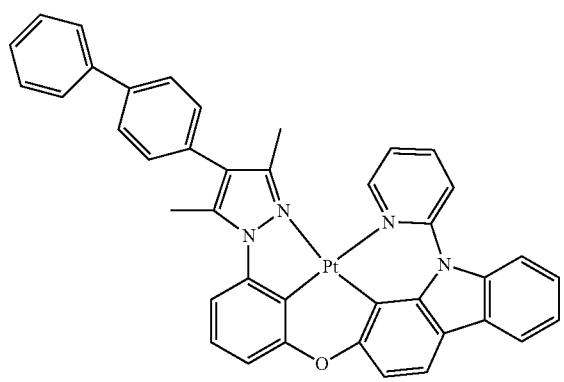
M-b-8
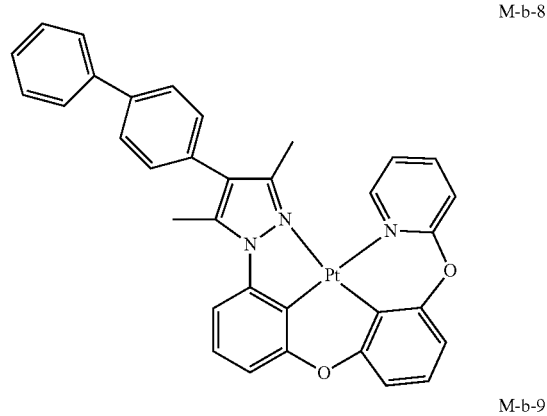
M-b-9
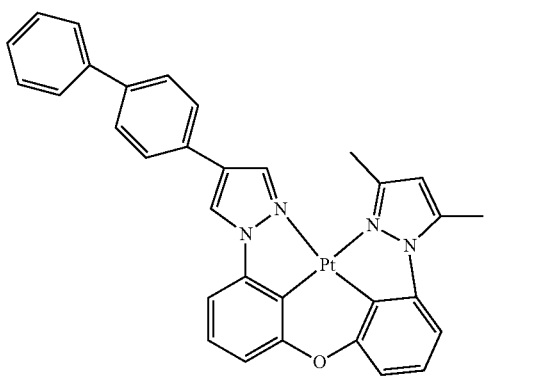
M-b-10
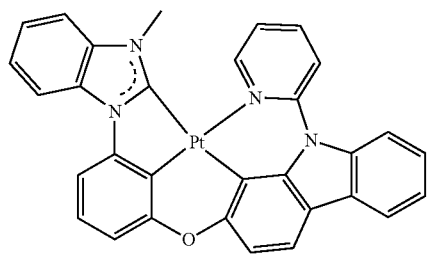
M-b-11
M-b-12
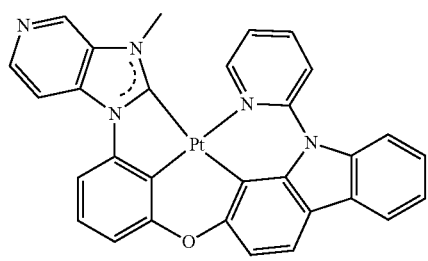
M-b-12
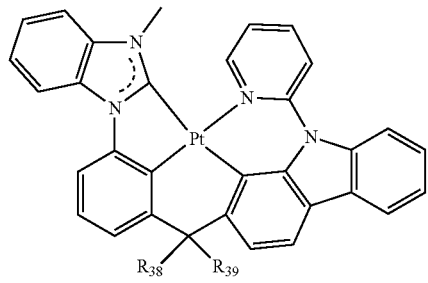
M-b-13

M-b-14

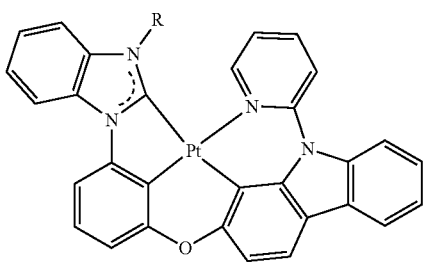

In the compounds, R, $R_{38}$, and $R_{39}$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroacryl group having 2 to 30 ring-forming carbon atoms.

The emission layer EML may further include a compound represented by any one among Formula F-a to Formula F-c below. The compound represented by Formula F-a to Formula F-c below may be used as a fluorescence dopant material.

Formula F-a

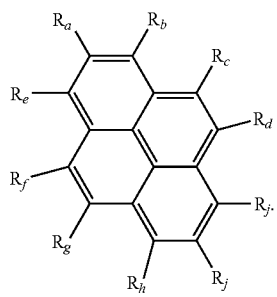

In Formula F-a, two selected from among $R_a$ to $R_j$ may each independently be substituted with

*—$NAr_1Ar_2$.

The others, which may be not substituted with

*—$NAr_1Ar_2$, among $R_a$ to $R_j$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In

*—$NAr_1Ar_2$, $Ar_1$ and $Ar_2$ may be each independently a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

Formula F-b]

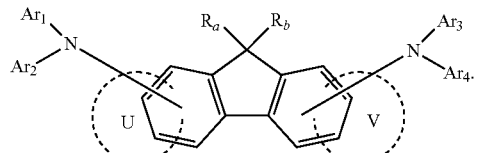

In Formula F-b, $R_a$ and $R_b$ may be each independently a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula F-b, U and V may be each independently a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may be each independently 0 or 1. For example, in Formula F-b when the number of U or V is 1, one ring forms a condensed ring at a part described as U or V, and when the number of U or V is 0, a ring described as U or V may not be present. For example, when the number of U is 0 and the number of V is 1, or when the number of U is 1 and the number of V is 0, the condensed ring having a fluorene core of Formula F-b may be a four-ring cyclic compound. In one or more embodiments, when each number of U and V is 0, the condensed ring of Formula F-b may be a three-ring cyclic compound. In one or more embodiments, when each number of U and V is 1, the condensed ring having a fluorene core of Formula F-b may be a five-ring cyclic compound.

Formula F-c

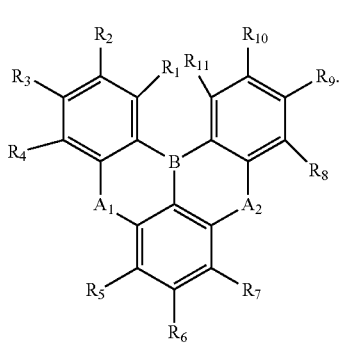

In Formula F-c, $A_1$ and $A_2$ may be each independently O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may be each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or bonded to an adjacent group to form a ring.

In Formula F-c, $A_1$ and $A_2$ may each independently be bonded to substituents of an adjacent ring to form a condensed ring. For example, when $A_1$ and $A_2$ may be each independently $NR_m$, $A_1$ may be bonded to $R_4$ or $R_5$ to form a ring. In one or more embodiments, $A_2$ may be bonded to $R_7$ or $R_8$ to form a ring.

In one or more embodiments, the emission layer EML may further include, as a dopant material, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), 4,4'-bis[2-(4-(N,N-diphenylamino)phenyl)vinyl]biphenyl(DPAVBi), perylene and the derivatives thereof (e.g., 2,5,8,11-tetra-t-butylperylene (TBP)), pyrene and the derivatives thereof (e.g., 1,1-dipyrene, 1,4-dipyrenylbenzene, 1,4-bis(N,N-diphenylamino)pyrene), etc.

The emission layer EML may further include a phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), or thulium (Tm) may be used as a phosphorescence dopant. For example, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as a phosphorescence dopant. However, the embodiments of the present disclosure are not limited thereto.

In each organic electroluminescence device ED of embodiments illustrated in FIGS. 3 to 6, the electron transport region ETR may be provided on the emission layer EML. The electron transport region ETR may include at least one of the hole blocking layer HBL, the electron transport layer ETL, or the electron injection layer EIL, but the embodiments of the present disclosure are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of the electron injection layer EIL or the electron transport layer ETL, and may have a single layer structure formed of an electron injection material and an electron transport material. In one or more embodiments, the electron transport region ETR may have a single layer structure formed of a plurality of different materials, or may have a structure in which an electron transport layer ETL/electron injection layer EIL, a hole blocking layer HBL/electron transport layer ETL/electron injection layer EIL may be stacked in order from the emission layer EML, but the embodiments of the present disclosure are not limited thereto. The electron transport region ETR may have a thickness, for example, from about 1,000 Å to about 1,500 Å.

The electron transport region ETR may be formed by using various methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1 below.

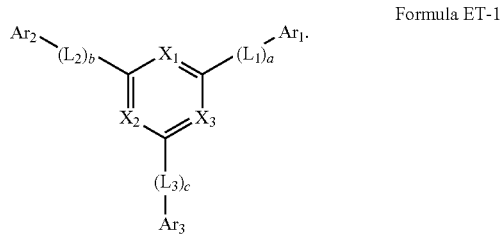

Formula ET-1

In Formula ET-1, at least one among $X_1$ to $X_3$ may be N, and the rest may be $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may be each independently a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may be each independently an integer of 0 to 10. In Formula ET-1, $L_1$ to $L_3$ may be each independently a direct linkage, a substituted or unsubstituted arylene group having 6 to 30 ring-forming carbon atoms, or a substituted or unsubstituted heteroarylene group having 2 to 30 ring-forming carbon atoms. Meanwhile, when a to c are an integer of 2 or more, $L_1$ to $L_3$ may be each independently a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, the embodiments of the present disclosure are not limited thereto, and the electron transport region ETR may include, for example, diphenyl[4-(triphenylsilyl)phenyl]phosphine oxide (TSPO1), tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), 1,3-bis[3,5-di(pyridin-3-yl)phenyl]benzene (BmPyPhB), or a mixture thereof.

In one or more embodiments, the electron transport regions ETR may include a metal halide such as LiF, NaCl, CsF, RbCl, RbI, CuI, or KI, a lanthanide metal such as Yb, and a co-deposited material of the metal halide and the lanthanide metal. For example, the electron transport region ETR may include KI:Yb, RbI:Yb, etc. as a co-deposited material. Meanwhile, the electron transport region ETR may be formed using a metal oxide such as $Li_2O$ or BaO, or 8-hydroxyl-lithium quinolate (Liq), etc., but the embodiments of the present disclosure are not limited thereto. The electron transport region ETR may also be formed of a mixture material of an electron transport material and an insulating organometallic salt. The organometallic salt may be a material having an energy band gap of about 4 eV or more. For example, the organometallic salt may include, for example, one or more of metal acetates, metal benzoates, metal acetoacetates, metal acetylacetonates, and/or metal stearates.

The electron transport region ETR may further include at least one of 2,9-dimethyl-4,7-diphenyl-1,10-phenanthroline (BCP), or 4,7-diphenyl-1,10-phenanthroline (Bphen) in addition to the above-described materials, but the embodiments of the present disclosure are not limited thereto.

The electron transport region ETR may include the above-described compounds of the electron transport region in at least one of the electron injection layer EIL, the electron transport layer ETL, or the hole blocking layer HBL.

When the electron transport region ETR includes the electron transport layer ETL, the electron transport layer ETL may have a thickness of about 100 Å to about 1,000 Å, for example, about 150 Å to about 500 Å. If the thickness of the electron transport layer ETL satisfies the aforementioned range, satisfactory electron transport characteristics may be obtained without a substantial increase in driving voltage. When the electron transport region ETR includes the electron injection layer EIL, the electron injection layer EIL may have a thickness of about 1 Å to about 100 Å, for example, about 3 Å to about 90 Å. If the thickness of the electron injection layer EIL satisfies the above-described range, satisfactory electron injection characteristics may be obtained without a substantial increase in driving voltage.

The second electrode EL2 may be provided on the electron transport region ETR. The second electrode EL2 may be a common electrode. The second electrode EL2 may be a cathode or an anode, but the embodiments of the present disclosure are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is the transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, or a compound or mixture thereof (e.g., AgMg, AgYb, or MgAg). In some embodiments, the second electrode EL2 may have a multi-layer structure including a reflective film or a transflective film formed of the above-described materials, and a transparent conductive film formed of ITO, IZO, ZnO, ITZO, etc. For example, the second electrode EL2 may include the above-described one or more metal materials, one or more combinations of at least two metal materials of the above-described metal materials, one or more oxides of the above-described metal materials, and/or the like.

In one or more embodiments, the second electrode EL2 may be connected with an auxiliary electrode. If the second electrode EL2 is connected with the auxiliary electrode, the resistance of the second electrode EL2 may decrease.

Meanwhile, a capping layer CPL may be further disposed on the second electrode EL2 of the organic electroluminescence device ED according to one or more embodiments. The capping layer CPL may include a multilayer or a single layer.

In one or more embodiments, the capping layer CPL may be an organic layer or an inorganic layer. For example, when the capping layer CPL may include an inorganic material, the inorganic material may include an alkaline metal compound such as LiF, an alkaline earth metal compound such as $MgF_2$, SiON, $SiN_x$, and/or SiOy, etc.

For example, when the capping layer CPL may include an organic material, the organic material may include α-NPD, NPB, TPD, m-MTDATA, $Alq_3$, CuPc, N4,N4,N4',N4'-tetra(biphenyl-4-yl)biphenyl-4,4'-diamine (TPD15), 4,4',4"-tris(carbazol-9-yl)triphenylamine (TCTA), etc., or an epoxy resin, or acrylate such as methacrylate. However, the embodiments of the present disclosure are not limited thereto, and the capping layer CPL may include at least one among Compounds P1 to P5 below.

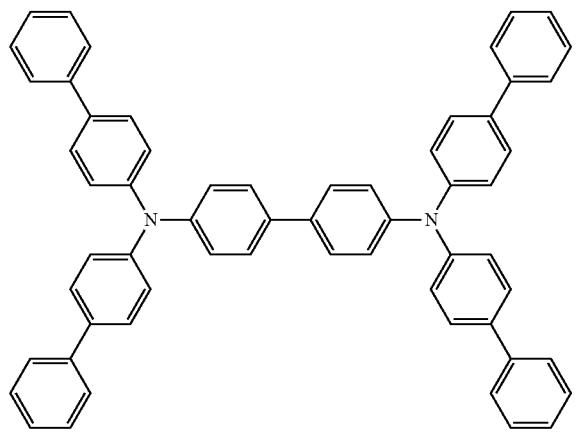

P1

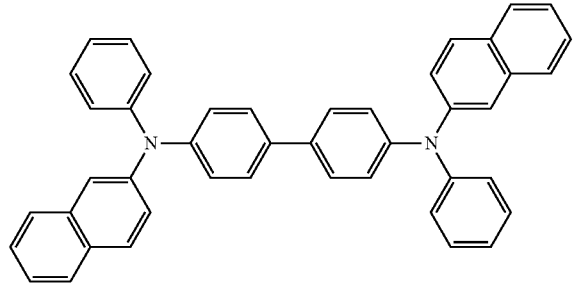

P2

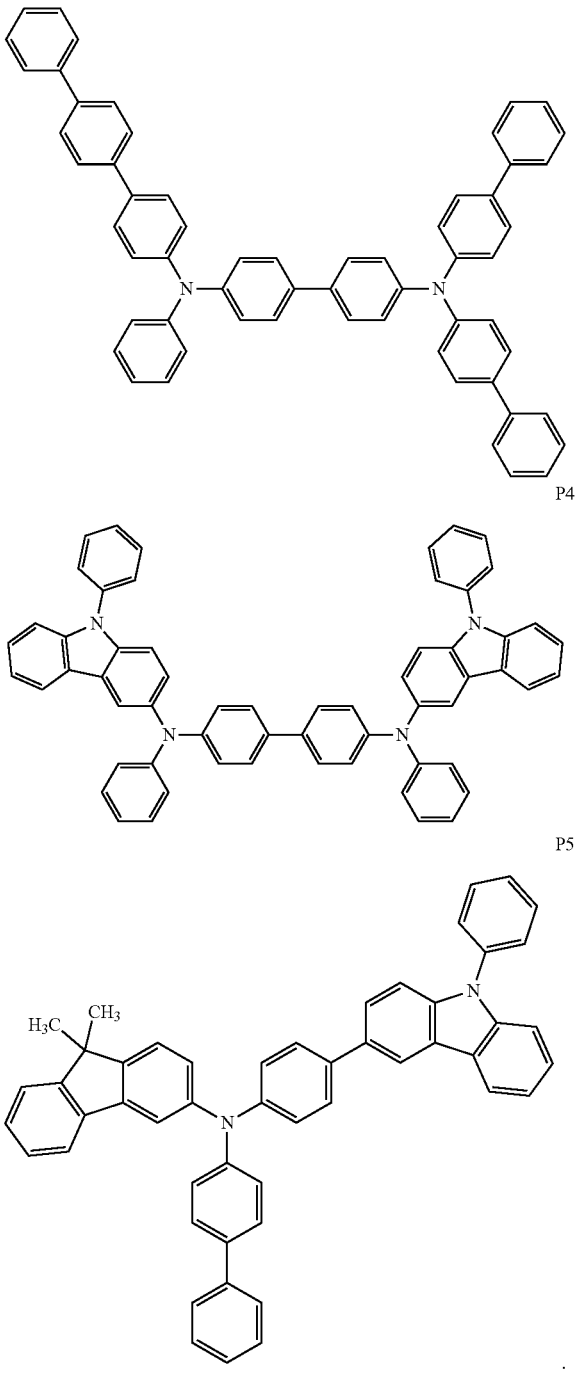

including a display device layer DP-ED, a light control layer CCL disposed on the display panel DP, and a color filter layer CFL.

Figure 7:
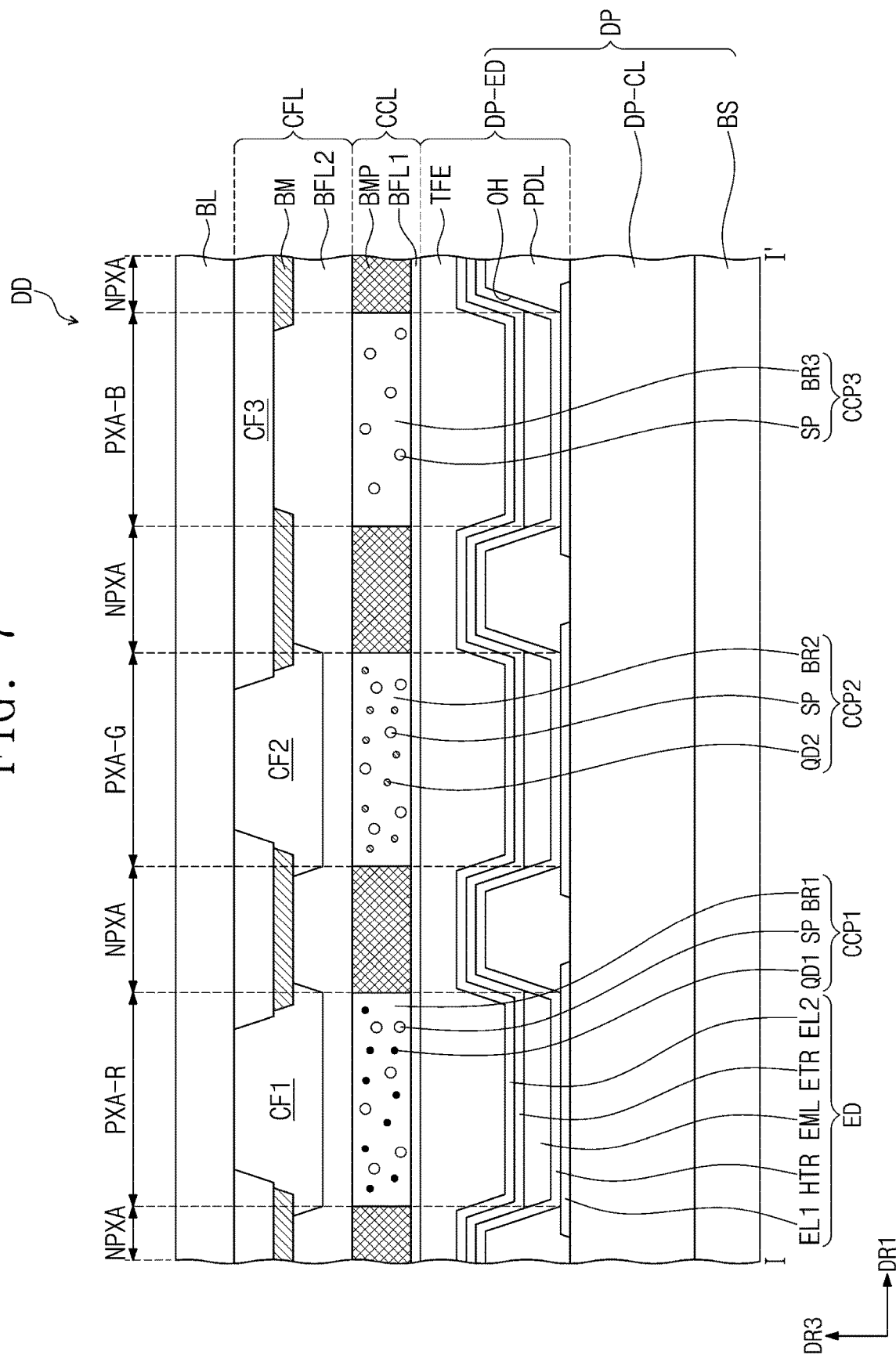
FIG. 7 is a cross-sectional view of a display apparatus according to one or more embodiments of the present disclosure.

In one or more embodiments illustrated in FIG. 7, the display panel DP may include a base layer BS, a circuit layer DP-CL provided on the base layer BS, and the display device layer DP-ED, and the display device layer DP-ED may include an organic electroluminescence device ED.

The organic electroluminescence device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. Meanwhile, the structures of the organic electroluminescence devices of FIGS. 3 to 6 as described above may be equally (e.g. substantially equally) applied to the structure of the organic electroluminescence device ED shown in FIG. 7.

Referring to FIG. 7, the emission layer EML may be disposed in an opening OH defined in a pixel defining film PDL. For example, the emission layer EML which may be divided by the pixel defining film PDL and provided corresponding to each light emitting regions PXA-R, PXA-G, and PXA-B may emit light in the same wavelength range. In the display apparatus DD of one or more embodiments, the emission layer EML may emit blue light. Alternatively, in one or more embodiments, the emission layer EML may be provided as a common layer in the entire light emitting regions PXA-R, PXA-G, and PXA-B.

The light control layer CCL may be disposed on the display panel DP. The light control layer CCL may include a light conversion body. The light conversion body may be a quantum dot, a phosphor, or the like. The light conversion body may emit provided light by converting the wavelength thereof. That is, the light control layer CCL may a layer containing the quantum dot or a layer containing the phosphor.

The emission layer EML may include a quantum dot material. The core of the quantum dot may be a Group II-VI compound, a Group III-VI compound, a Group I-III-IV compound, a Group III-V compound, a Group III-II-V compound, a Group IV-VI compound, a Group IV element, a Group IV compound, or a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and/or $In_2Se_3$, a ternary compound such as $InGaS_3$ and/or $InGaSe_3$, or any combination thereof.

A Group compound may be a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, and/or a quaternary compound such as $AgInGaS_2$ and/or $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. Meanwhile, the Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

In this case, a binary compound, a ternary compound, or a quaternary compound may be present in particles in a uniform (e.g. substantially uniform) concentration distribution, or may be present in the same particle in a partially different concentration distribution. In one or more embodiments, the quantum dot may have a core/shell structure in which one quantum dot surrounds another quantum dot. In a core/shell structure, the interface of the core and the shell may have a concentration gradient in which the concentration of an element present in the shell becomes lower towards the core.

In some embodiments, a quantum dot may have the above-described core-shell structure including a core containing nanocrystals and a shell surrounding the core. The shell of the quantum dot may serve as a protection layer to prevent or reduce the chemical deformation of the core so as to maintain semiconductor properties, and/or a charging layer to impart electrophoresis properties to the quantum dot. The shell may be a single layer or a multilayer. An example of the shell of the quantum dot may include a metal or non-metal oxide, a semiconductor compound, or a combination thereof.

For example, the metal or non-metal oxide may be a binary compound such as $SiO_2$, $Al_2O_3$, $TiO_2$, $ZnO$, $MnO$, $Mn_2O_3$, $Mn_3O_4$, $CuO$, $FeO$, $Fe_2O_3$, $Fe_3O_4$, $CoO$, $Co_3O_4$, and/or $NiO$, or a ternary compound such as $MgAl_2O_4$, $CoFe_2O_4$, $NiFe_2O_4$, and/or $CoMn_2O_4$, but the embodiments of the present disclosure are not limited thereto.

Also, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but the embodiments of the present disclosure are not limited thereto.

The quantum dot may have a full width of half maximum (FWHM) of a light emission wavelength spectrum of about 45 nm or less, for example about 40 nm or less, or more for example about 30 nm or less, and color purity or color reproducibility may be improved in the above ranges. In one or more embodiments, light emitted through such a quantum dot may be emitted in all directions, and thus a wide viewing angle may be improved.

In one or more embodiments, although the form of a quantum dot may not be particularly limited as long as it is a form commonly used in the art, for example, a quantum dot in the form of spherical, pyramidal, multi-arm, and/or cubic nanoparticles, nanotubes, nanowires, nanofibers, nanoplates, etc. may be used.

The quantum dot may control the color of emitted light according to the particle size thereof. Accordingly, the quantum dot may have various luminous colors such as blue, red, and green.

The light control layer CCL may include a plurality of light control units CCP1, CCP2 and CCP3. The light control units CCP1, CCP2, and CCP3 may be spaced apart from one another.

Referring to FIG. 7, divided patterns BMP may be disposed between the light control units CCP1, CCP2 and CCP3 which may be spaced apart from each other, but the embodiments of the present disclosure are not limited thereto. FIG. 7 illustrates that the divided patterns BMP do not overlap the light control units CCP1, CCP2 and CCP3, but at least a portion of the edges of the light control units CCP1, CCP2 and CCP3 may overlap the divided patterns BMP.

The light control layer CCL may include a first light control unit CCP1 containing a first quantum dot QD1 which converts first color light provided from the organic electroluminescence device ED into second color light, a second light control unit CCP2 containing a second quantum dot QD2 which converts the first color light into third color light, and a third light control unit CCP3 which transmits the first color light.

In one or more embodiments, the first light control unit CCP1 may provide red light that may be the second color light, and the second light control unit CCP2 may provide green light that may be the third color light. The third light control unit CCP3 may provide blue light by transmitting the blue light that may be the first color light provided in the organic electroluminescence device ED. For example, the first quantum dot QD1 may be a red quantum dot, and the second quantum dot QD2 may be a green quantum dot. The same as described above may be applied with respect to the quantum dots QD1 and QD2.

In one or more embodiments, the light control layer CCL may further include a scatterer SP. The first light control unit CCP1 may include the first quantum dot QD1 and the scatterer SP, the second light control unit CCP2 may include the second quantum dot QD2 and the scatterer SP, and the third light control unit CCP3 may not include any quantum dot but include the scatterer SP.

The scatterer SP may be inorganic particles. For example, the scatterer SP may include at least one of $TiO_2$, $ZnO$, $Al_2O_3$, $SiO_2$, or hollow silica. The scatterer SP may include any one of $TiO_2$, $ZnO$, $Al_2O_3$, $SiO_2$, or hollow silica, or may be a mixture of at least two materials selected from among $TiO_2$, $ZnO$, $Al_2O_3$, $SiO_2$, and hollow silica.

The first light control unit CCP1, the second light control unit CCP2, and the third light control unit CCP3 each may include a corresponding one of base resins BR1, BR2, and BR3 in which the quantum dots QD1 and QD2 and the scatterer SP may be dispersed. In one or more embodiments, the first light control unit CCP1 may include the first quantum dot QD1 and the scatterer SP dispersed in a first base resin BR1, the second light control unit CCP2 may include the second quantum dot QD2 and the scatterer SP dispersed in a second base resin BR2, and the third light control unit CCP3 may include the scatterer SP dispersed in a third base resin BR3. The base resins BR1, BR2, and BR3 may be media in which the quantum dots QD1 and QD2 and the scatterer SP may be dispersed, and may be formed of various resin compositions, which may be generally referred to as a binder. For example, the base resins BR1, BR2, and BR3 may be acrylic-based resins, urethane-based resins, silicone-based resins, epoxy-based resins, etc. The base resins BR1, BR2, and BR3 may be transparent resins. In one or more embodiments, the first base resin BR1, the second base resin BR2, and the third base resin BR3 each may be the same as or different from each other.

The light control layer CCL may include a barrier layer BFL1. The barrier layer BFL1 may serve to prevent or reduce the penetration of moisture and/or oxygen (hereinafter, referred to as 'moisture/oxygen'). The barrier layer BFL1 may be disposed on the light control units CCP1, CCP2, and CCP3 to prevent or reduce the light control units CCP1, CCP2 and CCP3 exposure to moisture/oxygen. Meanwhile, the barrier layer BFL1 may cover the light control units CCP1, CCP2, and CCP3. In one or more embodiments, the barrier layer BFL2 may be provided between the light control units CCP1, CCP2, and CCP3 and the color filter layer CFL.

The barrier layers BFL1 and BFL2 may include at least one inorganic layer. That is, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. Meanwhile, the barrier layers BFL1 and BFL2 may further include an organic film. The barrier layers BFL1 and BFL2 may be formed of a single layer or a plurality of layers.

In the display apparatus DD of one or more embodiments, the color filter layer CFL may be disposed on the light control layer CCL. For example, the color filter layer CFL may be directly disposed on the light control layer CCL. In this case, the barrier layer BFL2 may be omitted.

The color filter layer CFL may include a light shielding unit BM and filters CF-B, CF-G, and CF-R. The color filter layer CFL may include a first filter CF1 configured to transmit the second color light, a second filter CF2 configured to transmit the third color light, and a third filter CF3 configured to transmit the first color light. For example, the first filter CF1 may be a red filter, the second filter CF2 may be a green filter, and the third filter CF3 may be a blue filter. The filters CF1, CF2, and CF3 each may include a polymeric photosensitive resin and a pigment and/or dye. The first filter CF1 may include a red pigment and/or dye, the second filter CF2 may include a green pigment and/or dye, and the third filter CF3 may include a blue pigment and/or dye. However, the embodiments of the present disclosure are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

Furthermore, In one or more embodiments, the first filter CF1 and the second filter CF2 may be a yellow filter. The first filter CF1 and the second filter CF2 may not be separated but be provided as one filter.

The light shielding unit BM may be a black matrix. The light shielding unit BM may include an organic light shielding material and/or an inorganic light shielding material containing a black pigment and/or dye. The light shielding unit BM may prevent or reduce light leakage, and may separate boundaries between the adjacent filters CF1, CF2, and CF3. In one or more embodiments, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

A base substrate BL may be disposed on the color filter layer CFL. The base substrate BL may be a member which provides a base surface in which the color filter layer CFL, the light control layer CCL, and the like may be disposed. The base substrate BL may be a glass substrate, a metal substrate, a plastic substrate, etc. However, the embodiments of the present disclosure are not limited thereto, and the base substrate BL may be an inorganic layer, an organic layer, or a composite material layer. In one or more embodiments, the base substrate BL may be omitted.

Figure 8:
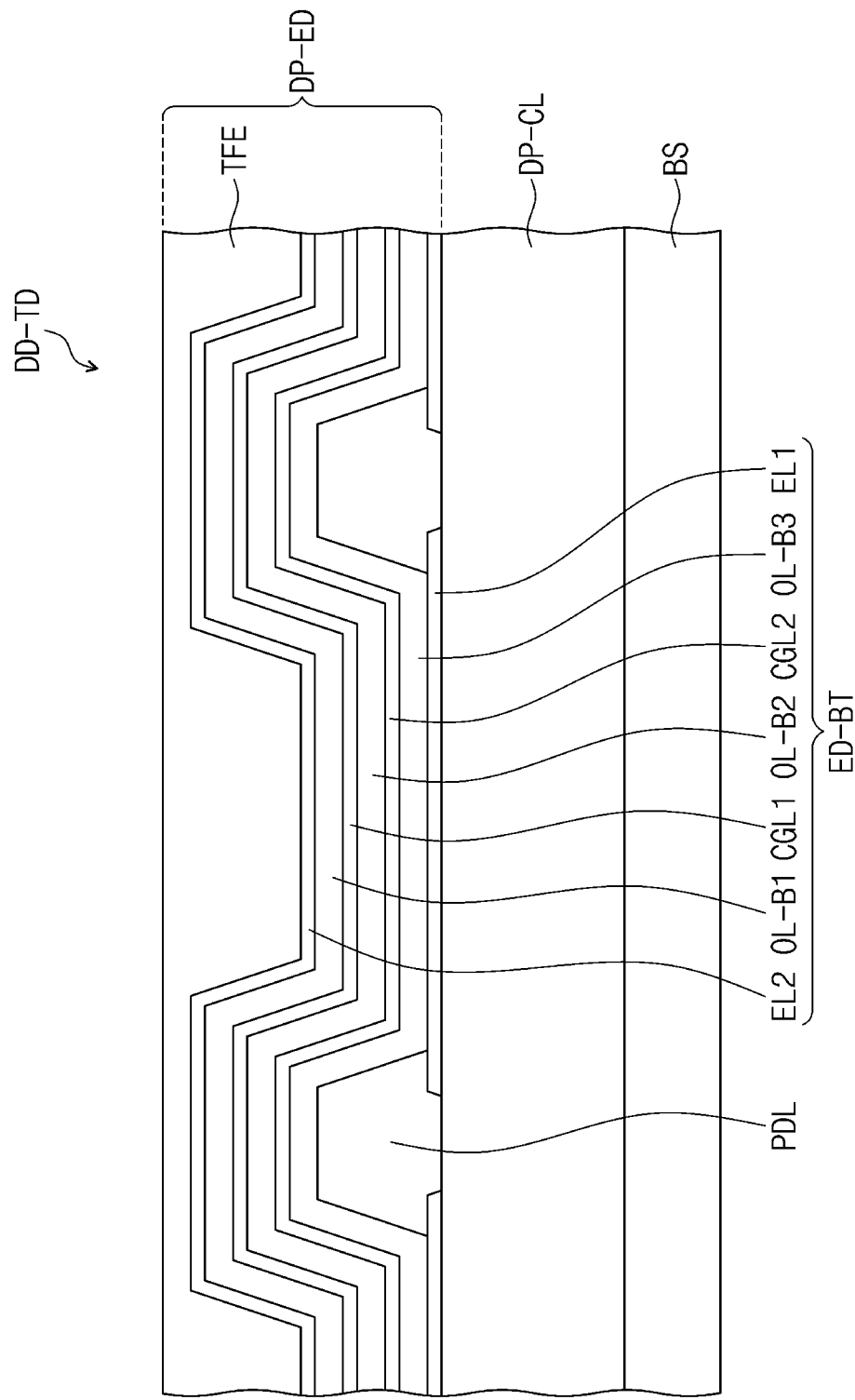
FIG. 8 is a cross-sectional view of a display apparatus according to one or more embodiments of the present disclosure.

FIG. 8 is a cross-sectional view illustrating a part of a display apparatus according to one or more embodiments. FIG. 8 illustrates a cross-sectional view of a part corresponding to the display panel DP of FIG. 7. In the display apparatus DD-TD of one or more embodiments, the organic electroluminescence device ED-BT may include a plurality of light emitting structures OL-B1, OL-B2, and OL-B3. The organic electroluminescence device ED-BT may include a first electrode EL1 and a second electrode EL2 which face each other, and the plurality of light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR disposed with the emission layer EML (FIG. 7) therebetween.

That is, the organic electroluminescence device ED-BT included in the display apparatus DD-TD of one or more embodiments may be an organic electroluminescence device having a tandem structure and including a plurality of emission layers. When the organic electroluminescence device ED includes a plurality of emission layers, at least one emission layer EML may include the organometallic compound of one or more embodiments as described above.

In one or more embodiments illustrated in FIG. 8, all light respectively emitted from the light emitting structures OL-B1, OL-B2, and OL-B3 may be blue light. However, the embodiments of the present disclosure are not limited thereto, and the light respectively emitted from the light emitting structures OL-B1, OL-B2, and OL-B3 may have wavelength ranges different from each other. For example, the organic electroluminescence device ED-BT including the plurality of light emitting structures OL-B1, OL-B2, and OL-B3 which emit light having wavelength ranges different from each other may emit white light.

A charge generation layer CGL may be disposed between the neighboring light emitting structures OL-B1, OL-B2, and OL-B3. The charge generation layer CGL may include a p-type charge generation layer and/or an n-type charge generation layer.

Hereinafter, the present disclosure will be described in more detail through specific Examples and Comparative Examples. Examples below are only illustrations for assisting the understanding of the present disclosure, and the scope of the present disclosure is not limited thereto.

SYNTHETIC EXAMPLES

A compound according to one or more embodiments of the present disclosure may be synthesized, for example, as follows. However, a synthetic method of the compound according to one or more embodiments of the present disclosure is not limited thereto.

1. Synthesis of Compound BD1

1.1 Synthesis of Intermediate BD1-1

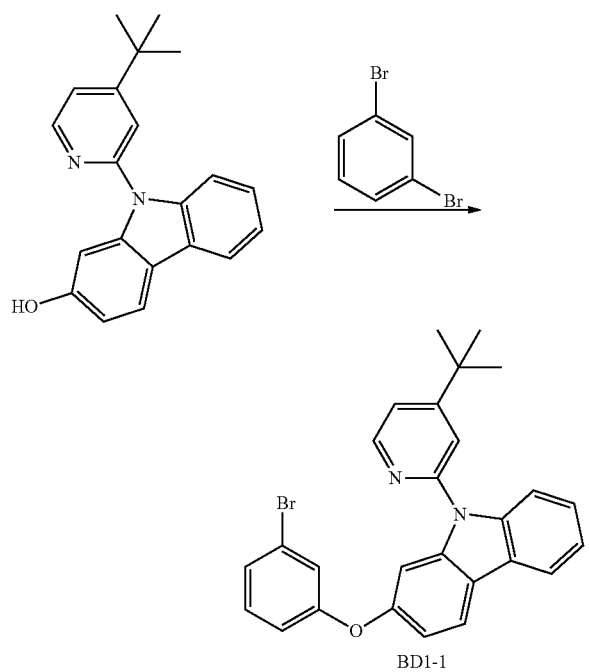

9-(4-(tert-butyl)pyridin-2-yl)-9H-carbazol-2-ol (1.0 eq), 1,3-dibromobenzene (2.5 eq), CuI (0.01 eq), $K_2CO_3$ (2.0 eq) and L-proline (0.02 eq) were dissolved in N,N-dimethylformamide (0.1 M), and then stirred at about 160° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD1-1 (yield 70%) by using column chromatography.

1.2 Synthesis of Intermediate BD1-2

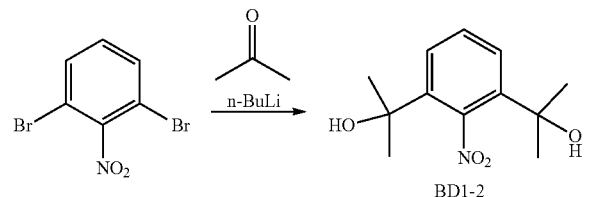

1,3-dibromo-2-nitrobenzene was dissolved in THF (0.1 M), and then n-butyllithium (2.5 M in hexane, 3.0 eq) was slowly added dropwise thereto at about −78° C. and stirred for about 1 hour. Acetone (3.0 eq) was added to the reactant and stirred at room temperature for about 24 hours. The resultant product was extracted three times using dichloromethane and water to obtain an organic layer. The obtained organic layer was dried over magnesium sulfate, and then concentrated to synthesize Intermediate BD1-2 (yield 80%).

1.3 Synthesis of Intermediate BD1-3

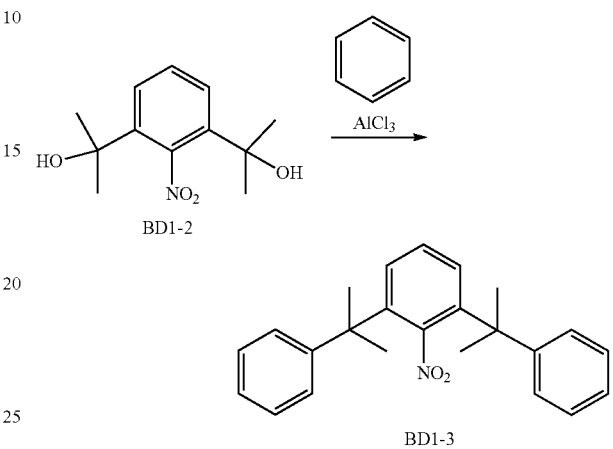

Intermediate BD1-2 was dissolved in benzene (0.1 M), and then $AlCl_3$ (5.0 eq) was added thereto at room temperature and stirred for about 48 hours. After slowly adding water thereto, the resultant product was extracted three times using dichloromethane and water to obtain an organic layer. The obtained organic layer was dried over magnesium sulfate, and then concentrated to synthesize Intermediate BD1-3 (yield 50%) by using column chromatography.

1.4 Synthesis of Intermediate BD1-4

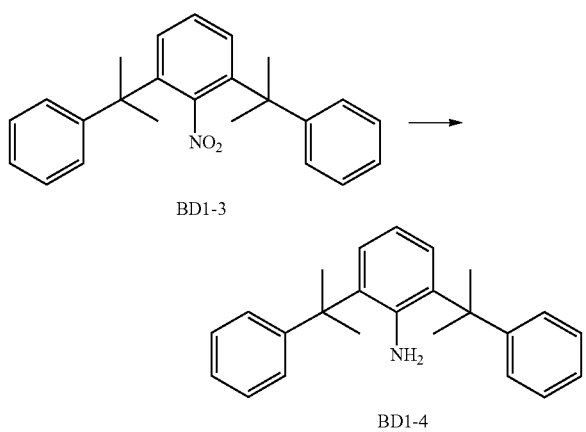

Intermediate BD1-3, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD1-4 (yield 90%) by using column chromatography.

1.5 Synthesis of Intermediate BD1-5

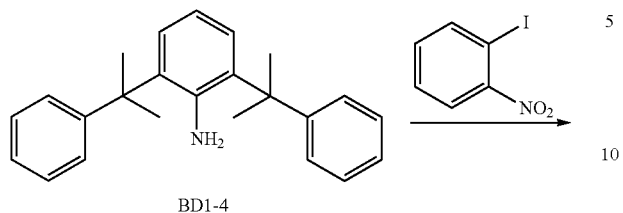

Intermediate BD1-4 (1.0 eq), 1-iodo-2-nitrobenzene (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD1-5 (yield 81%) by using column chromatography.

1.6 Synthesis of Intermediate BD1-6

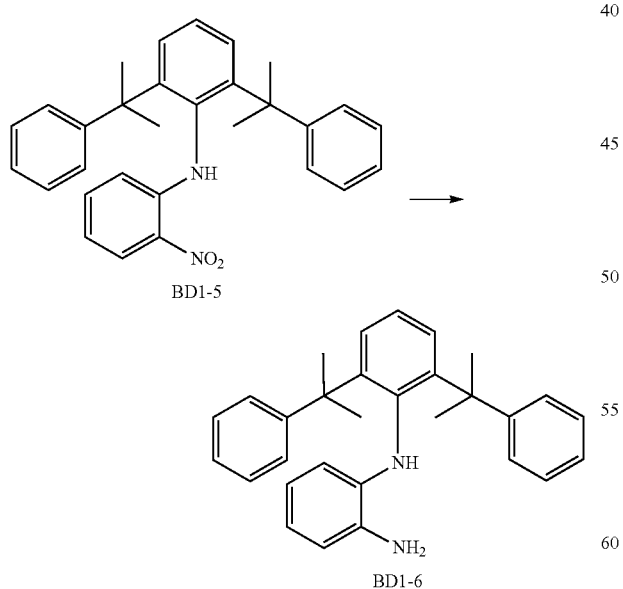

Intermediate BD1-5, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD1-6 (yield 85%) by using column chromatography.

1.7 Synthesis of Intermediate BD1-7

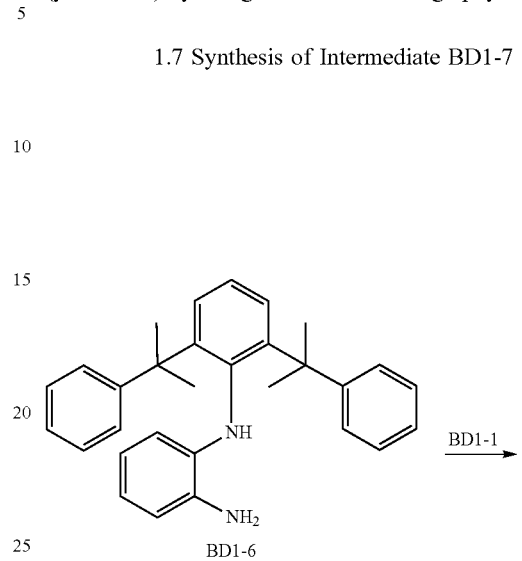

Intermediate BD1-1 (1.0 eq), Intermediate BD1-6 (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD1-7 (yield 88%) by using column chromatography.

1.8 Synthesis of Intermediate BD1-8

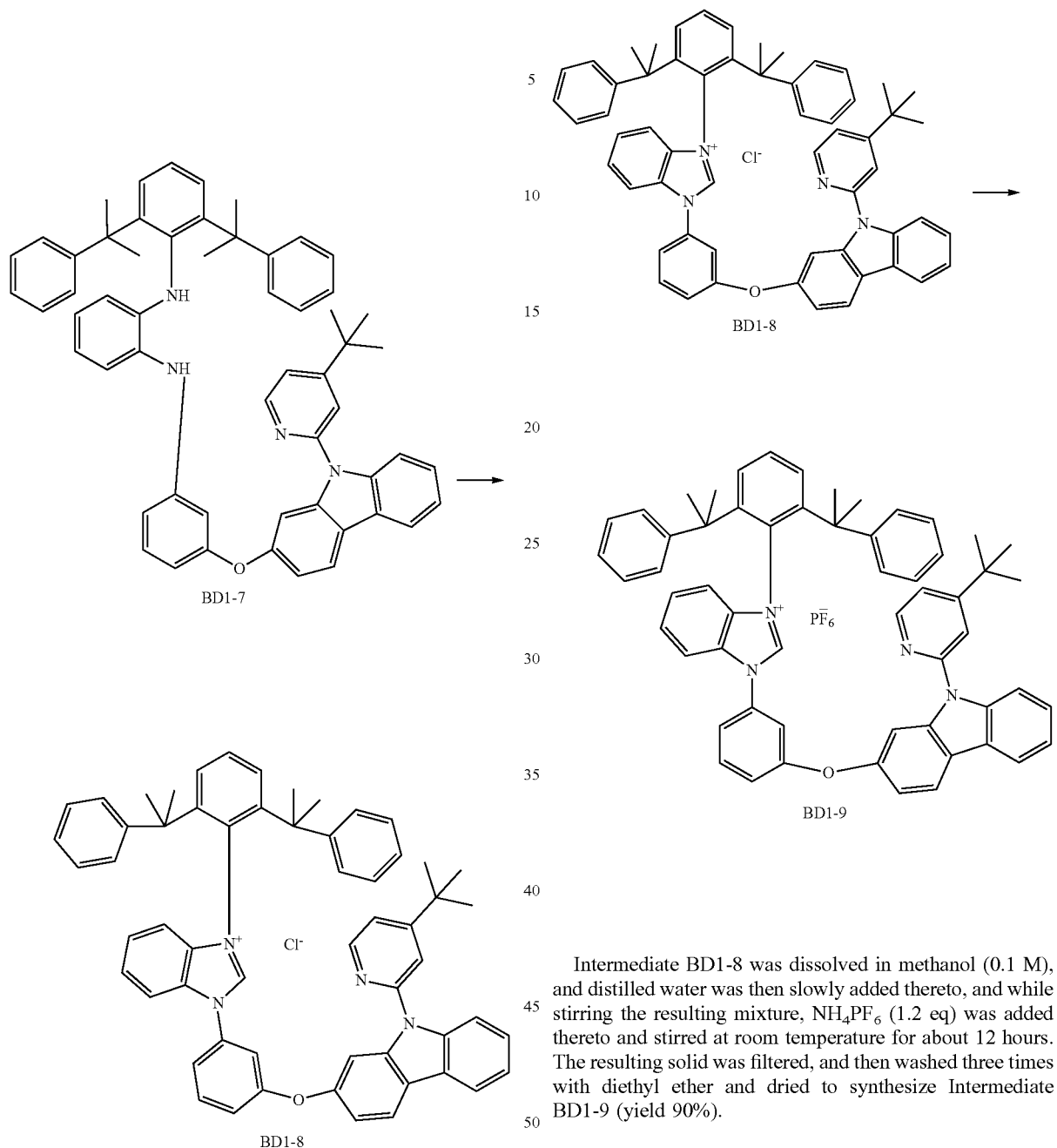

A mixture of Intermediate BD1-7 (1.0 eq), triethylorthoformate (50 eq), and HCl (25 eq) was stirred at about 80° C. for about 12 hours. The reaction mixture was cooled to room temperature, and triethylorthoformate was then removed, and the reaction mixture was extracted three times using ethyl acetate and water to obtain an organic layer. The obtained organic layer was dried over magnesium sulfate, and then concentrated to synthesize Intermediate BD1-8 (yield 92%) by using column chromatography.

Intermediate BD1-8 was dissolved in methanol (0.1 M), and distilled water was then slowly added thereto, and while stirring the resulting mixture, $NH_4PF_6$ (1.2 eq) was added thereto and stirred at room temperature for about 12 hours. The resulting solid was filtered, and then washed three times with diethyl ether and dried to synthesize Intermediate BD1-9 (yield 90%).

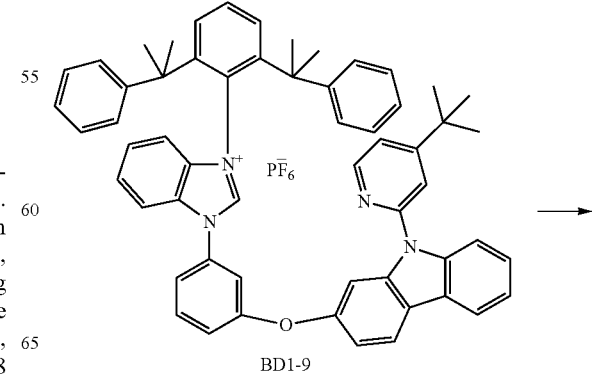

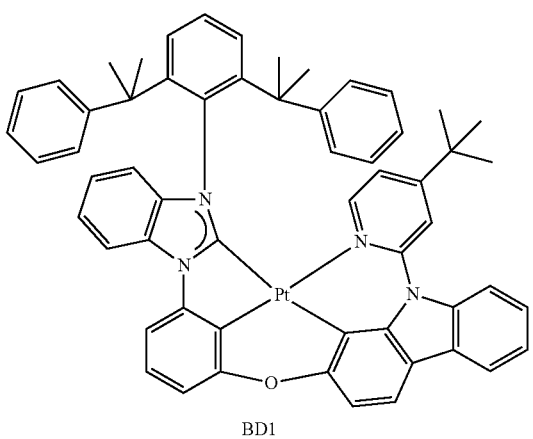

BD1

Intermediate BD1-9 (1.0 eq), dichloro(1,2-dicyclooctadiene)platinum (Pt(COD)Cl₂) (1.1 eq), and sodium acetate (2.0 eq) were dissolved in dioxane (0.1 M) and then stirred at about 120° C. for about 72 hours. The reaction mixture was cooled to room temperature, and then was extracted three times using dichloromethane and water to obtain an organic layer. The obtained organic layer was dried over magnesium sulfate, and then concentrated to synthesize Compound BD1 (yield 21%) by using column chromatography.

2. Synthesis of Compound BD14

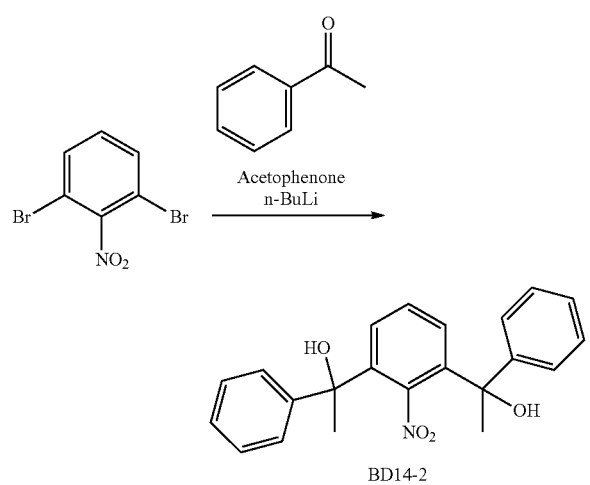

1,3-dibromo-2-nitrobenzene was dissolved in THF (0.1 M), and then n-butyllithium (2.5 M in hexane, 3.0 eq) was slowly added dropwise thereto at about −78° C. and stirred for about 1 hour. Acetophenone (3.0 eq) was added to the reactant and stirred at room temperature for about 24 hours. The resultant product was extracted three times using dichloromethane and water to obtain an organic layer. The obtained organic layer was dried over magnesium sulfate, and then concentrated to synthesize Intermediate BD14-2 (yield 81%).

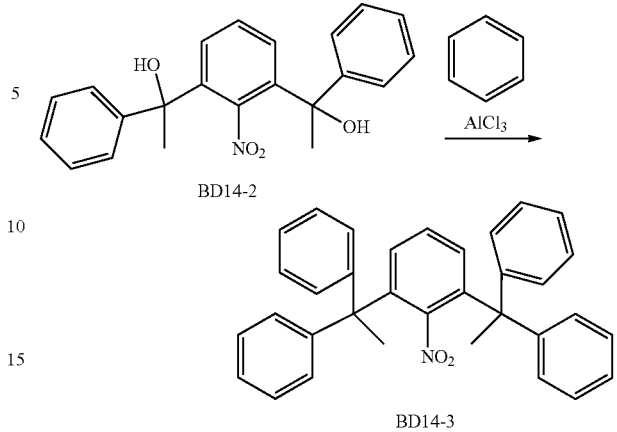

Intermediate BD14-2 was dissolved in benzene (0.1 M), and then AlCl₃ (5.0 eq) was added thereto at room temperature and stirred for about 48 hours. After slowly adding water thereto, the resultant product was extracted three times using dichloromethane and water to obtain an organic layer. The obtained organic layer was dried over magnesium sulfate, and then concentrated to synthesize Intermediate BD14-3 (yield 40%) by using column chromatography.

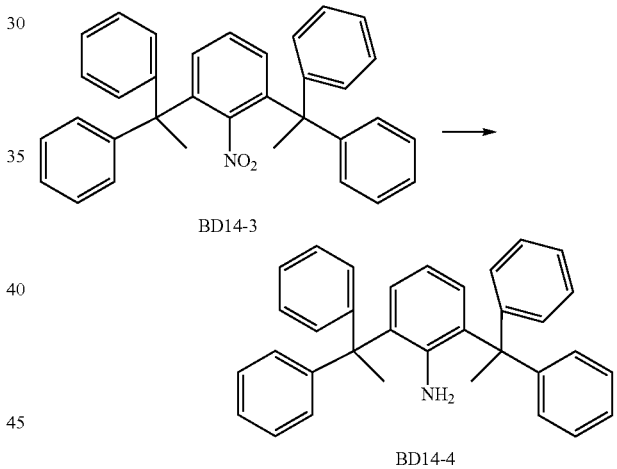

Intermediate BD14-3, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD14-4 (yield 80%) by using column chromatography.

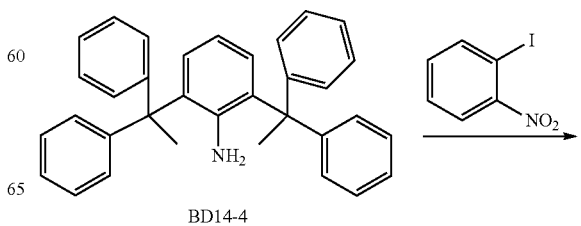

-continued

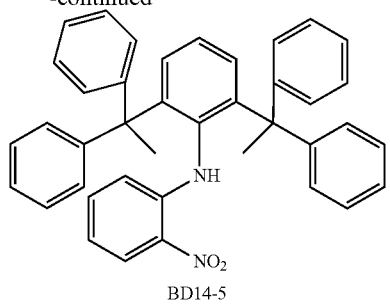
BD14-5

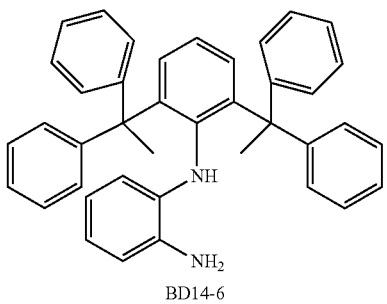
BD14-6

Intermediate BD14-4 (1.0 eq), 1-iodo-2-nitrobenzene (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD14-5 (yield 71%) by using column chromatography.

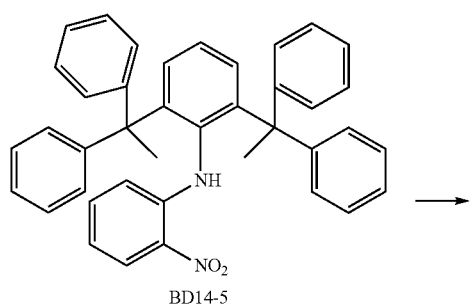
BD14-5

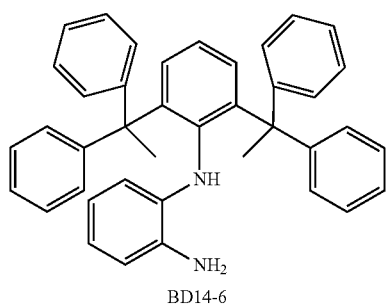
BD14-6

Intermediate BD14-5, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD14-6 (yield 85%) by using column chromatography.

BD1-1 →

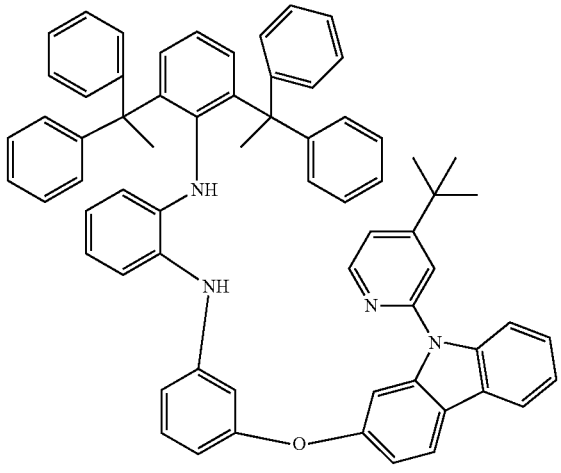
BD14-7

Intermediate BD1-1 (1.0 eq), Intermediate BD14-6 (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD14-7 (yield 80%) by using column chromatography.

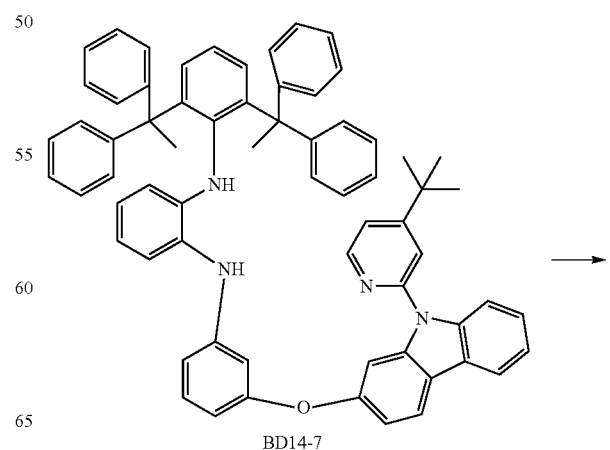
BD14-7

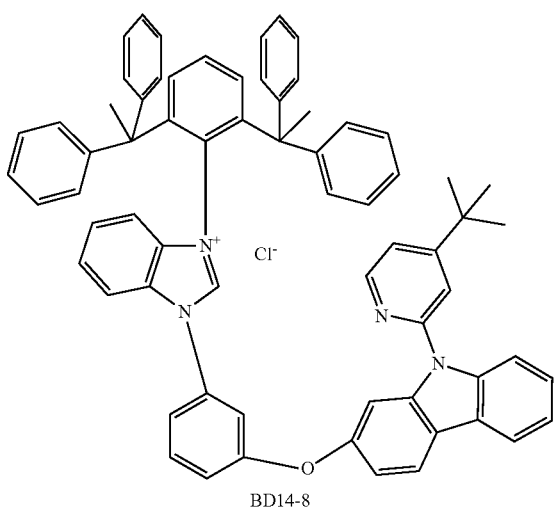

BD14-8

A mixture of Intermediate BD14-7 (1.0 eq), triethylorthoformate (50 eq), and HCl (25 eq) was stirred at about 80° C. for about 12 hours. The reaction mixture was cooled to room temperature, and triethylorthoformate was then removed, and the reaction mixture was extracted three times using ethyl acetate and water to obtain an organic layer. The obtained organic layer was dried over magnesium sulfate, and then concentrated to synthesize Intermediate BD14-8 (yield 97%) by using column chromatography.

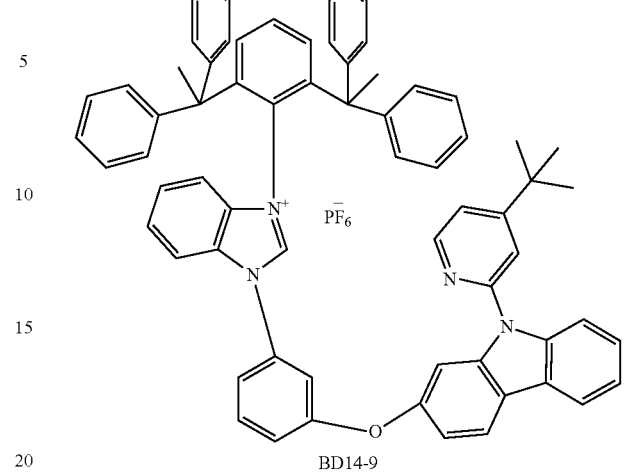

BD14-9

Intermediate BD14-8 was dissolved in methanol (0.1 M), and distilled water was then slowly added thereto, and while stirring the resulting mixture, $NH_4PF_6$ (1.2 eq) was added thereto and stirred at room temperature for about 12 hours. The resulting solid was filtered, and then washed three times with diethyl ether and dried to synthesize Intermediate BD14-9 (yield 84%).

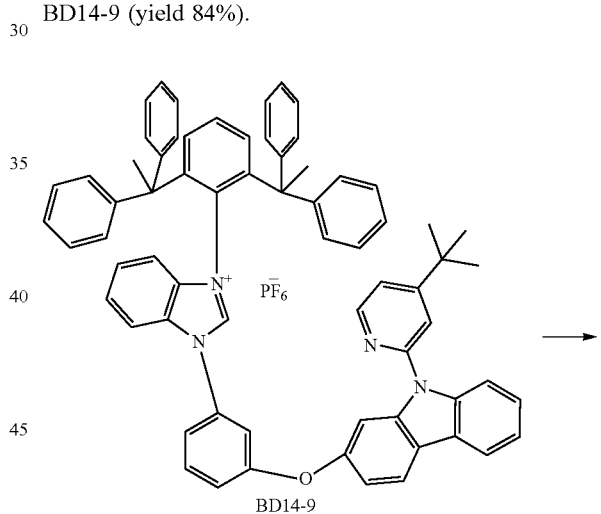

BD14-9

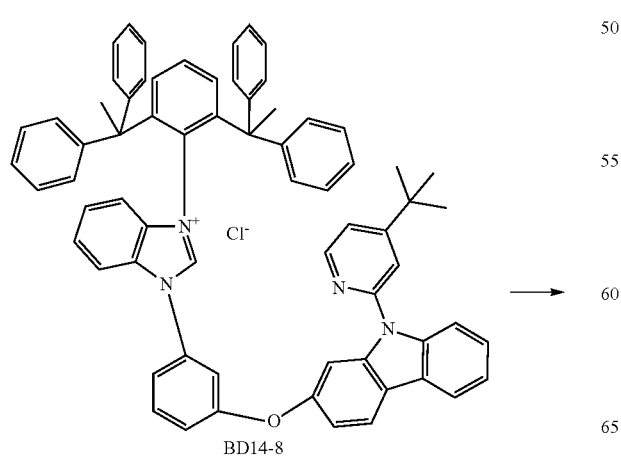

BD14-8

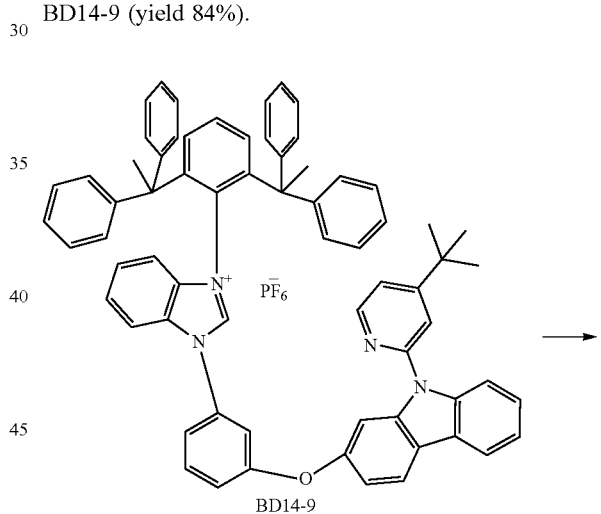

BD14

Intermediate BD14-9 (1.0 eq), dichloro(1,2-dicyclooctadiene)platinum (Pt(COD)Cl$_2$) (1.1 eq), and sodium acetate (2.0 eq) were dissolved in dioxane (0.1 M) and then stirred at about 120° C. for about 72 hours. The reaction mixture was cooled to room temperature, and then was extracted three times using dichloromethane and water to obtain an organic layer. The obtained organic layer was dried over magnesium sulfate, and then concentrated to synthesize Compound BD14 (yield 28%) by using column chromatography.

3. Synthesis of Compound BD22

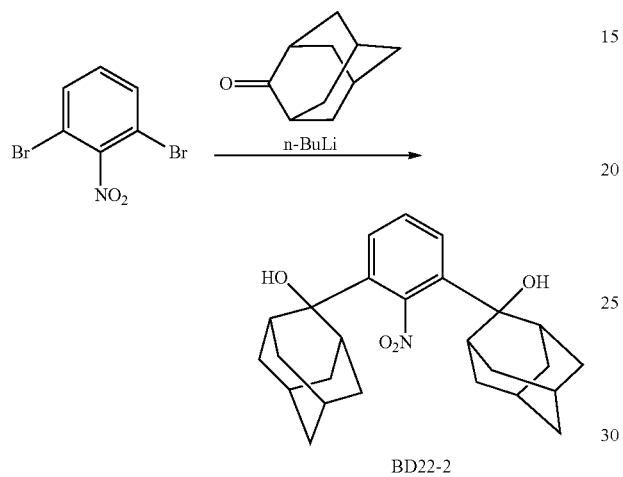

BD22-2

1,3-dibromo-2-nitrobenzene was dissolved in THF (0.1 M), and then n-butyllithium (2.5 M in hexane, 3.0 eq) was slowly added dropwise thereto at about −78° C. and stirred for about 1 hour. (1r,3r,5r,7r)-adamantan-2-one (3.0 eq) was added to the reactant and stirred at room temperature for about 24 hours. The resultant product was extracted three times using dichloromethane and water to obtain an organic layer. The obtained organic layer was dried over magnesium sulfate, and then concentrated to synthesize Intermediate BD22-2 (yield 70%).

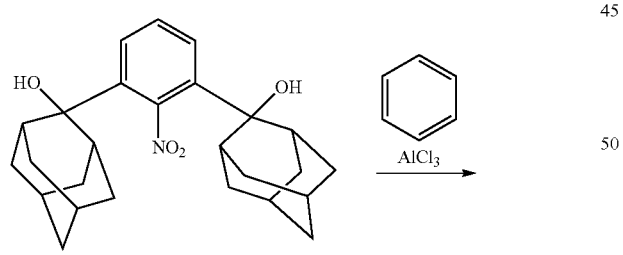

BD22-3

Intermediate BD22-2 was dissolved in benzene (0.1 M), and then AlCl$_3$ (5.0 eq) was added thereto at room temperature and stirred for about 48 hours. After slowly adding water thereto, the resultant product was extracted three times using dichloromethane and water to obtain an organic layer. The obtained organic layer was dried over magnesium sulfate, and then concentrated to synthesize Intermediate BD22-3 (yield 80%) by using column chromatography.

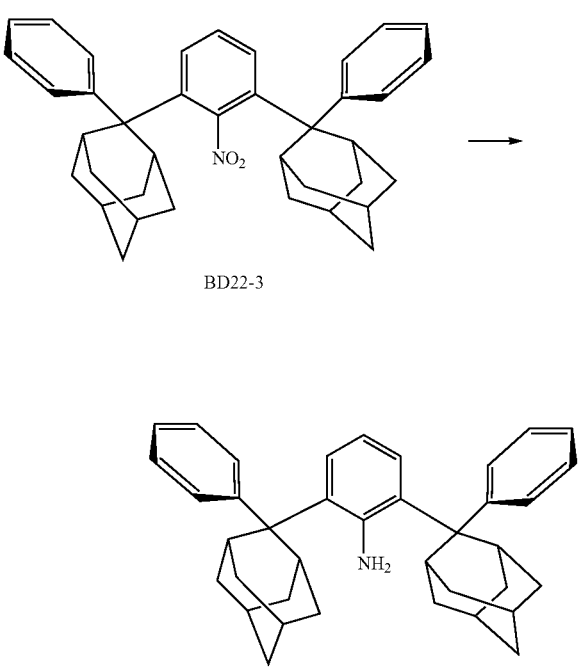

BD22-3

BD22-4

Intermediate BD22-3, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD22-4 (yield 71%) by using column chromatography.

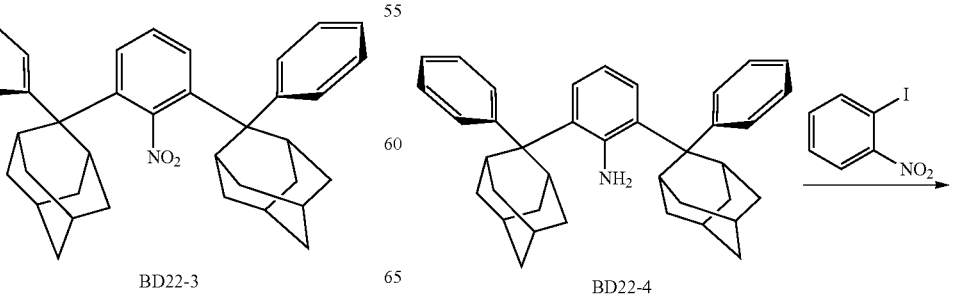

BD22-4

-continued

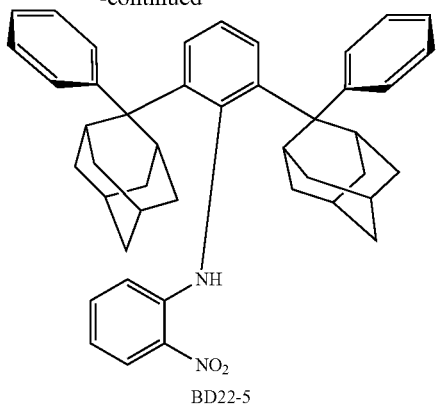
BD22-5

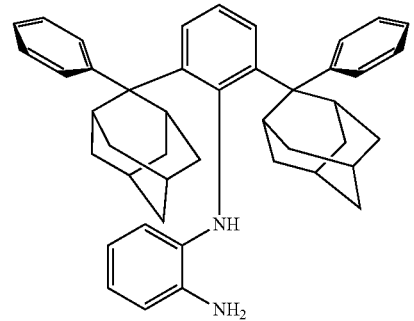
BD22-6

Intermediate BD22-4 (1.0 eq), 1-iodo-2-nitrobenzene (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD22-5 (yield 64%) by using column chromatography.

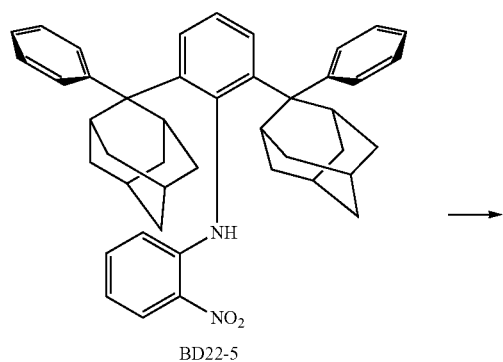
BD22-5

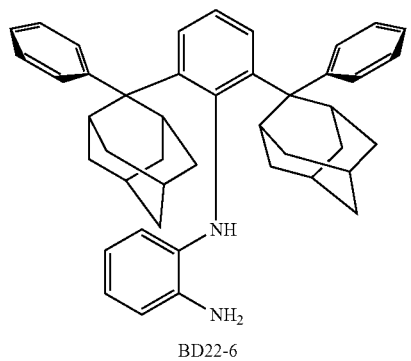
BD22-6

Intermediate BD22-5, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD22-6 (yield 85%) by using column chromatography.

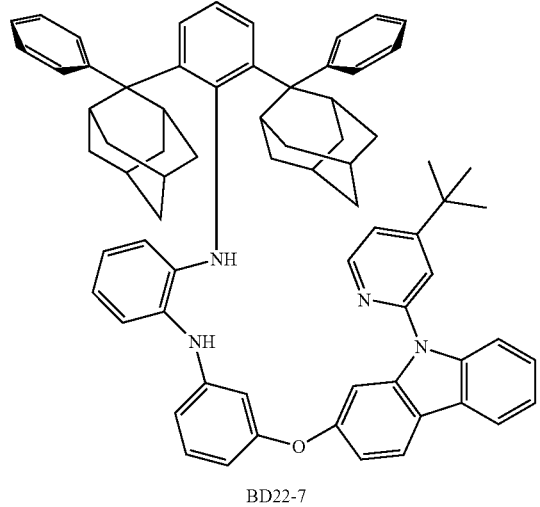
BD22-7

Intermediate BD1-1 (1.0 eq), Intermediate BD22-6 (1.2 eq), Pd$_2$(dba)$_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD22-7 (yield 78%) by using column chromatography.

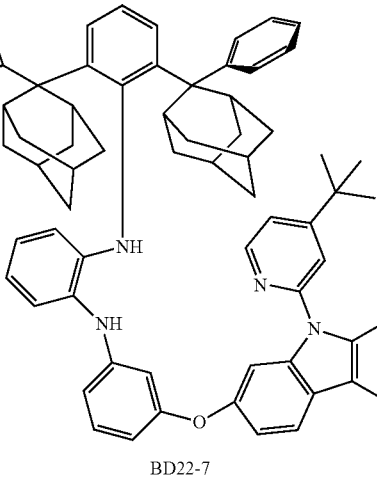
BD22-7

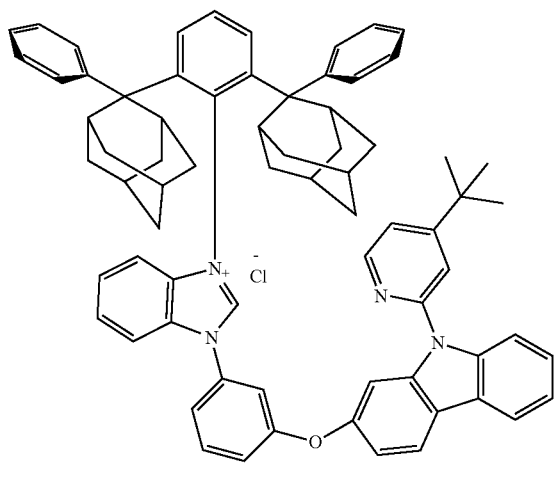

BD22-8

A mixture of Intermediate BD22-7 (1.0 eq), triethylorthoformate (50 eq), and HCl (25 eq) was stirred at about 80° C. for about 12 hours. The reaction mixture was cooled to room temperature, and triethylorthoformate was then removed, and the reaction mixture was extracted three times using ethyl acetate and water to obtain an organic layer. The obtained organic layer was dried over magnesium sulfate, and then concentrated to synthesize Intermediate BD22-8 (yield 70%) by using column chromatography.

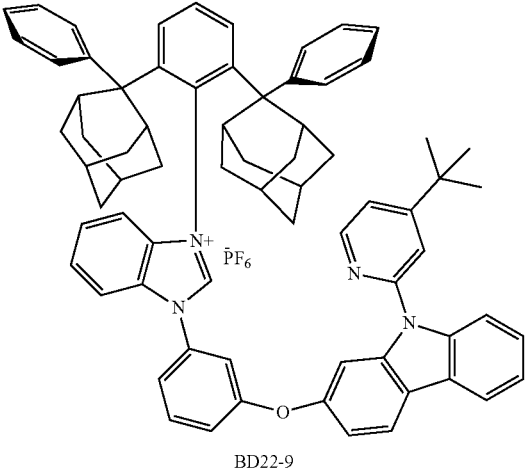

BD22-9

Intermediate BD22-8 was dissolved in methanol (0.1 M), and distilled water was then slowly added thereto, and while stirring the resulting mixture, $NH_4PF_6$ (1.2 eq) was added thereto and stirred at room temperature for about 12 hours. The resulting solid was filtered, and then washed three times with diethyl ether and dried to synthesize Intermediate BD22-9 (yield 80%).

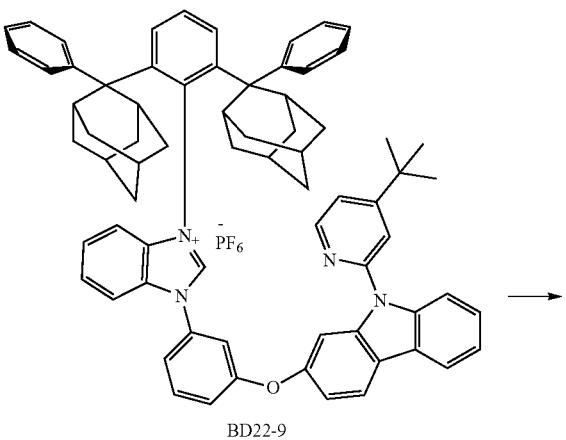

BD22-9

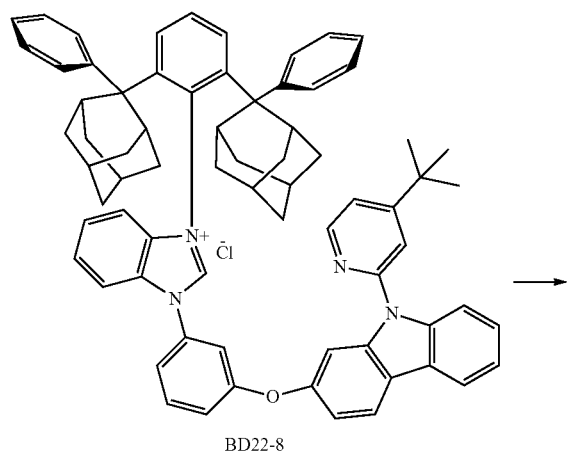

BD22-8

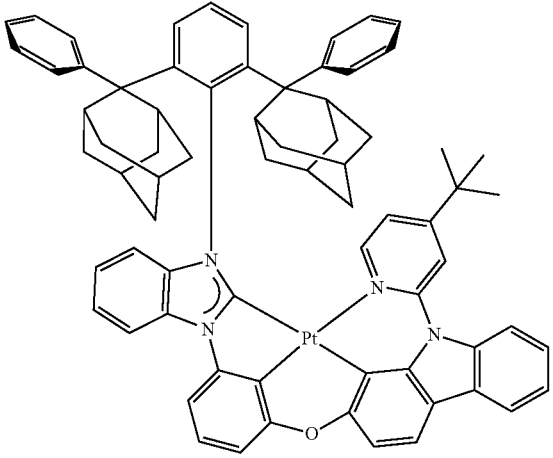

BD22

149

Intermediate BD22-9 (1.0 eq), dichloro(1,2-dicyclooctadiene)platinum (Pt(COD)Cl$_2$) (1.1 eq), and sodium acetate (2.0 eq) were dissolved in dioxane (0.1 M) and then stirred at about 120° C. for about 72 hours. The reaction mixture was cooled to room temperature, and then was extracted three times using dichloromethane and water to obtain an organic layer. The obtained organic layer was dried over magnesium sulfate, and then concentrated to synthesize Compound BD22 (yield 35%) by using column chromatography.

4. Synthesis of Compound BD25

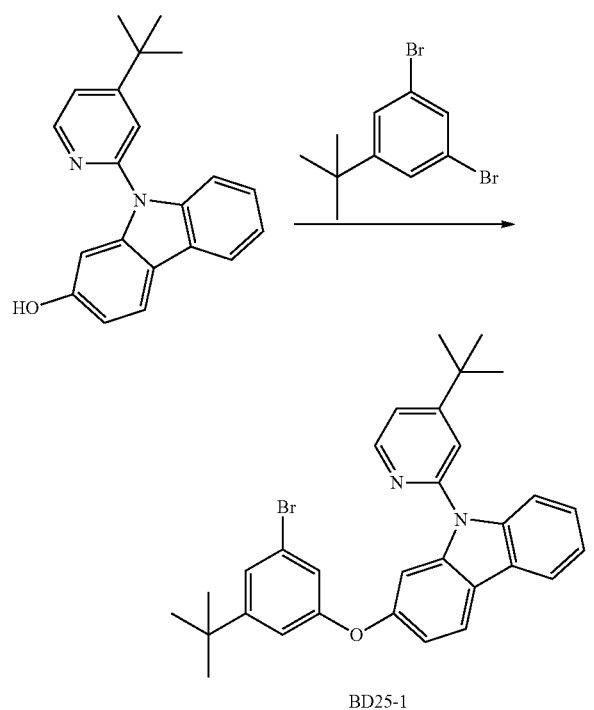

BD25-1

9-(4-(tert-butyl)pyridin-2-yl)-9H-carbazol-2-ol (1.0 eq), 1,3-dibromo-5-(tert-butyl)benzene (2.5 eq), CuI (0.01 eq), K$_2$CO$_3$ (2.0 eq), and L-proline (0.02 eq) were dissolved in N,N-dimethylformamide (0.1 M), and then stirred at about 160° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD25-1 (yield 70%) by using column chromatography.

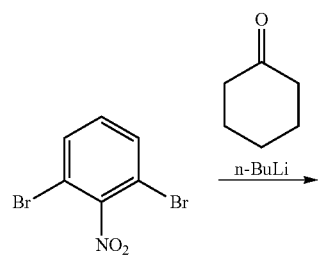

150

-continued

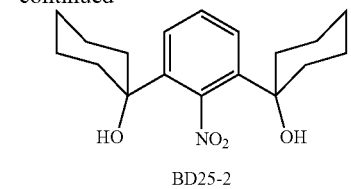

BD25-2

1,3-dibromo-2-nitrobenzene was dissolved in THF (0.1 M), and then n-butyllithium (2.5 M in hexane, 3.0 eq) was slowly added dropwise thereto at about −78° C. and stirred for about 1 hour. Cyclohexanone (3.0 eq) was added to the reactant and stirred at room temperature for about 24 hours. The resultant product was extracted three times using dichloromethane and water to obtain an organic layer.

The obtained organic layer was dried over magnesium sulfate, and then concentrated to synthesize Intermediate BD25-2 (yield 80%).

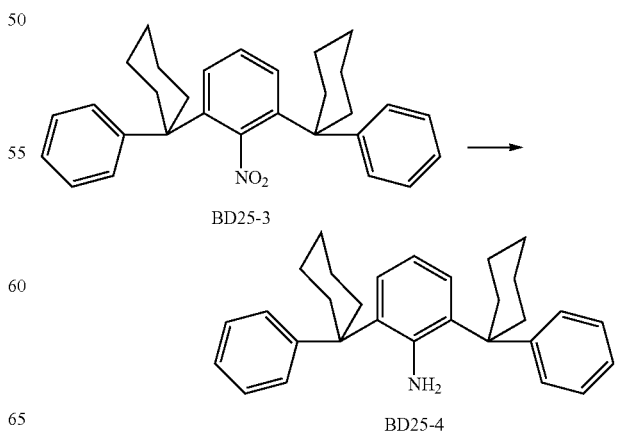

Intermediate BD25-2 was dissolved in benzene (0.1 M), and then AlCl$_3$ (5.0 eq) was added thereto at room temperature and stirred for about 48 hours. After slowly adding water thereto, the resultant product was extracted three times using dichloromethane and water to obtain an organic layer. The obtained organic layer was dried over magnesium sulfate, and then concentrated to synthesize Intermediate BD25-3 (yield 50%) by using column chromatography.

Intermediate BD25-3, Sn (2.5 eq), and HCl (2.0 eq) were dissolved in EtOH, and then stirred at about 80° C. for about 12 hours. The reaction mixture was cooled to room temperature, and then was extracted three times using dichloromethane and water to obtain an organic layer. The obtained organic layer was dried over magnesium sulfate, and then concentrated to synthesize Intermediate BD25-4 (yield 90%) by using column chromatography.

12 hours. The reaction mixture was cooled to room temperature, and then was extracted three times using dichloromethane and water to obtain an organic layer. The obtained organic layer was dried over magnesium sulfate, and then concentrated to synthesize Intermediate BD25-6 (yield 85%) by using column chromatography.

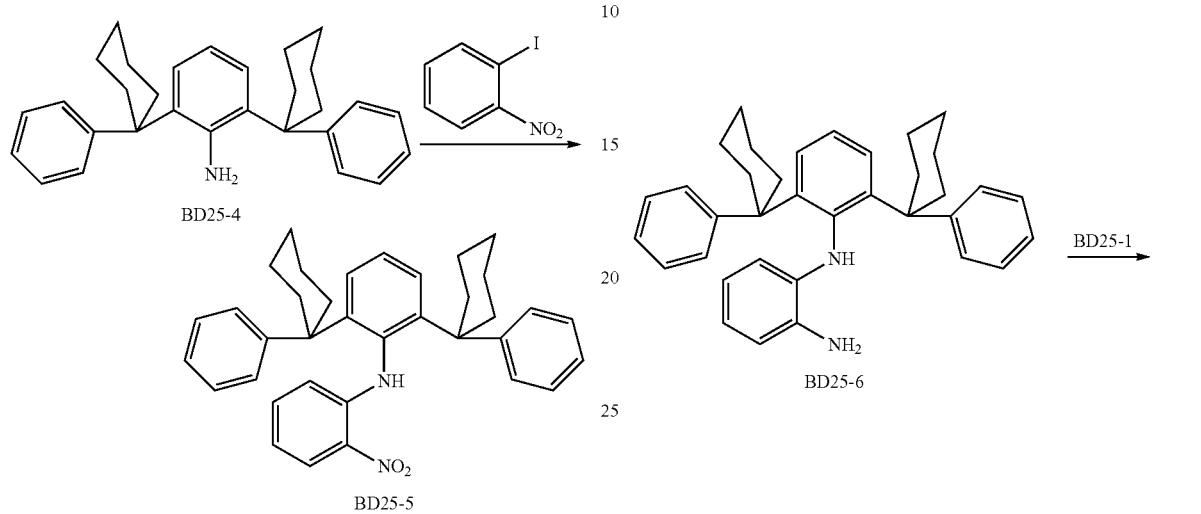

Intermediate BD25-4 (1.0 eq), 1-iodo-2-nitrobenzene (1.2 eq), $Pd_2(dba)_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD25-5 (yield 81%) by using column chromatography.

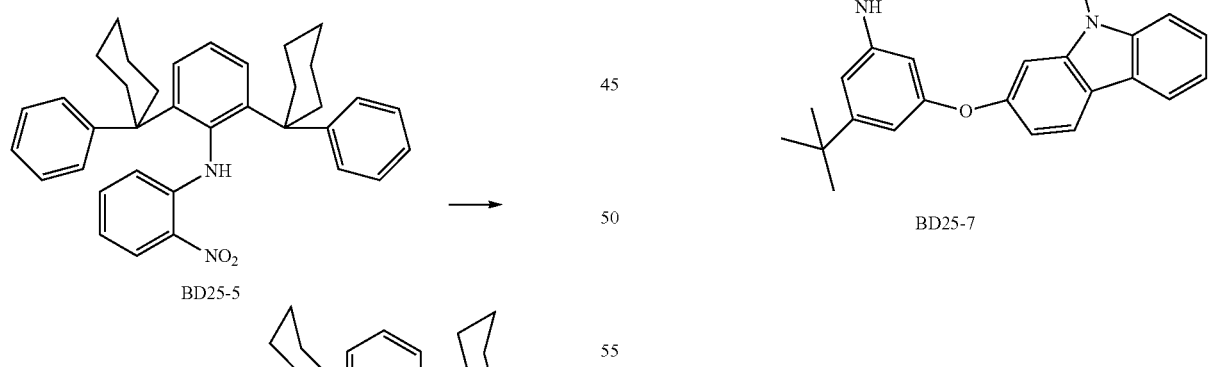

Intermediate BD25-5, Sn (2.5 eq), and HCl (2.0 eq) were dissolved in EtOH, and then stirred at about 80° C. for about Intermediate BD25-1 (1.0 eq), Intermediate BD1-6 (1.2 eq), $Pd_2(dba)_3$ (0.05 eq), Sphos (0.05 eq), and sodium tert-butoxide (2.0 eq) were dissolved in toluene (0.05 M), and then stirred at about 120° C. for about 24 hours. The reaction mixture was cooled to room temperature, and then was extracted three times using dichloromethane and water to obtain an organic layer. The obtained organic layer was dried over magnesium sulfate, and then concentrated to synthesize Intermediate BD25-7 (yield 88%) by using column chromatography.

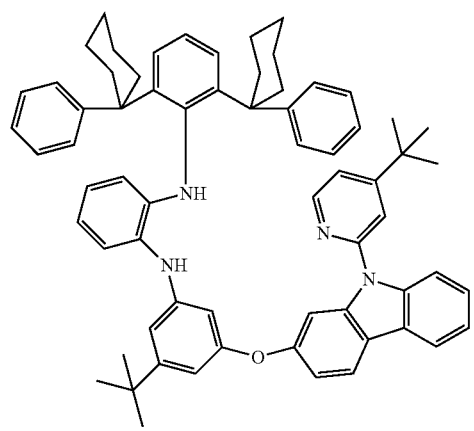

BD25-7

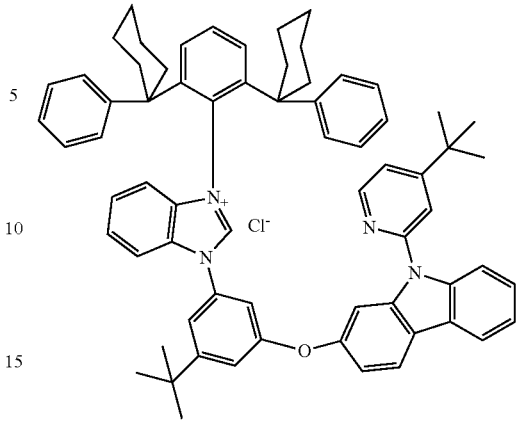

BD25-8

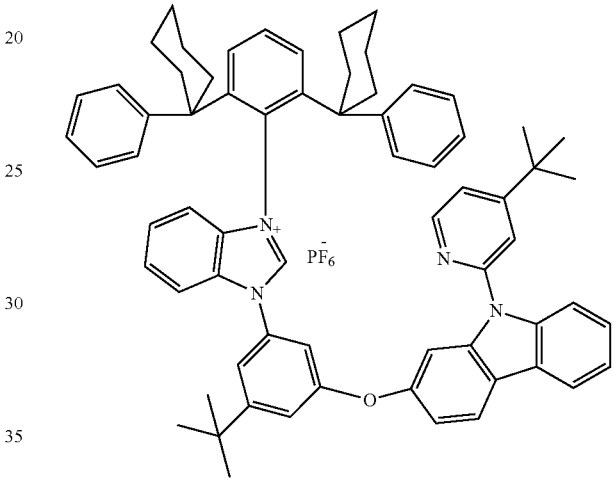

BD25-9

A mixture of Intermediate BD25-7 (1.0 eq), triethylorthoformate (50 eq), and HCl (25 eq) was stirred at about 80° C. for about 12 hours. The reaction mixture was cooled to room temperature, and triethylorthoformate was then removed, and the reaction mixture was extracted three times using ethyl acetate and water to obtain an organic layer. The obtained organic layer was dried over magnesium sulfate, and then concentrated to synthesize Intermediate BD25-8 (yield 92%) by using column chromatography.

BD25-8

Intermediate BD25-8 was dissolved in methanol (0.1 M), and distilled water was then slowly added thereto, and while stirring the resulting mixture, $NH_4PF_6$ (1.2 eq) was added thereto and stirred at room temperature for about 12 hours. The resulting solid was filtered, and then washed three times with diethyl ether and dried to synthesize Intermediate BD25-9 (yield 90%).

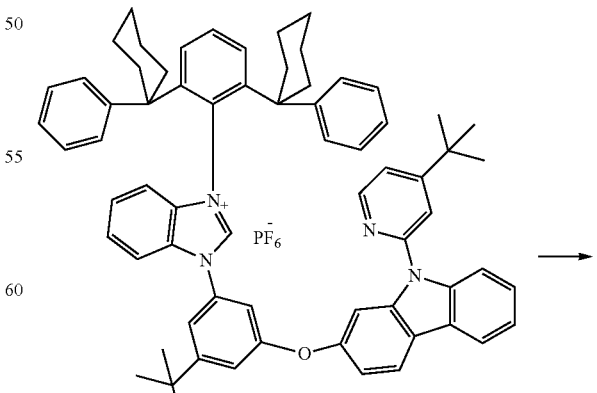

BD25-9

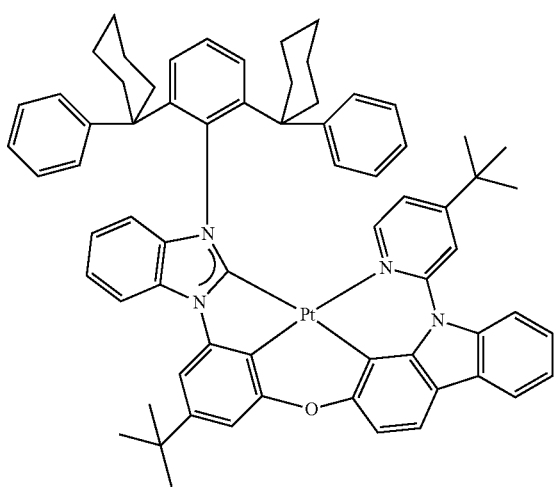

BD25

Intermediate BD25-9 (1.0 eq), dichloro(1,2-dicyclooctadiene)platinum (Pt(COD)Cl$_2$) (1.1 eq), and sodium acetate (2.0 eq) were dissolved in dioxane (0.1 M) and then stirred at about 120° C. for about 72 hours. The reaction mixture was cooled to room temperature, and then was extracted three times using dichloromethane and water to obtain an organic layer. The obtained organic layer was dried over magnesium sulfate, and then concentrated to synthesize Compound BD25 (yield 21%) by using column chromatography.

$^1$H NMR and MS/FAB in synthesized compounds of Synthetic Examples 1 to 4 above are shown in Table 1 below. The synthetic methods of other compounds may be easily recognized by those skilled in the art with reference to the above synthetic path and raw materials.

TABLE 1

| Compound No. | $^1$H NMR (DMSO, 400 MHz) | MS/FAB found | calc. |
|---|---|---|---|
| BD1 | 8.60-8.55 (m, 3H), 8.23 (t, 1H), 8.08 (d, 1H), 7.94 (d, 1H), 7.71 (t, 1H), 7.51 (t, 1H), 7.40-7.10 (m, 22H), 1.69 (s, 12H), 1.32 (s, 9H) | 1014.37 | 1015.16 |
| BD14 | 8.64-8.60 (m, 3H), 8.26 (t, 1H), 8.01 (d, 1H), 7.88(d, 1H), 7.72 (t, 1H), 7.49 (t, 1H), 7.40-7.10 (m, 22H), 6.99-6.80 (m, 10H) 1.69 (s, 6H), 1.32 (s, 9H) | 1138.40 | 1139.30 |
| BD22 | 8.59-8.48 (m, 3H), 8.17 (t, 1H), 8.00 (d, 1H), 7.74 (d, 1H), 7.68 (t, 1H), 7.47 (t, 1H), 7.41-7.20 (m, 22H), 1.72 (t, 10H), 1.41 (m, 8H), 1.32 (s, 9H), 1.07(t, 10H) | 1198.50 | 1199.44 |
| BD25 | 8.69-8.57 (m, 3H), 8.42 (t, 1H), 8.21 (d, 1H), 8.01 (d, 1H), 7.74 (t, 1H), 7.54 (t, 1H), 7.47-7.04 (m, 21H), 1.66 (m, 10H), 1.32 (s, 18H), 1.14 (m, 10) | 1150.50 | 1151.40 |

Manufacture of Organic Electroluminescence Device

Organic electroluminescence devices were manufactured using Example Compounds and Comparative Example Compounds below as an emission layer material.

Example Compounds

BD1

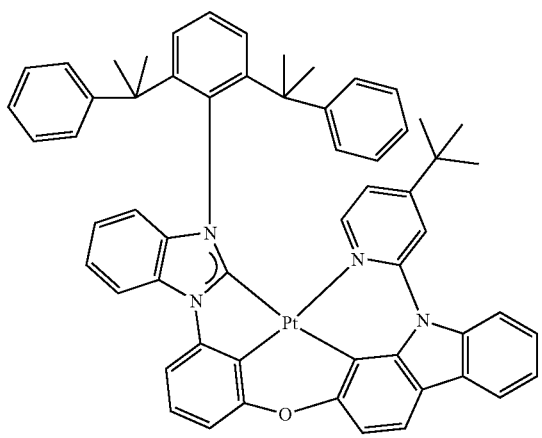

BD14

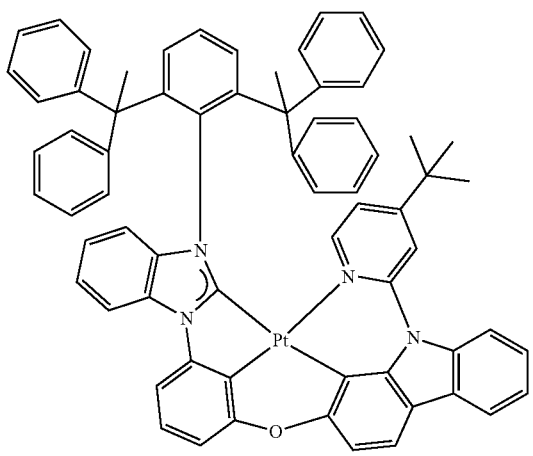

BD22

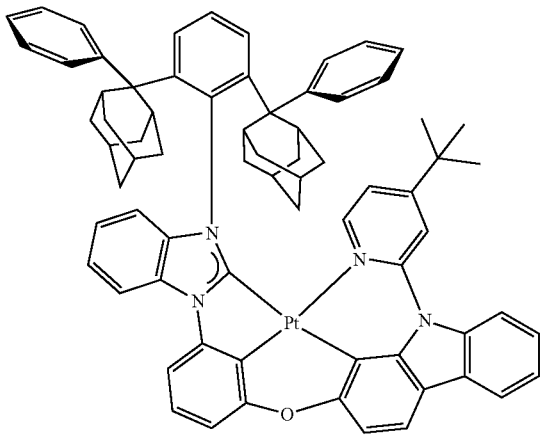

BD25

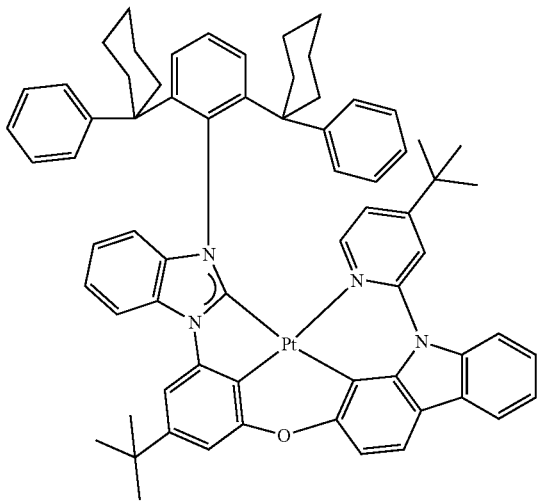

Comparative Example Compounds

A

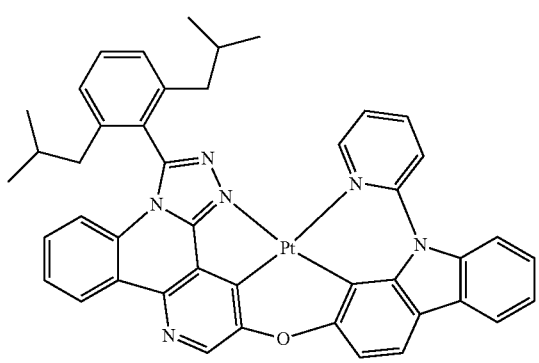

B

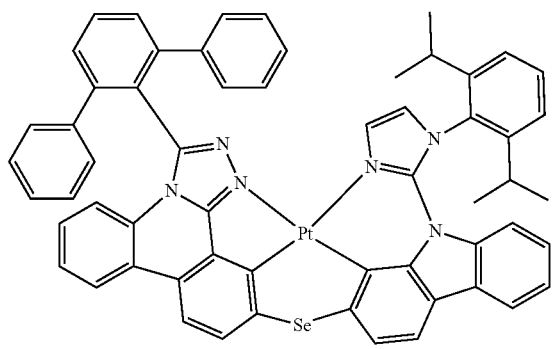

C

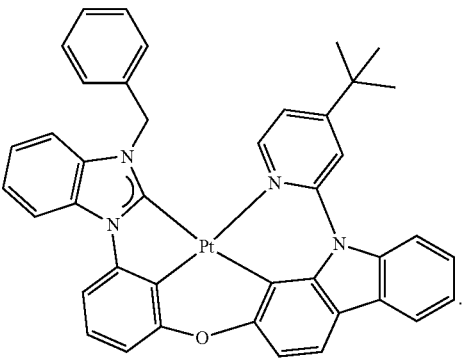

The organic electroluminescence devices of Examples and Comparative Examples were manufactured by the following method.

Example 1

A glass substrate made by Corning Co., on which an ITO electrode of about 15Ω/cm² (1200 Å) may be formed as an anode, was cut to a size of about 50 mm×50 mm×0.7 mm, cleansed by ultrasonic waves using isopropyl alcohol and pure water for about 5 minutes, and then irradiated with ultraviolet rays for about 30 minutes and exposed to ozone and cleansed. The glass substrate was installed on a vacuum deposition apparatus.

2-TNATA was deposited in vacuum on the upper portion of the ITO electrode (anode) of the glass substrate to form a 600 Å-thick hole injection layer, and 4,4'-bis[N-(1-naphthyl)-N-phenyl amino biphenyl (hereinafter, NPB) was deposited in vacuum on the upper portion of the hole injection layer to form a 300 Å-thick hole transport layer.

A dopant (Compound BD1) and a host (ETH66: HTH29=1:1) were co-deposited on the upper portion of the hole transport layer at a weight ratio of 10:90 to form a 300 Å-thick emission layer.

Diphenyl(4-(triphenylsilyl)phenyl)-phosphine oxide (TSP01) was deposited in vacuum on the upper portion of the emission layer to form a 50 Å-thick hole blocking layer, Alq₃ was deposited in vacuum on the upper portion of the hole blocking layer to form a 300 Å-thick electron transport layer, LiF was then deposited in vacuum on the upper portion of the electron transport layer to form a 10 Å-thick electron injection layer, and then Al was deposited in vacuum on the upper portion of the electron injection layer to form a 3000 Å-thick cathode, thereby manufacturing an organic electroluminescence device.

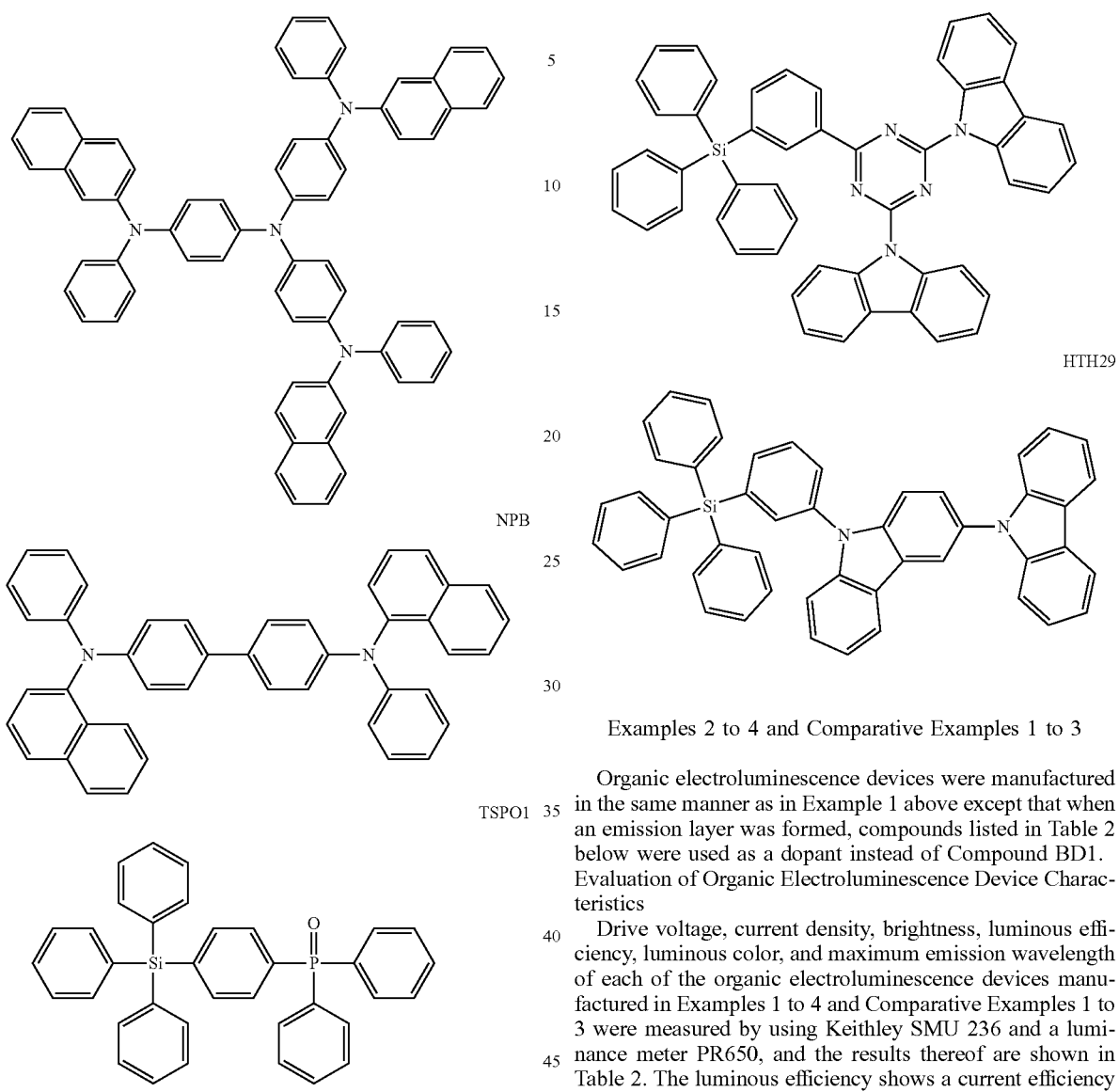

Examples 2 to 4 and Comparative Examples 1 to 3

Organic electroluminescence devices were manufactured in the same manner as in Example 1 above except that when an emission layer was formed, compounds listed in Table 2 below were used as a dopant instead of Compound BD1.

Evaluation of Organic Electroluminescence Device Characteristics

Drive voltage, current density, brightness, luminous efficiency, luminous color, and maximum emission wavelength of each of the organic electroluminescence devices manufactured in Examples 1 to 4 and Comparative Examples 1 to 3 were measured by using Keithley SMU 236 and a luminance meter PR650, and the results thereof are shown in Table 2. The luminous efficiency shows a current efficiency value with respect to a current density of 50 mA/cm$^2$.

TABLE 2

|  | Emission layer Dopant | Driving voltage (V) | Current density (mA/cm$^2$) | Brightness (cd/m$^2$) | Efficiency (cd/A) | Luminous color | Emission wavelength (nm) |
| --- | --- | --- | --- | --- | --- | --- | --- |
| Example 1 | BD1 | 3.3 | 50 | 15 | 120 | Blue | 456 |
| Example 2 | BD14 | 3.4 | 50 | 15 | 110 | Blue | 459 |
| Example 3 | BD22 | 3.2 | 50 | 15 | 96 | Blue | 461 |
| Example 4 | BD25 | 3.3 | 50 | 15 | 97 | Blue | 459 |
| Comparative Example 1 | Compound A | 4.0 | 50 | 15 | 55 | Blue | 461 |
| Comparative Example 2 | Compound B | 4.2 | 50 | 15 | 57 | Blue | 464 |
| Comparative Example 3 | Compound C | 4.0 | 50 | 15 | 30 | Blue | 450 |

Referring to the results of Table 2, it may be confirmed that Examples of the organic luminescence device using the organometallic compound according to embodiments of the present disclosure as an emission layer material exhibit low drive voltages and relatively high luminous efficiencies compared to Comparative Examples.

The organometallic compound represented by Formula 1 according to one or more embodiments of the present disclosure may include the group represented by Formula 2 in a particular position, thereby causing an electronic control effect and a steric hindrance effect at the same time, and thus when the organometallic compound is utilized as an emission layer dopant of the organic electroluminescence device, high luminous efficiency and blue light with high color purity may be achieved.

The group represented by Formula 2 may include a substituent having an electron donor property between $Ar_1$ and $Ar_2$ and between $Ar_2$ and $Ar_3$. The group represented by Formula 2 having such a structure may be located at a part corresponding to LUMO of the organometallic compound of one or more embodiments, thereby increasing a LUMO energy level to have a wide energy band-gap, and thus deep blue light may be provided. Also, Formula 2 may exhibit a steric hindrance characteristic by including a substituent between $Ar_1$ and $Ar_2$ and between $Ar_2$ and $Ar_3$. Accordingly, because out-of-plane distortions may be induced in the organometallic compound, excimer or exciplex formation caused by the intermolecular interaction may be suppressed, and thus blue light with high color purity may be achieved. In one or more embodiments, because the intermolecular interaction may be reduced due to the steric hindrance characteristic, the exciton quenching phenomenon caused by the intermolecular stacking may be suppressed, and thus a luminous efficiency characteristic may be also improved.

It may be confirmed that Comparative Example 1 may include a phenyl group, at which an alkyl group having an electron donor property may be substituted, at the ortho-position as a terminal substituent of a ligand, and thus may be further blue-shifted than Comparative Example 2, but the steric hindrance characteristic may be reduced compared to Examples, thereby reducing luminous efficiency. Comparative Example 2 may include three phenyl groups as a terminal substituent of a ligand, but does not further include a substituent having an electron donor property, and thus the emission wavelength may be red-shifted compared to Examples, and because the steric hindrance characteristic may be relatively weaker than Examples, luminous efficiency may be also reduced. For Comparative Example 3, a substituent having an electron donor property may be directly substituted to a ligand and thus blue-shifted, but because Comparative Example 3 does not further include a substituent having a steric hindrance characteristic, luminous efficiency may be significantly reduced compared to Examples.

The organic electroluminescence device of one or more embodiments may include an organometallic compound in the emission layer, thereby improving luminous efficiency and service life characteristics of the organic electroluminescence device.

The organometallic compound of one or more embodiments may improve luminous efficiency and service life characteristics of the organic electroluminescence device.

Although the embodiments of the present disclosure are described, those with ordinary skill in the technical field to which the present disclosure pertains will understood that the present disclosure may be carried out in other specific forms without changing the technical idea or essential features. Therefore, the above-described embodiments are to be understood in all aspects as illustrative and not restrictive and modifications can be made by one ordinary skilled in the art within the spirit and scope of the present disclosure as hereinafter claimed by the following claims and equivalents thereof.

What is claimed is:

1. An organic electroluminescence device comprising:
   a first electrode;
   a hole transport region on the first electrode;
   an emission layer on the hole transport region;
   an electron transport region on the emission layer; and
   a second electrode on the electron transport region,
   wherein the emission layer comprises an organometallic compound represented by Formula 1:

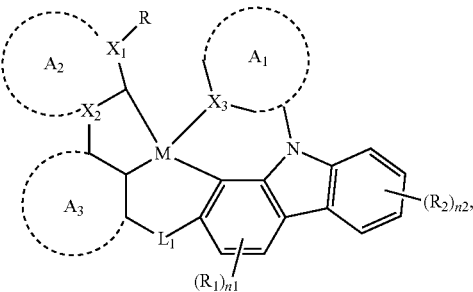

Formula 1 wherein, in Formula 1,
M is Pt, Pd, Ni, Au, Ag, Be, Mg, Al, Ca, Ti, Mn, Co, Zn, Ga, Zr, Ru, Rh, or Cu,
$L_1$ is $CR_3R_4$, $NR_5$, O, $SiR_6R_7$, $BR_8$, or $PR_9$,
$X_1$ to $X_3$ are each independently $CR_{10}$ or N,
ring $A_1$ to ring As are each independently a substituted or unsubstituted monocyclic or polycyclic hydrocarbon ring group having 6 to 30 ring-forming carbon atoms, or a substituted or unsubstituted monocyclic or polycyclic heterocyclic group having 2 to 30 ring-forming carbon atoms,
$R_1$ to $R_{10}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
n1 is an integer of 0 to 2,
n2 is an integer of 0 to 4, and
R is represented by Formula 2:

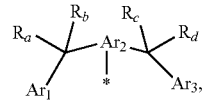

Formula 2 and
wherein, in Formula 2,
$Ar_1$ and $Ar_3$ are each independently a substituted or unsubstituted aryl group having 6 to 30 ring-forming carbon atoms, or a substituted or unsubstituted heteroaryl group having 2 to 30 ring-forming carbon atoms, Ar₂ is a substituted or unsubstituted trivalent aryl group having 6 to 30 ring-forming carbon atoms, or a substituted or unsubstituted trivalent heteroaryl group having 2 to 30 ring-forming carbon atoms, $R_a$ to $R_d$ are each independently a substituted or unsubstituted amine group, a substituted or unsubstituted alkoxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or $R_a$ and $R_b$ are bonded to each other to form a ring and/or $R_c$ and $R_d$ are bonded to each other to form a ring, provided that, when Ar₂ is a trivalent phenyl group not substituted with any additional substituents, then $R_a$ to $R_d$ are not all methyl groups at the same time, and "—*" is the bonding position with Formula 1.

2. The organic electroluminescence device of claim 1, wherein the emission layer is to emit phosphorescence.

3. The organic electroluminescence device of claim 1, wherein the emission layer comprises a host and a dopant, and the dopant comprises an organometallic compound represented by Formula 1.

4. The organic electroluminescence device of claim 1, wherein Formula 2 is represented by Formula 2-1 or Formula 2-2:

Formula 2-1

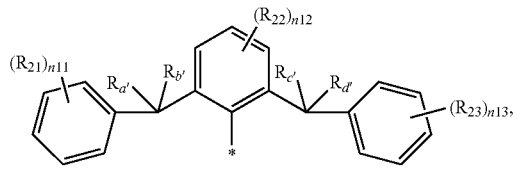

Formula 2-2

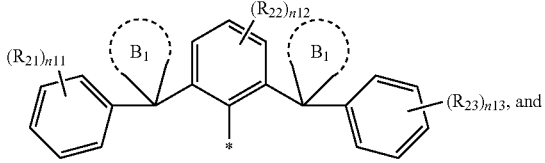

and wherein, in Formula 2-1 and Formula 2-2, $R_{21}$ to $R_{23}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, $R_{a'}$ to $R_{d'}$ are each independently a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, provided that, when n12 is 0, then $R_{a'}$ to $R_{d'}$ are not all methyl groups at the same time, ring B₁ and ring B₂ are each independently a substituted or unsubstituted cycloalkyl having 3 to 20 carbon atoms, a substituted or unsubstituted hetero cycloalkyl having 2 to 20 carbon atoms, a substituted or unsubstituted bicycloalkyl having 4 to 20 carbon atoms, a substituted or unsubstituted hetero bicycloalkyl having 3 to 20 carbon atoms, a substituted or unsubstituted tricycloalkyl having 6 to 20 carbon atoms, or a substituted or unsubstituted hetero tricycloalkyl having 5 to 20 carbon atoms, n11 and n13 are each independently an integer of 0 to 5, and n12 is an integer of 0 to 3.

5. The organic electroluminescence device of claim 4, wherein ring B₁ and ring B₂ are each independently represented by any one among Formula 3-1 to Formula 3-5:

Formula 3-1

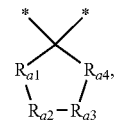

Formula 3-2

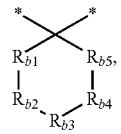

Formula 3-3

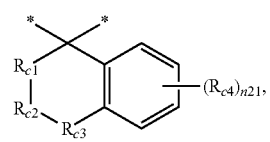

Formula 3-4

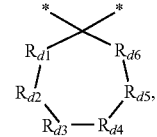

Formula 3-5

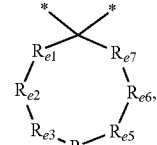

and wherein, in Formula 3-1 to Formula 3-5, $R_{a1}$ to $R_{a4}$, $R_{b1}$ to $R_{b5}$, $R_{c1}$ to $R_{c3}$, $R_{d1}$ to $R_{d6}$, and $R_{e1}$ to $R_{e7}$ are each independently $CR_{31}R_{32}$, or $NR_{33}$, $R_{31}$ to $R_{32}$ are each independently a hydrogen atom, a deuterium atom, a halogen atom, a substituted or unsubstituted alkyl group having 1 to 30 carbon atoms, a substituted or unsubstituted amine group, a substituted or unsubstituted aryl group having 6 to 30 ring-forming carbon atoms, or a substituted or unsubstituted heteroaryl group having 2 to 30 ring-forming carbon atoms, $R_{33}$ and $R_{c4}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, at least any two groups among $R_{a1}$ to $R_{a4}$, at least any two groups among $R_{b1}$ to $R_{b5}$, at least any two groups among $R_{c1}$ to $R_{c3}$, at least any two groups among $R_{d1}$ to $R_{d6}$, or at least any two groups among $R_{e1}$ to $R_{e7}$ are bonded to each other to form bicycloalkyl, hetero bicycloalkyl, tricycloalkyl, or hetero tricycloalkyl, and n21 is an integer of 0 to 4.

6. The organic electroluminescence device of claim 1, wherein Formula 1 is represented by Formula 4:

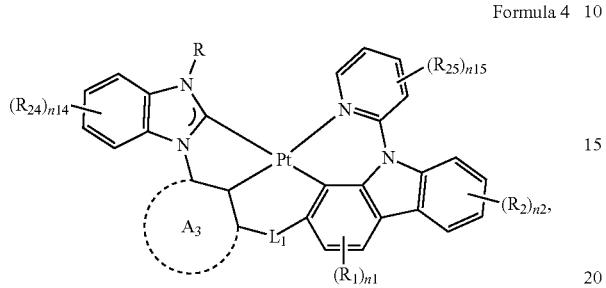

Formula 4 and
wherein, in Formula 4,
$R_{24}$ and $R_{25}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
n14 and n15 are each independently an integer of 0 to 4, and
$L_1$, ring $A_3$, R, $R_1$, $R_2$, n1, and n2 are the same as defined in Formula 1.

7. The organic electroluminescence device of claim 6, wherein Formula 4 is represented by Formula 5:

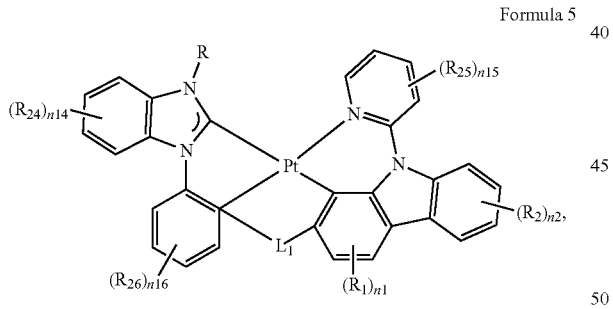

Formula 5 and
wherein, in Formula 5,
$R_{26}$ is a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
n16 is an integer of 0 to 3, and
$L_1$, R, $R_1$, $R_2$, n1, n2, $R_{24}$, $R_{25}$, n14, and n15 are the same as defined in Formula 4.

8. An organic electroluminescence device comprising:
a first electrode;
a hole transport region on the first electrode;
an emission layer on the hole transport region;
an electron transport region on the emission layer; and
a second electrode on the electron transport region,
wherein the emission layer comprises a host and a dopant,
the dopant comprises an organometallic compound represented by Formula 1, and
the host comprises:
a first host represented by Formula 6; and
a second host represented by Formula 7:

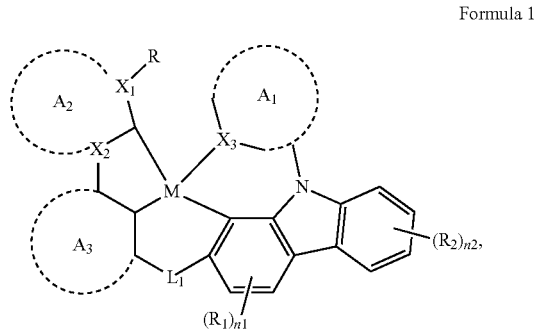

Formula 1 wherein, in Formula 1,
M is Pt, Pd, Ni, Au, Ag, Be, Mg, Al, Ca, Ti, Mn, Co, Zn, Ga, Zr, Ru, Rh, or Cu,
$L_1$ is $CR_3R_4$, $NR_5$, O, $SiR_6R_7$, $BR_8$, or $PR_9$,
$X_1$ to $X_3$ are each independently $CR_{10}$ or N,
ring $A_1$ to ring $A_5$ are each independently a substituted or unsubstituted monocyclic or polycyclic hydrocarbon ring group having 6 to 30 ring-forming carbon atoms, or a substituted or unsubstituted monocyclic or polycyclic heterocyclic group having 2 to 30 ring-forming carbon atoms,
$R_1$ to $R_{10}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
n1 is an integer of 0 to 2,
n2 is an integer of 0 to 4, and
R is represented by Formula 2:

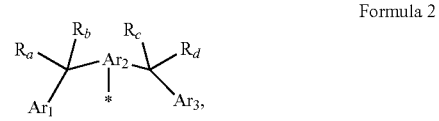

Formula 2 and
wherein, in Formula 2,
$Ar_1$ and $Ar_3$ are each independently a substituted or unsubstituted aryl group having 6 to 30 ring-forming carbon atoms, or a substituted or unsubstituted heteroaryl group having 2 to 30 ring-forming carbon atoms,
$Ar_2$ is a substituted or unsubstituted trivalent aryl group having 6 to 30 ring-forming carbon atoms, or a substituted or unsubstituted trivalent heteroaryl group having 2 to 30 ring-forming carbon atoms,
$R_a$ to $R_d$ are each independently a substituted or unsubstituted amine group, a substituted or unsubstituted alkoxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or $R_a$ and $R_b$ are bonded to each other to form a ring and/or $R_c$ and $R_d$ are bonded to each other to form a ring, and "—*" is the bonding position with Formula 1,

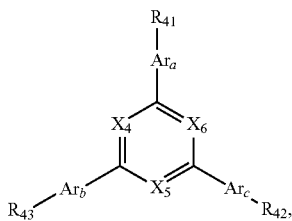

Formula 6 wherein, in Formula 6, $X_4$ and $X_6$ are each independently N, or $CR_{44}$, wherein, at least one among $X_4$ to $X_6$ is N, $Ar_a$ to $Ar_c$ are each independently a direct linkage, a substituted or unsubstituted arylene group having 6 to 30 ring-forming carbon atoms, or a substituted or unsubstituted heteroarylene group having 2 to 30 ring-forming carbon atoms, or are bonded to an adjacent group to form a ring, $R_{41}$ to $R_{43}$ are each independently a hydrogen atom, a deuterium atom, a halogen atom, a substituted or unsubstituted silyl group, a substituted or unsubstituted oxy group, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, $R_{44}$ is a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,

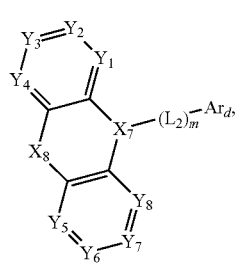

Formula 7 and wherein, in Formula 7, $Y_1$ to $Y_8$ are each independently $CR_{51}$ or N, $X_7$ is N or $CR_{52}$, $X_8$ is a direct linkage, $SiR_{53}R_{54}$, or $CR_{55}R_{56}$, $R_{51}$ is a hydrogen atom, a deuterium atom, a halogen atom, a cyano group, a substituted or unsubstituted silyl group, a substituted or unsubstituted oxy group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or is bonded to an adjacent group to form a ring, $R_{52}$ to $R_{56}$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, $L_2$ is a direct linkage, a substituted or unsubstituted arylene group having 6 to 30 ring-forming carbon atoms, or a substituted or unsubstituted heteroarylene group having 2 to 30 ring-forming carbon atoms, and/or is bonded to an adjacent group to form a ring, $Ar_d$ is a substituted or unsubstituted silyl group, a substituted or unsubstituted phosphine oxide group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or is bonded to an adjacent group to form a ring, and m is an integer of 0 to 2.

9. The organic electroluminescence device of claim 3, wherein the emission layer further comprises a thermally activated delayed fluorescence dopant, and the thermally activated delayed fluorescence dopant is represented by Formula 8:

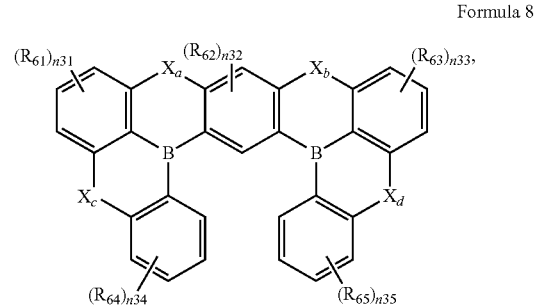

Formula 8 and wherein, in Formula 8, $X_a$ to $X_d$ are each independently $NR_{66}$, O, or S, $R_{61}$ to $R_{65}$ are each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or are bonded to an adjacent group to form a ring, $R_{66}$ is a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or is bonded to an adjacent group to form a ring, n31 and n33 are each independently an integer of 0 to 3, n32 is an integer of 0 to 2, and n34 and n35 are each independently an integer of 0 to 4.

10. The organic electroluminescence device of claim 1, wherein the organometallic compound represented by Formula 1 is any one among compounds represented by Compound Group 1:
Compound Group 1
BD2
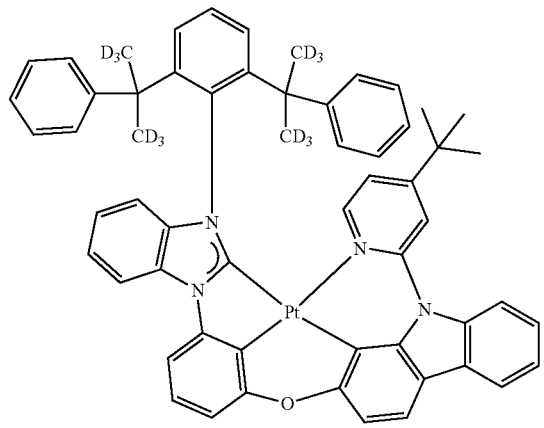
BD3
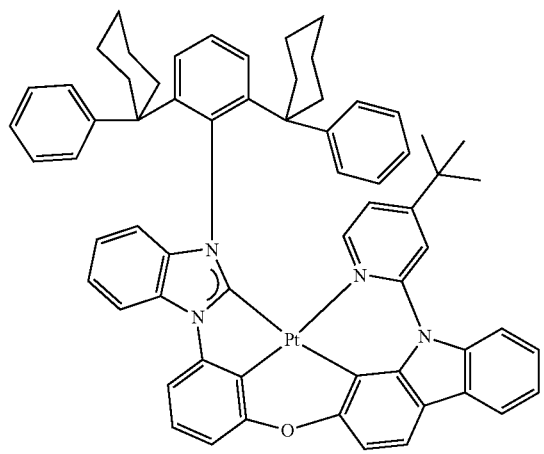
BD4
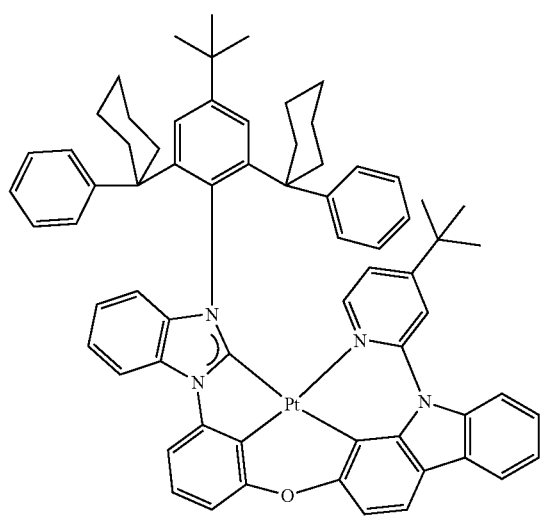
-continued
BD5
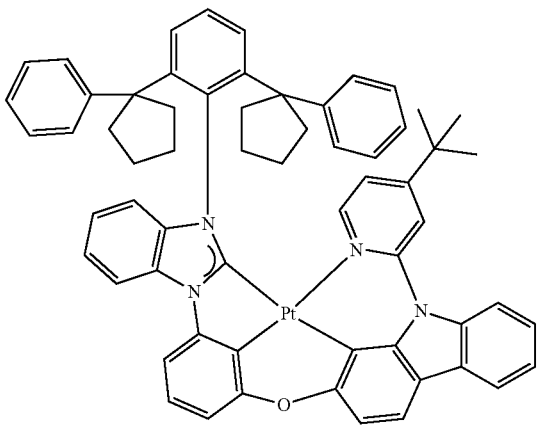
BD6
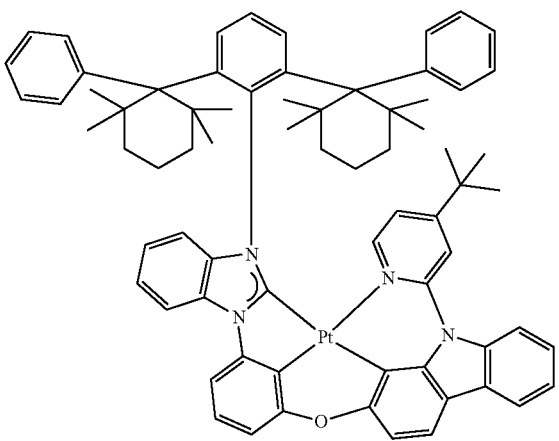
BD7
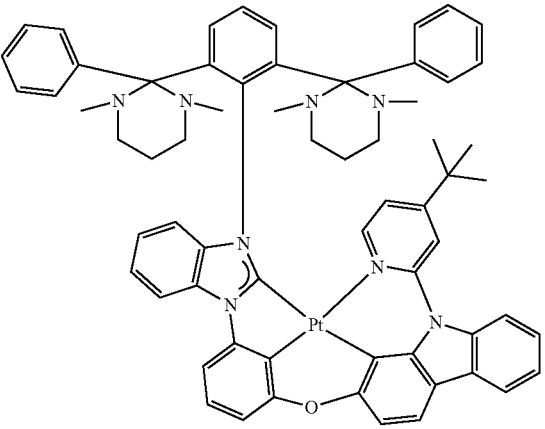

BD8
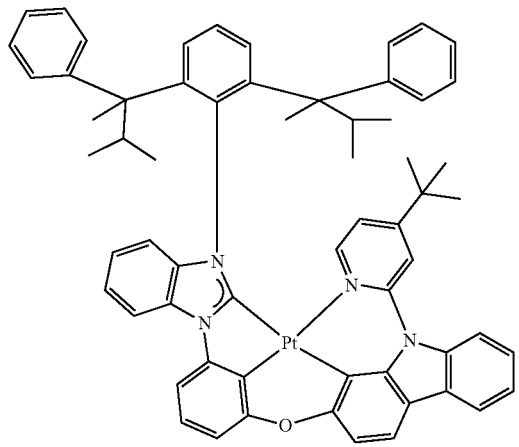
BD11
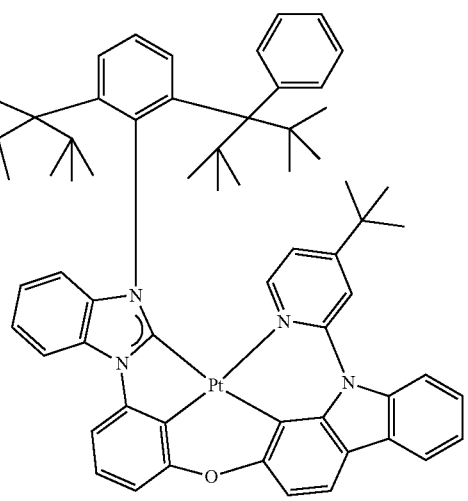
BD9
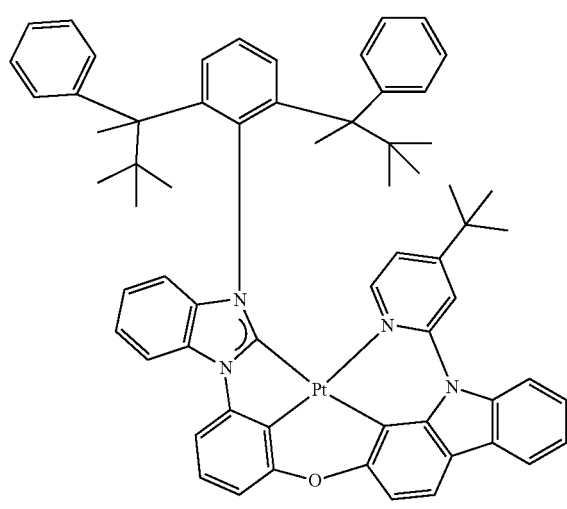
BD12
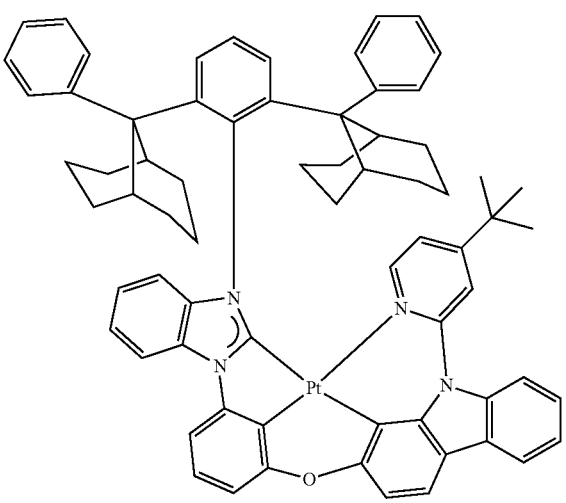
BD10
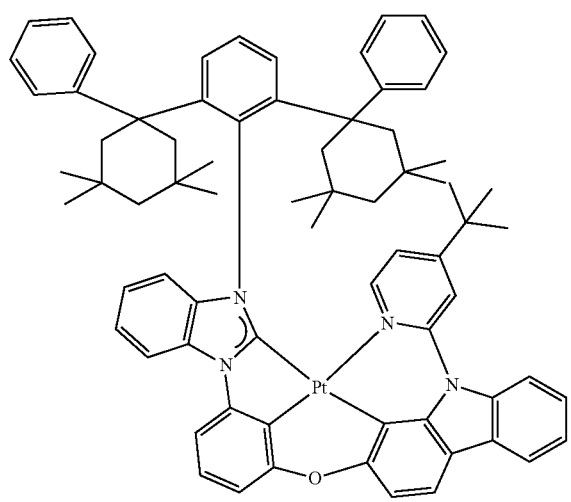
BD13
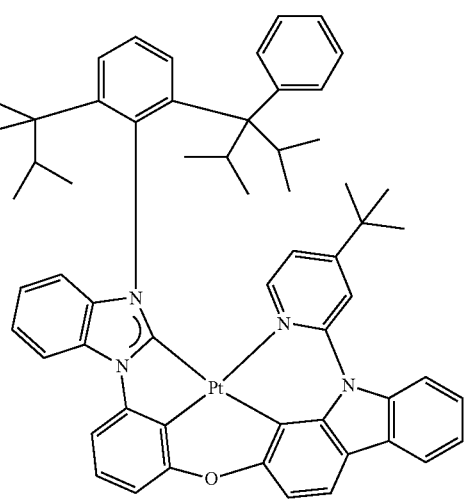

BD14
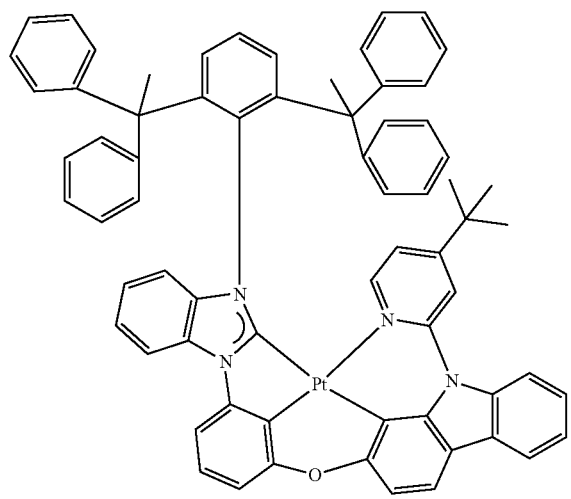
BD17
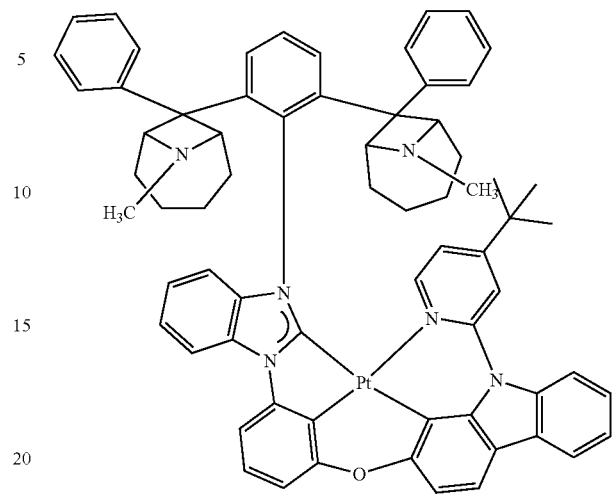
BD15
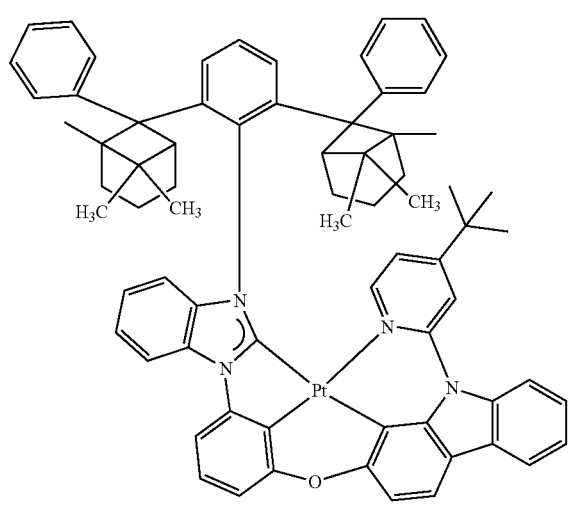
BD18
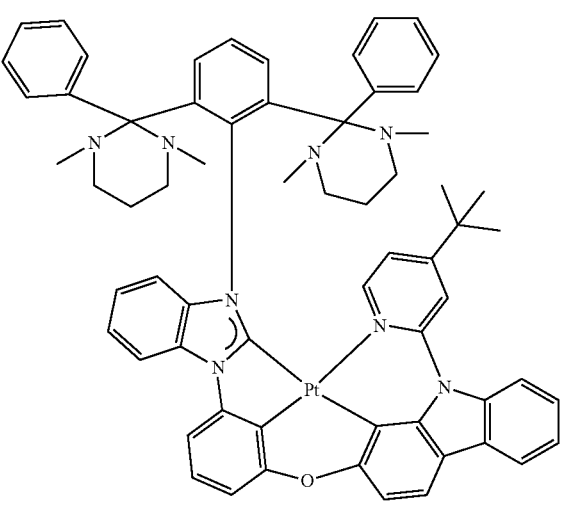
BD16
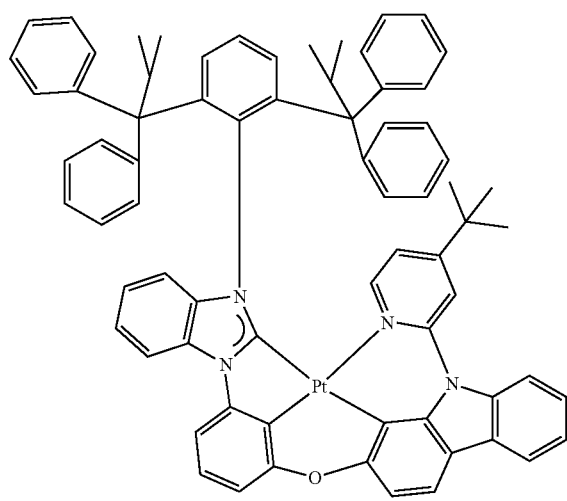
BD19
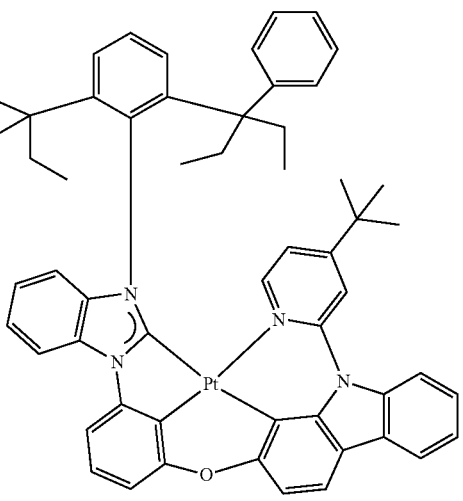

BD20
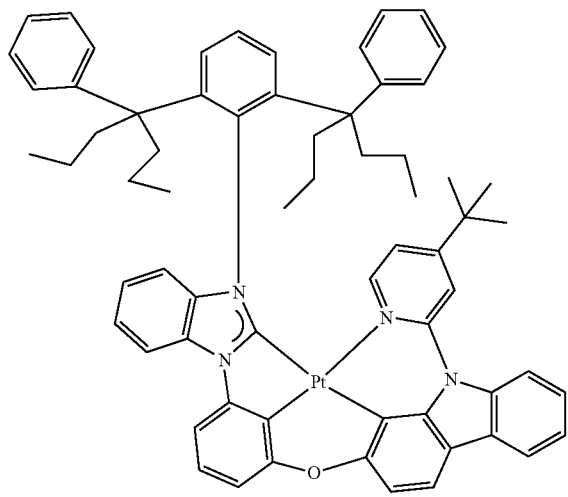
BD24
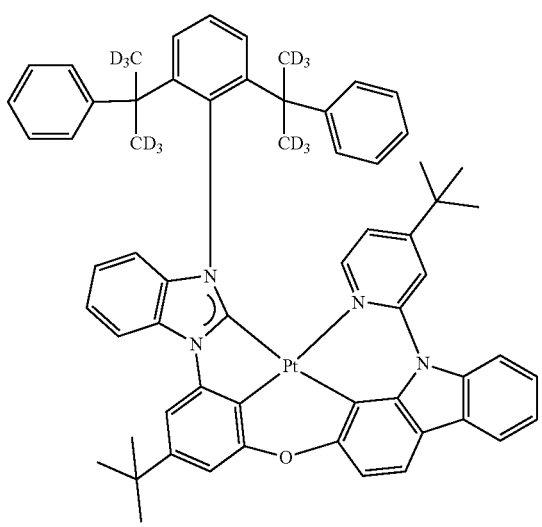
BD21
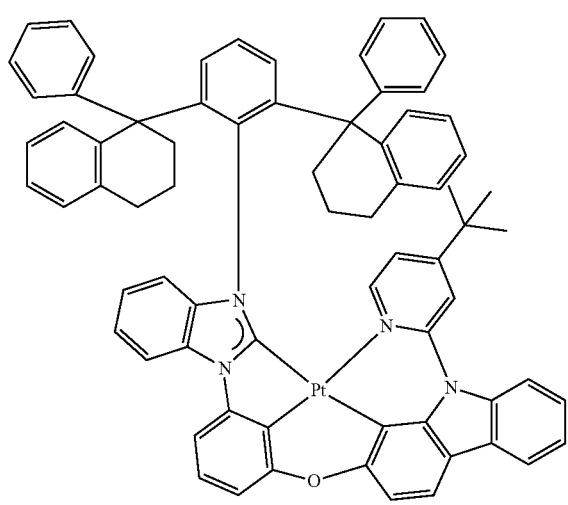
BD25
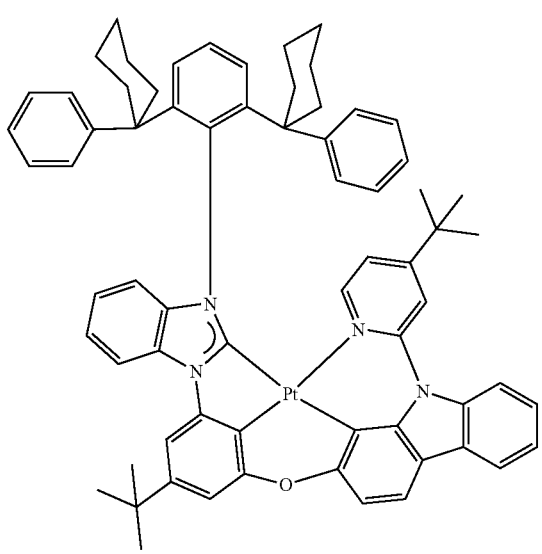
BD22
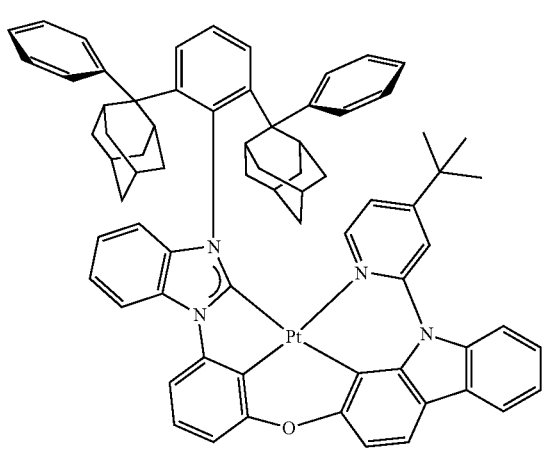
BD26
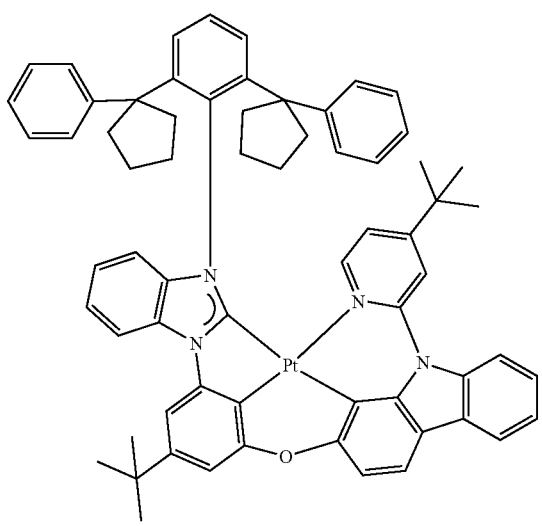

-continued
BD27
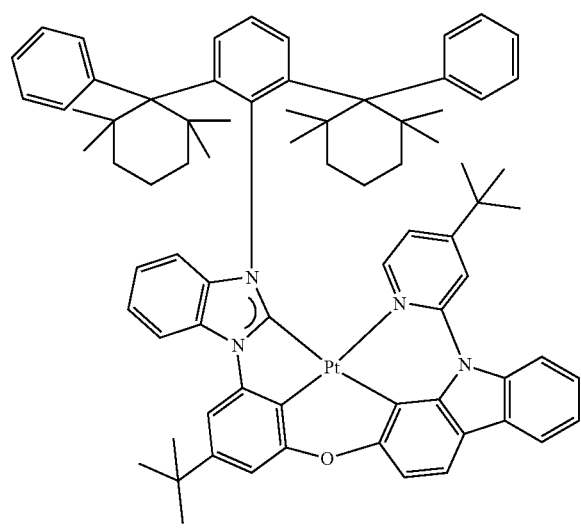
BD28
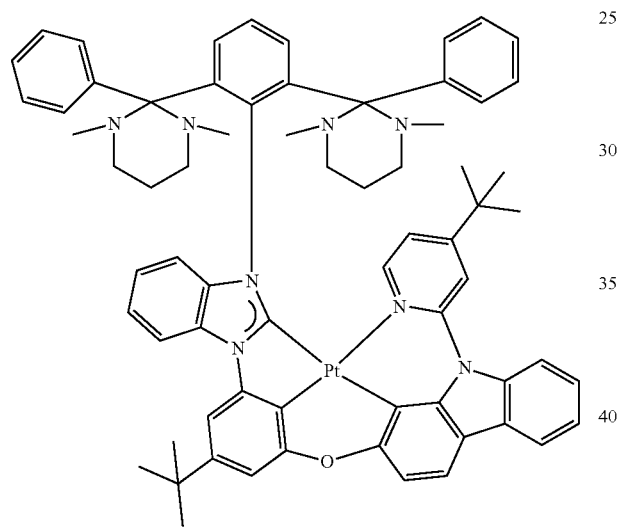
BD29
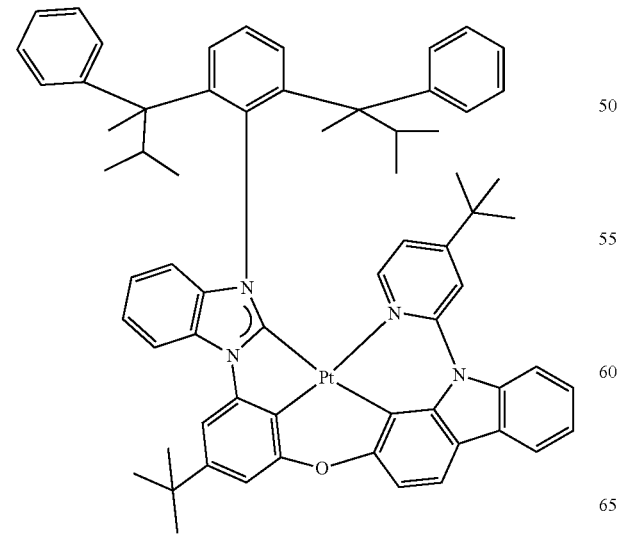
-continued
BD30
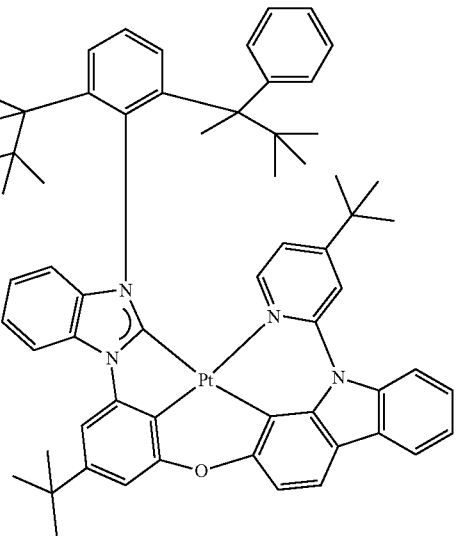
BD31
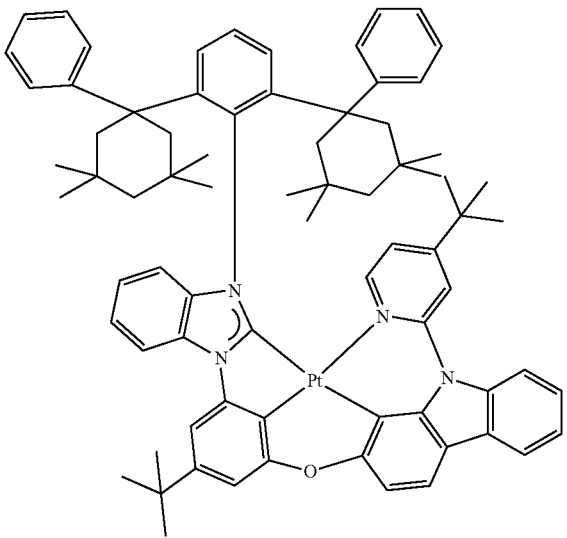

BD32
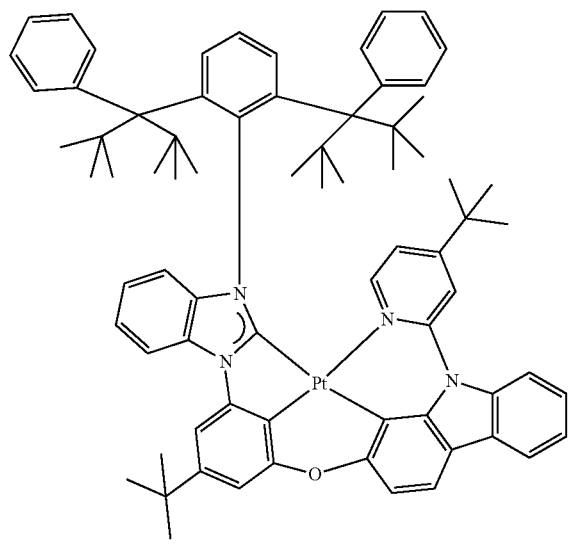
BD34
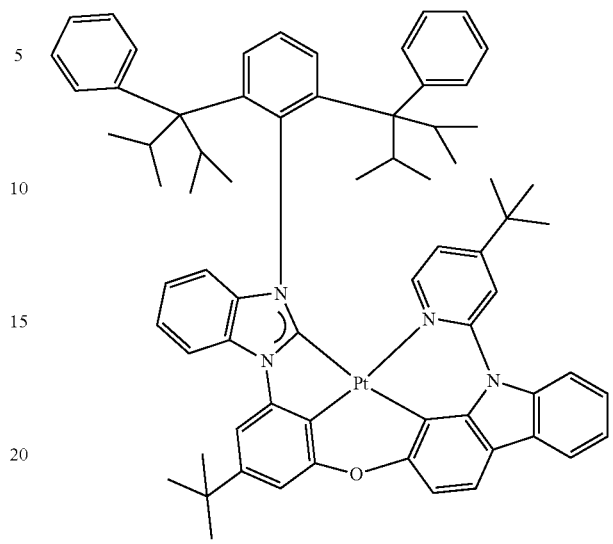
BD33
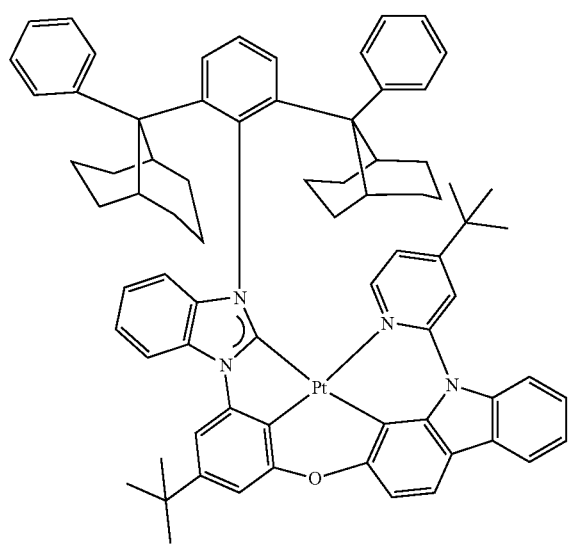
BD35
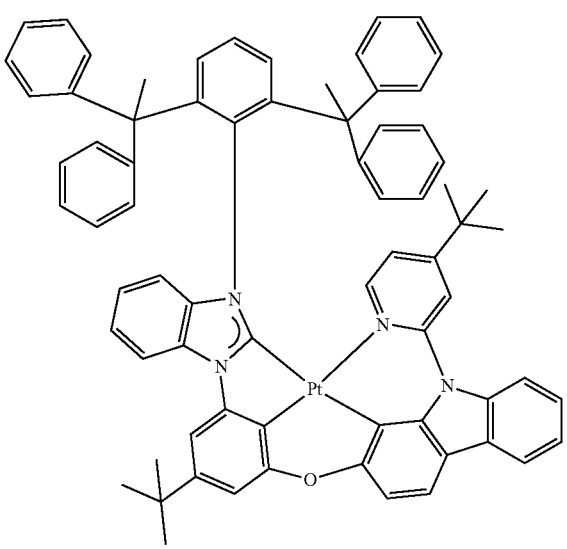

BD36
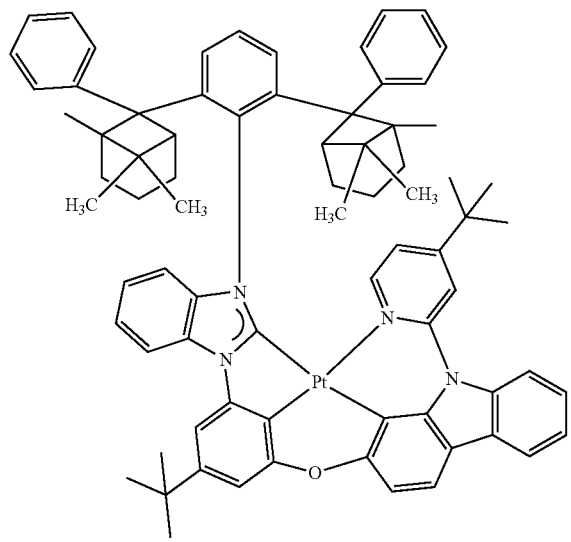
BD38
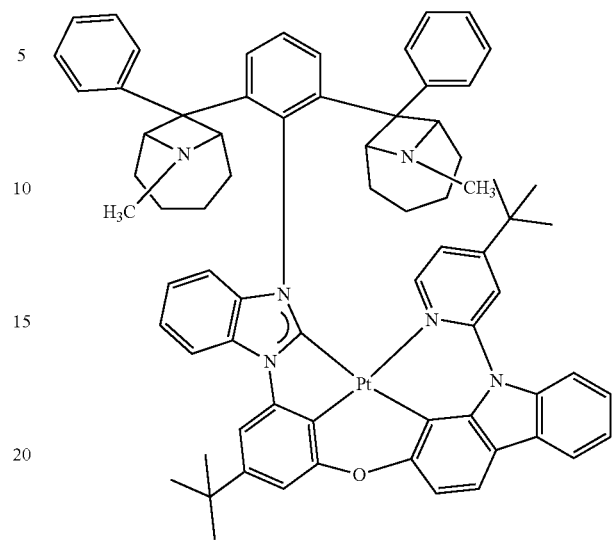
BD37
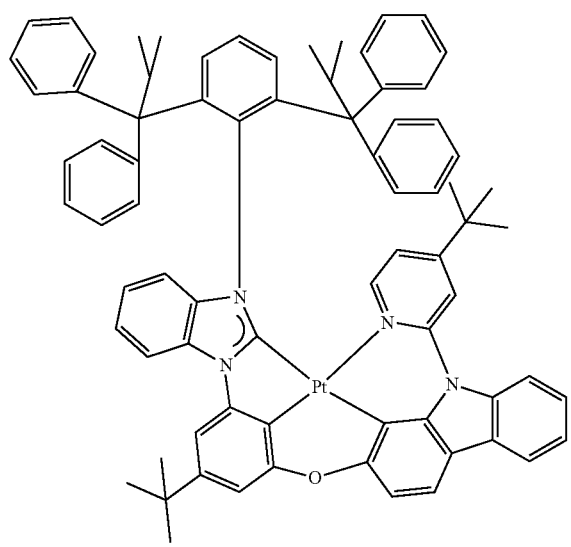
BD39
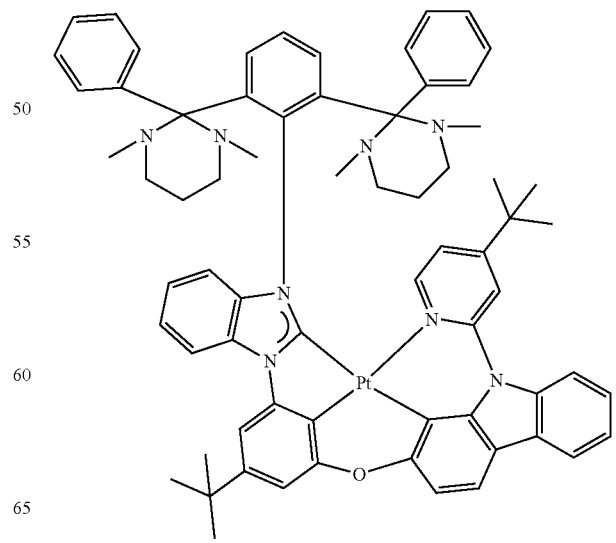

BD40
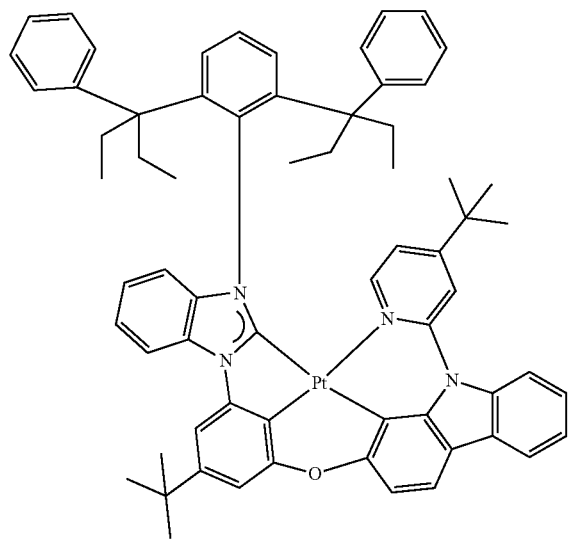
BD43
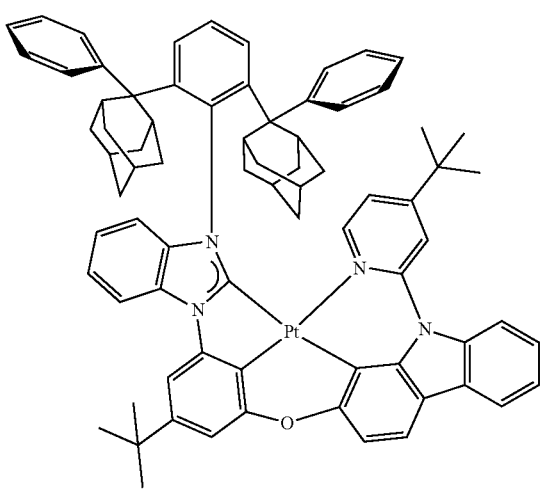
BD41
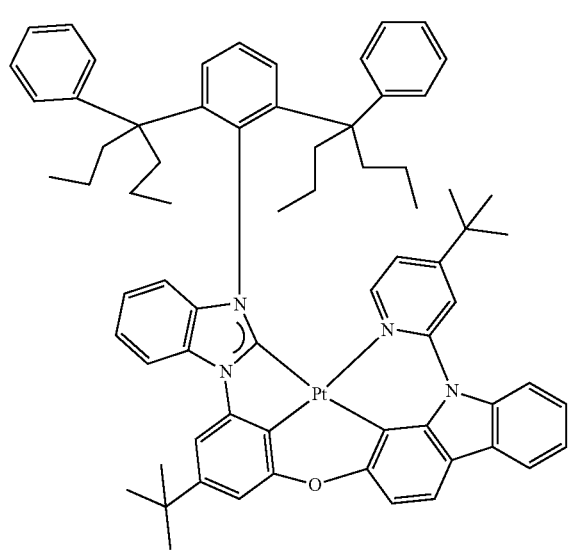
BD44
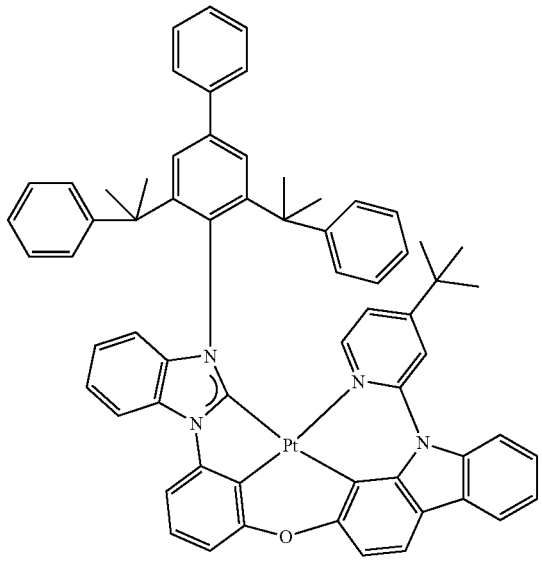
BD42
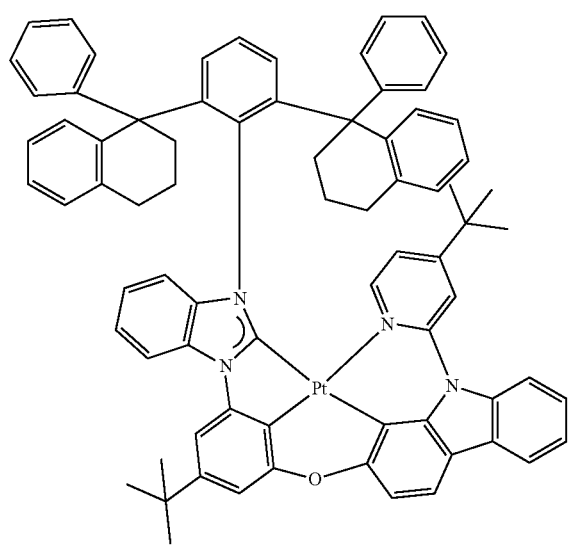
BD45
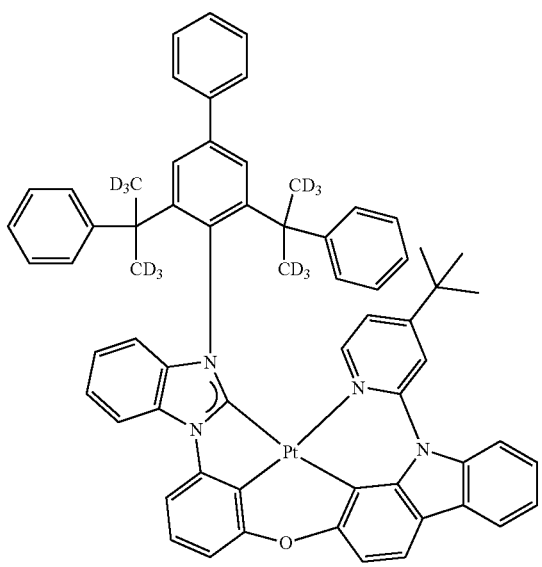

BD46
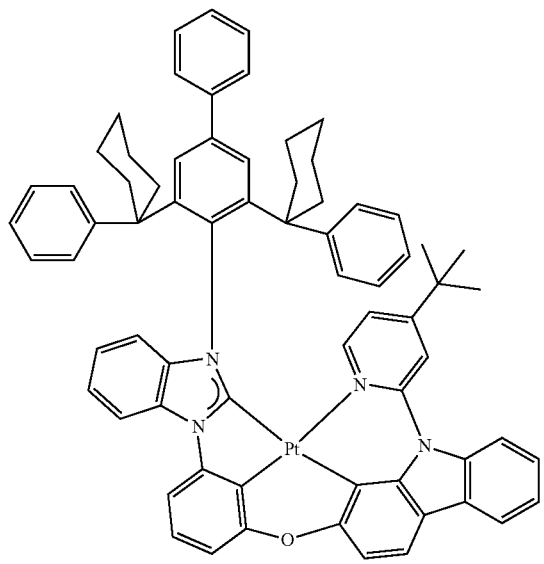
BD48
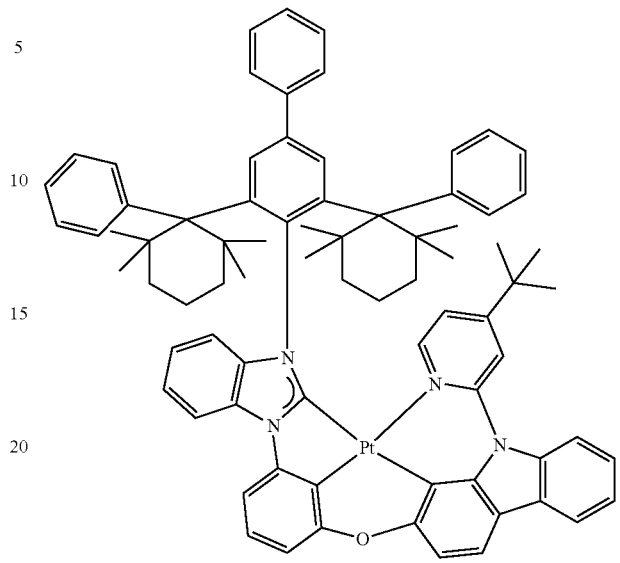
BD47
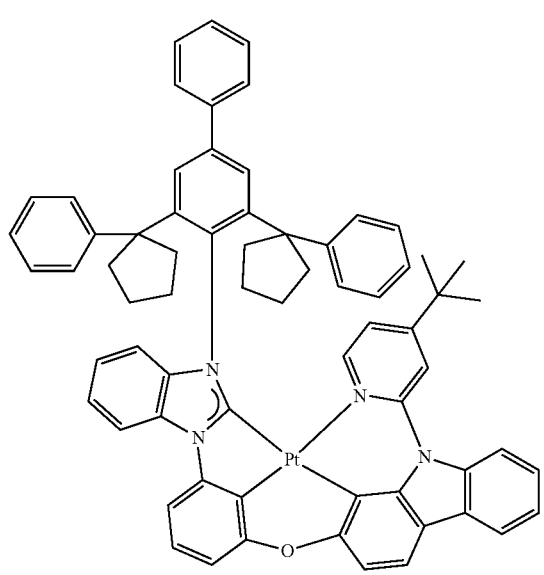
BD49
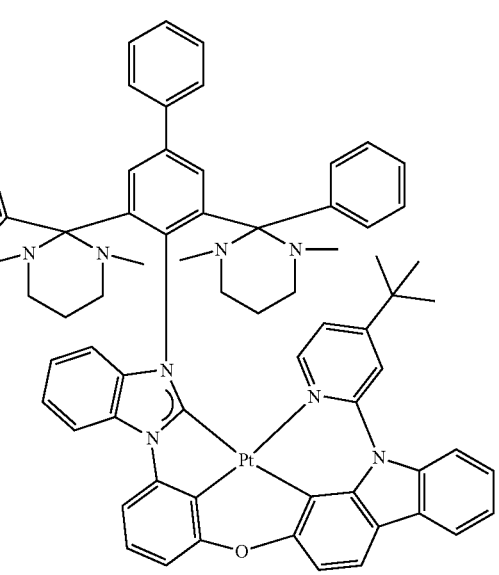

BD50
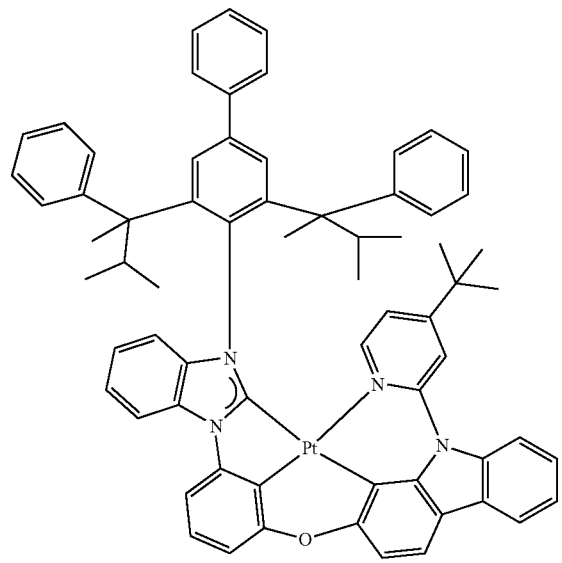
BD52
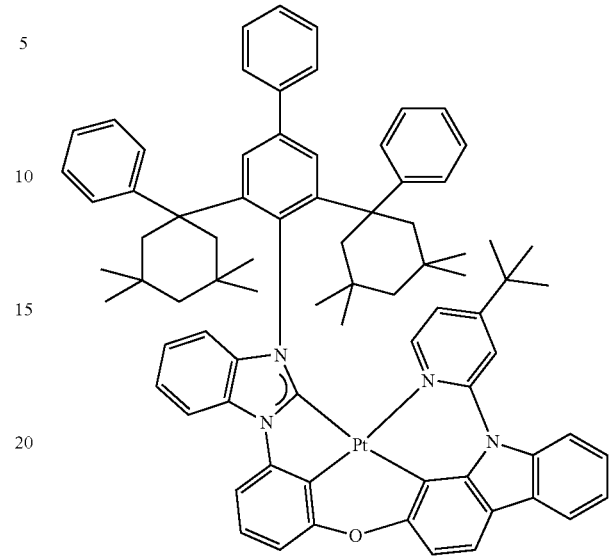
BD51
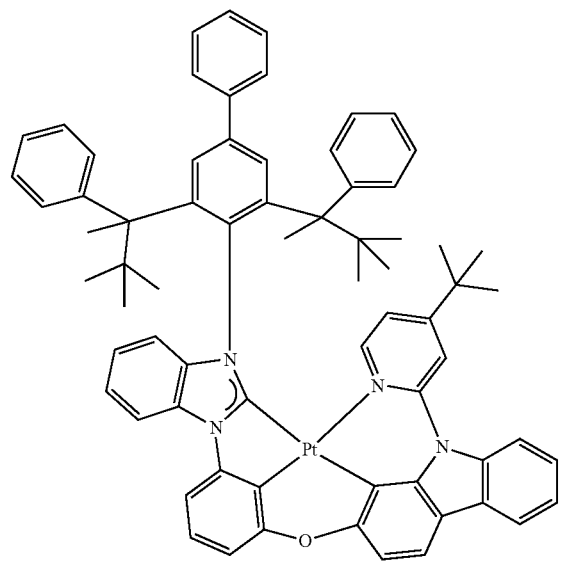
BD53
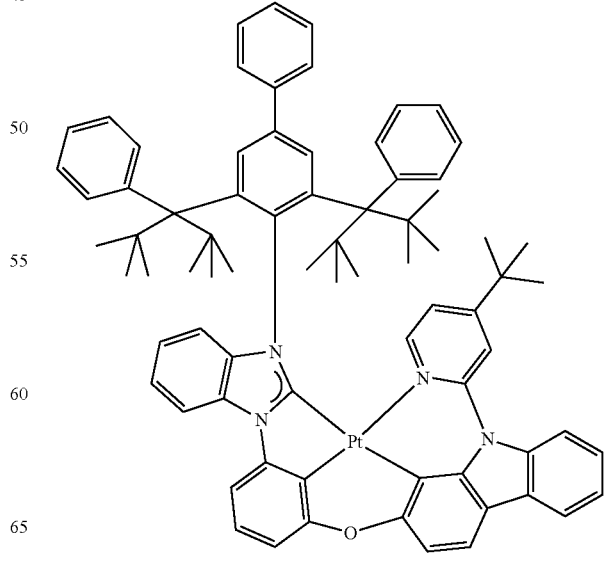

-continued
BD54
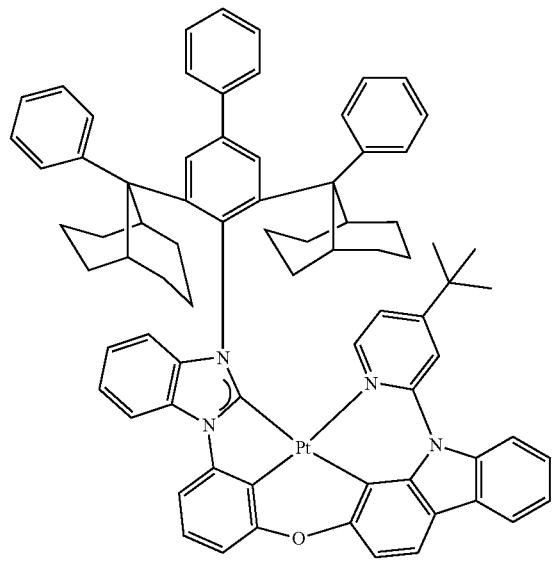
BD56
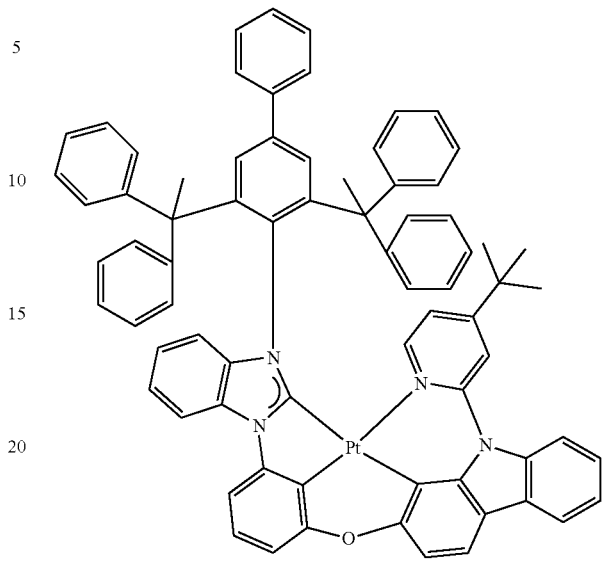
BD55
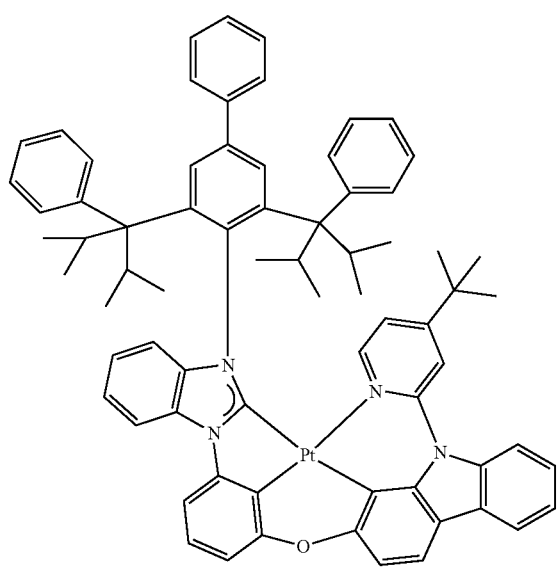
BD57
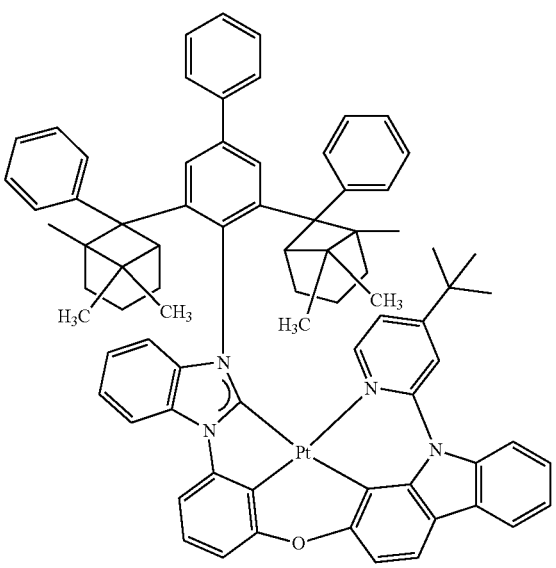

BD58
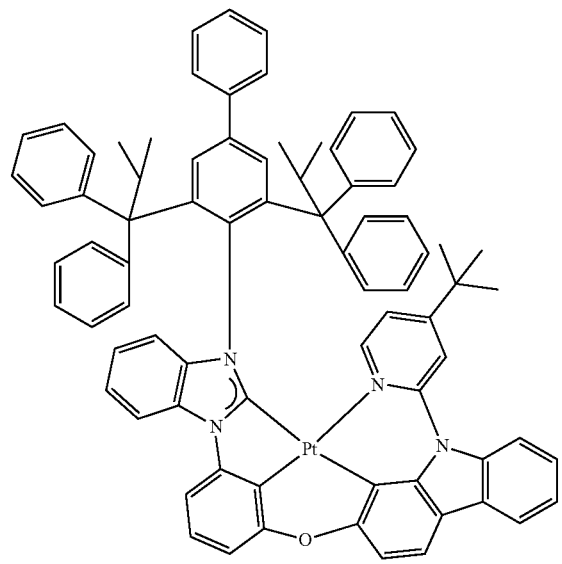
BD60
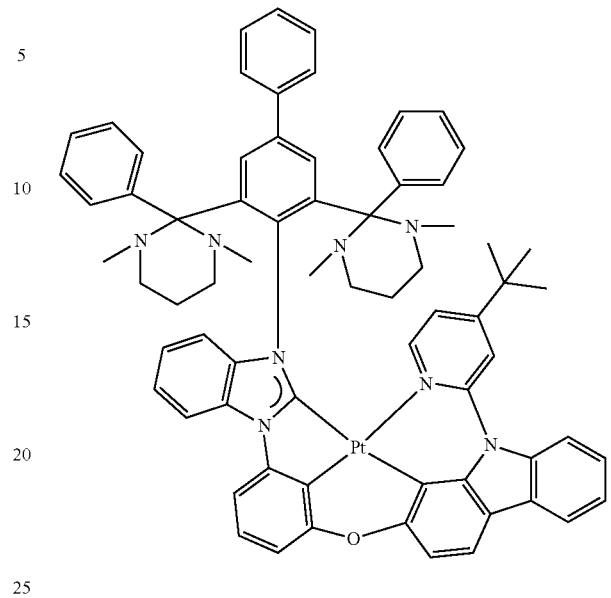
BD59
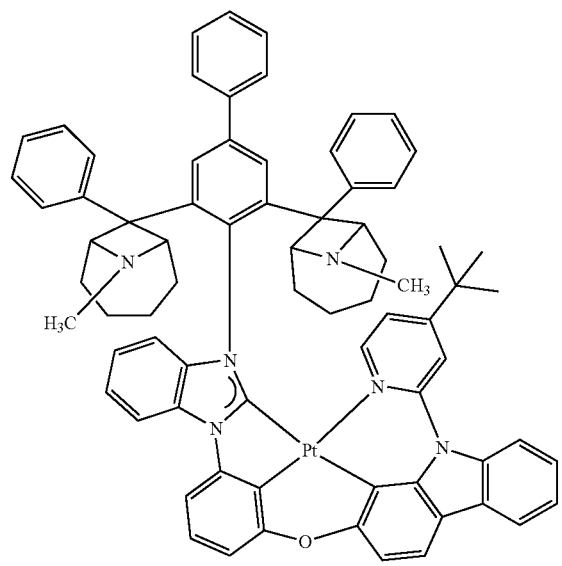
BD61
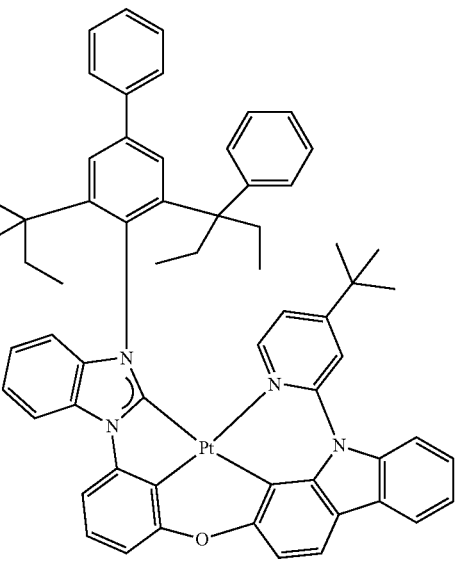

11. The organic electroluminescence device of claim 8, wherein the first host represented by Formula 6 is any one among compounds represented by Compound Group 2:
Compound Group 2
ETH1
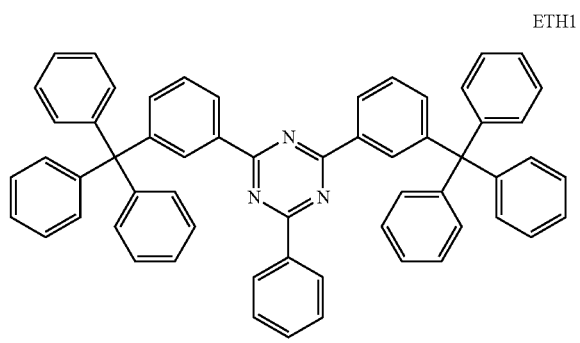
ETH2
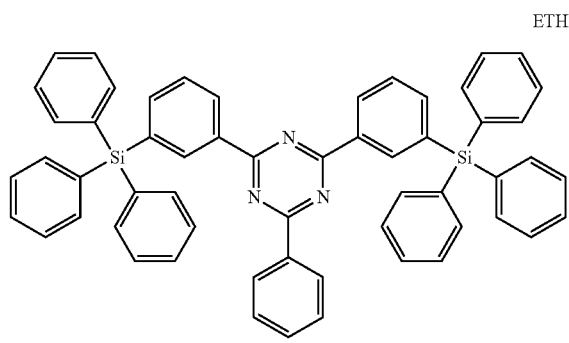
ETH3
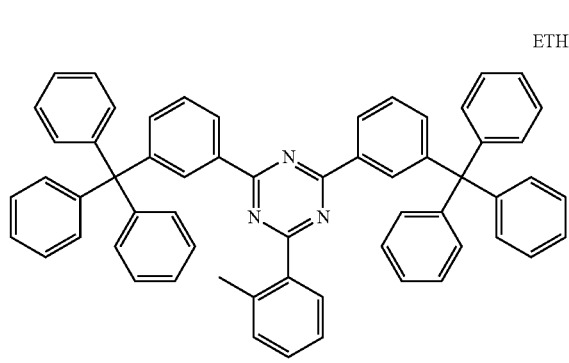
ETH4
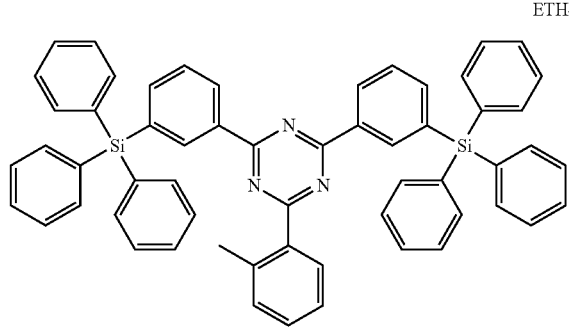
-continued
ETH5
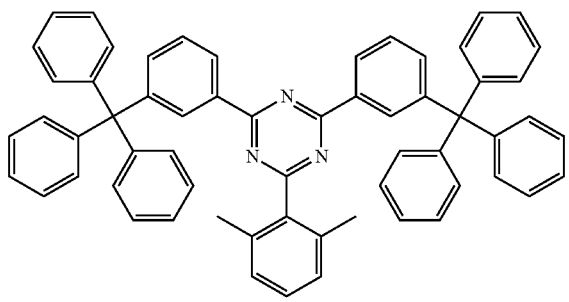
ETH6
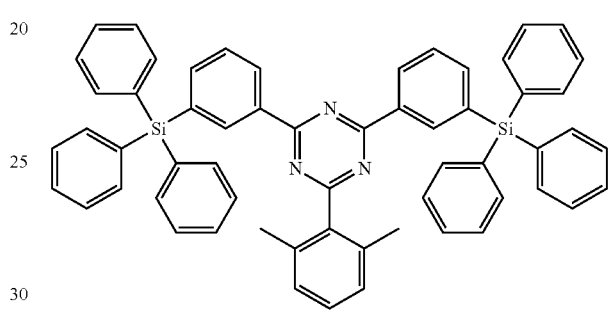
ETH7
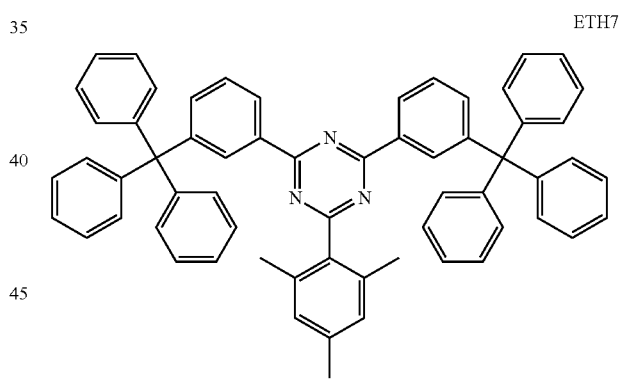
ETH8
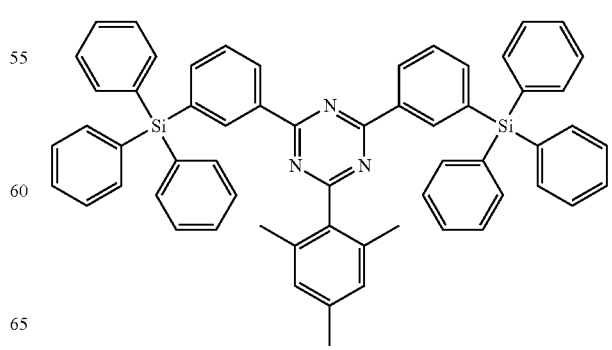

ETH9
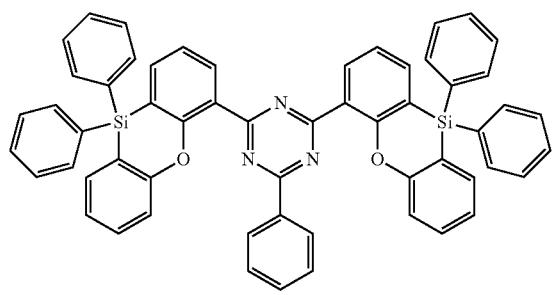
ETH10
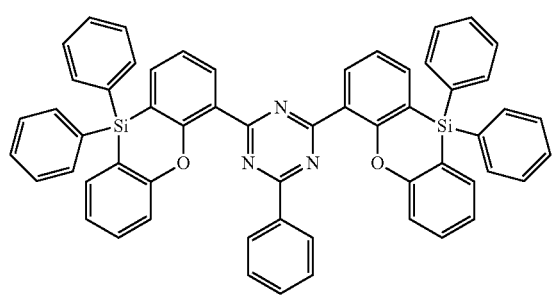
ETH11
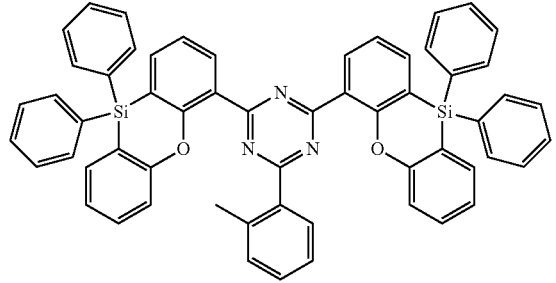
ETH12
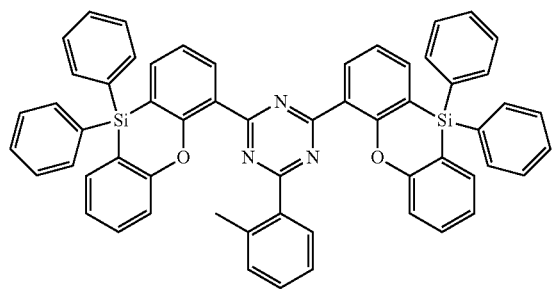
ETH13
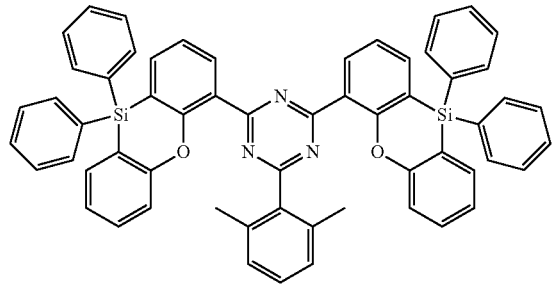
ETH14
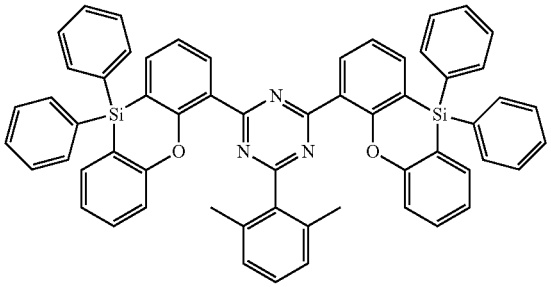
ETH15
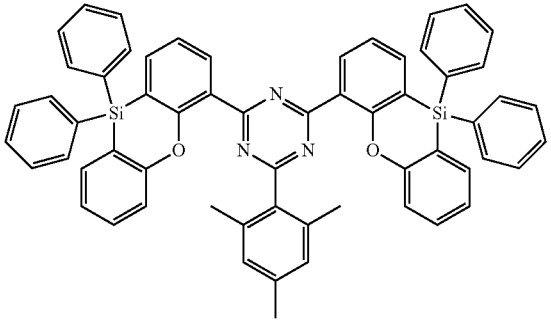
ETH16
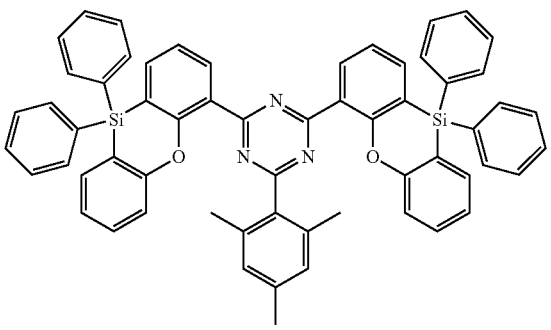
ETH17
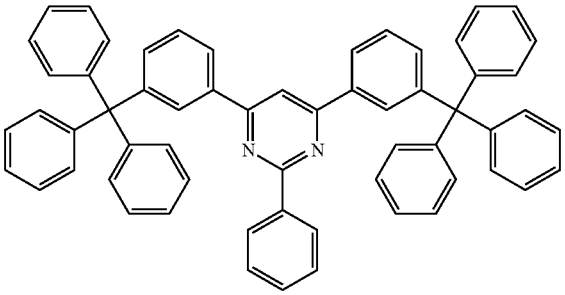
ETH18
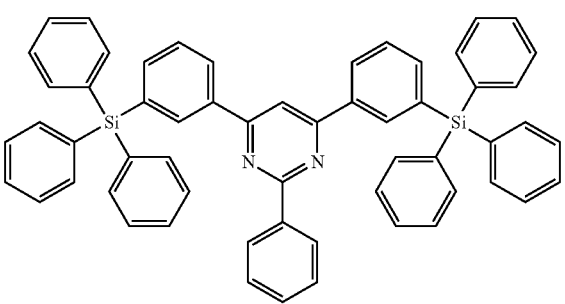

ETH19
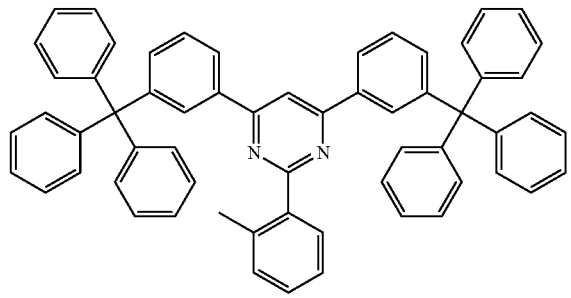
ETH20
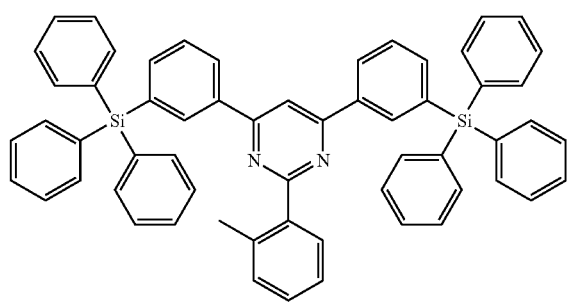
ETH21
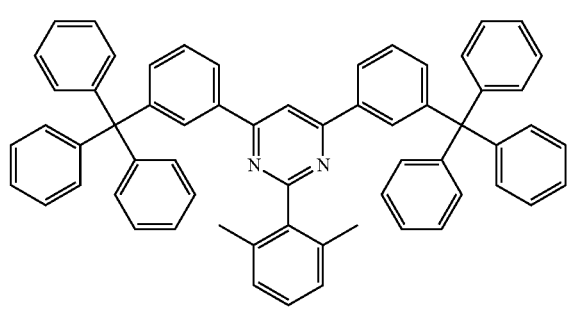
ETH22
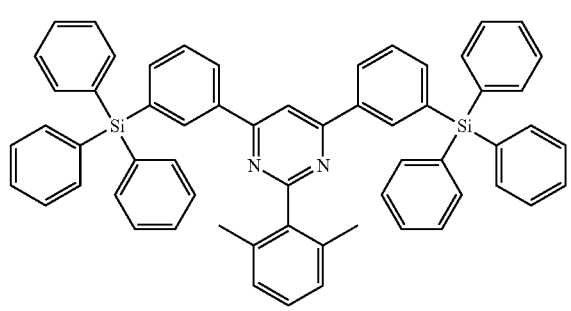
ETH23
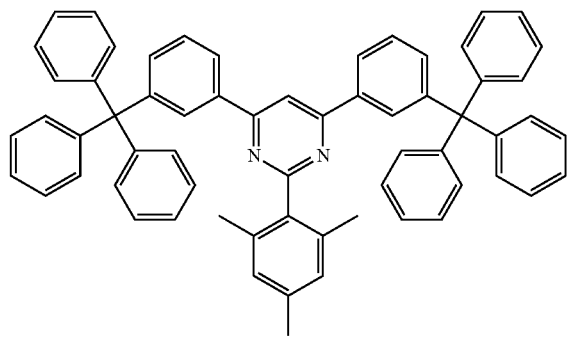
ETH24
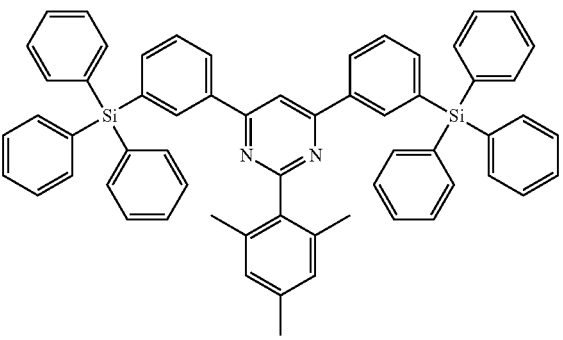
ETH25
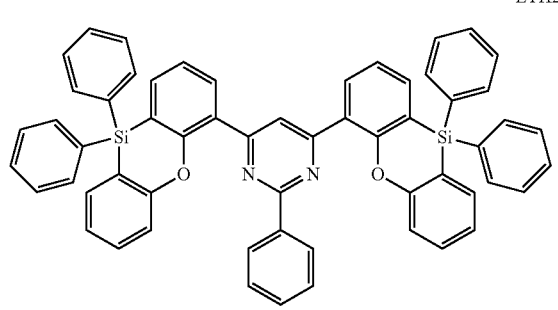
ETH26
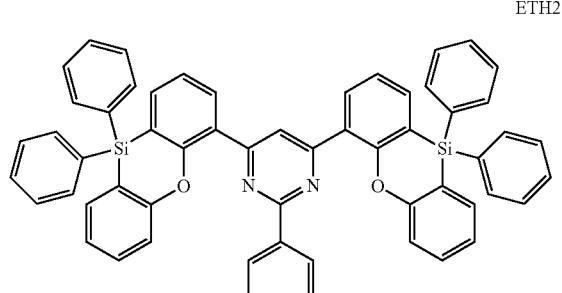
ETH27
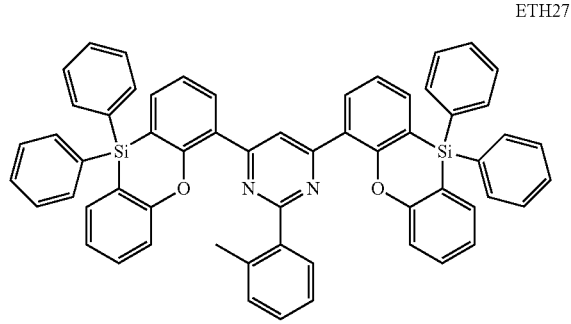
ETH28
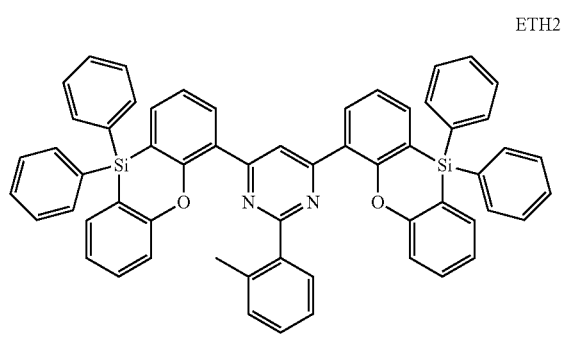

ETH29
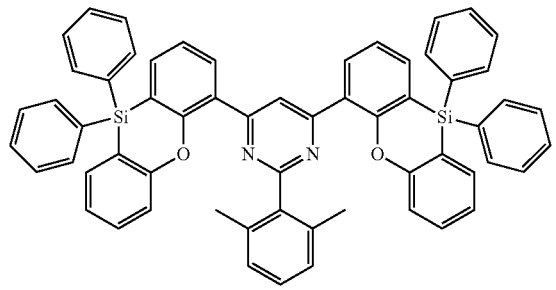
ETH30
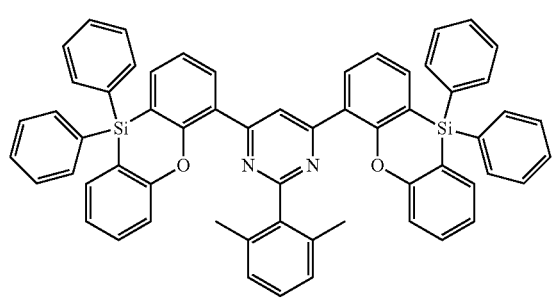
ETH31
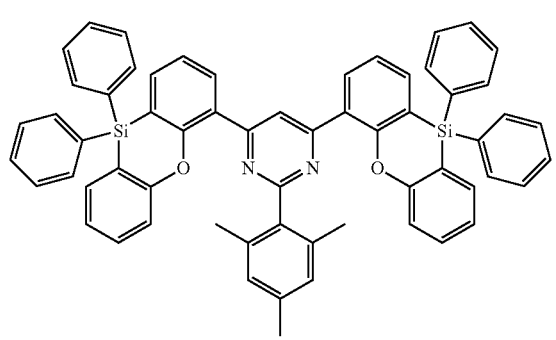
ETH32
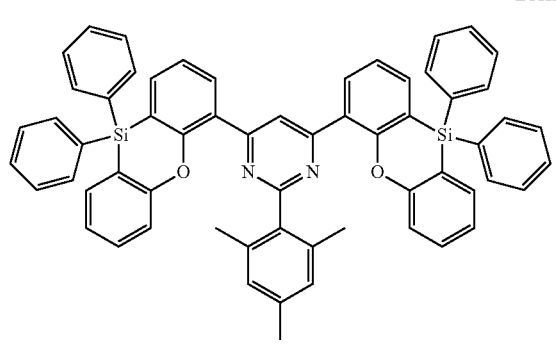
ETH33
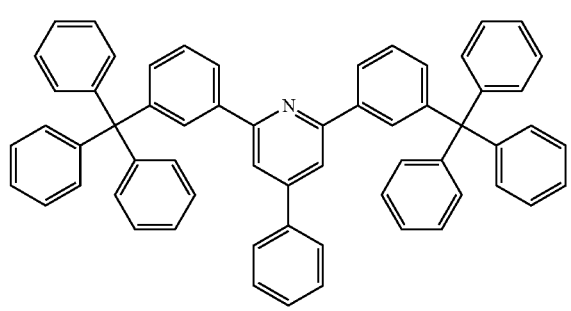
ETH34
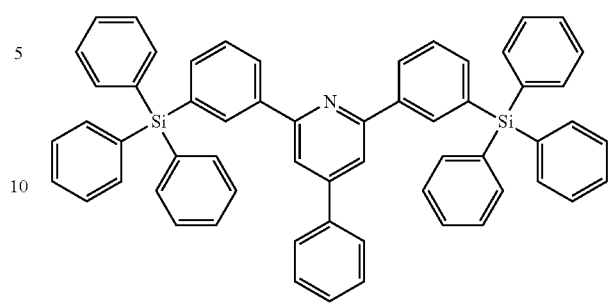
ETH35
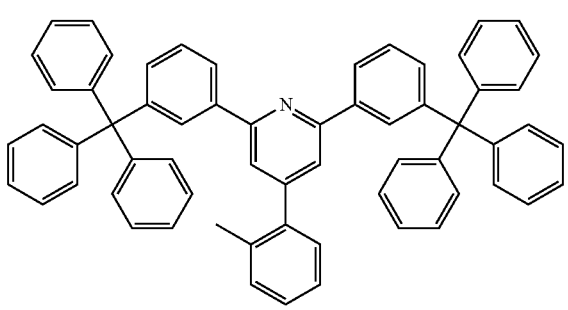
ETH36
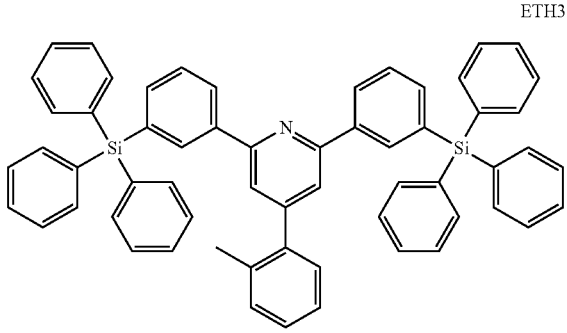
ETH37
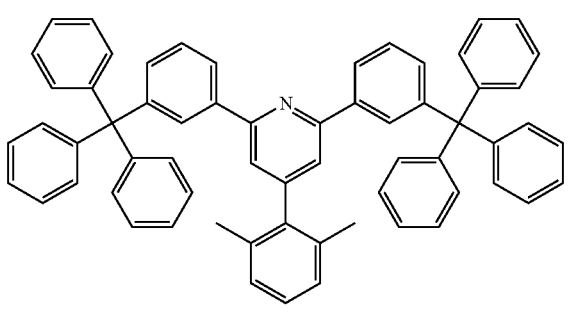
ETH38
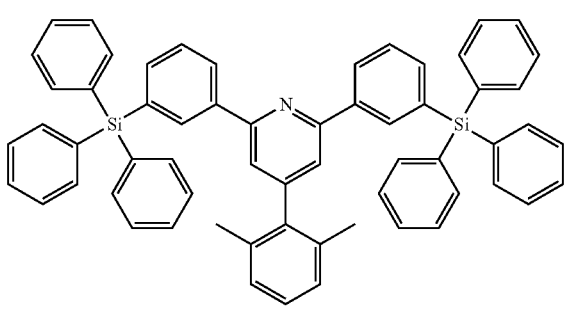

ETH39
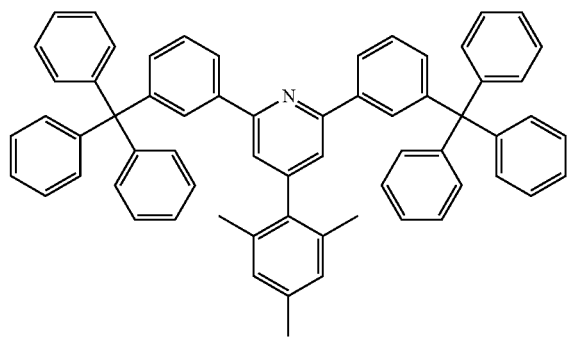
ETH40
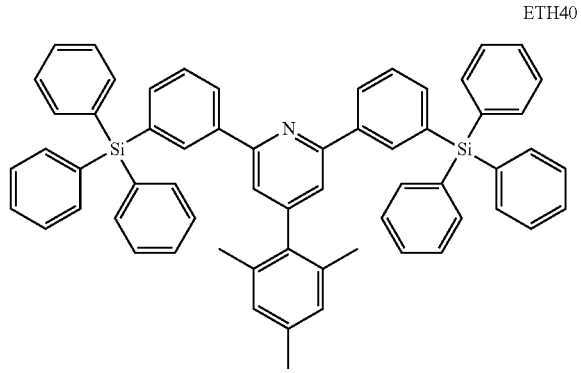
ETH41
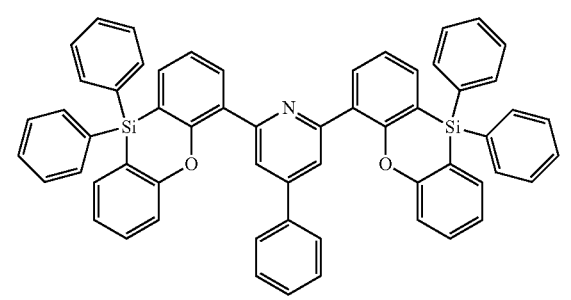
ETH42
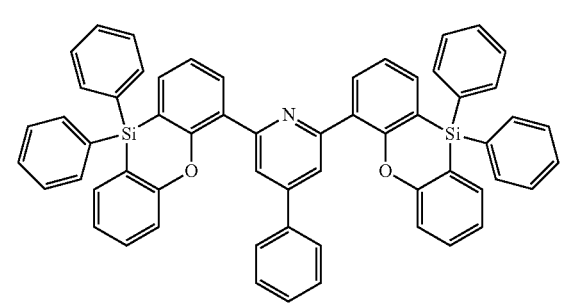
ETH43
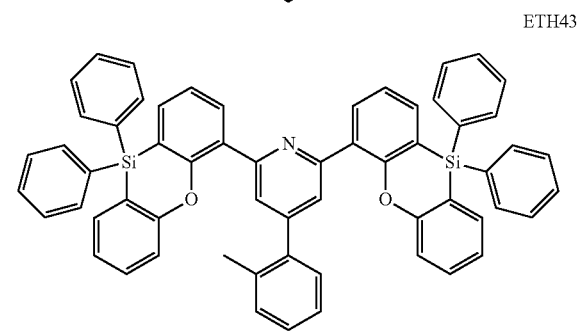
ETH44
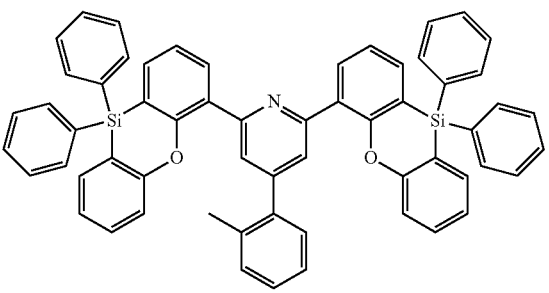
ETH45
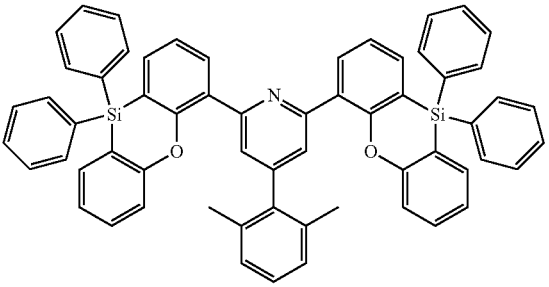
ETH46
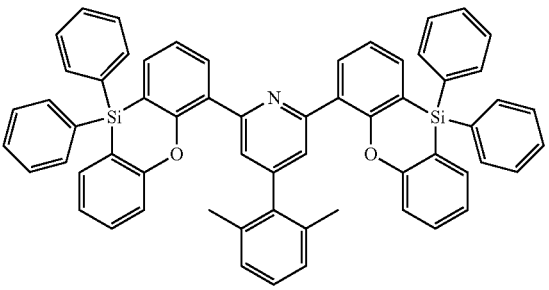
ETH47
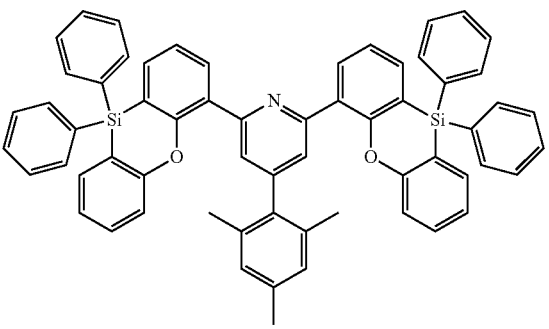
ETH48
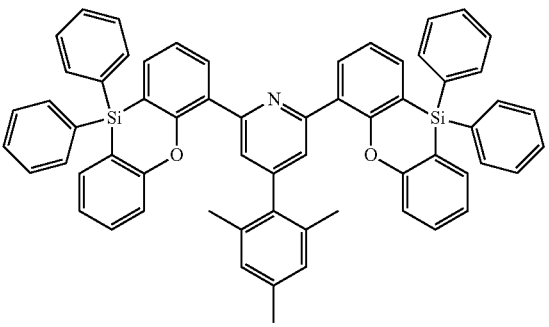

ETH49
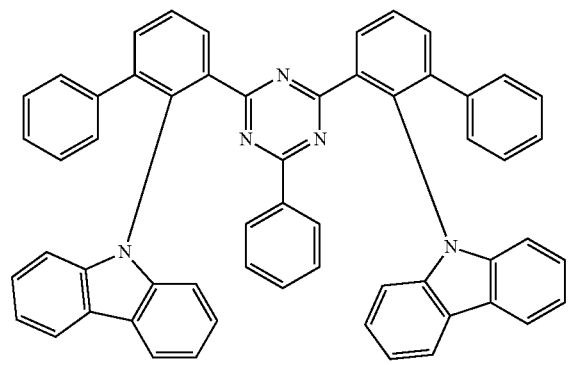
ETH50
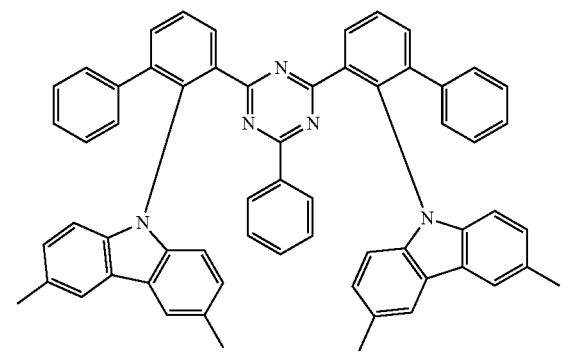
ETH51
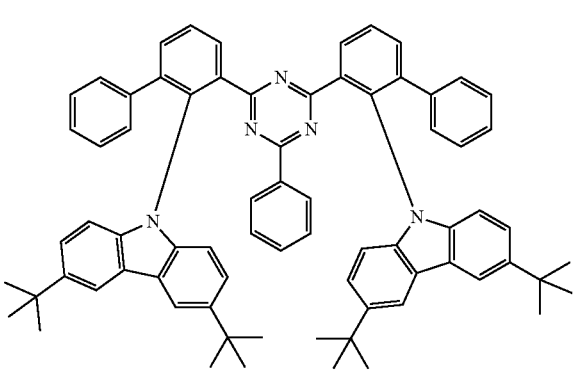
ETH52
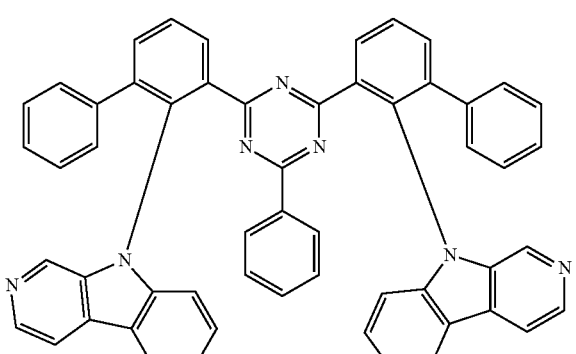
ETH53
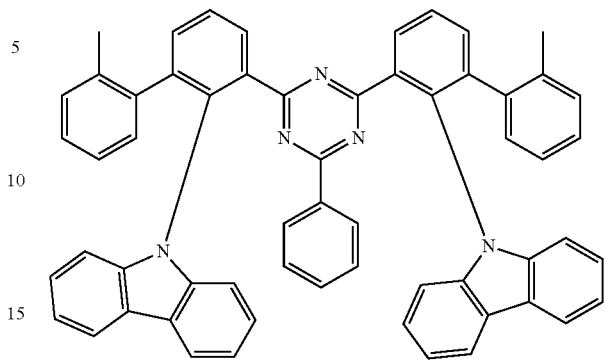
ETH54
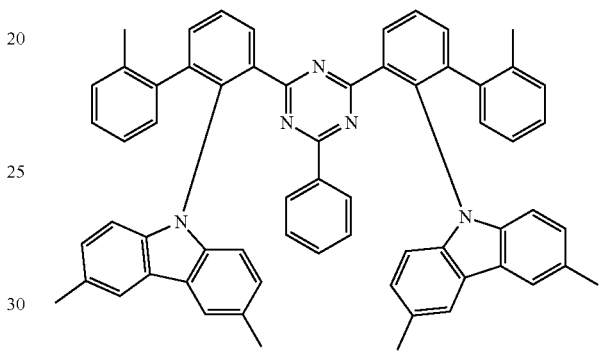
ETH55
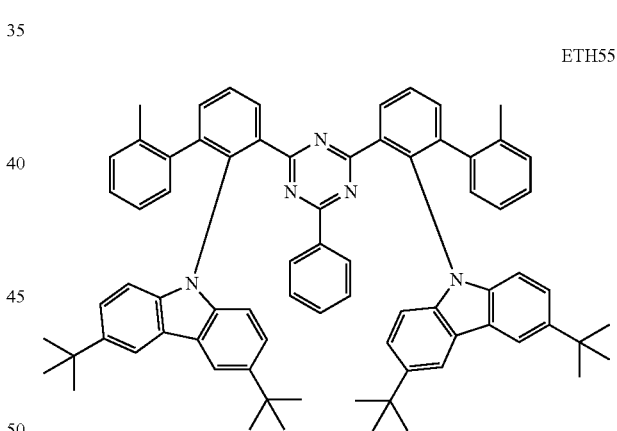
ETH56
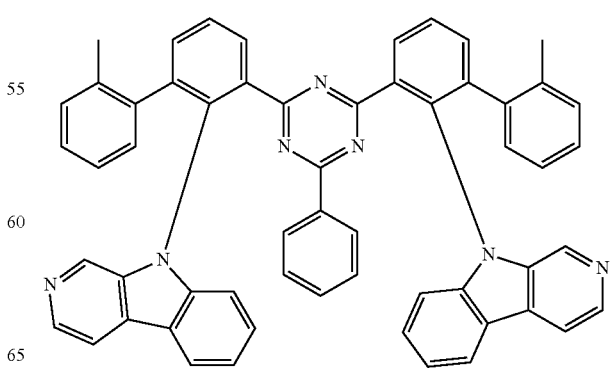

ETH57
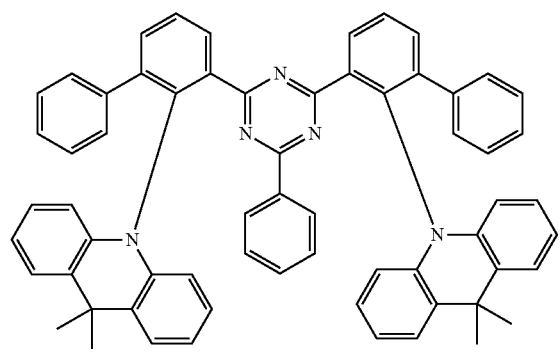
ETH58
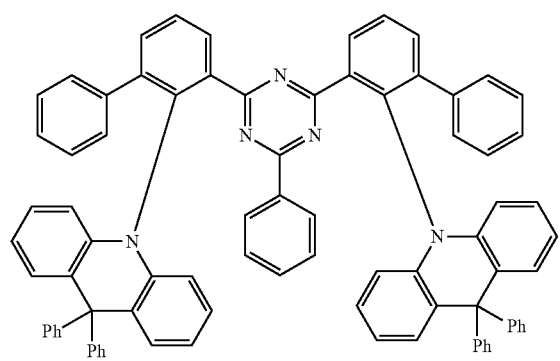
ETH59
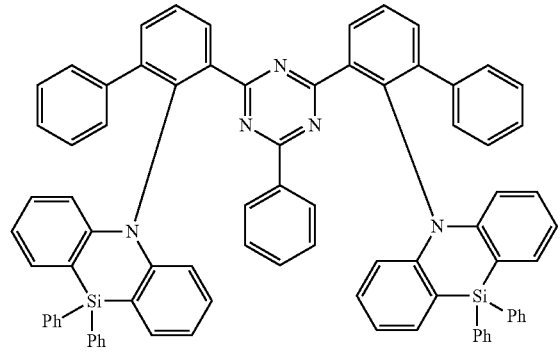
ETH60
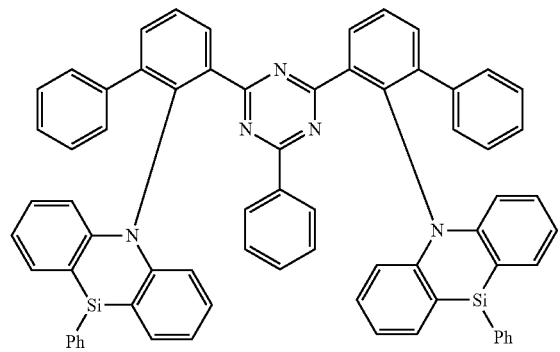
ETH61
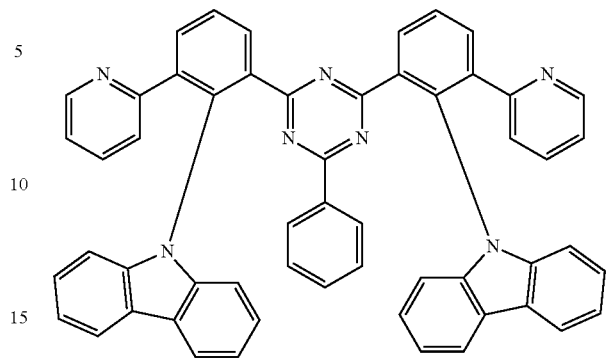
ETH62
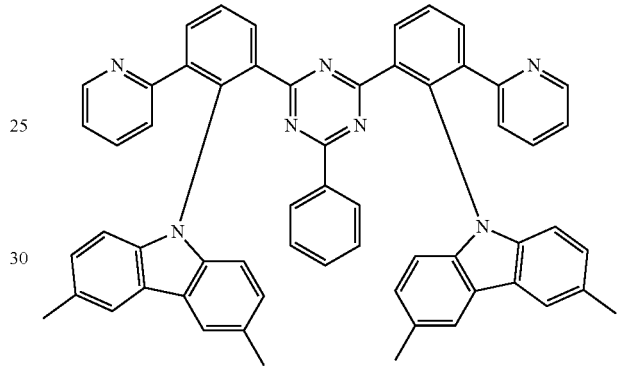
ETH63
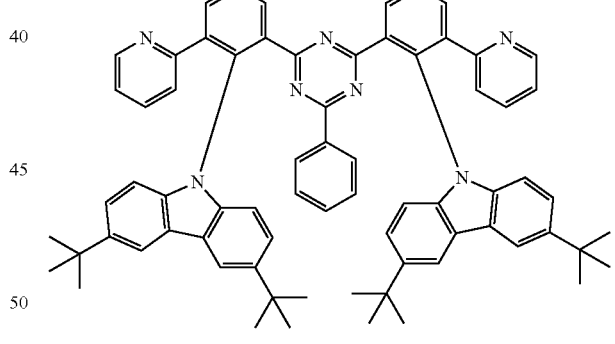
ETH64
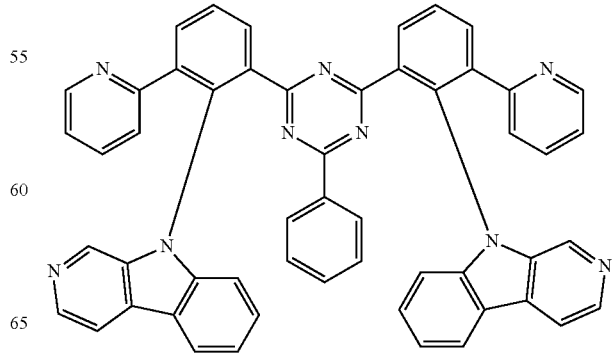

ETH65
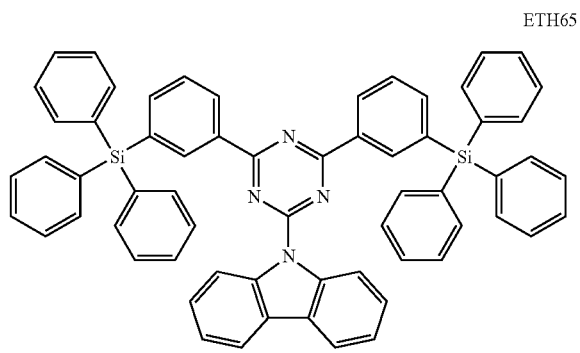
ETH69
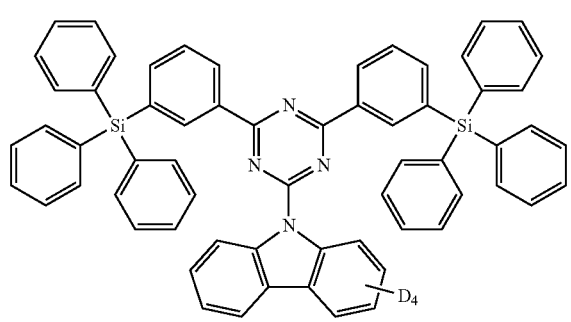
ETH66
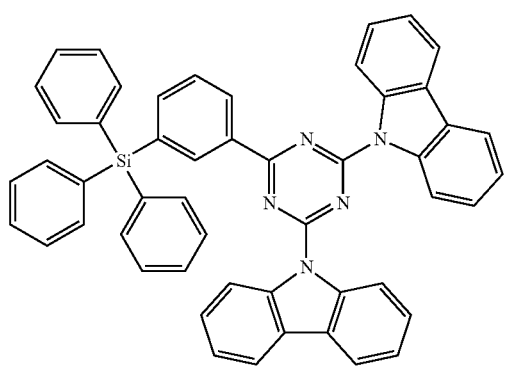
ETH70
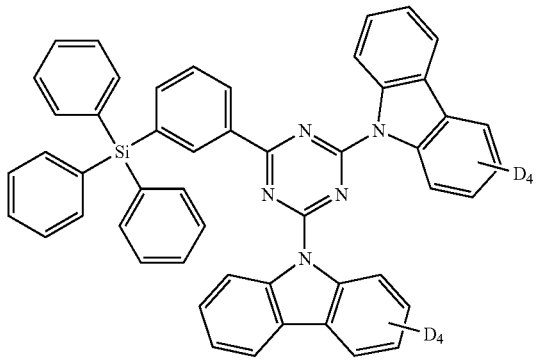
ETH67
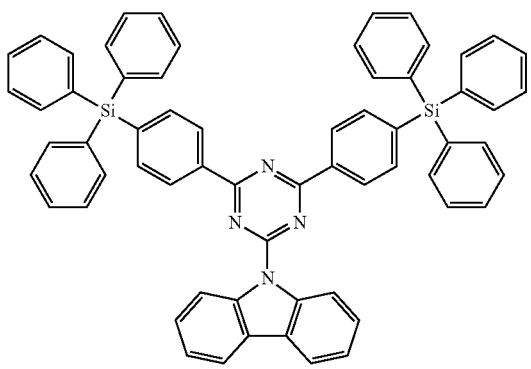
ETH71
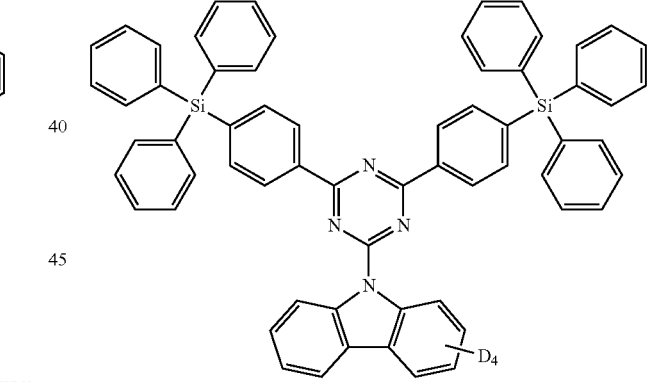
ETH68
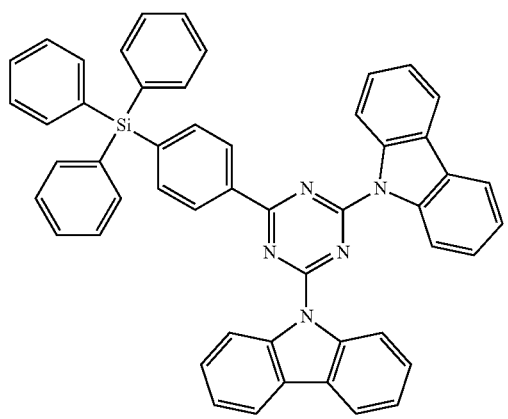
ETH72
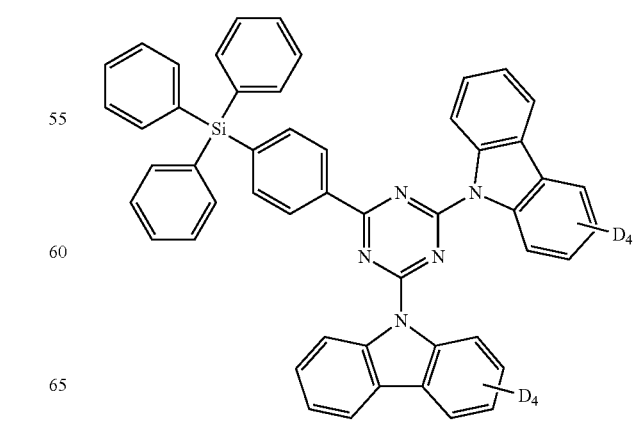

ETH73
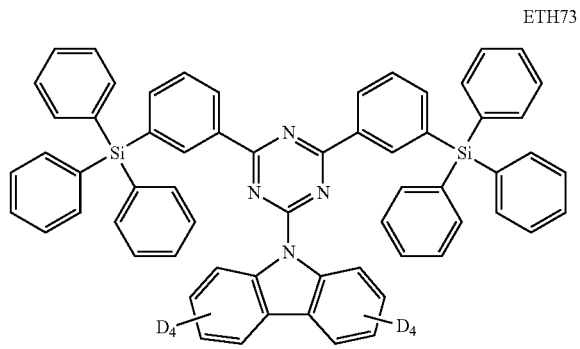
ETH74
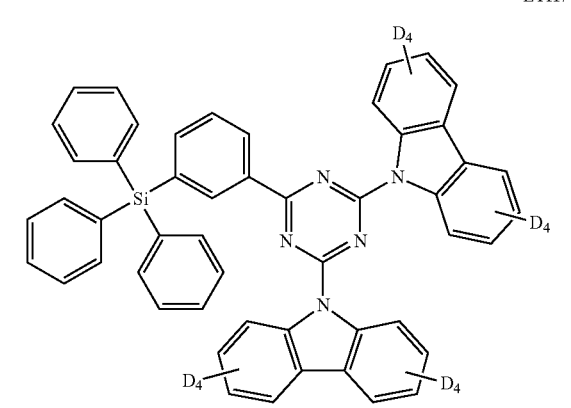
ETH75
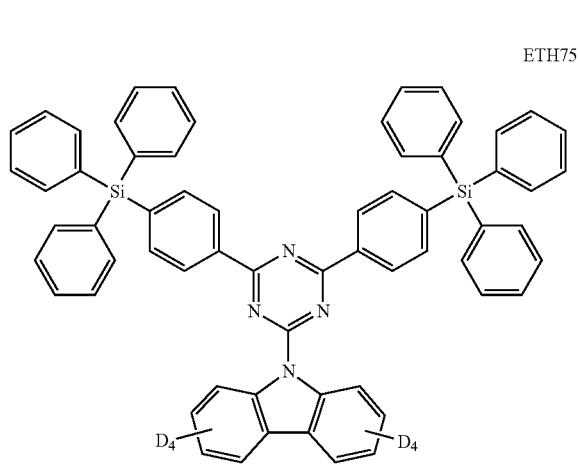
ETH76
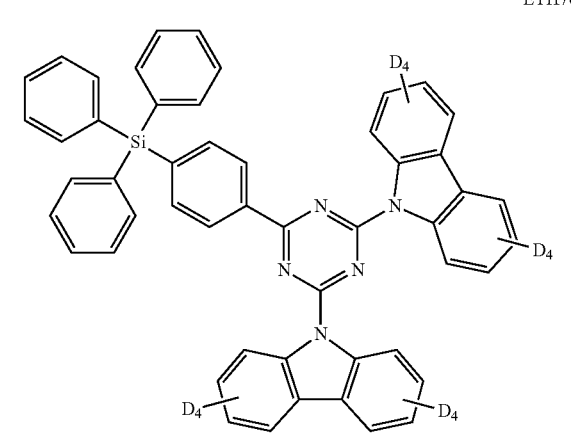
ETH77
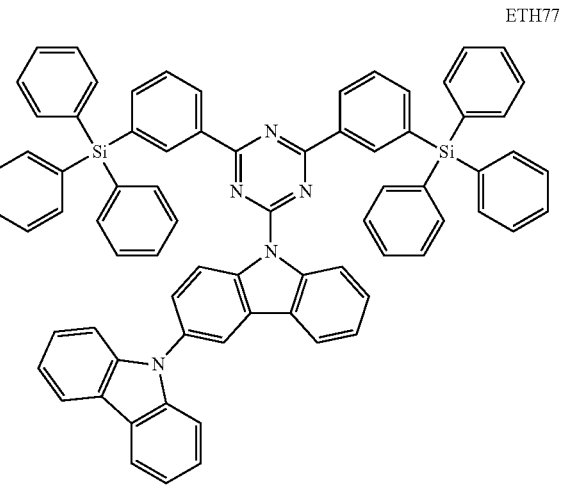
ETH78
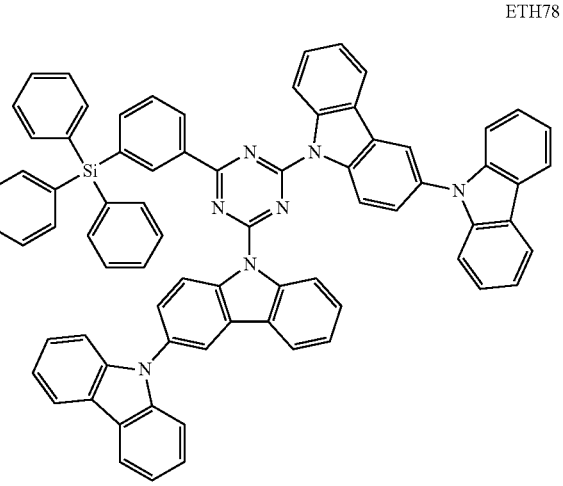
ETH79
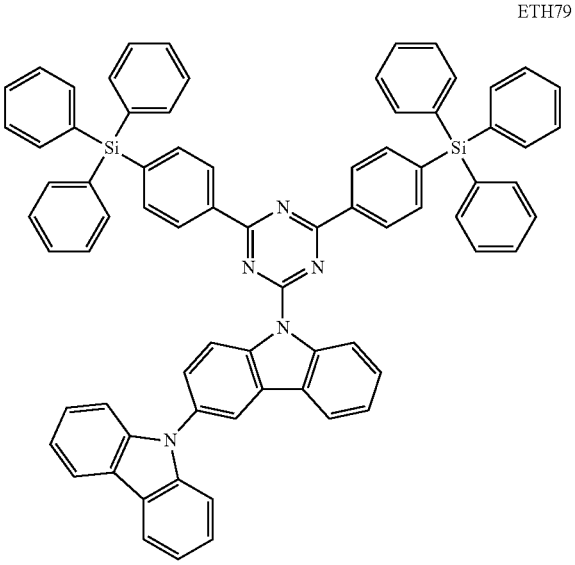

ETH80
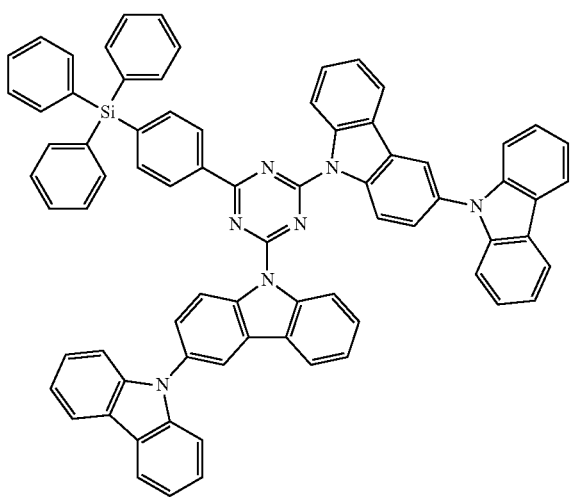
ETH81
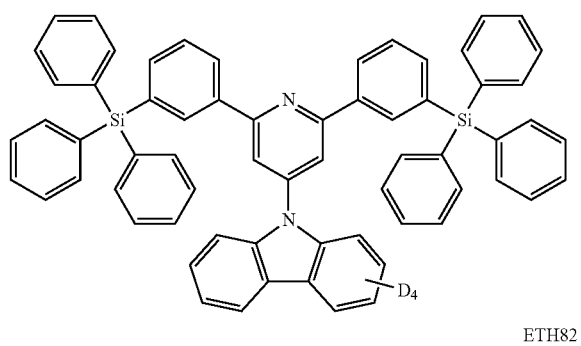
ETH82
ETH83
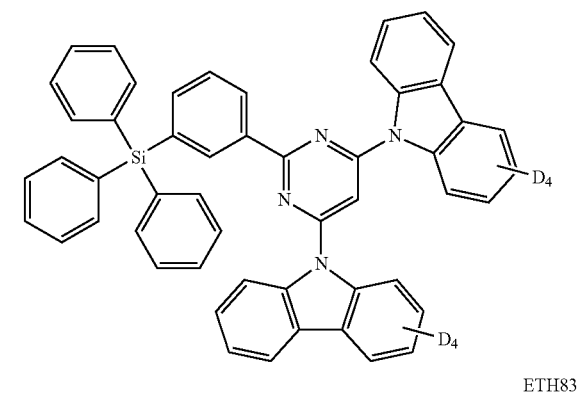
ETH84
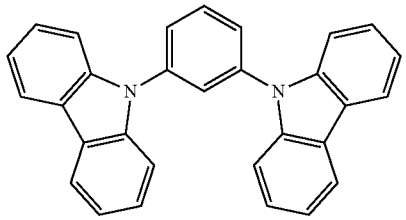
12. The organic electroluminescence device of claim 8, wherein the second host represented by Formula 7 is any one among compounds represented by Compound Group 3:
Compound Group 3
HTH1
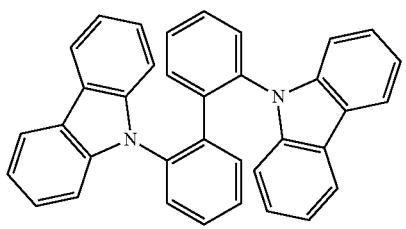
HTH2
HTH3
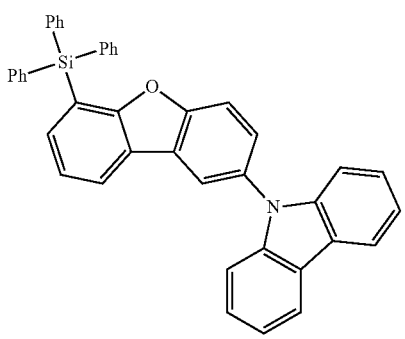

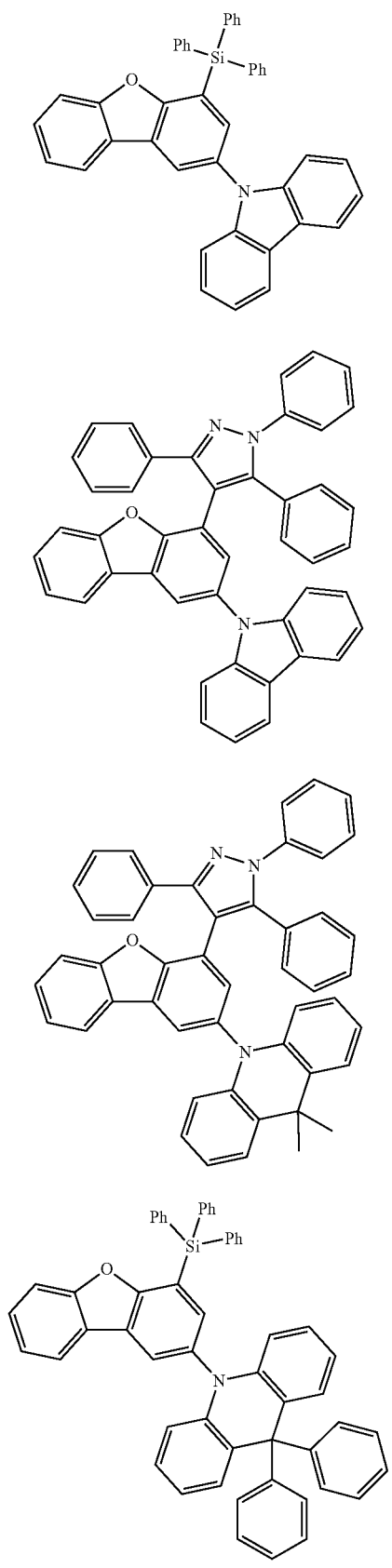
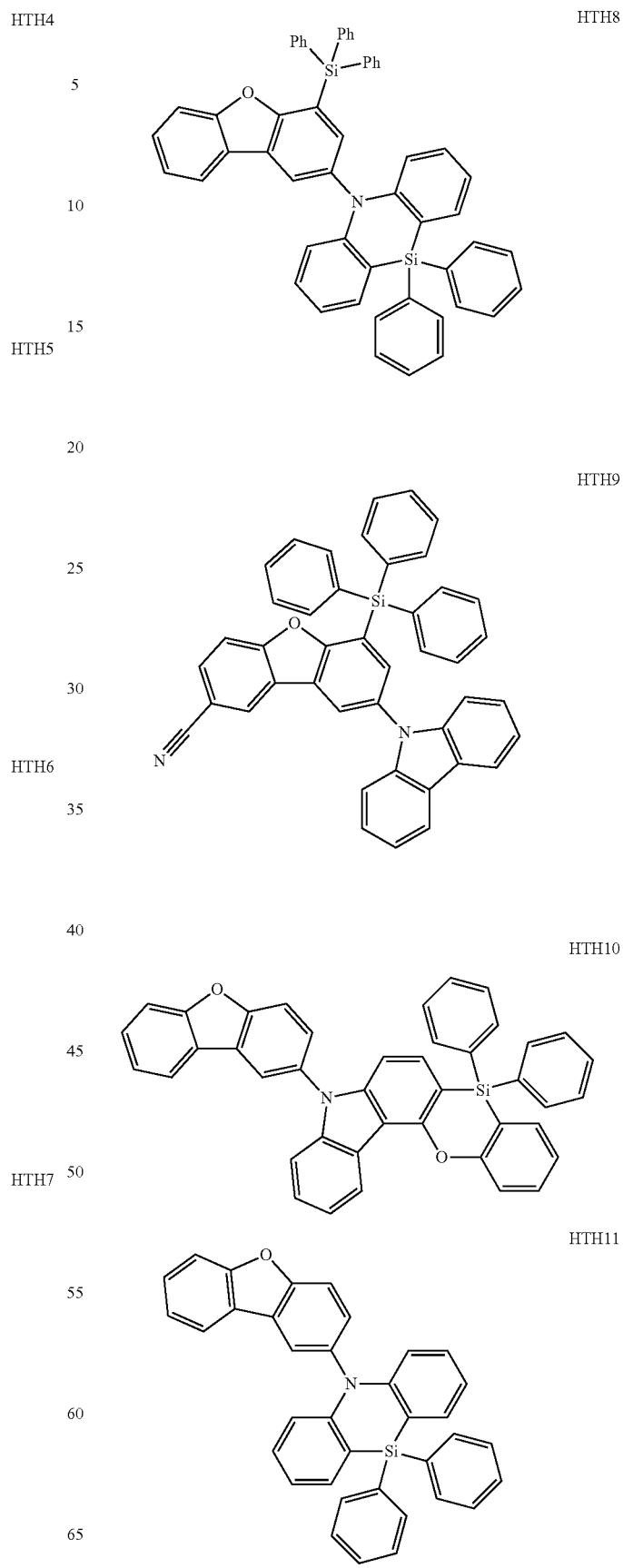

HTH12
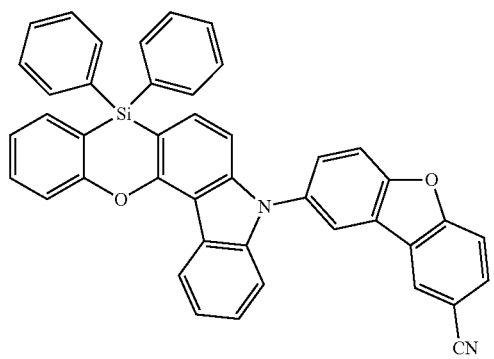
HTH13
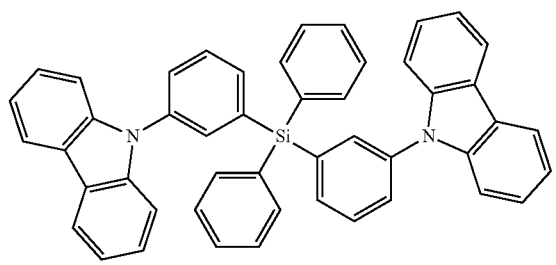
HTH14
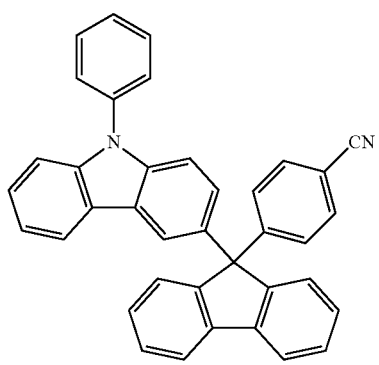
HTH15
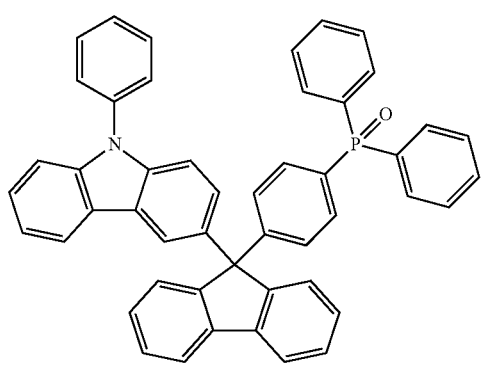
HTH16
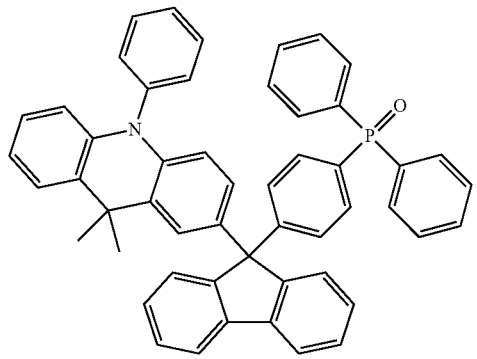
HTH17
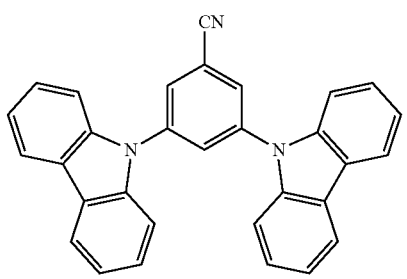
HTH18
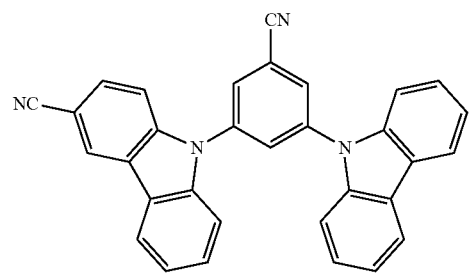
HTH19
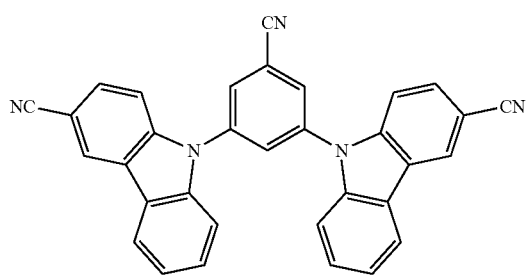
HTH20
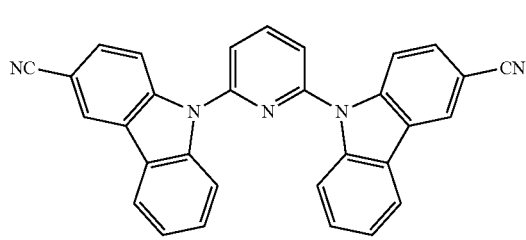

-continued
HTH21
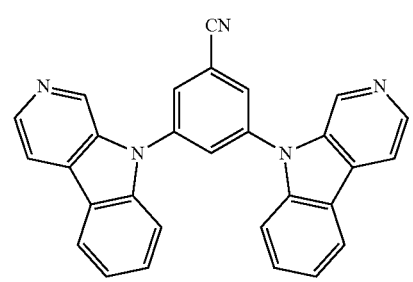
HTH22
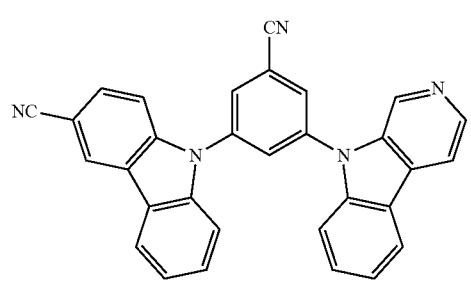
HTH23
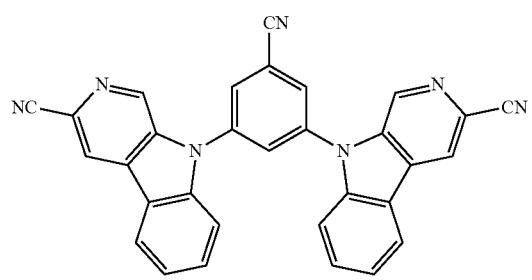
HTH24
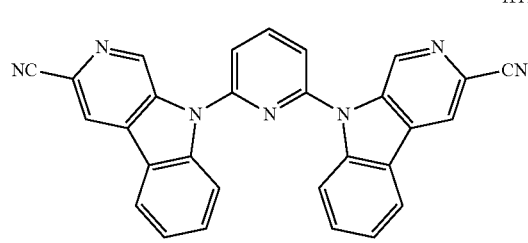
HTH25
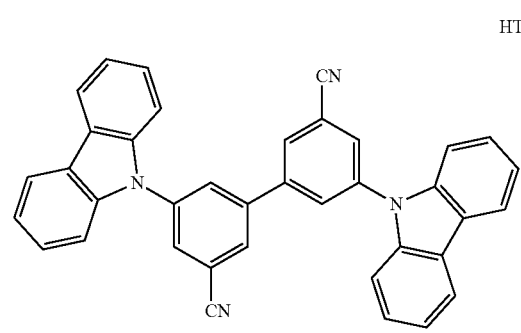
-continued
HTH26
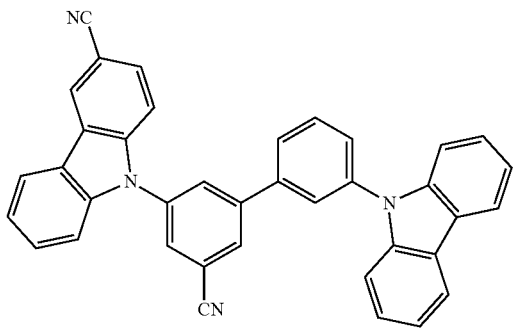
HTH27
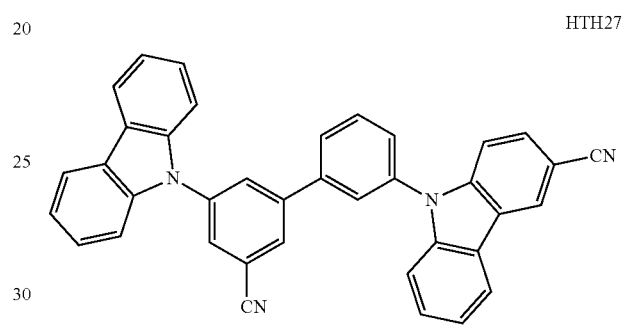
HTH28
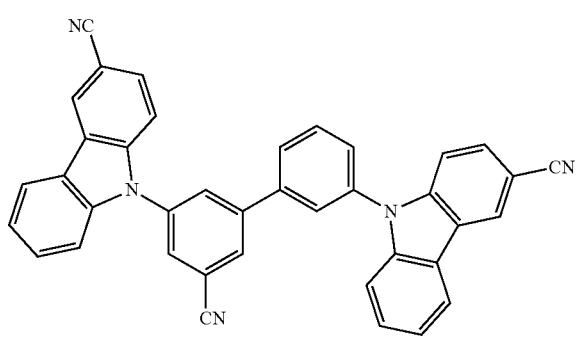
HTH29
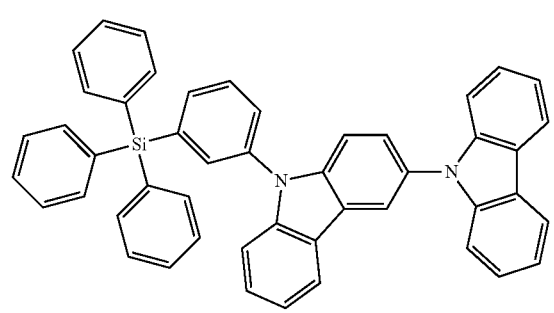

HTH30
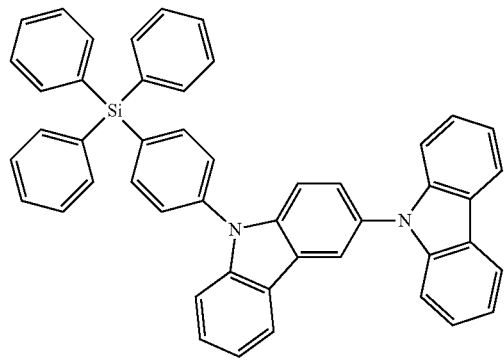
HTH31
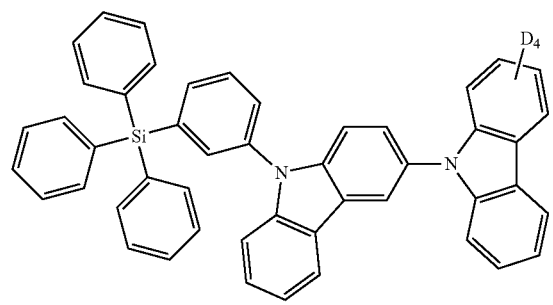
HTH32
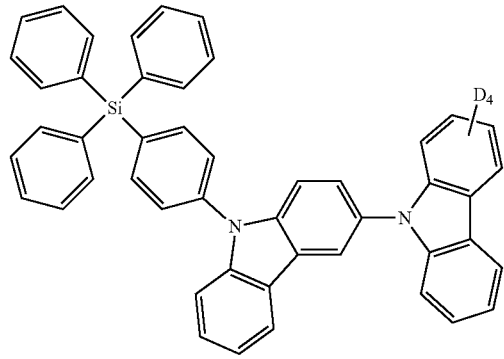
HTH33
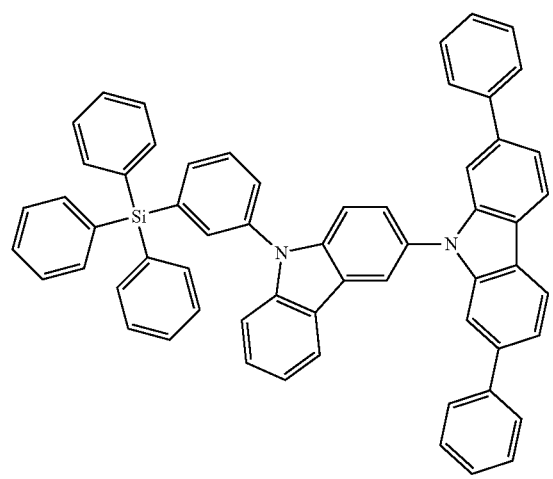
HTH34
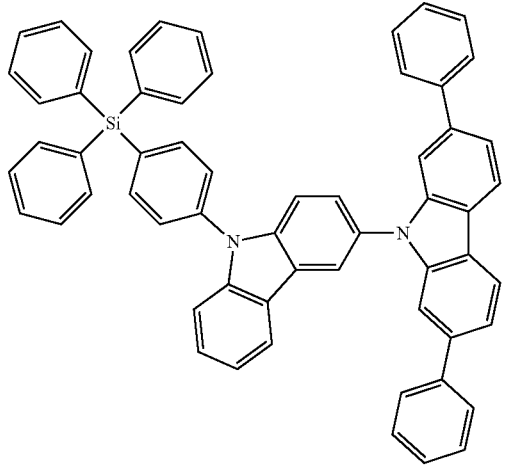
HTH35
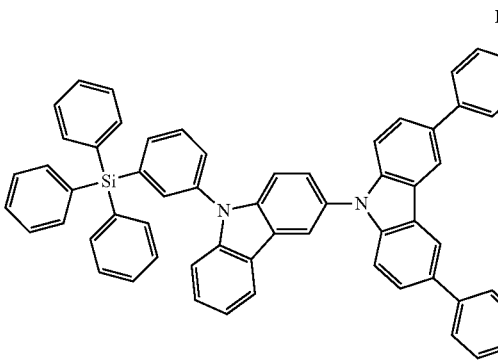
HTH36
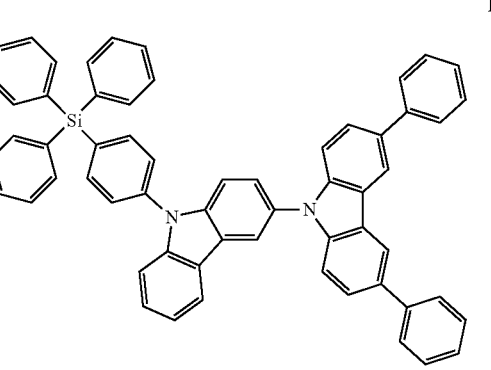
HTH37
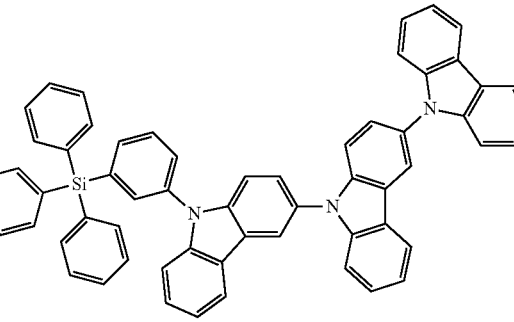

HTH38
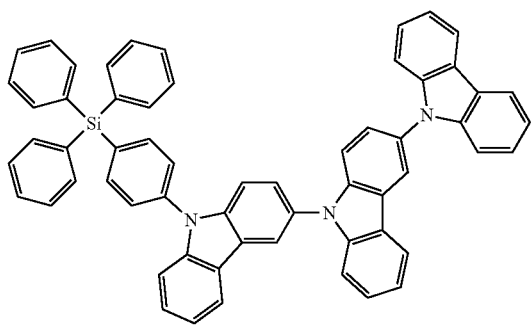
HTH39
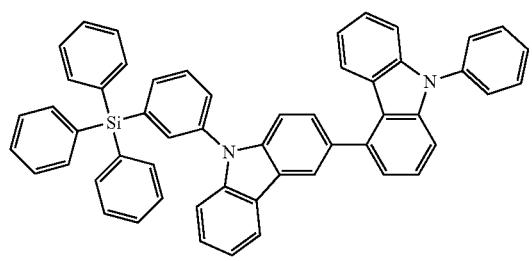
HTH40
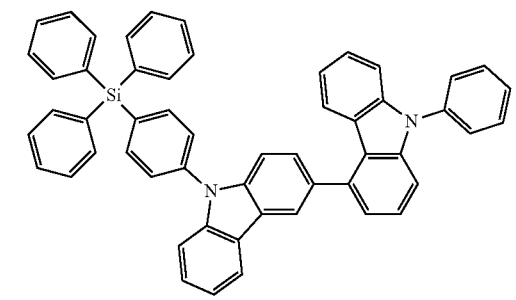
HTH41
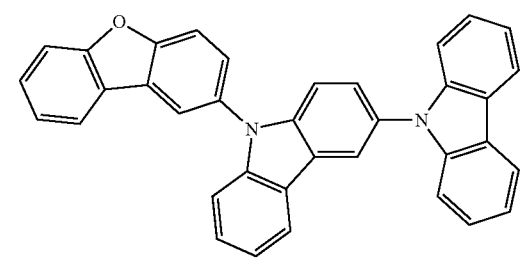
HTH42
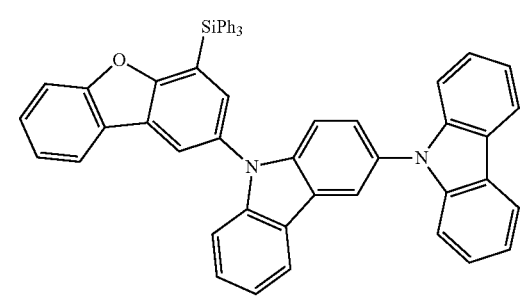
HTH43
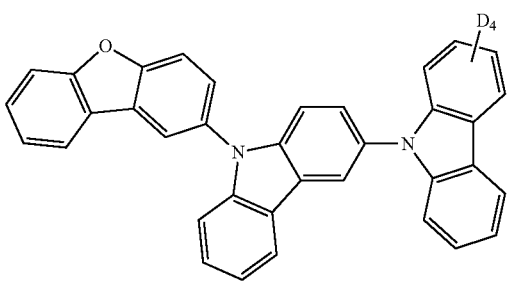
HTH44
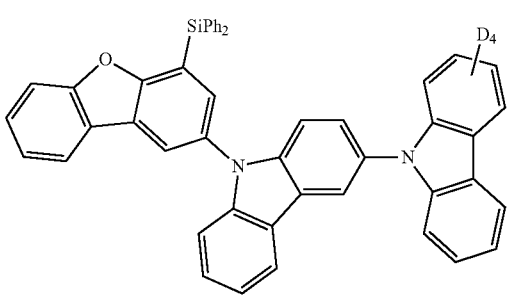
HTH45
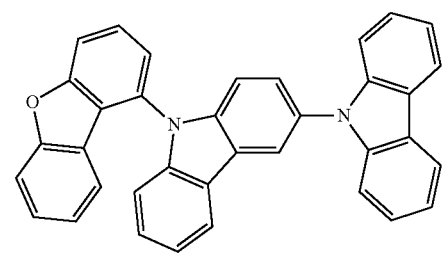
HTH46
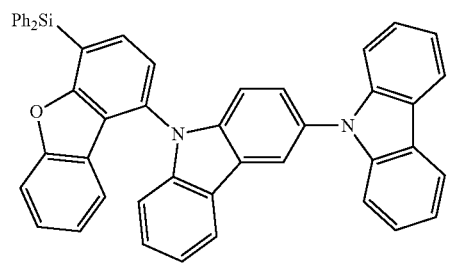
HTH47
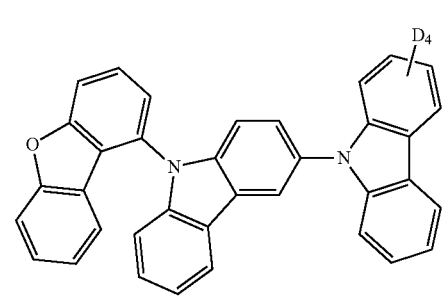

-continued
HTH48 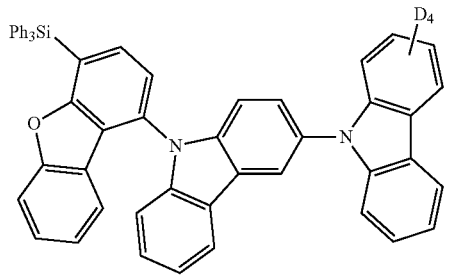
HTH49 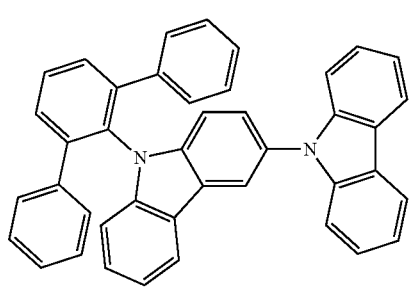
HTH50 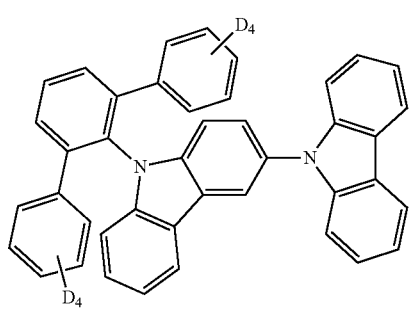
HTH51 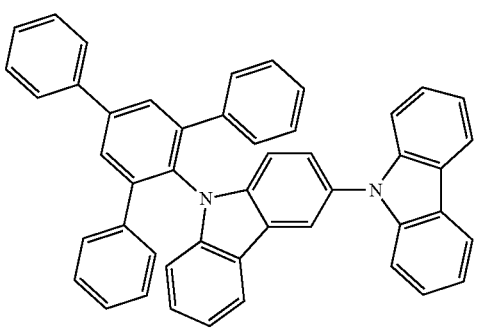
HTH52 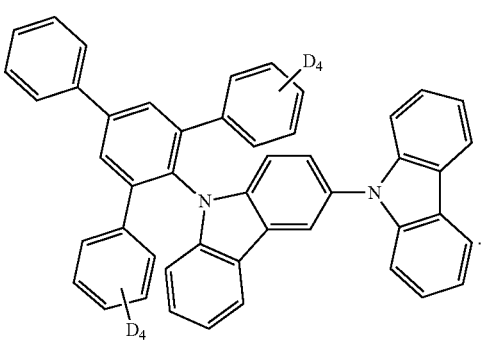
13. The organic electroluminescence device of claim 9, wherein the thermally activated delayed fluorescence dopant represented by Formula 8 is any one among compounds represented by Compound Group 4:
Compound Group 4
DFD1
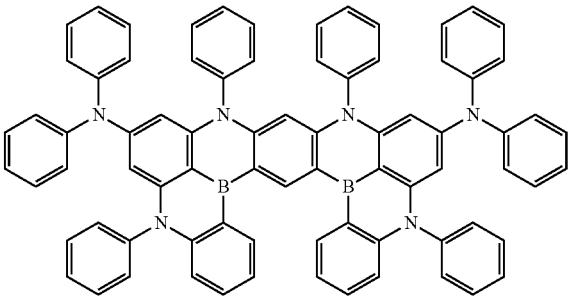
DFD2
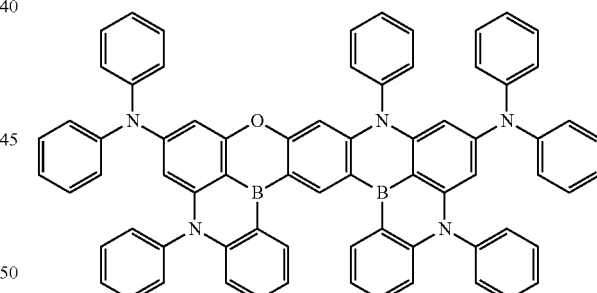
DFD3
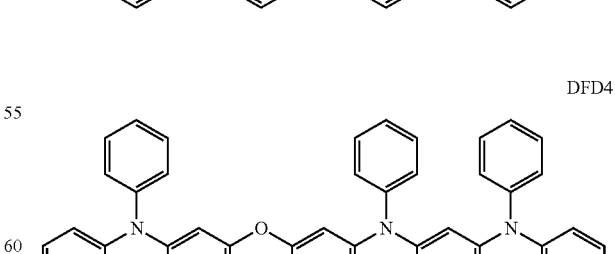
DFD4
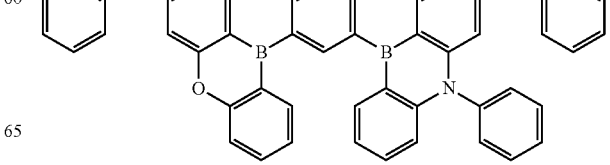

DFD5
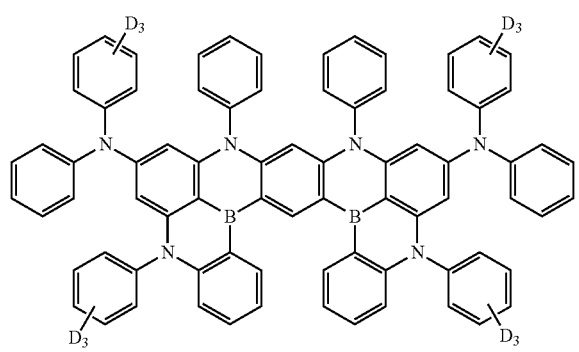
DFD9
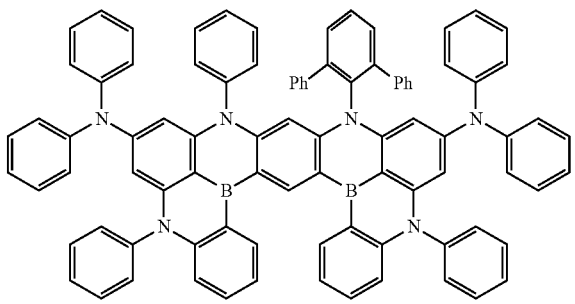
DFD6
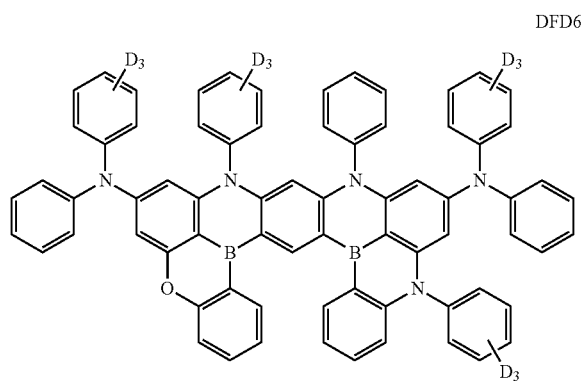
DFD10
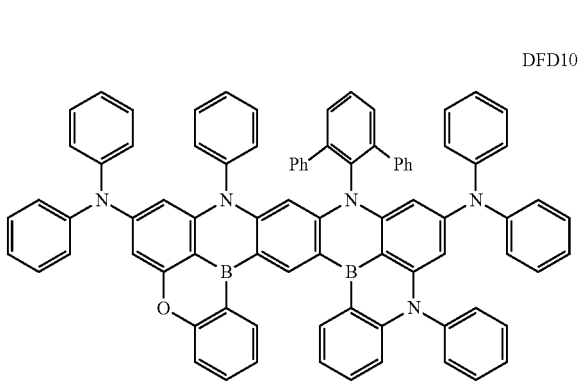
DFD7
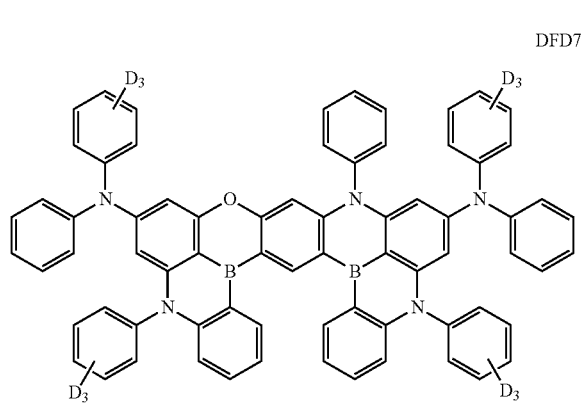
DFD11
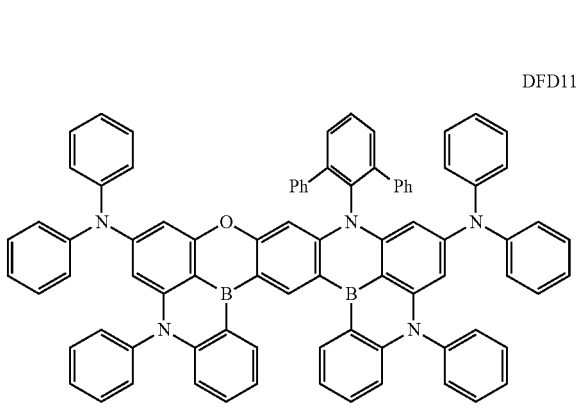
DFD8
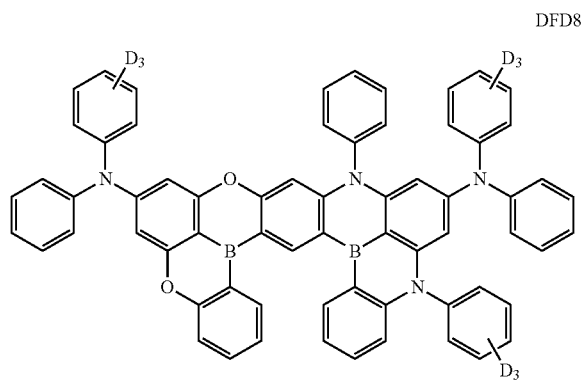
DFD12
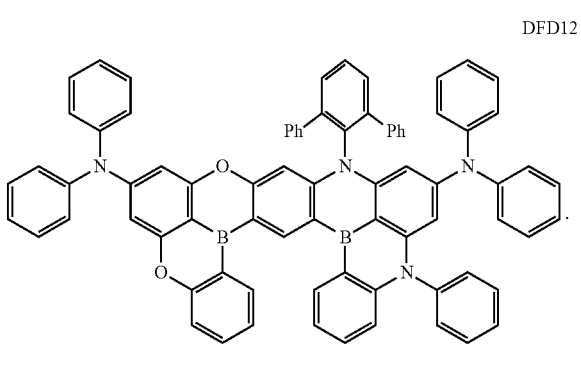

14. An organometallic compound represented by Formula 1:

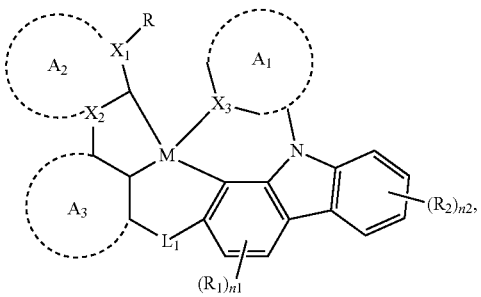

Formula 1 and
wherein, in Formula 1,
M is Pt, Pd, Ni, Au, Ag, Be, Mg, Al, Ca, Ti, Mn, Co, Zn, Ga, Zr, Ru, Rh, or Cu,
$L_1$ is $CR_3R_4$, $NR_5$, O, $SiR_6R_7$, $BR_8$, or $PR_9$,
$X_1$ to $X_3$ are each independently $CR_{10}$ or N,
ring $A_1$ to ring $A_3$ are each independently a substituted or unsubstituted monocyclic or polycyclic hydrocarbon ring group having 6 to 30 ring-forming carbon atoms, or a substituted or unsubstituted monocyclic or polycyclic heterocyclic group having 2 to 30 ring-forming carbon atoms,
$R_1$ to $R_{10}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
n1 is an integer of 0 to 2,
n2 is an integer of 0 to 4, and
R is represented by Formula 2-below:

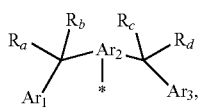

Formula 2 and
wherein, in Formula 2,
$Ar_1$ and $Ar_3$ are each independently a substituted or unsubstituted aryl group having 6 to 30 ring-forming carbon atoms, or a substituted or unsubstituted heteroaryl group having 2 to 30 ring-forming carbon atoms,
$Ar_2$ is a substituted or unsubstituted trivalent aryl group having 6 to 30 ring-forming carbon atoms, or a substituted or unsubstituted trivalent heteroaryl group having 2 to 30 ring-forming carbon atoms,
$R_a$ to $R_d$ are each independently a substituted or unsubstituted amine group, a substituted or unsubstituted alkoxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or $R_a$ and $R_b$ are bonded to each other to form a ring and/or $R_c$ and $R_d$ are bonded to each other to form a ring,
provided that, when $Ar_2$ is a trivalent phenyl group not substituted with any additional substituents, then Ra to Ra are not all methyl groups at the same time, and
"—*" is the bonding position with Formula 1.

15. The organometallic compound of claim 14, wherein Formula 2 is represented by Formula 2-1 or Formula 2-2:

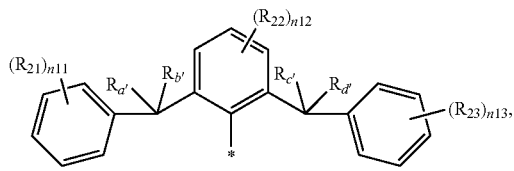

Formula 2-1

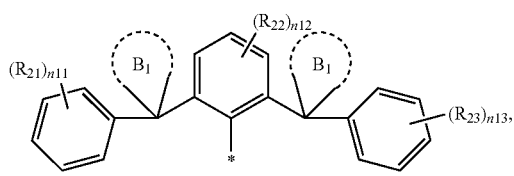

Formula 2-2 and
wherein, in Formula 2-1 and Formula 2-2,
$R_{21}$ to $R_{23}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms,
$R_{a'}$ to $R_{d'}$ are each independently a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, provided that, when n12 is 0, then $R_{a'}$ to $R_{d'}$ are not all methyl groups at the same time,
ring $B_1$ and ring $B_2$ are each independently a substituted or unsubstituted cycloalkyl having 3 to 20 carbon atoms, a substituted or unsubstituted hetero cycloalkyl having 2 to 20 carbon atoms, a substituted or unsubstituted bicycloalkyl having 4 to 20 carbon atoms, a substituted or unsubstituted hetero bicycloalkyl having 3 to 20 carbon atoms, a substituted or unsubstituted tricycloalkyl having 6 to 20 carbon atoms, or a substituted or unsubstituted hetero tricycloalkyl having 5 to 20 carbon atoms,
n11 and n13 are each independently an integer of 0 to 5, and
n12 is an integer of 0 to 3.

16. The organometallic compound of claim 15, wherein ring $B_1$ and ring $B_2$ are each independently represented by any one among Formula 3-1 to Formula 3-5:

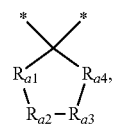

Formula 3-1

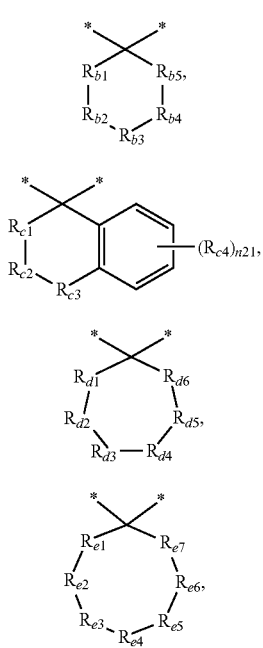

Formula 3-2

Formula 3-3

Formula 3-4

Formula 3-5 and wherein, in Formula 3-1 to Formula 3-5, $R_{a1}$ to $R_{a4}$, $R_{b1}$ to $R_{b5}$, $R_{c1}$ to $R_{c3}$, $R_{d1}$ to $R_{d6}$, and $R_{e1}$ to $R_{e7}$ are each independently $CR_{31}R_{32}$, or $NR_{33}$, $R_{31}$ to $R_{32}$ are each independently a hydrogen atom, a deuterium atom, a halogen atom, a substituted or unsubstituted alkyl group having 1 to 30 carbon atoms, a substituted or unsubstituted amine group, a substituted or unsubstituted aryl group having 6 to 30 ring-forming carbon atoms, or a substituted or unsubstituted heteroaryl group having 2 to 30 ring-forming carbon atoms, $R_{33}$ and $R_{c4}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, at least any two groups among $R_{a1}$ to $R_{a4}$, at least any two groups among $R_{b1}$ to $R_{b5}$, at least any two groups among $R_{c1}$ to $R_{c3}$, at least any two groups among $R_{d1}$ to $R_{d6}$, or at least any two groups among $R_{e1}$ to $R_{e7}$ are bonded to each other to form bicycloalkyl, hetero bicycloalkyl, tricycloalkyl, or hetero tricycloalkyl, and n21 is an integer of 0 to 4.

17. The organometallic compound of claim 15, wherein $R_a'$ to $R_d'$ are each independently a substituted or unsubstituted alkyl group having 1 to 10 carbon atoms, or a substituted or unsubstituted aryl group having 6 to 20 ring-forming carbon atoms, and ring $B_1$ and ring $B_2$ are each independently a substituted or unsubstituted cyclopentane, a substituted or unsubstituted cyclohexane, a substituted or unsubstituted hexahydropyrimidine, a substituted or unsubstituted cycloheptane, a substituted or unsubstituted tetraline, a substituted or unsubstituted bicyclo[3.3.1]nonyl, or a substituted or unsubstituted tricyclo[3.3.1.13.7]decane.

18. The organometallic compound of claim 14, wherein Formula 1-above is represented by Formula 4:

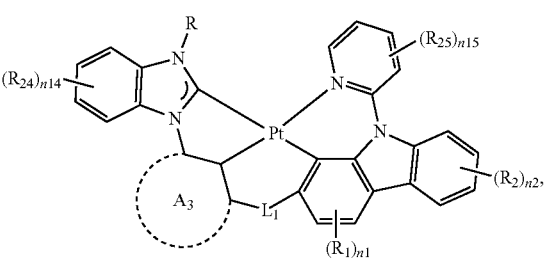

Formula 4 and wherein, in Formula 4, $R_{24}$ and $R_{25}$ are each independently a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, n14 and n15 are each independently an integer of 0 to 4, and $L_1$, ring $A_3$, R, $R_1$, $R_2$, n1, and n2 are the same as defined in Formula 1.

19. The organometallic compound of claim 18, wherein Formula 4 is represented by Formula 5:

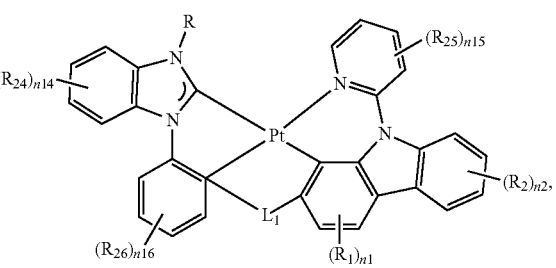

Formula 5 and wherein, in Formula 5 above, $R_{26}$ is a hydrogen atom, a deuterium atom, a halogen atom, a substituted or unsubstituted alkyl group having 1 to 30 carbon atoms, a substituted or unsubstituted aryl group having 6 to 30 ring-forming carbon atoms, or a substituted or unsubstituted heteroaryl group having 2 to 30 ring-forming carbon atoms, n16 is an integer of 0 to 3, and $L_1$, R, $R_1$, $R_2$, n1, n2, $R_{24}$, $R_{25}$, n14, and n15 are the same as defined in Formula 4.

20. The organometallic compound of claim 14, wherein the organometallic compound represented by Formula 1 is any one among compounds represented by Compound Group 1:

Compound Group 1
BD2
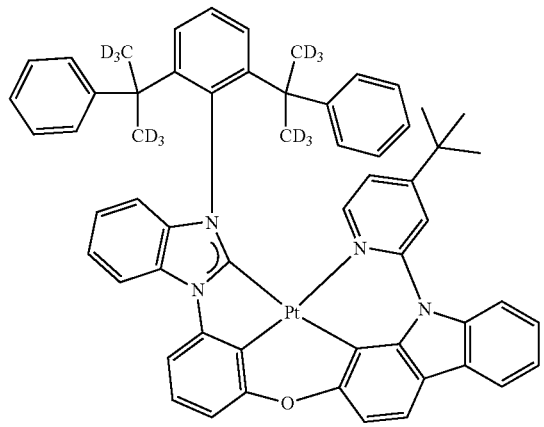
BD3
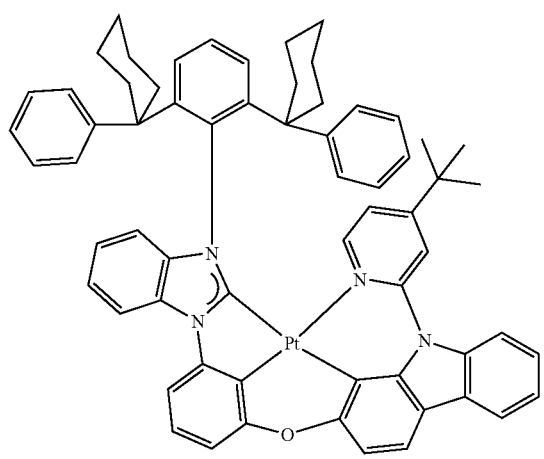
BD4
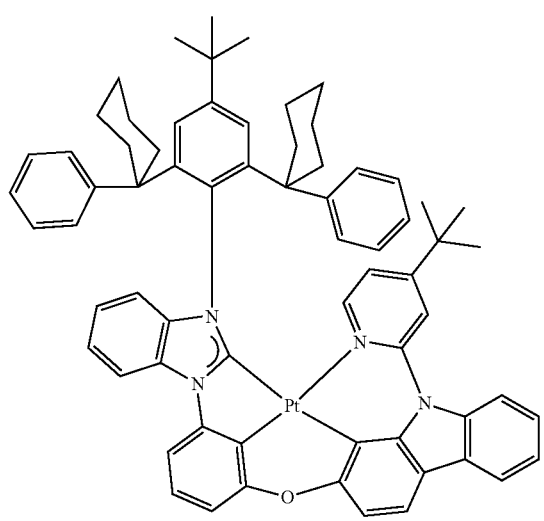
-continued
BD5
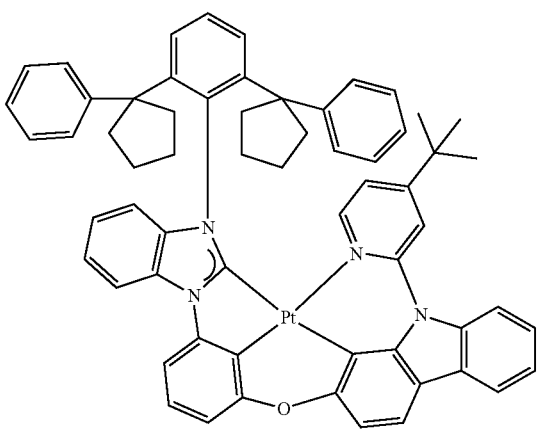
BD6
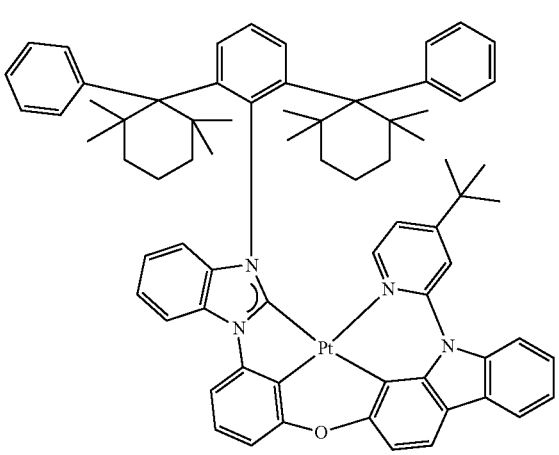
BD7
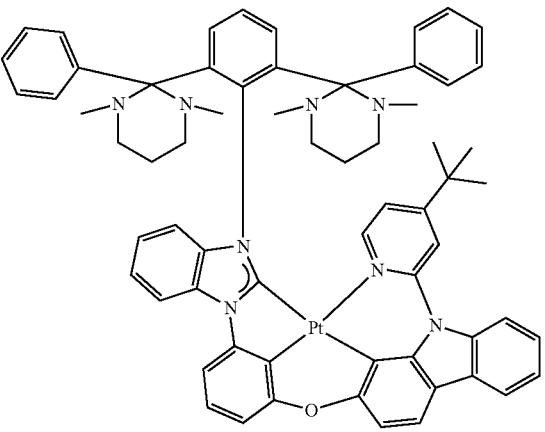

BD8
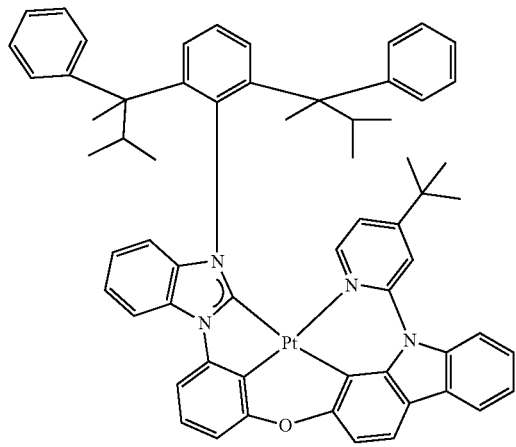
BD11
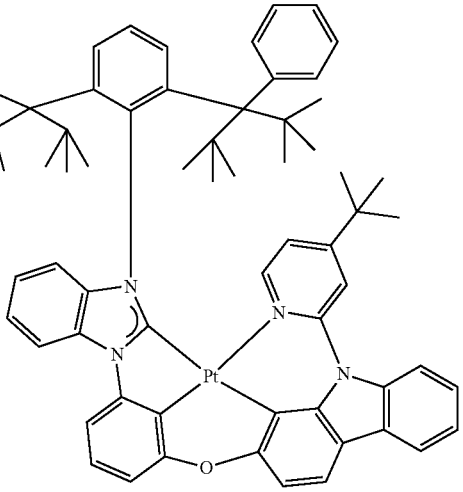
BD9
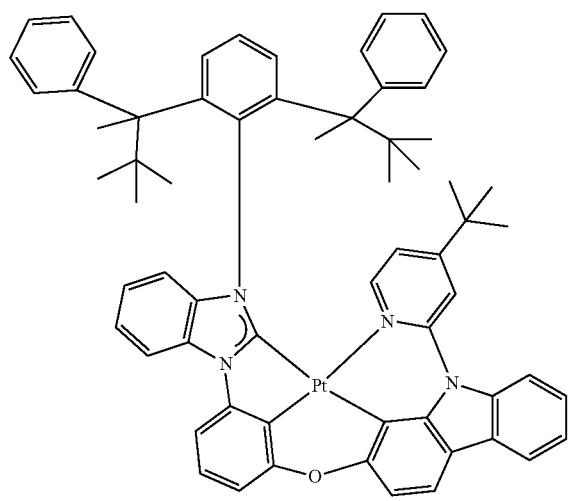
BD12
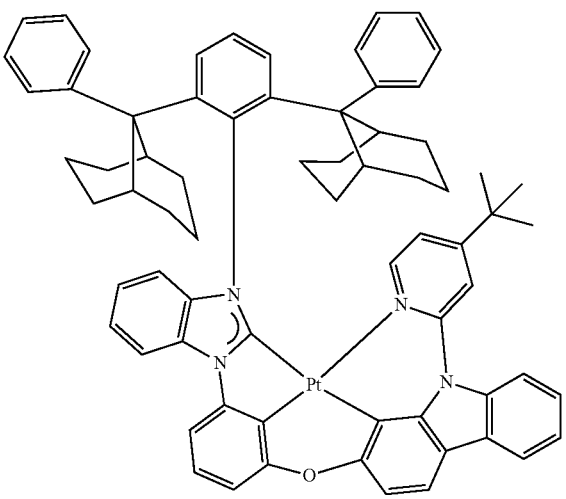
BD10
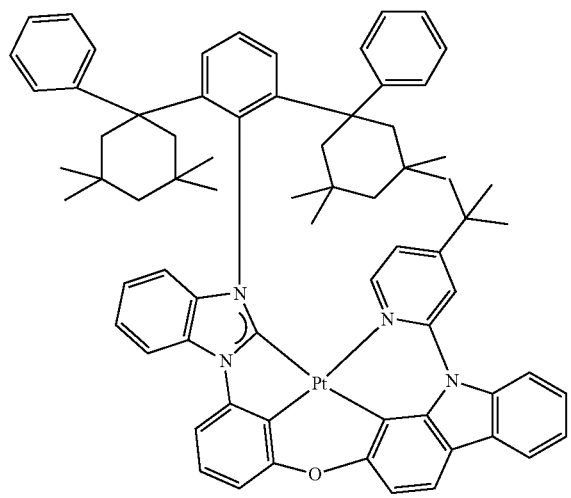
BD13
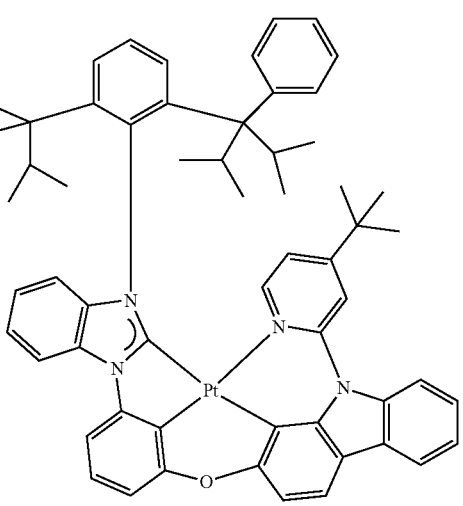

BD14
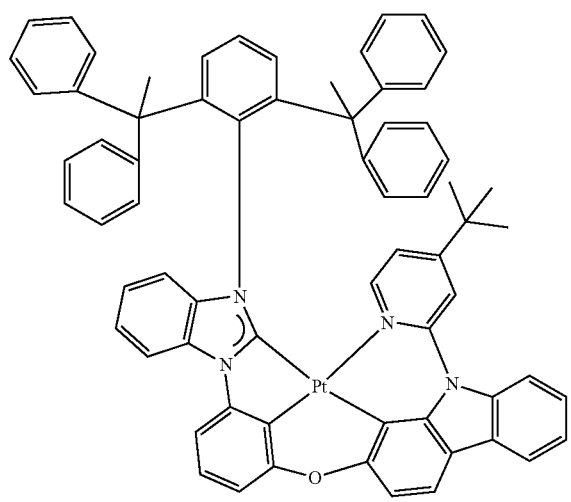
BD15
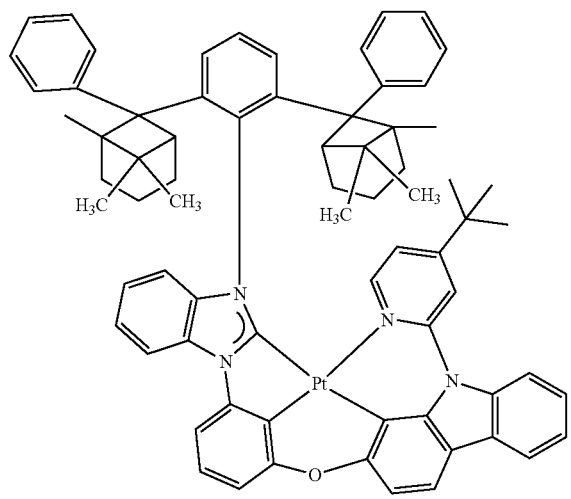
BD16
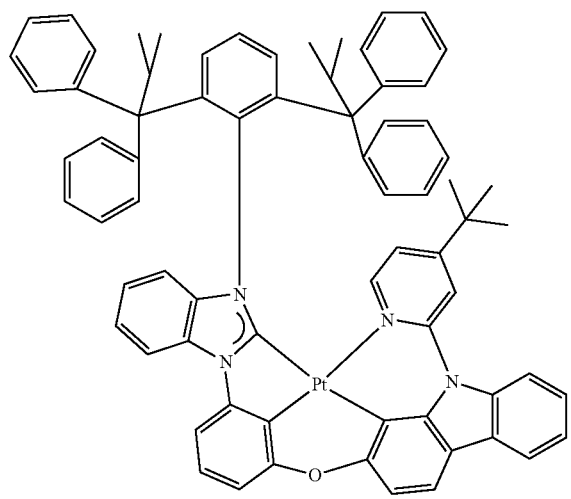
BD17
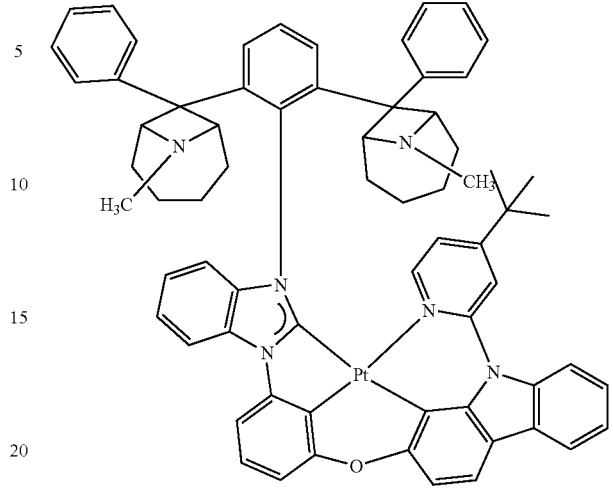
BD18
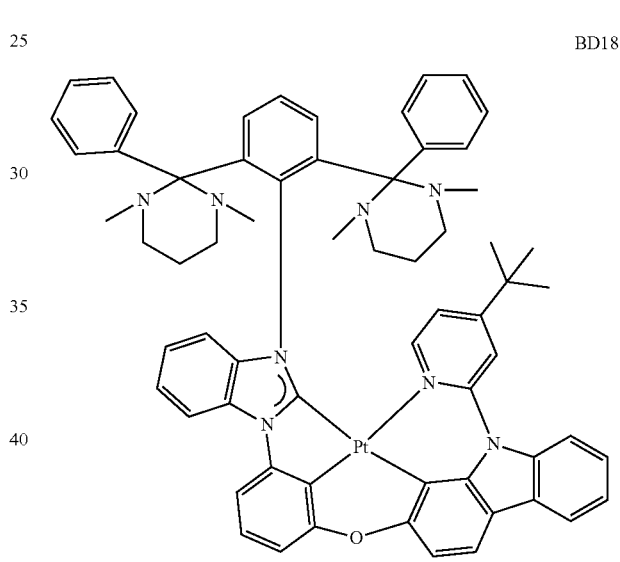
BD19
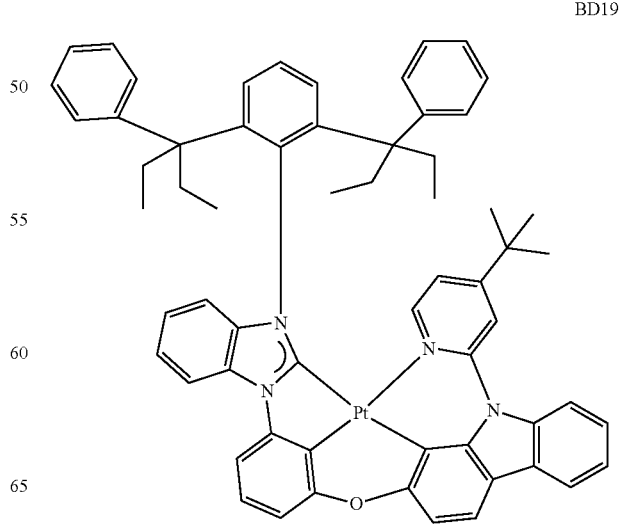

BD20
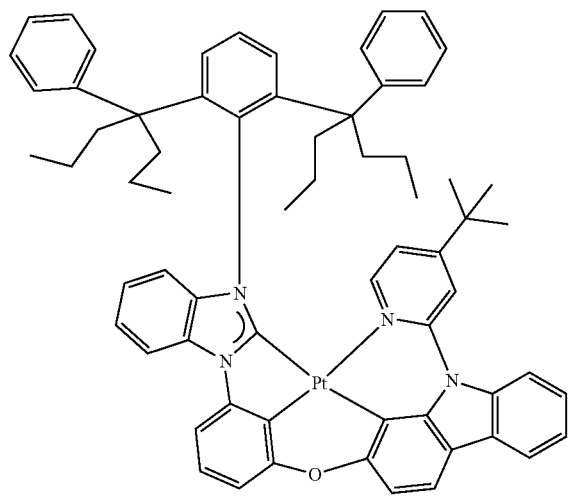
BD24
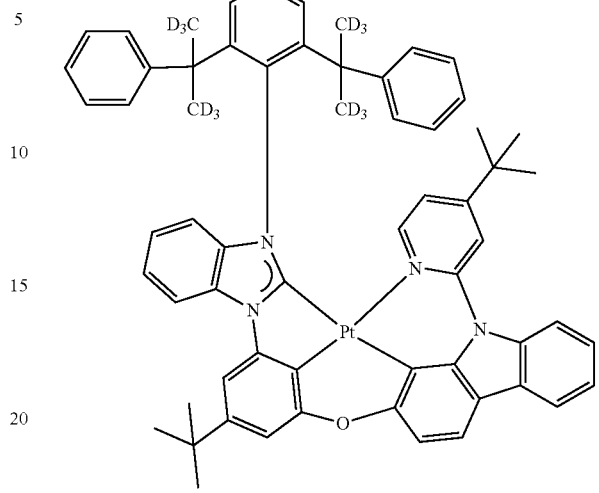
BD21
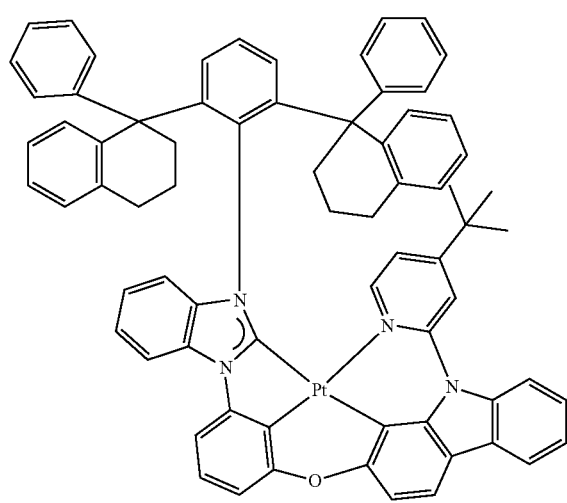
BD25
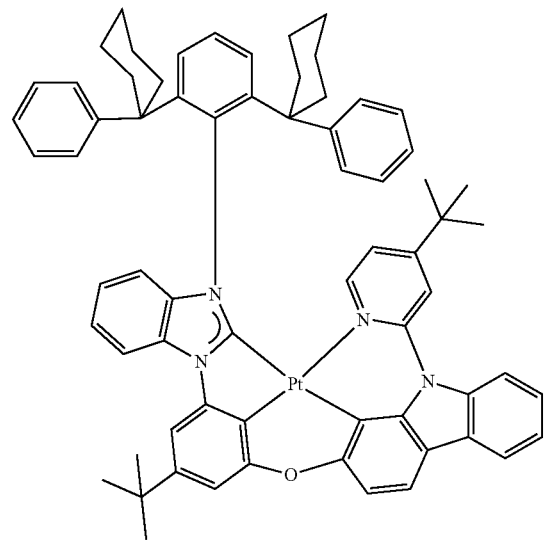
BD22
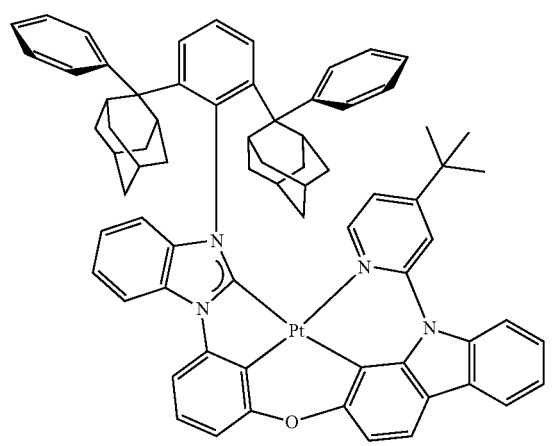
BD26
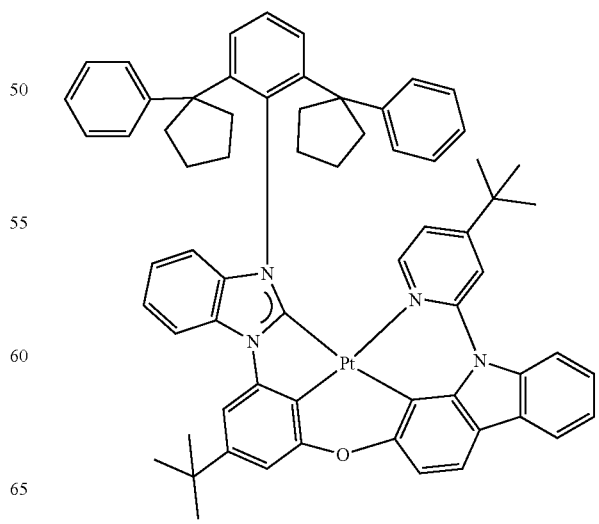

-continued
BD27
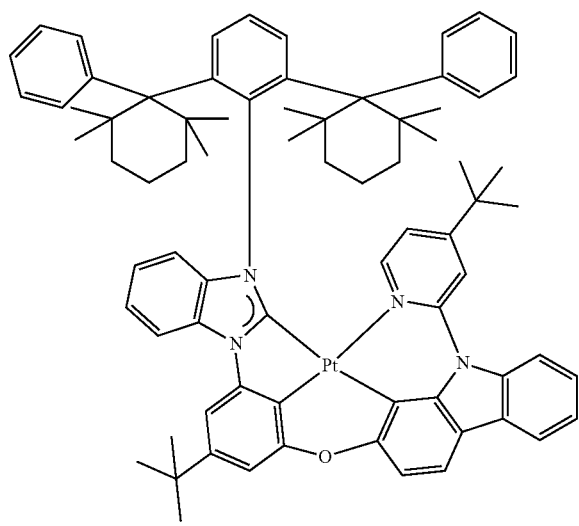
BD28
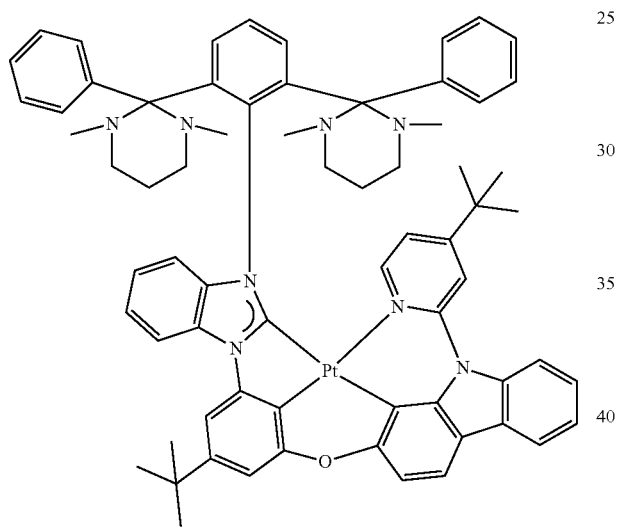
BD29
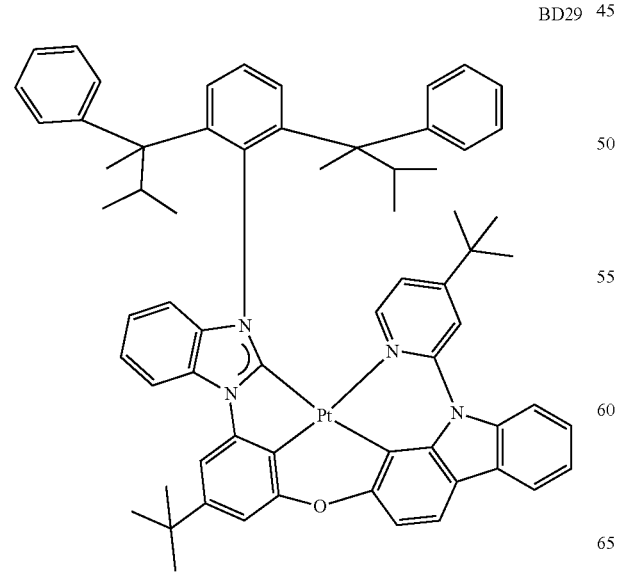
-continued
BD30
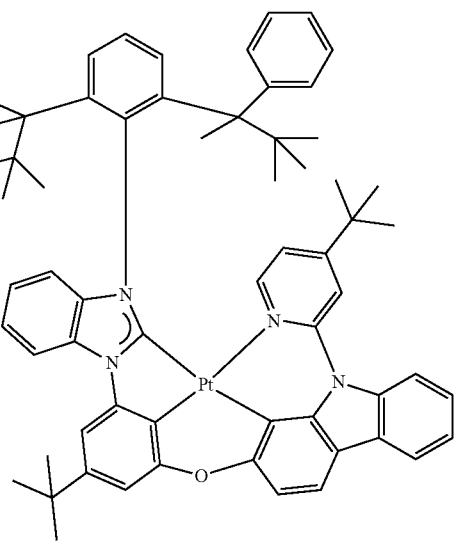
BD31
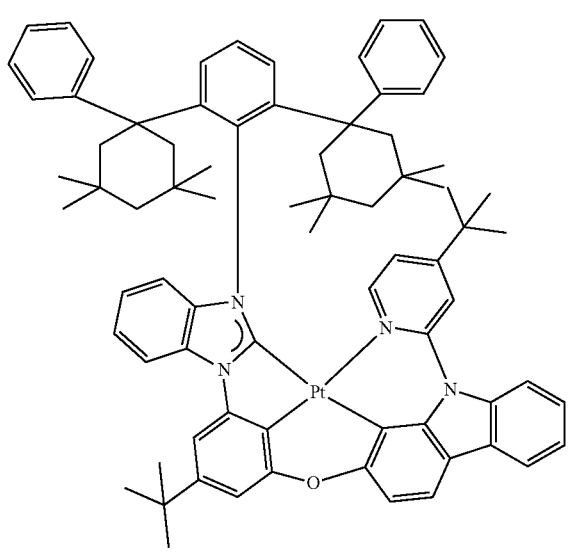

BD32
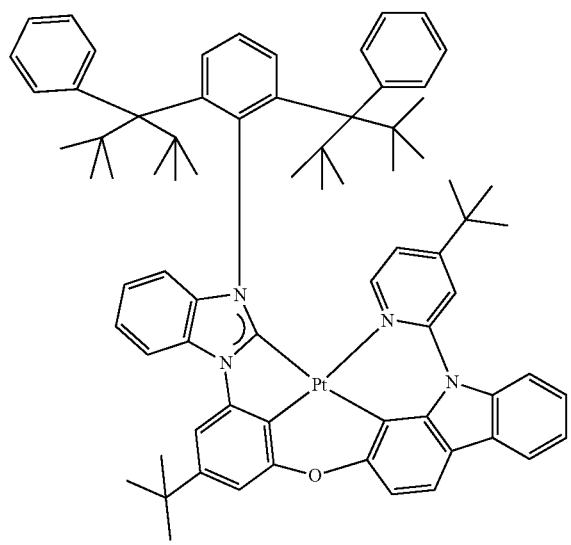
BD34
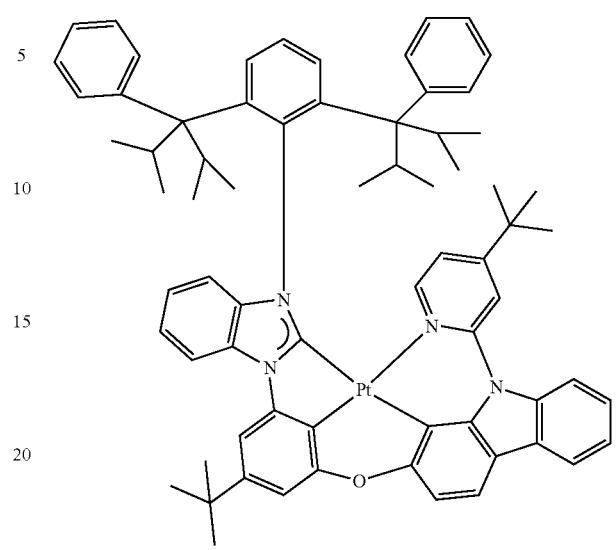
BD33
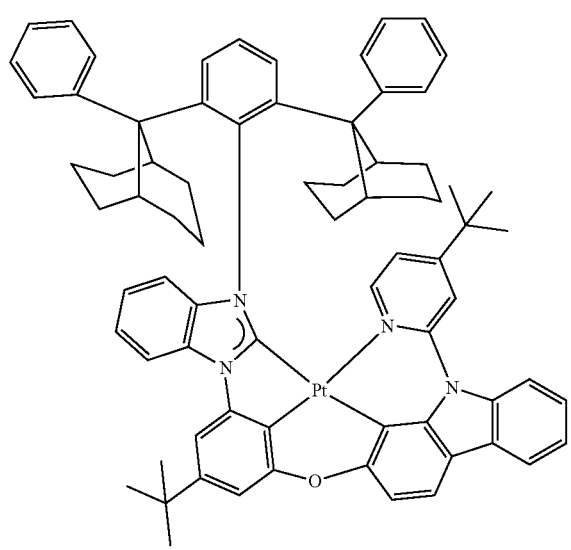
BD35
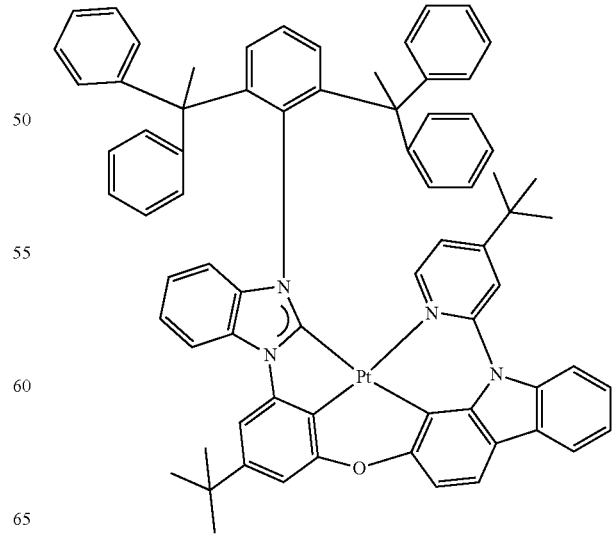

BD36
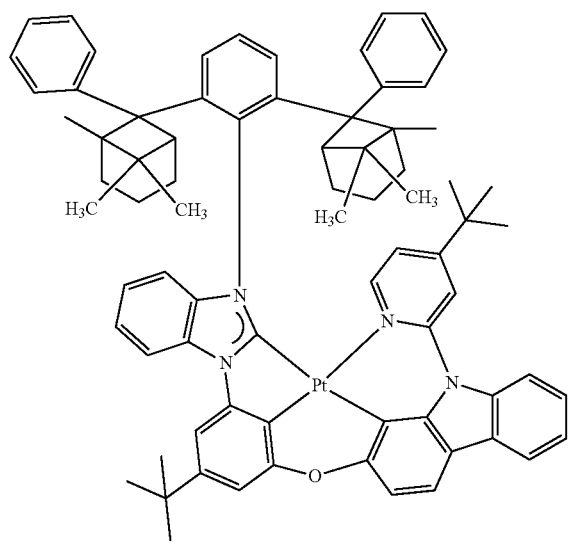
BD38
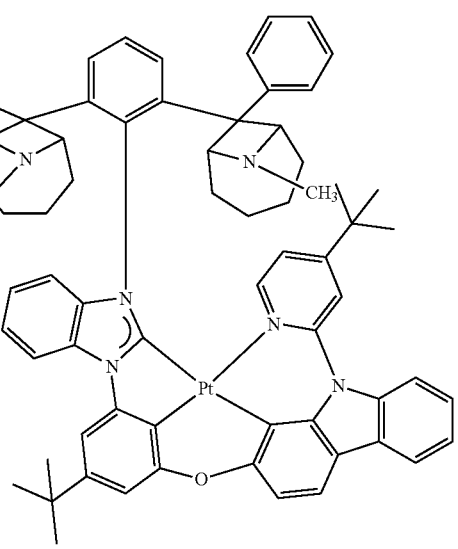
BD37
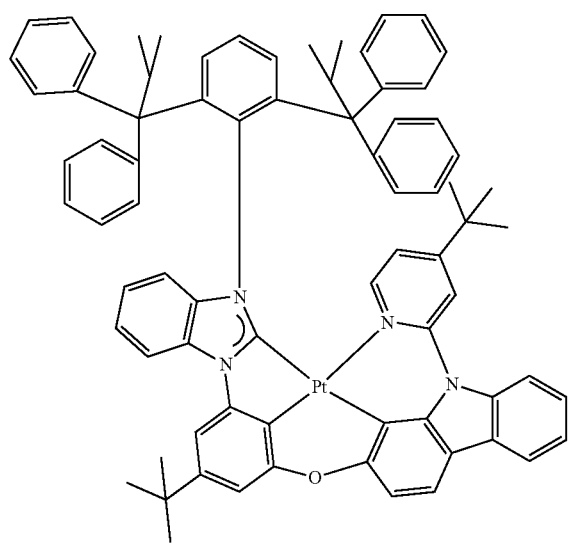
BD39
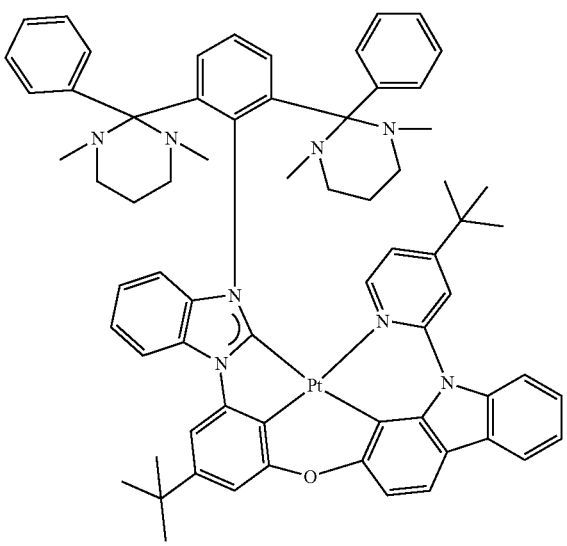

BD40
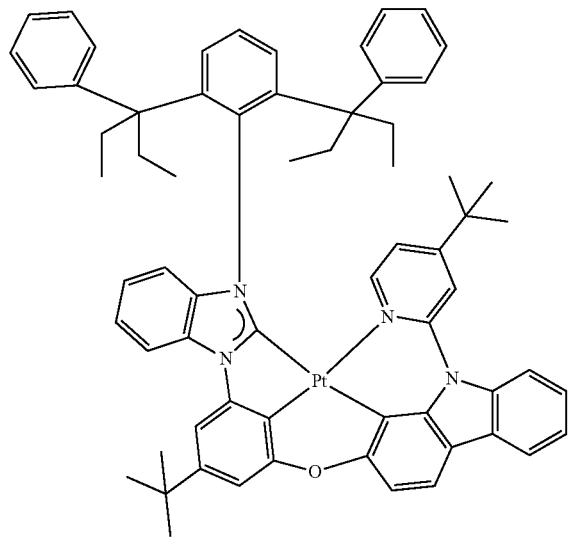
BD41
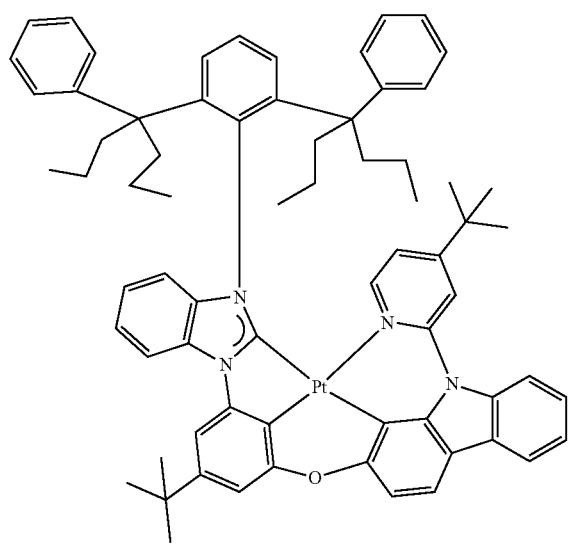
BD42
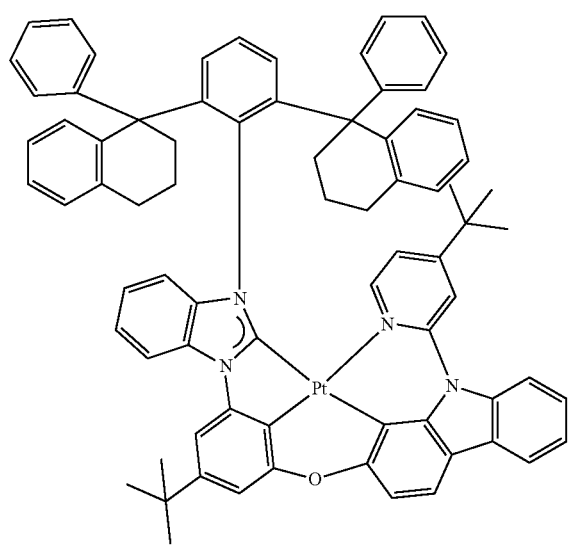
BD43
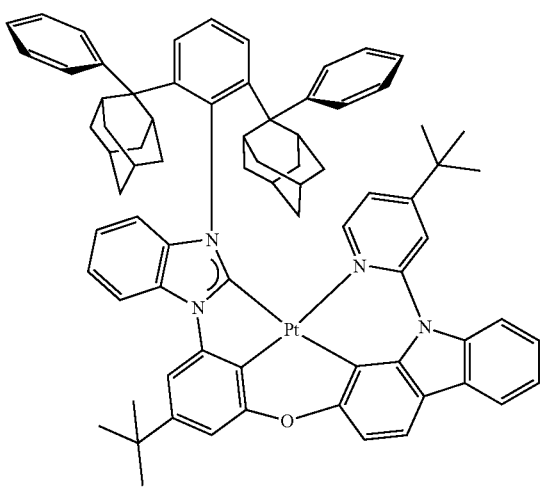
BD44
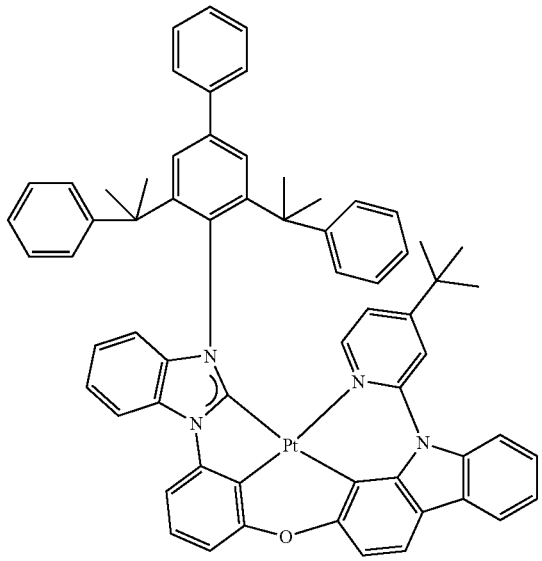
BD45
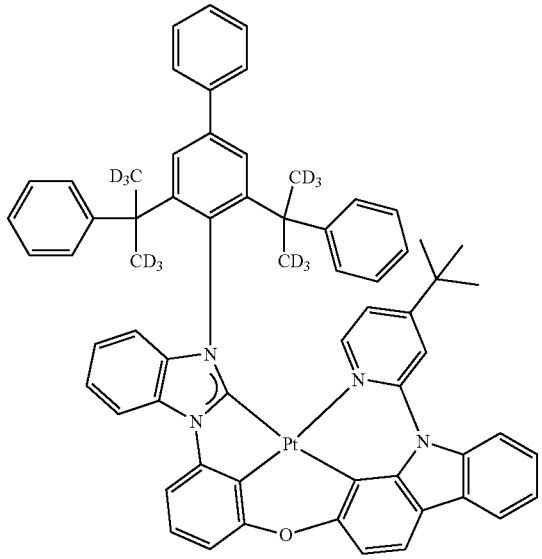

BD46
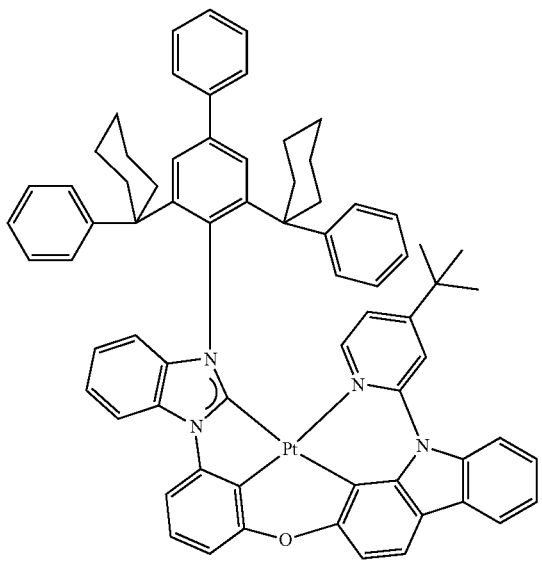
BD48
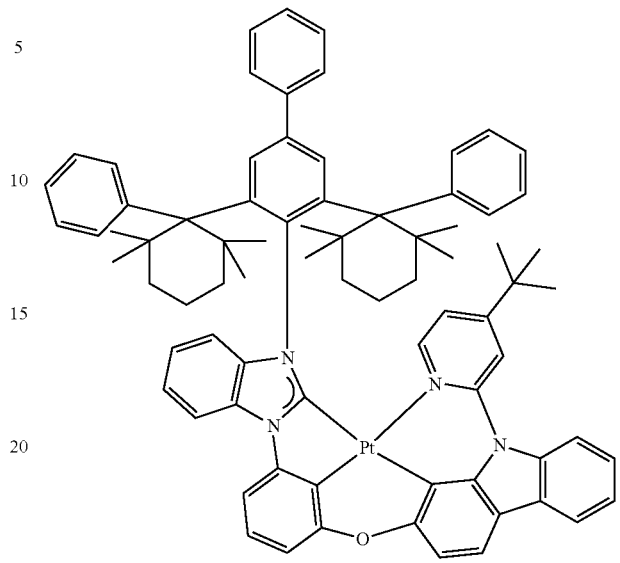
BD47
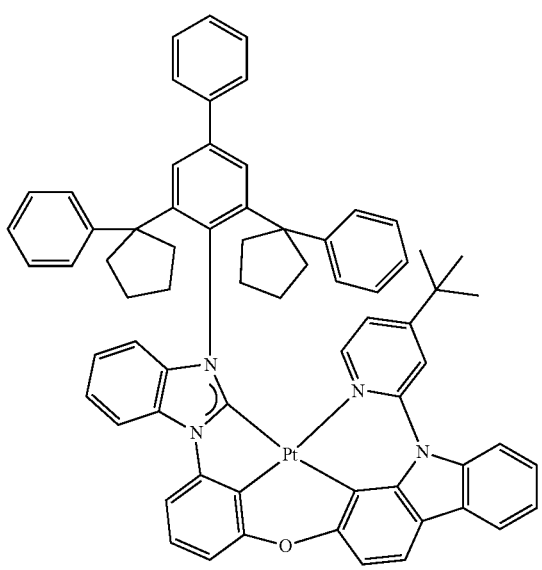
BD49
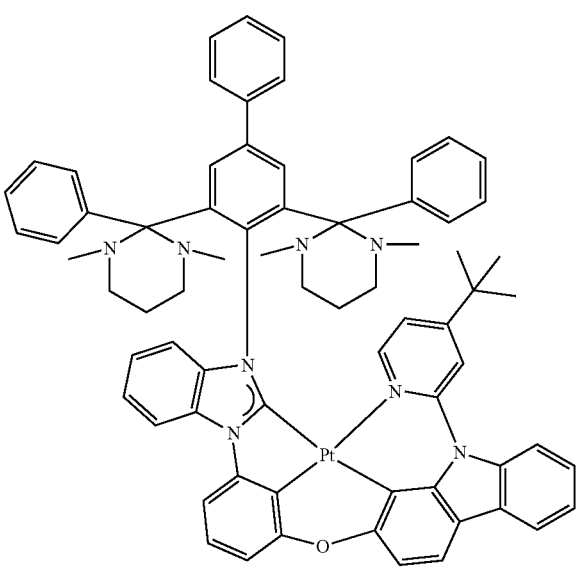

BD50
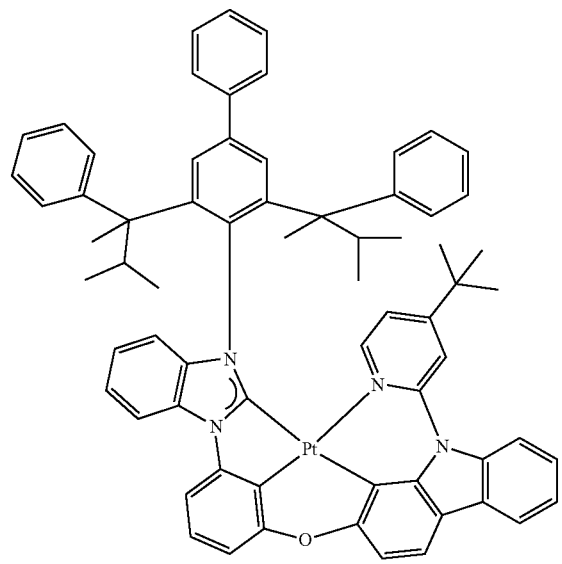
BD52
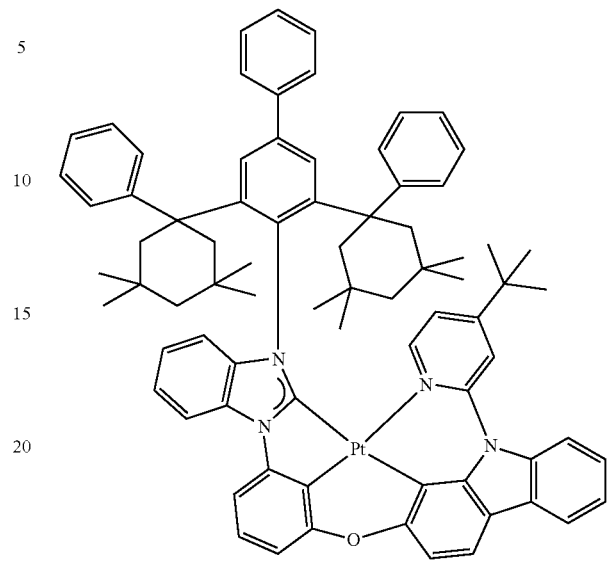
BD51
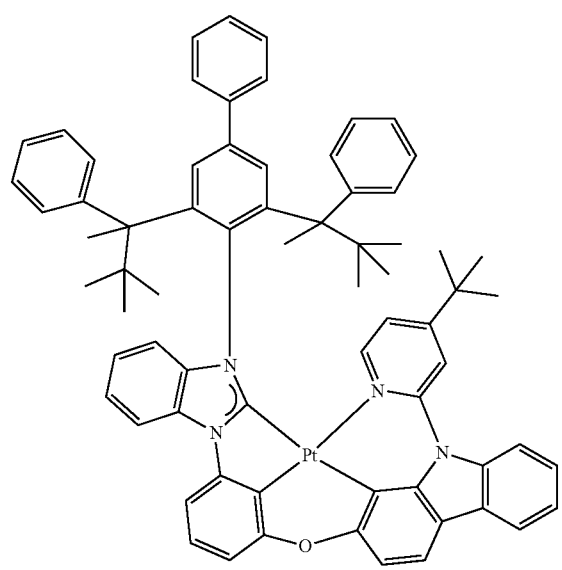
BD53
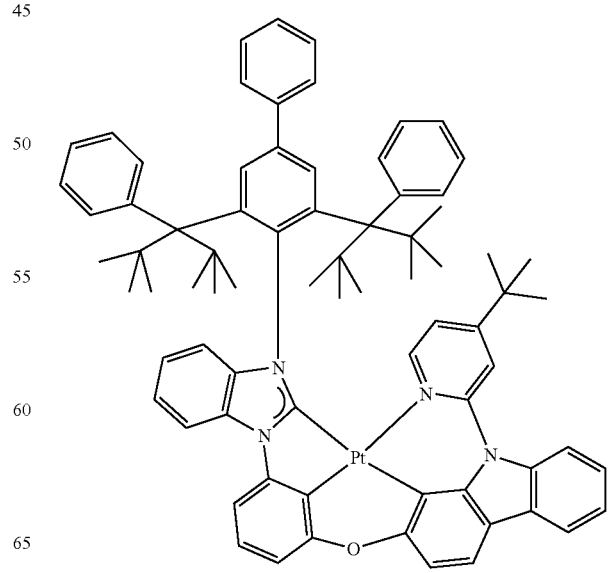

BD54
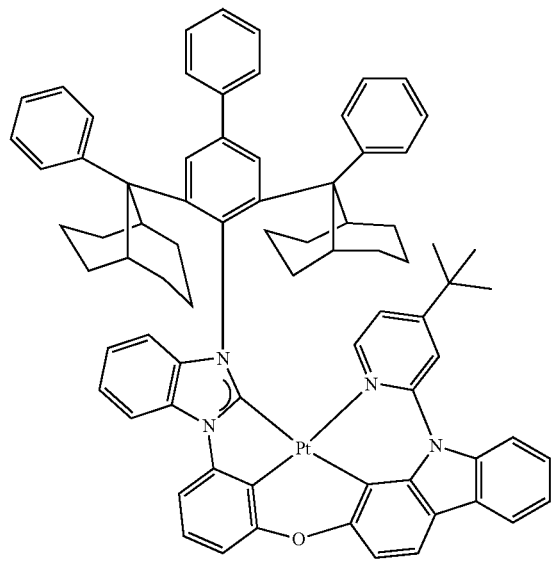
BD56
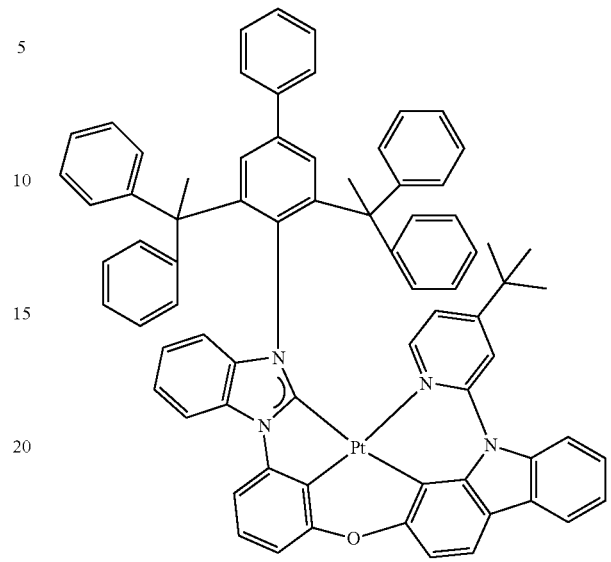
BD55
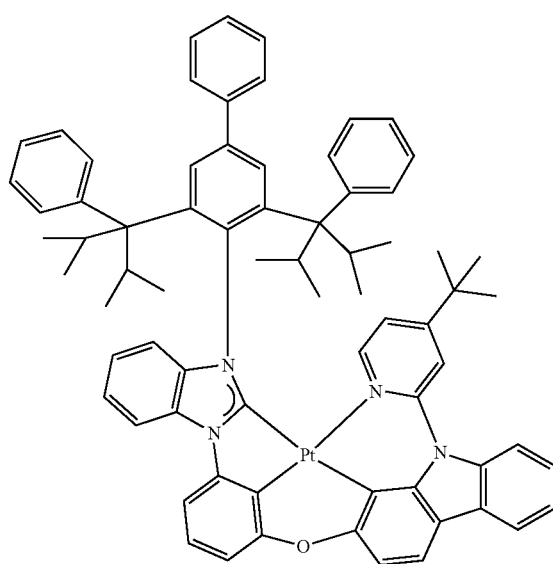
BD57
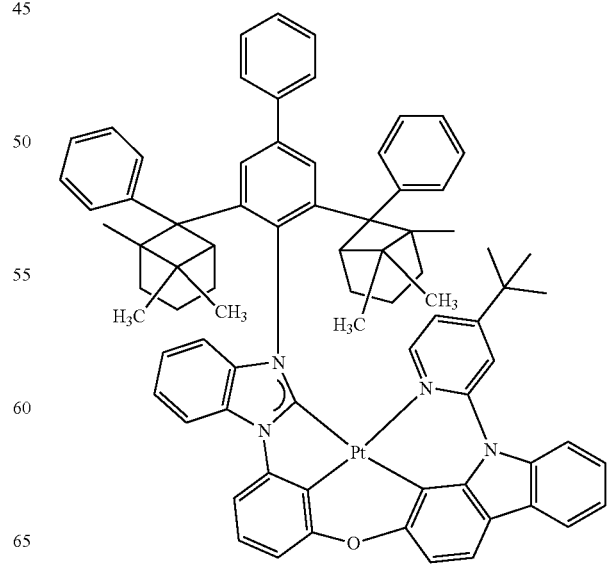

BD58
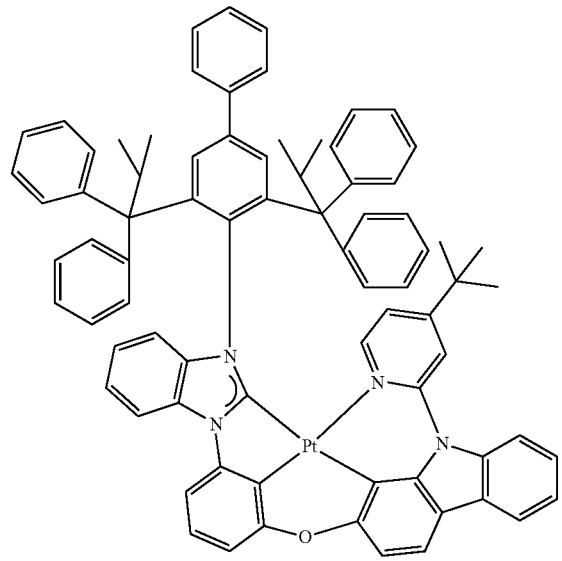
BD60
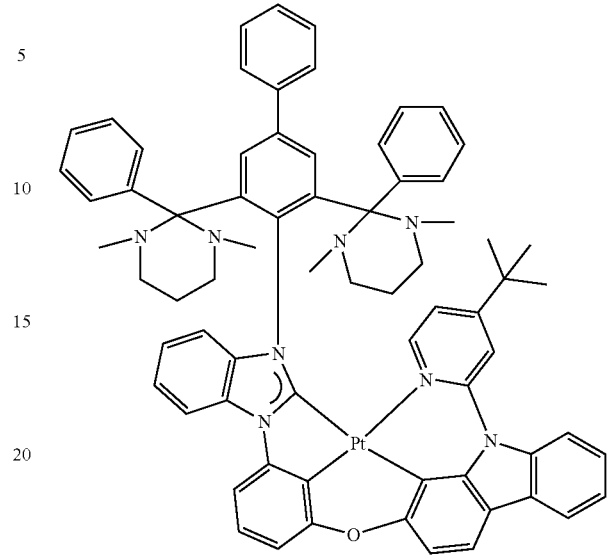
BD59
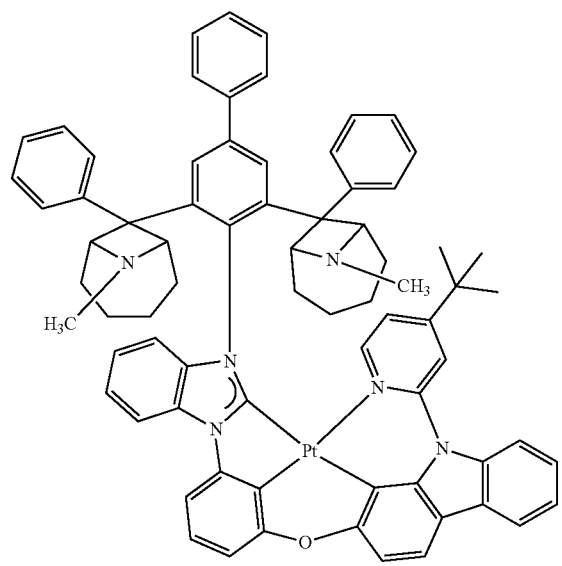
BD61
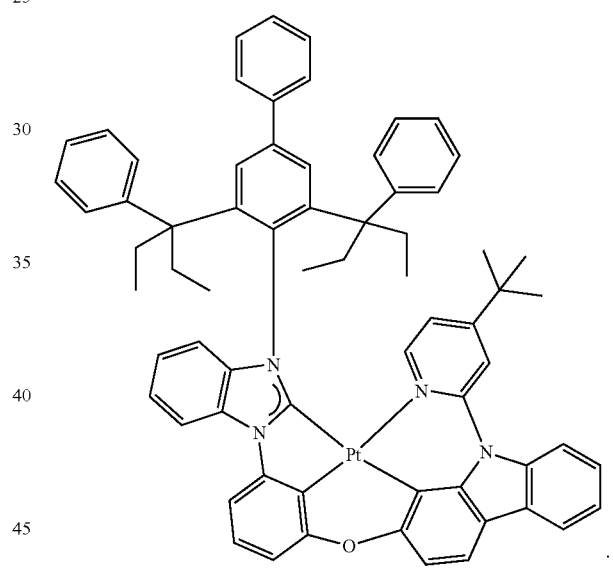
* * * * *

UNITED STATES PATENT AND TRADEMARK OFFICE
CERTIFICATE OF CORRECTION

Page 1 of 5

PATENT NO. : 12,250,874 B2
APPLICATION NO. : 17/447249
DATED : March 11, 2025
INVENTOR(S) : Eunsoo Ahn et al.

It is certified that error appears in the above-identified patent and that said Letters Patent is hereby corrected as shown below:

In the Claims

In Column 162, Line 37, in Claim 1, delete "As" and insert -- $A_3$ --.

In Column 163, Lines 40-46, in Claim 4, Formula 2-2, delete

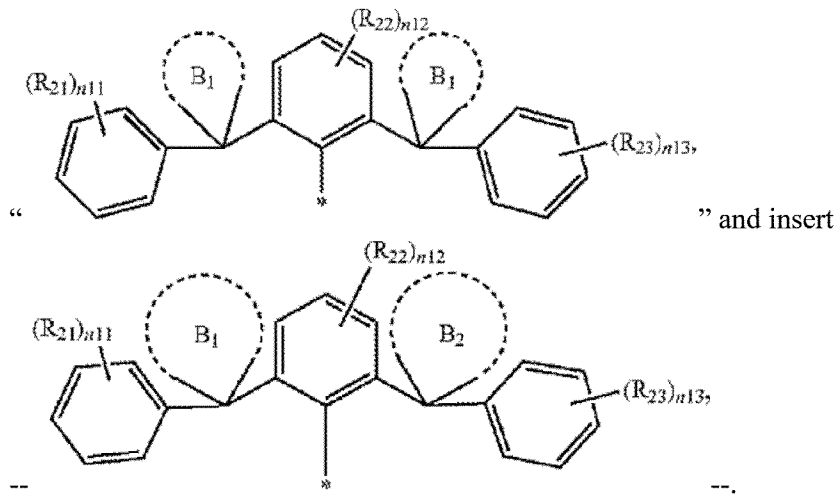

" and insert

" and insert

-- --.

In Column 163, Line 48, in Claim 4, above "wherein," delete "and".

In Column 166, Line 29, in Claim 8, delete "As" and insert -- $A_3$ --.

Signed and Sealed this
Twenty-ninth Day of July, 2025

Coke Morgan Stewart
*Acting Director of the United States Patent and Trademark Office*

In Column 205, Lines 54-66, in Claim 11, Compound ETH60, delete
" 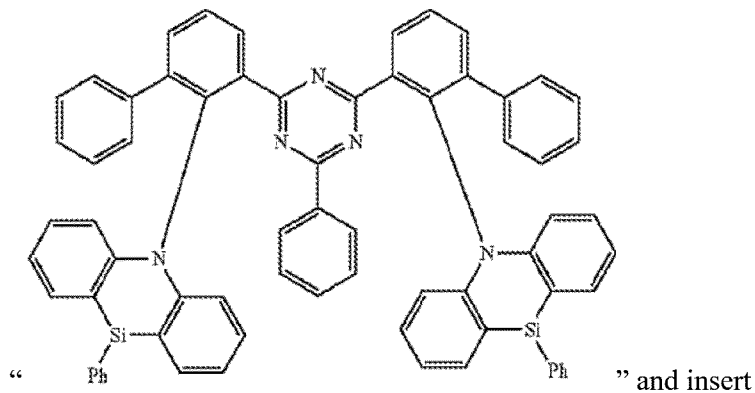 " and insert
-- 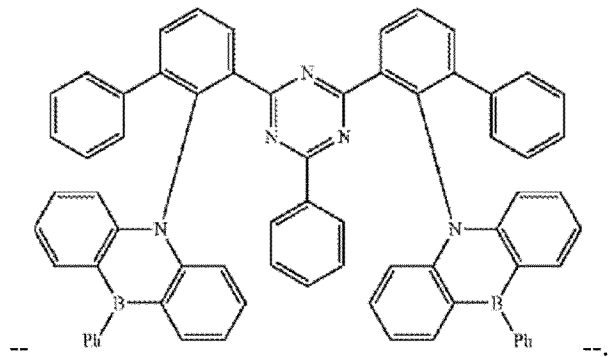 --.
In Column 222, Lines 17-28, in Claim 12, Compound HTH44, delete
" 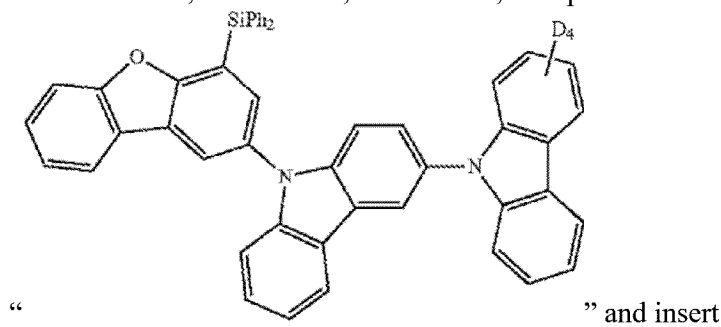 " and insert
-- 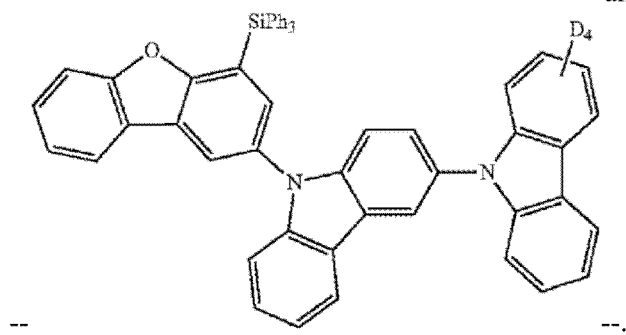 --.

CERTIFICATE OF CORRECTION (continued)
U.S. Pat. No. 12,250,874 B2

In Column 222, Lines 46-55, in Claim 12, Compound HTH46, delete

" 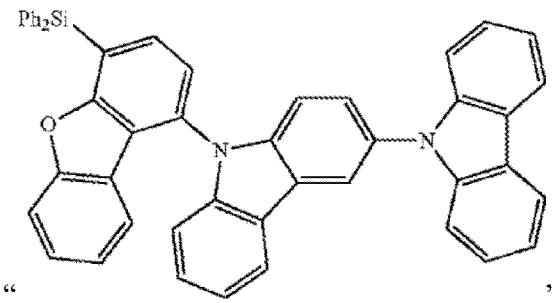 " and insert

-- 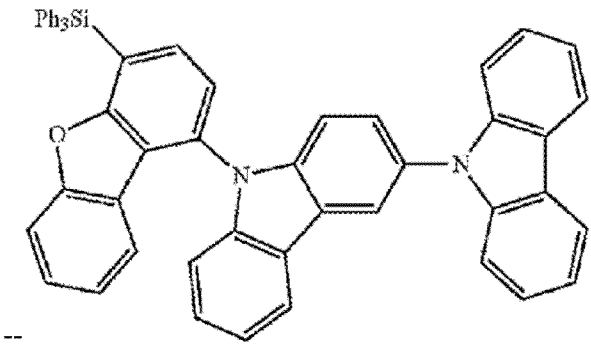 --.

In Column 225, Lines 3-15, in Claim 13, Compound DFD5, delete

" 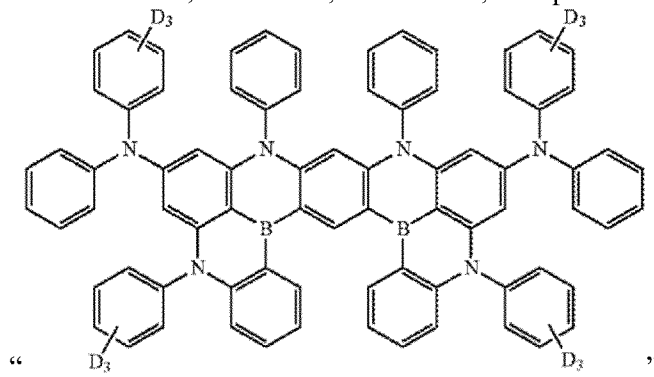 " and insert

-- 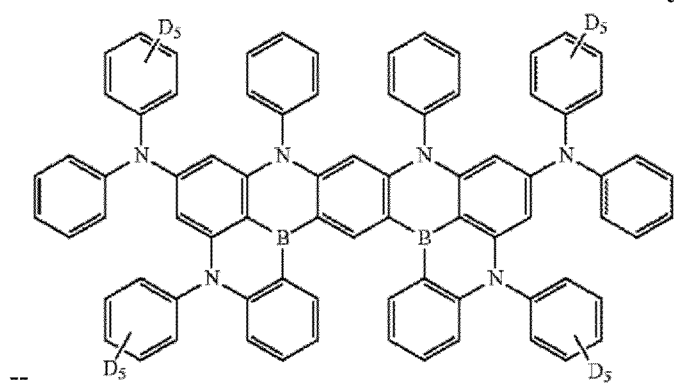 --.

CERTIFICATE OF CORRECTION (continued)
U.S. Pat. No. 12,250,874 B2

In Column 225, Lines 20-32, in Claim 13, Compound DFD6, delete

" 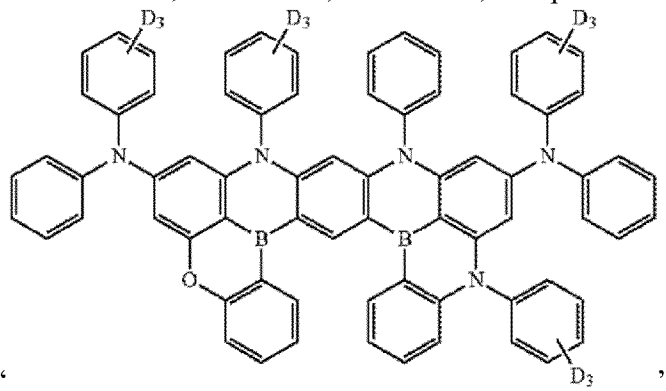 " and insert

-- 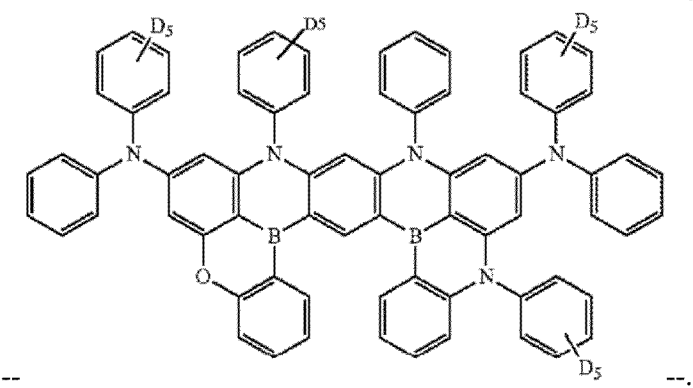 --.

In Column 225, Lines 37-49, in Claim 13, Compound DFD7, delete

" 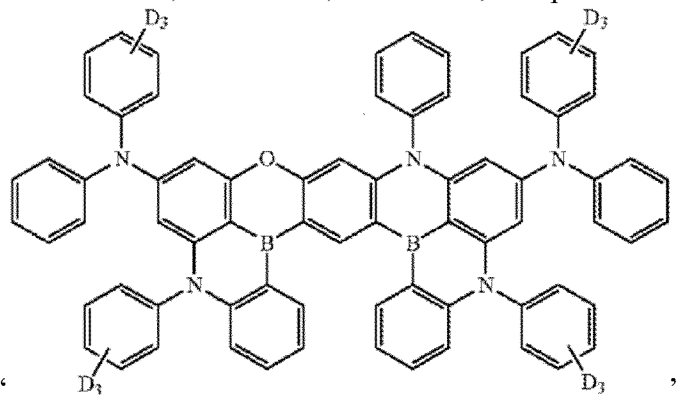 " and insert

-- 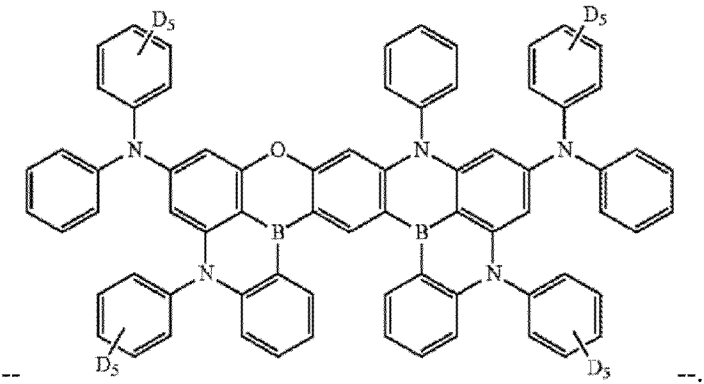 --.

In Column 225, Lines 55-67, in Claim 13, Compound DFD8, delete
" 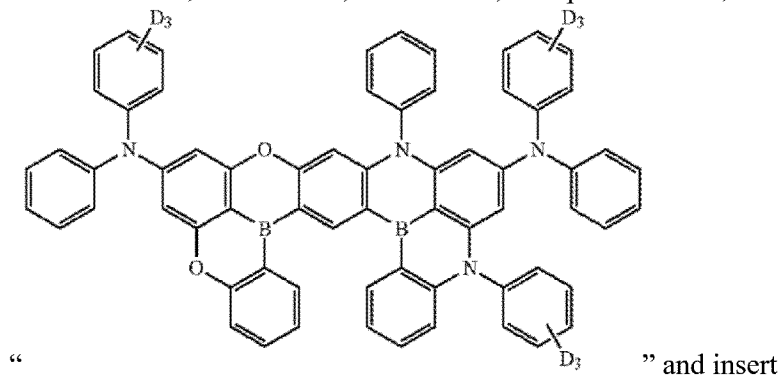 " and insert
-- 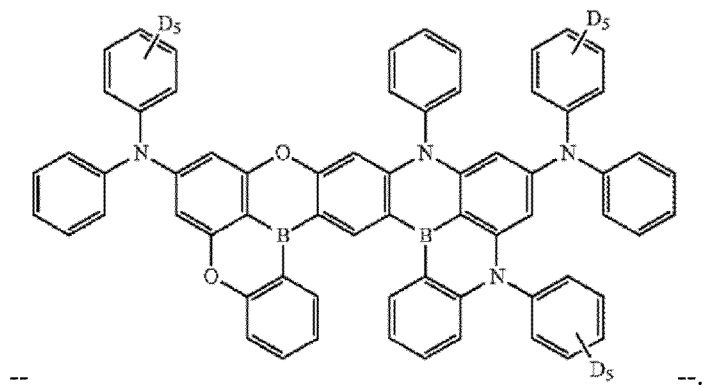 --.
In Column 227, Line 40, in Claim 14, delete "2-below:" and insert -- 2: --.
In Column 228, Lines 4-5, in Claim 14, delete "Ra to Ra" and insert -- $R_a$ to $R_d$ --.
In Column 228, Lines 20-25, in Claim 15, Formula 2-2, delete
" 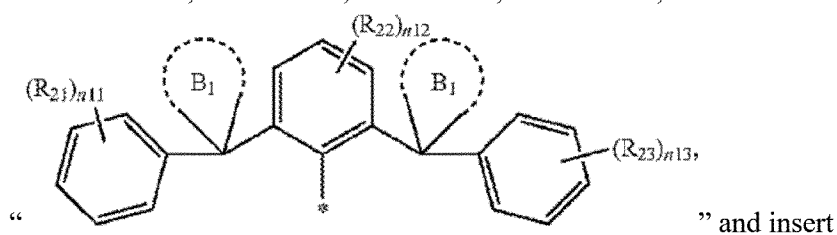 " and insert
-- 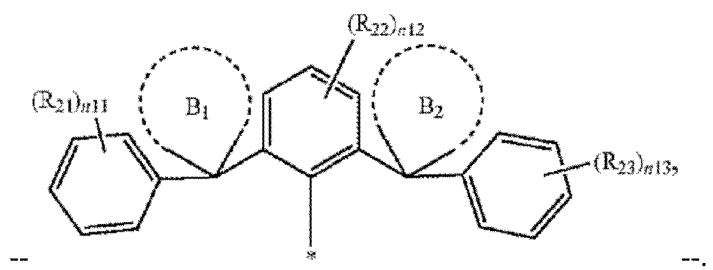 --.
In Column 230, Line 2, in Claim 18, delete "1-above" and insert -- 1 --.